United States Patent
Dennis, Jr. et al.

(10) Patent No.: US 9,822,400 B2
(45) Date of Patent: Nov. 21, 2017

(54) METHODS FOR TREATING, DIAGNOSING, AND MONITORING RHEUMATOID ARTHRITIS

(71) Applicant: Genentech, Inc., South San Francisco, CA (US)

(72) Inventors: Glynn Dennis, Jr., Fairfieled, CA (US); Flavius Martin, Hayward, CA (US); Michael J. Townsend, San Jose, CA (US)

(73) Assignee: GENENTECH, INC., South San Francisco, CA (US)

( * ) Notice: Subject to any disclaimer, the term of this patent is extended or adjusted under 35 U.S.C. 154(b) by 167 days.

(21) Appl. No.: 14/248,135

(22) Filed: Apr. 8, 2014

(65) Prior Publication Data

US 2014/0341887 A1 Nov. 20, 2014

Related U.S. Application Data

(62) Division of application No. 12/874,972, filed on Sep. 2, 2010, now Pat. No. 8,728,730.

(60) Provisional application No. 61/252,424, filed on Oct. 16, 2009, provisional application No. 61/275,948, filed on Sep. 3, 2009.

(51) Int. Cl.
| | |
|---|---|
| G01N 33/53 | (2006.01) |
| C12Q 1/68 | (2006.01) |
| A61K 38/16 | (2006.01) |
| G01N 33/564 | (2006.01) |
| C07K 16/28 | (2006.01) |

(52) U.S. Cl.
CPC ............ *C12Q 1/6837* (2013.01); *A61K 38/16* (2013.01); *C07K 16/2887* (2013.01); *C12Q 1/686* (2013.01); *C12Q 1/6883* (2013.01); *G01N 33/564* (2013.01); *C12Q 2600/106* (2013.01); *C12Q 2600/112* (2013.01); *C12Q 2600/158* (2013.01); *G01N 2800/102* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,434,227 A | 2/1984 | Unger |
| 5,484,892 A | 1/1996 | Tedder et al. |
| 5,595,721 A | 1/1997 | Kaminski et al. |
| 5,677,180 A | 10/1997 | Robinson et al. |
| 5,736,137 A | 4/1998 | Anderson et al. |
| 6,110,695 A | 8/2000 | Gunn et al. |
| 6,139,832 A | 10/2000 | Li et al. |
| 6,183,744 B1 | 2/2001 | Goldenberg |
| 6,485,719 B1 | 11/2002 | Li et al. |
| 6,818,406 B2 | 11/2004 | Goronzy et al. |
| 7,074,403 B1 | 7/2006 | Goldenberg et al. |
| 7,105,149 B1 | 9/2006 | Dalla-Favera |
| 7,332,302 B2 | 2/2008 | Li et al. |
| 7,390,884 B2 | 6/2008 | Segal et al. |
| 8,728,730 B2 | 5/2014 | Dennis, Jr. et al. |
| 2003/0027136 A1 | 2/2003 | Goronzy et al. |
| 2003/0166551 A1* | 9/2003 | Matsuzawa ........ C07K 14/5759 435/7.1 |
| 2003/0219433 A1 | 11/2003 | Hansen et al. |
| 2003/0224386 A1 | 12/2003 | Guild et al. |
| 2004/0009479 A1 | 1/2004 | Wohlgemuth et al. |
| 2004/0258682 A1 | 12/2004 | Leung et al. |
| 2005/0070689 A1 | 3/2005 | Dixit et al. |
| 2005/0095243 A1 | 5/2005 | Chan et al. |
| 2005/0163775 A1 | 7/2005 | Chan et al. |
| 2005/0202421 A1 | 9/2005 | Hirsch et al. |
| 2006/0024295 A1 | 2/2006 | Brunetta |
| 2006/0094056 A1 | 5/2006 | Chappell et al. |
| 2006/0110387 A1 | 5/2006 | Brunetta |
| 2006/0286556 A1 | 12/2006 | Segal et al. |
| 2007/0071760 A1 | 3/2007 | Broly et al. |
| 2007/0105133 A1 | 5/2007 | Clarke et al. |
| 2008/0014201 A1 | 1/2008 | Bugelski et al. |
| 2008/0044419 A1 | 2/2008 | Yayon |
| 2008/0108509 A1 | 5/2008 | Haupl et al. |
| 2008/0199481 A1 | 8/2008 | Barker et al. |
| 2008/0227704 A1 | 9/2008 | Kamens |
| 2008/0279849 A1 | 11/2008 | Segal et al. |
| 2008/0292632 A1 | 11/2008 | Pastan et al. |
| 2009/0083867 A1 | 3/2009 | Ferguson et al. |
| 2009/0136512 A1 | 5/2009 | Bugelski et al. |
| 2009/0202474 A1 | 8/2009 | Chockalingam et al. |
| 2009/0204489 A1 | 8/2009 | Behrens et al. |
| 2010/0086942 A1 | 4/2010 | Barker et al. |
| 2010/0261881 A1 | 10/2010 | Beator et al. |

FOREIGN PATENT DOCUMENTS

| | | |
|---|---|---|
| EP | 0 175 270 B1 | 3/1986 |
| EP | 0 869 180 A1 | 10/1998 |

(Continued)

OTHER PUBLICATIONS

Handbook of Chemistry and Physics, 49th Edition, 1968, Weast (ed.), The Chemical Rubber Co., Cleveland, Ohio, p. A-245.*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Arthritis & Rheumatism. 2008 Annual Scientific Meeting, 43rd Annual Meeting Association of Rheumatology Health Professionals, Oct. 24-29, 2008, San Francisco, *Arthritis & Rheumatism* 58(9)(Suppl.):S451-S452, (Sep. 2008).

(Continued)

*Primary Examiner* — James Martinell
(74) *Attorney, Agent, or Firm* — Morrison & Foerster LLP

(57) ABSTRACT

Methods of identifying, diagnosing, and prognosing rheumatoid arthritis are provided, as well as methods of treating rheumatoid arthritis. Also provided are methods for identifying effective rheumatoid arthritis therapeutic agents and predicting responsiveness to rheumatoid arthritis therapeutic agents.

17 Claims, 18 Drawing Sheets

(56) References Cited

FOREIGN PATENT DOCUMENTS

| | | |
|---|---|---|
| EP | 1 476 120 B1 | 11/2004 |
| EP | 1 504 035 B1 | 2/2005 |
| RU | 2005122655 A | 1/2006 |
| WO | WO-96/24668 | 8/1996 |
| WO | WO-96/39522 | 12/1996 |
| WO | WO-98/18921 A1 | 5/1998 |
| WO | WO-98/27114 | 6/1998 |
| WO | WO-99/12964 | 3/1999 |
| WO | WO-99/28468 | 6/1999 |
| WO | WO-99/33980 | 7/1999 |
| WO | WO-00/40716 | 7/2000 |
| WO | WO-01/12812 A2 | 2/2001 |
| WO | WO-01/87979 A2 | 11/2001 |
| WO | WO-02/02641 A1 | 1/2002 |
| WO | WO-02/16312 | 2/2002 |
| WO | WO02/16412 A2 | 2/2002 |
| WO | WO-02/24909 A2 | 3/2002 |
| WO | WO-02/38766 A2 | 5/2002 |
| WO | WO-02/066516 A2 | 8/2002 |
| WO | WO-02/080010 A1 | 10/2002 |
| WO | WO-02/092620 A2 | 11/2002 |
| WO | WO-03/002607 | 1/2003 |
| WO | WO-03/014294 A2 | 2/2003 |
| WO | WO-03/024991 A2 | 3/2003 |
| WO | WO-03/035846 | 5/2003 |
| WO | WO-03/072736 A2 | 9/2003 |
| WO | WO-03/072827 | 9/2003 |
| WO | WO-2004/035607 A2 | 4/2004 |
| WO | WO-2004/056312 A2 | 7/2004 |
| WO | WO-2004/056864 A1 | 7/2004 |
| WO | WO-2005/000351 A2 | 1/2005 |
| WO | WO-2006/039238 A2 | 4/2006 |
| WO | WO-2006/068867 A1 | 6/2006 |
| WO | WO-2007/014238 A2 | 2/2007 |
| WO | WO-2007/038501 | 4/2007 |
| WO | WO-2007/122402 A1 | 11/2007 |
| WO | WO-2007/124414 A2 | 11/2007 |
| WO | WO-2007/135568 | 11/2007 |
| WO | WO-2008/056198 | 5/2008 |
| WO | WO-2008/079361 A2 | 7/2008 |
| WO | WO-2008/102123 A1 | 8/2008 |
| WO | WO-2008/104608 | 9/2008 |
| WO | WO-2008/121940 A1 | 10/2008 |
| WO | WO-2008/122007 A1 | 10/2008 |
| WO | WO-2008/132176 | 11/2008 |
| WO | WO-2008/154423 | 12/2008 |
| WO | WO-2009/030226 A2 | 3/2009 |
| WO | WO-2009/030226 A3 | 3/2009 |
| WO | WO-2010/120561 | 10/2010 |

OTHER PUBLICATIONS

Szodoray et al. "Apoptotic Effect of Rituximab on Peripheral Blood B Cells in Rheumatoid Arthritis," *Scandinavian Journal of Immunology* 60:209-218, (2004).

I. Rioja Pastor et al. "[SAT0075-AHP] B-Lymphocyte chemoattractant (BLC/CXCL13): A potential novel disease activity marker of rheumatoid arthritis", *Annals of the Rheumatic Diseases* 66(Suppl. 2):452, one page (2007).

"Guidelines for the Management of Rheumatoid Arthritis 2002 Update" Arthritis and Rheumatism 46(2):328-346 (Feb. 2002).

Abbas et al., "Immune response in silico (IRIS): immune-specific genes identified from a compendium of microarray expression data" Genes Immun 6:319-31 (2005).

Acosta-Rodriguez et al., "BAFF and LPS cooperate to induce B cells to become susceptible to CD95/Fas-mediated cell death" Eur. J. Immunol 37(4):990-1000 (2007).

Aggarwal et al., "Human Tumor Necrosis Factor" J Biol Chem 260(4):2345-2354 (1985).

Alamanosa et al., "Epidemiology of adult rheumatoid arthritis" Autoimmunity Reviews 4:130-136 (2005).

Alarcon et al., "Radiographic evidence of disease progression in methotrexate treated and nonmethotrexate disease modifying antirheumatic drug treated rheumatoid arthritis patients: a meta-analysis" J. Rheumatol 19(12):1868-73 (Dec. 1992).

Albert et al., "Modeling therapeutic strategies in rheumatoid arthritis: use of decision analysis and Markov models" J Rheumatol 27(3):644-52 (Mar. 2000).

Antoni et al., "The Infliximab Multinational Psoriatic Arthritis Controlled Trial (IMPACT): Results of Radiographic Analyses After 1 Year" Ann Rheum Dis 64(Suppl 111):107 (2005).

Arnett et al., "The American Rheumatism Association 1987 revised criteria for the classification of rheumatoid arthritis" Arthritis Rheum 31(3):315-24 (Mar. 1988).

Avouac et al., "Diagnostic and predictive value of anti-cyclic citrullinated protein antibodies in rheumatoid arthritis: a systematic literature review" Ann Rheum Dis 65(7):845-51 (Jul. 2006).

Badot et al., "Gene expression profiling in the synovium identifies a predictive signature of absence of response to adalimumab therapy in rheumatoid arthritis" Arthritis Research & Therapy (Epub Apr. 23, 2009), 11:R57 (2009).

Barrett et al., "NCBI GEO: archive for functional genomics data sets—10 years on" Nucleic Acids Research (Database issue), 39:D1005-D1010 (2011).

Bathon et al., "A Comparison of Etanercept and Methotrexate in Patients With Early Rheumatoid Arthritis" N Engl J Med 343:1586-93 (2000).

Batten et al., "BAFF Mediates Survival of Peripheral Immature B Lymphocytes" J Exp Med 192:1453-1465 (2000).

Bodmer et al., "The molecular architecture of the TNF superfamily" Trends Biochem Sci 27(1):19-26 (Jan. 2002).

Boers et al., "Randomised comparison of combined step-down prednisolone, methotrexate and sulphasalazine with sulphasalazine alone in early rheumatoid arthritis" Lancet 350:309-18 (Aug. 1997).

Bolstad et al., "A comparison of normalization methods for high density oligonucleotide array data based on variance and bias" Bioinformatics 19(2):185-193 (2003).

Bourgon et al., "Independent filtering increases detection power for high-throughput experiments" PNAS 107(21):9546-9551 (May 2010).

Breedveld et al., "Association between baseline radiographic damage and improvement in physical function after treatment of patients with rheumatoid arthritis" Ann Rheum Dis 64(1):52-5 (Jan. 2005).

Bresnihan et al., "Treatment of rheumatoid arthritis with recombinant human interleukin-1 receptor antagonist" Arthritis Rheum 41(12):2196-2204 (1998).

Bugatti et al., "Synovial Tissue Heterogeneity and Peripheral Blood Biomarkers" Curr Rheumatol Rep 13:440-448 (2011).

Bukhari et al., "Rheumatoid factor is the major predictor of increasing severity of radiographic erosions in rheumatoid arthritis: results from the Norfolk Arthritis Register Study, a large inception cohort" Arthritis Rheum 46(4):906-12 (Apr. 2002).

Campbell et al., "Severe inflammatory arthritis and lymphadenopathy in the absence of TNF" J. Clin. Invest. 107:1519-1527 (2001).

Cañete, J.D. et al. (2009). "Clinical significance of synovial lymphoid neogenesis and its reversal after anti-tumour necrosis factor alpha therapy in rheumatoid arthritis," Ann. Rheum. Dis. 68:751-756.

Chan A.C. et al. (2013). "Personalizing medicine for autoimmune and inflammatory diseases," Nat. Immunol. 14:106-109.

Chen, G. et al. (2002). "TNF-R1 signaling: a beautiful pathway," Science 296:1634-1635.

Cheema et al., "Elevated Serum B Lymphocyte Stimulator Levels in Patients With Systemic Immune-Based Rheumatic Diseases" Arthritis Rheum 44:1313-1319 (2001).

Childs et al., "Efficacy of Etanercept for Wear Debris-Induced Osteolysis" Journal of Bone and Mineral Research 16(2):338-347 (2001).

Choy, E. (2012). "Understanding the dynamics: pathways involved in the pathogenesis of rheumatoid arthritis," Rheumatology 51(Suppl 5):v3-v11.

Claudio et al., "BAFF-induced NEMO-independent processing of NF-kB2 in maturing B cells" Nature Immunol 3(10):958-965 (Oct. 2002).

Cohen et al., "Rituximab for rheumatoid arthritis refractory to anti-tumor necrosis factor therapy: Results of a multicenter, ran-

(56) References Cited

OTHER PUBLICATIONS domized, double-blind, placebo-controlled, phase III trial evaluating primary efficacy and safety at twenty-four weeks" Arthritis & Rheumatism 54(9):2793-2806 (Sep. 2006).
Cooke et al., "Solution Structure of Human Insulin-Like Growth Factor 1: A Nuclear Magnetic Resonance and Restrained Molecular Dynamics Study" Biochemistry—US 30:5484-5491 (1991).
International Search Report and Written Opinion for International Patent Application No. PCT/US10/47734 (2011).
Corsiero, E. et al. (2012). "Role of lymphoid chemokines in the development of functional ectopic lymphoid structures in rheumatic autoimmune diseases," Immunol. Lett. 145: 62-67.
Csuka et al., "Treatment of intractable rheumatoid arthritis with combined cyclophosphamide, azathioprine, and hydroxychloroquine. A follow-up study" J Am Medical Assn 255(17):2315-9 (May 1986).
Cuchacovich et al., "Precision of the Larsen and the Sharp Methods of Assessing Radiologic Change in Patients With Rheumatoid Arthritis" Arthritis and Rheumatism 35(7):736-739 (Jul. 1992).
Deng et al. "Role of CTLA-4 Ig in Rat Arthritis Models," Acad. J. Sec. Mil. Med. Univ. 22(12):1160-1162, (EnglishTranslation of the Abstract Only.) (Dec. 2001).
Dennis G., Jr. et al. (2003). "DAVID: Database for Annotation, Visualization, and Integrated Discovery," Genome biology 4(5):P3.
Dennis et al. "Synovial Phenotypes in Reheumatoid Arthritis Correlate With Response to Biologic Therapeutics," Arthritis Research & Therapy 16(R90):1-18 (2014).
Di Franco et al., "Relationship of rheumatoid factor isotype levels with joint lesions detected by magnetic resonance imaging in early rheumatoid arthritis" Rev Rhum Engl Ed 66(5):251-5 (May 1999).
Douni et al., "Transgenic and knockout analyses of the role of TNF in immune regulation and disease pathogenesis" J. Inflamm 47(Suppl 27-38) (1996).
Drossaers-Bakker et al., "A Comparison of Three Radiologic Scoring Systems for the Long-Term Assessment of Rheumatoid Arthritis" Arthritis & Rheumatism 43(7):1465-1472 (Jul. 2000).
Edgar et al., "Gene Expression Omnibus: NCBI genen expression and hybridization array data repository" Nucleic Acids Research 30(1):207-210 (2002).
Edmonds et al., "Antirheumatic Drugs: A Proposed New Classification" Arthritis and Rheumatism 363(3):360-340 (Mar. 1993).
Edwards et al., "Do self-perpetuating B lymphocytes drive human autoimmune disease?" Immunology 97(2):188-96 (Jun. 1999).
Emery, P. et al. (2008). "IL-6 receptor inhibition with tocilizumab improves treatment outcomes in patients with rheumatoid arthritis refractory to anti-tumour necrosis factor biologicals: results from a 24-week multicentre randomised placebo-controlled trial," Ann. Rheum. Dis. 67:1516-1523.
Emery et al., "Efficacy and safety of different doses and retreatment of rituximab: a randomised, placebo-controlled trial in patients who are biological naïve with active rheumatoid arthritis and an inadequate response to methotrexate (Study Evaluating Rituximab's Efficacy in MTX iNadequate rEsponders (SERENE))" Ann Rheum Dis 69:1629-1635 (2010).
Feldmann et al., "Rheumatoid Arthritis" Cell 85:307-310 (May 1996).
Felson et al., "American College of Rheumatology Preliminary definition of improvement in rheumatoid arthritis" Arthritis Rheum. 38(6):727-735 (Jun. 1995).
Fex et al., "Development of radiographic damage during the first 5-6 yr of rheumatoid arthritis. A prospective follow-up study of a Swedish cohort" Br J Rheumatol. 35(11):1106-15 (Nov. 1996).
Finis et al., "Analysis of Pigmented Villonodular Synovitis With Genome-Wide Complementary DNA Microarray and Tissue Array Technology Reveals Insight Into Potential Novel Therapeutic Approaches" Arthritis & Rheumatism 54(3):1009-1019 (Mar. 2006).
Forre, "Radiologic evidence of disease modification in rheumatoid arthritis patients treated with cyclosporine. Results of a 48-week multicenter study comparing low-dose cyclosporine with placebo. Norwegian Arthritis Study Group" Arthritis Rheum 37(10):1506-12 (Oct. 1994).
Fraser, "The Waaler-Rose Test: Anatomy of the Eponym" Seminars in Arthritis and Rheumatism 18(1):61-71 (Aug. 1988).
Frijters et al., "CoPub: a literature-based keyword enrichment tool for microarray data analysis" Nucleic Acids Research (Web Server issue doi:10.1093/nar/gkn215. Published online Apr. 28, 2008), 36:W406-W410 (2008).
Gabay, C. et al. (May 4, 2013). "Tocilizumab monotherapy versus adalimumab monotherapy for treatment of rheumatoid arthritis (ADACTA): a randomised, double-blind, controlled phase 4 trial," Lancet 381(9877):1541-1550.
Genovese et al., "Etanercept versus methotrexate in patients with early rheumatoid arthritis: two-year radiographic and clinical outcomes" Arthritis Rheum 46(6):1443-50 (Jun. 2002).
Genovese et al., "Safety and Clinical Activity of Ocrelizumab (a Humanized Antibody Targeting CD20+ B Cells) in Combination with Methotrexate (MTX) in Moderate-Severe Rheumatoid Arthritis (RA) Patients (pts) (Ph I/II Action Study)" Arthritis Rheum (Abstract 6), 54(Supp 9):S66-S67 (Sep. 2006).
Gentleman, R.C. et al. (2004). "Bioconductor: open software development for computational biology and bioinformatics," Genome Biology 5: R80, 16 pages.
Gleissner et al., "CXC Chemokine Ligand 4 Induces a Unique Transcriptome in Monocyte-Derived Macrophages" J Immunol 184:4810-4818 (2010).
Goldring et al., "Mechanisms of bone loss in inflammatory arthritis: diagnosis and therapeutic implications" Arthritis Res 2:33-37 (2000).
Goronzy et al., "Rheumatoid arthritis" Immunological Reviews 204:55-73 (2005).
Graudal et al., "Radiographic Progression in Rheumatoid Arthritis" Arthritis & Rheumatism 41(8):1470-1480 (Aug. 1998).
Groom et al., "Association of BAFF/BLyS overexpression and altered B cell differentiation with Sjogren's syndrome" J Clin Invest 109:59-68 (2002).
Gross et al., "TACI and BCMA are receptors for a TNF homologue implicated in B-cell autoimmune disease" Nature 404:995-999 (2000).
Gunn et al., "A B-cell-homing chemokine made in lymphoid follicles activates Burkitt's lymphoma receptor=1" Nature 391:799-803 (Feb. 1998).
Hackstadt, A.J. et al. (Jan. 8, 2009). "Filtering for increased power for microarray data analysis," BMC Bioinformatics 10:11, 12 pages.
Hagmann, "Doing Immunology on a Chip" Science 290:82-83 (Oct. 2000).
Hannonen et al., "Sulfasalazine in early rheumatoid arthritis. A 48-week double-blind, prospective, placebo-controlled study" Arthritis Rheum 36(11):1501-9 (Nov. 1993).
Hardy et al., "B Cell Development Pathways" Annu. Rev. Immunol. 19:595-621 (2001).
Harris et al., "Reciprocal regulation of polarized cytokine production by effector B and T cells" Nature Immunology 1(6):475-482 (Dec. 2000).
Hatzivassiliou et al., "IRTA1 and IRTA2, novel immunoglobulin superfamily receptors expressed in B cells and involved in chromosome 1q21 abnormalities in B cell malignancy" Immunity 14(3):277-289 (Mar. 2001).
Heliovaara et al., "Rheumatoid factor, chronic arthritis and mortality" Annals of the Rheumatic Diseases 54:811-814 (1995).
Hochberg et al., "More Powerful Procedures for Multiple Significance Testing" Statistics in Medicine 9:811-818 (1990).
Hofbauer et al., "The Roles of Osteoprotegerin and Osteoprotegerin Ligand in the Paracrine Regulation of Bone Resorption" Journal of Bone and Mineral Research 15(1):2-12 (2000).
Hogan, V.E. et al. (2012). "Pretreatment synovial transcriptional profile is associated with early and late clinical response in rheumatoid arthritis patients treated with rituximab," Ann. Rheum. Dis. 71(11):1888-1894.

(56) References Cited

OTHER PUBLICATIONS

Huber et al., "Identification of intra-group, inter-individual, and gene-specific variances in mRNA expression profiles in the rheumatoid arthritis synovial membrane" Arthritis Research & Therapy 10:R98 (2008).
Hueber et al. "Proteomic Analysis of Secreted Proteins in Early Rheumatoid Arthritis: Anti-Citrulline Autoreactivity is Associated With up Regulation of Proinflammatory cytokines," Ann. Rheum. Dis. 66:712-719 (2007, e-pub. Jul. 19, 2006).
Hueber et al. "Antigen Microarray Profiling of Autoantibodies in Rheumatoid Arthritis," Arthritis & Rheumatism 52(9):2645-2655 (Sep. 2005).
Hueber et al., "Blood autoantibody and cytokine profiles predict response to anti-tumor necrosis factor therapy in rheumatoid arthritis" Arthritis Research & Therapy 11:R76 (2009).
Hulsmans et al., "The Course of Radiologic Damage During the First Six Years of Rheumatoid Arthritis" Arthritis & Rheumatism 43(9):1927-1940 (Sep. 2000).
Irizarry, "Exploration, normalization, and summaries of high density oligonucleotide array probe level data" Biostatistics 4:249-264 (2003).
Ise et al., "Elevation of soluble CD307 (IRTA2/FcRH5) protein in the blood and expression on malignant cells of patients with multiple myeloma, chronic lymphocytic leukemia, and mantle cell lymphoma" Leukemia 21:169-174 (2007).
Ise et al., "Immunoglobulin Superfamily Receptor Translocation Associated 2 Protein on Lymphoma Cell Lines and Hairy Cell Leukemia Cells Detected by Novel Monoclonal Antibodies" Clinical Cancer Research 11:87-96 (Jan. 2005).
Ise et al., "Sandwich ELISAs for soluble immunoglobulin superfamily receptor translocation-associated 2 (IRTA2)/FcRH5 (CD307) proteins in human sera" Clin Chem Lab Med 44(5):594-602 (2006).
Janeway et al., "The B Cell is the Initiating Antigen-Presenting Cell in Peripheral Lymph Nodes" The Journal of Immunology 138(4):1051-1055 (Feb. 1987).
Jeurissen et al., "Influence of methotrexate and azathioprine on radiologic progression in rheumatoid arthritis. A randomized, double-blind study" Ann Intern Med 114(12):999-1004 (1991).
Jimenez-Boj et al. (2005). "Interaction between synovial inflammatory tissue and bone marrow in rheumatoid arthritis," J. Immunol. 175(4):2579-2588.
Joint Committee, "A comparison of prednisolone with aspirin or other analgesics in the treatment of rheumatoid arthritis. A second report by the joint committee of the Medical Research Council and Nuffield Foundation on clinical trials of cortisone, ACTH, and other therapeutic measures in chronic rheumatic diseases" Ann Rheum Dis 19:331-7 (Dec. 1960).
Kaarela et al., "Continuous progression of radiological destruction in seropositive rheumatoid arthritis" J Rheumatol. 24(7):1285-7 (Jul. 1997).
Kayagaki et al., "BAFF/BLyS Receptor 3 Binds the B Cell Survival Factor BAFF Ligand through a Discrete Surgace Loop and Promotes Processing of NF-κB2" Immunity 10:515-524 (Oct. 2002).
Keystone et al., "Adalimumab (D2E7), a Fully Human Anti-TNF-α Monoclonal Antibody, Inhibits the Progression of Structural Joint Damage in Patients with Active RA Despite Concomitant Methotrexate Therapy" Arthritis Rheum (#468), 46(Suppl suppl 9):S205 (2002).
Keystone, "B cells in rheumatoid arthritis: from hypothesis to the clinic" Rheumatology 44(Suppl Suppl 2):ii8-ii12 (May 2005).
Khare et al., "Severe B cell hyperplasia and autoimmune disease in TALL-1 transgenic mice" P Natl Acad Sci USA 97(7):3370-3375 (Mar. 2000).
Kirwan et al., "The effect of glucocorticoids on joint destruction in rheumatoid arthritis. The Arthritis and Rheumatism Council Low-Dose Glucocorticoid Study Group" New Engl J Med 333(3):142-6 (Jul. 1995).
Kishimoto, T. (2005). "Interleukin-6: from basic science to medicine—40 years in immunology," Annu. Rev. Immunol. 23:1-21.

Klaasen et al., "The Relationship Between Synovial Lymphocyte Aggregates and the Clinical Response to Infliximab in Rheumatoid Arthritis" Arthritis & Rheumatism 60(11):3217-3224 (Nov. 2009).
Krenn, V. et al. (1997). "Endothelial cells are the major source of sICAM-1 in rheumatoid synovial tissue," Rheumatol. Int. 17:17-27.
Lal et al., "Inflammation and Autoantibody Markers Identify Rheumatoid Arthritis Patients With Enhanced Clinical Benefit Following Rituximab Treatment" Arthritis & Rheumatism 63(12):3681-3691 (Dec. 2011).
Landewe et al., "COBRA combination therapy in patients with early rheumatoid arthritis: long-term structural benefits of a brief intervention" Arthritis Rheum 46(2):347-56 (Feb. 2002).
Landewe et al., "Presentation and analysis of radiographic data in clinical trials and observational studies" Ann Rheum Dis 64:iv48-iv51 (2005).
Larsen et al., "Radiographic Evaluation of Rheumatoid Arthritis and Related Conditions by Standard Reference Films" Acta Radiologica Diagnosis 18:481-491 (Jul. 1977).
Lassere et al., "Smallest Detectable Difference in Radiological Progression" J Rheumatol 26:731-9 (1999).
Lazar A.A. et al. (2010). "Evaluation of treatment-effect heterogeneity using biomarkers measured on a continuous scale: subpopulation treatment effect pattern plot," J. Clin. Oncol. 28:4539-4544.
Lee et al., "Rheumatoid arthritis" The Lancet 358:903-911 (Sep. 2001).
Legler et al., "B Cell-attracting Chemokine 1, a Human CXC Chemokine Expressed in Lymphoid Tissues, Selectively Attracts B Lymphocytes via BLR1/CXCR5" J. Exp. Med. 187(4):655-660 (Feb. 1998).
Li, W. et al., "Inferring causal relationships among intermediate phenotypes and biomarkers: a case study of rheumatoid arthritis" Bioinformatics 22(12):1503-7 (Jun. 2006).
Lindberg et al., "Effect of infliximab on mRNA expression profiles in synovial tissue of rheumatoid arthritis patients" Arthritis Research & Therapy 8(6):R179 (2006).
Lindberg et al., "The Gene Expression Profile in the Synovium as a Predictor of the Clinical Response to Infliximab Treatment in Rheumatoid Arthritis" PLoS ONE 5(6):e11310 (Jun. 2010).
Lindstrom et al. "Biomarkers for rheumatoid arthritis: making it personal" Scand. J Clin Lab Invest Suppl. 70(Suppl. 242):79-84 (2010).
Lipsky et al., "Infliximab and methotrexate in the treatment of rheumatoid arthritis. Anti-Tumor Necrosis Factor Trial in Rheumatoid Arthritis with Concomitant Therapy Study Group" New Engl J Med 343(22):1594-1602 (Nov. 2000).
MacKay et al., "BAFF and APRIL: A Tutorial on B Cell Survival" Annu Rev Immunol 21:231-264 (2003).
Mackay et al., "Mice Transgenic for BAFF Develop Lymphocytic Disorders Along with Autoimmune Manifestations" J. Exp. Med. 190(11):1697-1710 (Dec. 1999).
Maini et al., "Infliximab (chimeric anti-tumour necrosis α factor monoclonal antibody) versus placebo in rheumatoid arthritis patients receiving concomitant methotrexate: a randomised phase III trial" Lancet 354:1932-39 (1999).
Mantovani, A. et al., "The chemokine system in diverse forms of macrophage activation and polarization" Trends Immunol 25(12):677-686 (Dec. 2004).
Marotte et al., "Circulating tumour necrosis factor-α bioactivity in rheumatoid arthritis patients treated with infliximab: link to clinical response" Arthritis Res Ther 7:R149-R155 (2005).
Martin and Chan, "B cell immunobiology in disease: evolving concepts from the clinic" Annu Rev Immunol 24:467-496 (2006).
Meeuwisse et al., "Identification of CXCL13 as a Marker for Rheumatoid Arthritis Outcome Using an In Silico Model of the Rheumatic Joint" Arthritis & Rheumatism 63(5):1265-1273 (May 2011).
Moore et al., "BLyS: Member of the Tumor Necrosis Factor Family and B Lymphocyte Stimulator," Science 285(5425):260-263 (1999).
Mottonen et al., "Comparison of combination therapy with single-drug therapy in early rheumatoid arthritis: a randomised trial. FIN-RACo trial group" Lancet 353:1568-73 (May 1999).

(56) References Cited

OTHER PUBLICATIONS

Mukhopadhyay et al., "Identification and Characterization of a Novel Cytokine, THANK, a TNF Homologue That Activates Apoptosis, Nuclear Factor-κB, and c-Jun NH $_2$-Terminal Kinase" J Biol Chem 274:15978-15981 (1999).
Nakayama et al., "BXMAS1 identifies a cluster of homologous genes differentially expressed in B cells" Biochem Bioph Res Co 285(3):830-837 (Jul. 20, 2001).
Nash et al., "Seronegative spondyloarthropathies: to lump or split?" Ann Rheum Dis 64(Suppl II):ii9-ii13 (2005).
Ngo et al., "A loss-of-function RNA interference screen for molecular targets in cancer" Nature 441:106-110 (2006).
O'Dell et al., "Treatment of rheumatoid arthritis with methotrexate alone, sulfasalazine and hydroxychloroquine, or a combination of all three medications" New Engl J Med 334(20):1287-91 (May 1996).
Oku et al., "Periostin and bone marrow fibrosis" Int J Hematol 88:57-63 (2008).
Oron et al., "Gene set enrichment analysis using linear models and diagnostics" Bioinformatics 24(22):2586-2591 (2008).
Ota, "Immunologic laboratory testing in clinical practice for rheumatoid arthritis" Rinsho Byori Jap J Clin Pathol 54(8):861-8 (Aug. 2006) Abstract only.
Parker et al., "Peripheral blood expression of nuclear factor-kappab-regulated genes is associated with rheumatoid arthritis disease activity and responds differentially to anti-tumor necrosis factor-alpha versus methotrexate" J Rheumatol 34:1817-1822 (2007).
Paulus et al., "Analysis of improvement in individual rheumatoid arthritis patients treated with disease-modifying antirheumatic drugs, based on the findings in patients treated with placebo" Athritis Rheum 33(4):477-484 (Apr. 1990).
Paulus et al., "Classifying Structural Joint Damage in Rheumatoid Arthritis as Progressive or Nonprogressive Using a Composite Definition of Joint Radiographic Change" Arthritis & Rheumatism 50(4):1083-1096 (Apr. 2004).
Paulus et al., "Monitoring radiographic changes in early rheumatoid arthritis" J Rheumatol. 23(5):801-5 (1996).
Pennica et al., "Human Tumour Necrosis Factor: Precursor Structure, Expression and Homology to Lymphotoxin" Nature 312:724-729 (1984).
Pillai et al., "Marginal zone B cells" Annu Rev Immunol 23:161-196 (2005).
Pinals et al., "Preliminary Criteria for Clinical Remission in Rheumatoid Arthritis" Arthritis and Rheumatism 24(10):1308-1315 (Oct. 1981).
Pincus et al., "Comparison of 3 quantitative measures of hand radiographs in patients with rheumatoid arthritis: Steinbrocker stage, Kaye modified Sharp score, and Larsen score" J Rheumatol. 24(11):2106-12 (Nov. 1997).
Plant et al., "Measurement and prediction of radiological progression in early rheumatoid arthritis" J Rheumatol. 21(10):1808-13 (Oct. 1994).
Plant et al., "Patterns of radiological progression in early rheumatoid arthritis: results of an 8 year prospective study" J Rheumatol 25(3):417-26 (Mar. 1998).
Press et al., "Monoclonal Antibody 1F5 (Anti-CD20) Serotherapy of Human B Cell Lymphomas" Blood 69(2):584-591 (Feb. 1987).
Priolo et al., "Radiographic changes in the feet of patients with early rheumatoid arthritis. GRISAR (Gruppo Reumatologi Italiani Studio Artrite Reumatoide)" J Rheumatol 24(11):2113-8 (Nov. 1997).
Pyrpasopoulou et al., "Response to Rituximab and Timeframe to Relapse in Rheumatoid Arthritis Patients" Mol Diagn Ther 14(1):43-48 (2010).
Rantapaa-Dahlqvist et al., "Antibodies against cyclic citrullinated peptide and IgA rheumatoid factor predict the development of rheumatoid arthritis" Arthritis Rheum 48(10):2741-9 (Oct. 2003).
Rioja et al., "Potential Novel Biomarkers of Disease Activity in Rheumatoid Arthritis Patients" Arthritis & Rheumatism 58(8):2257-2267 (Aug. 2008).
Rivera et al., "Role of B cells as antigen-presenting cells in vivo revisited: antigen-specific B cells are essential for T cell expansion in lymph nodes and for systemic T cell responses to low antigen concentrations" International Immunology 13(12):1583-1593 (2001).
Rosengren et al., "CXCL13 as a marker for outcome of rheumatoid arthritis: comment on the article by Meeuwisse et al" Arthritis & Rheumatism 63(11):3646-3647 (Nov. 2011).
Rosengren et al., "CXCL13: a novel biomarker of B-cell return following rituximab treatment and synovitis in patients with rheumatoid arthritis" Rheumatology 50:603-610 (2011).
Russell et al., "The role of anti-cyclic citrullinated peptide antibodies in predicting progression of palindromic rheumatism to rheumatoid arthritis" J Rheumatol 33(7):1240-2 (Jul. 2006).
Sakurai et al., "TACI attenuates antibody production costimulated by BAFF-R and CD40" Eur. J. Immunol 37:110-118 (2007).
Schellekens et al., "The diagnostic properties of rheumatoid arthritis antibodies recognizing a cyclic citrullinated peptide" Arthritis Rheum 43(1):155-63 (Jan. 2000).
Schiemann et al., "An Essential Role for BAFF in the Normal Development of B Cells Through a BCMA-Independent Pathway" Science 293:2111-2114 (2001).
Schneider et al., "BAFF, A Novel Ligand of the Tumor Necrosis Factor Family, Stimulates B Cell Growth" J Exp Med 189:1747-1756 (1999).
Scott et al., "Rheumatoid arthritis" Lancet 376:1094-1108 (2010).
Scott et al., "The links between joint damage and disability in rheumatoid arthritis" Rheumatology 39:122-132 (2000).
Sharp et al., "How many joints in the hands and wrists should be included in a score of radiologic abnormalities used to assess rheumatoid arthritis?" Arthritis Rheum. 28(12):1326-35 (Dec. 1985).
Sharp et al., "Methods of Scoring the Progression of Radiologic Changes in Rheumatoid Arthritis" Arthritis and Rheumatism (November-December), 14(6):706-720 (1971).
Sharp et al., "Treatment with leflunomide slows radiographic progression of rheumatoid arthritis: results from three randomized controlled trials of leflunomide in patients with active rheumatoid arthritis. Leflunomide Rheumatoid Arthritis Investigators Group" Arthritis Rheum 43(3):495-505 (Mar. 2000).
Shi et al., "Lymphoid Chemokine B Cell-Attracting Chemokine-1 (CXCL13) Is Expressed in Germinal Center of Ectopic Lymphoid Follicles Within the Synovium of Chronic Arthritis Patients" J. Immunol. 166:650-655 (2001).
Shu et al., "Tall-1 is a Novel Member of the TNF Family that is Down-Regulated by Mitogens" J Leukocyte Biol 65:680-683 (1999).
Silverman et al., "Roles of B cells in rheumatoid arthritis" Arthritis Res Ther 5(Suppl 4):S1-S6 (2003).
Slawski et al., "CMA—a comprehensive Bioconductor package for supervised classification with high dimensional data" BMC Bioinformatics 9:439 (2008).
Smolen et al., "[Sat0031] Patients with Early Rheumatoid Arthritis Achieved a Clinically Meaningful and Sustained Improvement in Physical Function After Treatment With Infliximab" Ann Rheum Dis 64(Suppl III):418 (Jun. 11, 2005).
Smolen et al., "Evidence of radiographic benefit of treatment with infliximab plus methotrexate in rheumatoid arthritis patients who had no clinical improvement: a detailed subanalysis of data from the anti-tumor necrosis factor trial in rheumatoid arthritis with concomitant therapy study" Arthritis Rheum 52(4):1020-30 (Apr. 2005).
Strand et al., "Treatment of Active Rheumatoid Arthritis With Leflunomide Compared With Placebo and Methotrexate" Arch Intern Med. 159:2542-2550 (1999).
Subramanian et al., "Gene set enrichment analysis: A knowledge-based approach for interpreting genome-wide expression profiles" PNAS 102(43):15545-15550 (Oct. 2005).
Sundberg et al., "The Immunomodulatory Benzodiazepine Bz-423 Inhibits B-Cell Proliferation by Targeting c-Myc Protein for Rapid and Specific Degradation" Cancer Research 66:1775-1782 (2006).

(56) References Cited

OTHER PUBLICATIONS

Suzuki et al., "Pvclust: an R package for assessing the uncertainty in hierarchical clustering" Bioinformatics 22(12):1540-1542 (2006).
Tak et al., "The Pathogenesis and Prevention of Joint Damage in Rheumatoid Arthritis: Advances from Synovial Biopsy and Tissue Analysis" Arthritis & Rheumatism 43(12):2619-2633 (Dec. 2000).
Takemura et al., "Lymphoid neogenesis in rheumatoid synovitis" J Immunol 167(2):1072-1080 (Jul. 15, 2001).
Takemura et al., "T cell activation in rheumatoid synovium is B cell dependent" J Immunol 167(8):4710-4718 (Oct. 15, 2001).
Teitelbaum, "Bone Resorption by Osteoclasts" Science 289:1504-1508 (Sep. 2000).
Thangarajh et al., "A Proliferation-inducing Ligand (APRIL) is Expressed by Astrocytes and is Increased in Multiple Sclerosis" Scandinavian Journal of Immunology 65:92-98 (2007).
The R Foundation for Statistical Computing (2012). R Development Team: R: A Language and Environment for Statistical Computing. Vienna, Austria: R Foundation for Statistical Computing.
Thompson et al., "BAFF-R a Newly Identified TNF Receptor That Specifically Interacts with BAFF" Science 293:2108-2111 (Sep. 2001).
Thornton et al., "DNA Microarray Analysis Reveals Novel Gene Expression Profiles in Collagen-Induced Arthritis" Clinical Immunology 105(2):155-168 (Nov. 2002).
Timmer et al., "Inflammation and Ectopic Lymphoid Structures in Rheumatoid Arthritis Synovial Tissues Dissected by Genomics Technology: Identification of the Interleukin-7 Signaling Pathway in Tissues With Lymphoid Neogenesis" Arthritis & Rheumatism 56(8):2492-2502 (Aug. 2007).
Tugwell et al., "OMERACT Conference on Outcome Measures in Rheumatoid Arthritis Clinical Trials: Introduction" The Journal of Rheumatology 20(3):528-530 (1993).
Valentine et al., "B3.9 Structure and function of the B-cell specific 35-37 kDa CD20 protein" Leukocyte Typing III (B-cell antigens—papers),:440-443 (1987).
van Baarsen et al., "Pharmacogenomics of infliximab treatment using peripheral blood cells of patients with rheumatoid arthritis" Genes and Immunity 11:622-629 (2010).
van Baarsen et al., "Synovial Tissue Heterogeneity in Rheumatoid Arthritis in Relation to Disease Activity and Biomarkers in Peripheral Blood" Arthritis & Rheumatism 62(6):1602-1607 (Jun. 2010).
van Baarsen et al., "Transcription profiling of rheumatic diseases" Arthritis Research & Therapy 11:207 (2009).
Van der Heijde et al., "[FRI0201] The effect of Infliximab Therapy on Spinal Inflammation Assessed by Magnetic Resonance Imaging in a Randomized, Placebo-Controlled Trial of 279 Patients With Ankylosing Spondylitis" Ann Rheum Dis 64(Suppl Suppl III):317 (Jul. 10, 2005).
Van der Heijde et al., "[FRI0208] The Effect of Infliximab Therapy on Bone Mineral Density in Patients with Ankylosing Spondylitis: Results from Assert" Ann Rheum Dis 64(Suppl III):319 (2005).
Van der Heijde et al., "[Sat0028] Effect of Infliximab and Methotrexate on Radiographic Progression in Patients with Early Rheumatoid Arthritis" Ann Rheum Dis 64(Suppl Suppl III):417 (Jun. 11, 2005).
van der Heijde et al., "ASessment in Ankylosing Spondylitis (ASAS) international working group: a model for psoriatic arthritis and psoriasis?" Ann Rheum Dis 64(Suppl II):ii108-ii109 (2005).
Van Der Heijde et al., "Biannual Radiographic Assessments of Hands and Feet in a Three-Year Prospective Followup of Patients with Early Rheumatoid Arthritis" Arthritis & Rheumatism 35(1):26-34 (Jan. 1992).
van der Heijde et al., "Effects of hydroxychloroquine and sulphasalazine on progression of joint damage in rheumatoid arthritis" Lancet 1(8646):1036-8 (May 13, 1989).
Van Der Heijde et al., "Efficacy and safety of infliximab in patients with ankylosing spondylitis: results of a randomized, placebo-controlled trial (ASSERT)." Arthritis Rheum 52(2):582-591 (Feb. 2005).
Van der Heijde et al., "How Should Treatment Effect on Spinal Radiographic Progression in Patients With Ankylosing Spondylitis Be Measured?" Arthritis Rheum 52(7):1979-85 (Jul. 2005).
van der Heijde et al., "Psoriatic arthritis imaging: a review of scoring methods" Ann Rheum Dis 64(Suppl II):ii61-ii64 (2005).
van der Heijde, "How to Read Radiographs According to the Sharp/van der Heijde Method" J RheumatoL 27:261-3 (2000).
Van der Heijde, "Plain X-rays in rheumatoid arthritis: overview of scoring methods, their reliability and applicability" Bailliere's Clinical Rheumatology 10(3):435-453 (Aug. 1996).
van der Pouw Kraan et al., "Discovery of distinctive gene expression profiles in rheumatoid synovium using cDNA microarray technology: evidence for the existence of multiple pathways of tissue destruction and repair" Genes and Immunity 4:187-196 (2003).
van der Pouw Kraan et al., "Responsiveness to anti-tumour necrosis factor α therapy is related to pre-treatment tissue inflammation levels in rheumatoid arthritis patients" Ann Rheum Dis 67:563-566 (2008).
van der Pouw Kraan et al., "Rheumatoid Arthritis Is a Heterogeneous Disease" Arthritis & Rheumatism 48(8):2132-2145 (Aug. 2003).
Van Everdingen et al., "Low-dose prednisone therapy for patients with early active rheumatoid arthritis: clinical efficacy, disease-modifying properties, and side effects: a randomized, double-blind, placebo-controlled clinical trial" Ann Intern Med 136(1):1-12 (Jan. 2002).
Vidal-Laliena et al., "Characterization of antibodies submitted to the B cell section of the 8th Human Leukocyte Differentiation Antigens Workshop by Flow cytometry and immunohistochemistry" Cellular Immunology 236:6-16 (2005).
Wassenberg et al., "Low Dose Prednisolone Therapy (LDPT) Retards Radiographically Detectable Destruction in Early Rheumatoid Arthritis" Arthritis Rheum 42:S243 (1999).
Weinblatt et al., "The effects of drug therapy on radiographic progression of rheumatoid arthritis. Results of a 36-week randomized trial comparing methotrexate and auranofin" Arthritis Rheum 36(5):613-9 (May 1993).
Weyand and Goronzy, "Ectopic Germinal Center Formation in Rheumatoid Synovitis" Ann NY Acad Sci 987:140-149 (2003).
Wijbrandts et al., "The clinical response to infliximab in rheumatoid arthritis is in part dependent on pretreatment tumor necrosis factor α expression in the synovium" Ann Rheum Dis 67:1139-1144 (2008).
Wilson et al., "cDNA Cloning of the B Cell Membrane Protein CD22: A Mediator of B-B Cell Interactions" J Exp Med 173:137-146 (Jan. 1991).
Wilson et al., "Genomic Structure and Chromosomal Mapping of the Human CD22 Gene" J Immunol 150(11):5013-5024 (Jun. 1993).
Witkowska, A.M. et al. (2004). "Soluble intercellular adhesion molecule-1 (sICAM-1): an overview," Eur. Cytokine Netw. 15:91-98.
Wolfe et al., "A Core Set of Domains for Longitudinal Observation Studies in Rheumatic Disorders: Consensus Report from Omeract 4" Arthritis Rheum. 41(Suppl No. 9):S204 (Sep. 1998).
Wolfe et al., "Radiographic Outcome of Recent-Onset Rheumatoid Arthritis" Arthritis & Rheumatism 41(9):1571-1582 (Sep. 1998).
Wolfe et al., "Radiographic progression predicts substantial income loss and work disability in rheumatoid arthritis" Arthritis Rheum. 43(Suppl 9):S403 (2000).
Yan et al., "Activation and accumulation of B cells in TACI-deficient mice" Nat Immunol 2(7):638-643 (Jul. 2001.
Yan et al., "Identification of a novel receptor for B lymphocyte stimulator that is mutated in a mouse strain with severe B cell deficiency" Curr Biol 11:1547-1552 (2001).
Yan et al., "Identification of a receptor for BLyS demonstrates a crucial role in humoral immunity" Nat Immunol 1:37-41 (2000).
Zhang et al., "Cutting Edge: A Role for B Lymphocyte Stimulator in Systemic Lupus Erythematosus" J Immunol 166:6-10 (2001).
Zheng et al., "CXCL13 Neutralization Reduces the Severity of Collagen-Induced Arthritis" Arthritis & Rheumatism 52(2):620-626 (Feb. 2005).

(56) References Cited

OTHER PUBLICATIONS

Sibilia et al. "Rituximab: A New Therapeutic Alternative in Rheumatoid Arthritis", *Joint Bone Spine*75(5):526-532, (Oct. 2008, e-pub. Jun. 20, 2008).

Taylor "Rituximab in the Treatment of Rheumatoid Arthritis," *Expert Review of Clinical Immunology*3(1)17-26, (Jan. 2007).

* cited by examiner

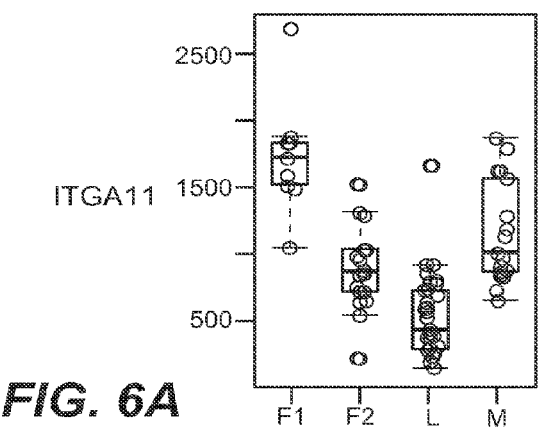
*FIG. 6A*
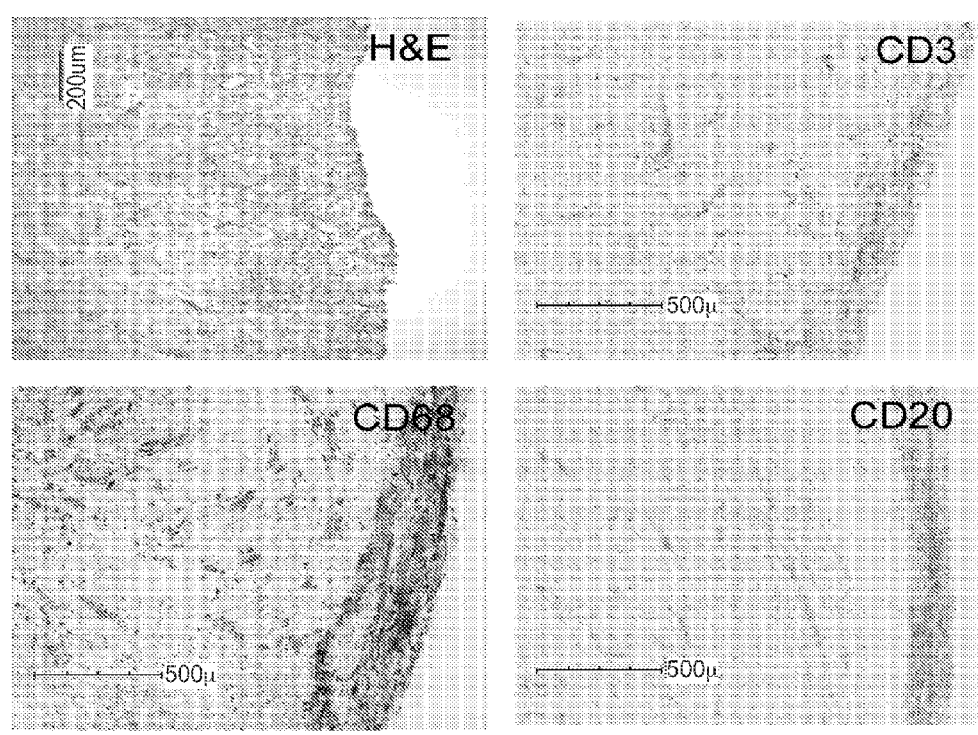
*FIG. 6B*  *FIG. 6C*
*FIG. 6D*  *FIG. 6E*

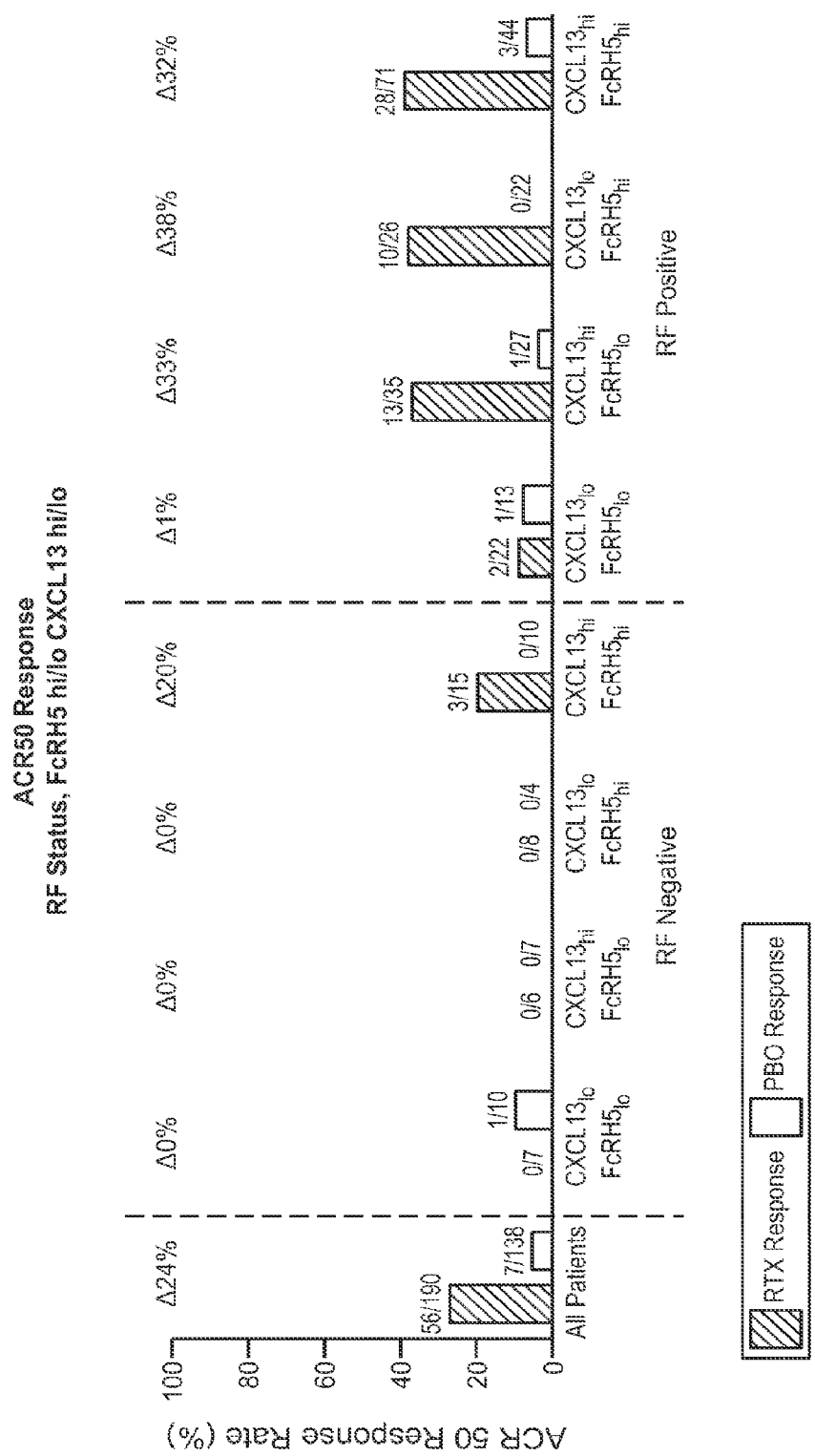

METHODS FOR TREATING, DIAGNOSING, AND MONITORING RHEUMATOID ARTHRITIS

CROSS REFERENCE TO RELATED APPLICATIONS

This application is a divisional application of U.S. patent application Ser. No. 12/874,972, filed Sep. 2, 2010, which claims the benefit of priority of provisional U.S. Application No. 61/275,948, filed Sep. 3, 2009 and provisional U.S. Application No. 61/252,424, filed Oct. 16, 2009, the contents of which are hereby incorporated by reference in their entirety.

FIELD

Methods of identifying, diagnosing, and prognosing rheumatoid arthritis are provided, as well as methods of treating rheumatoid arthritis. Also provided are methods for identifying effective rheumatoid arthritis therapeutic agents and predicting responsiveness to rheumatoid arthritis therapeutic agents.

BACKGROUND

Rheumatoid arthritis (RA) is a clinically important, chronic systemic autoimmune inflammatory disease affecting between 1.3 and 2.1 million persons in the United States (See, e.g., Alamanosa and Drosos, *Autoimmun. Rev.*, 4:130-136 (2005)). RA is an autoimmune disorder of unknown etiology. Most RA patients suffer a chronic course of disease that, even with currently available therapies, may result in progressive joint destruction, deformity, disability and even premature death. More than 9 million physician visits and more than 250,000 hospitalizations per year result from RA.

Diagnosis of RA typically relies on clinical and laboratory evaluation of a patient's signs and symptoms. Generally, laboratory evaluation of a patient suspected of having RA may include determination of the level of certain antibodies in serum known as rheumatoid factor (RF) and antibodies to cyclic citrullinated peptide (anti-CCP). (See, e.g., Schellekens et al., *Arthritis Rheum.*, 43:155-163 (2000); DiFranco et al., *Rev. Rheum. Engl. Ed.*, 66(5):251-255 (1999); Rantapaa-Dahlqvist et al., *Arthritis Rheum.*, 48:2741-2749 (2003); Li et al., *Bioinformatics* 22(12):1503-1507 (2006); Russell et al., *J. Rhematol.*, 33(7):1240-1242 (2006); Ota, *Rinsho byori. Jap. J. Clin. Pathol.*, 54(8)861-868 (2006); Avouac et al., *Ann. Rheum. Dis.*, 65(7):845-851 (2006)). While these antibodies are often found in the serum of RA patients, not all RA patients have them. An additional blood test known as the erythrocyte sedimentation rate (ESR) may also be used. An elevated ESR indicates the general presence of an inflammatory process, although not necessarily RA. Further blood tests may be used to assess the level of other factors, such as C-reactive protein (CRP) that have been associated with RA. In addition, radiographic analysis of affected joints may be performed. In sum, such currently available laboratory tests to diagnose RA are imprecise and imperfect.

In certain instances, diagnosis of RA is made if a patient satisfies certain American College of Rheumatology (ACR) criteria. Certain such criteria include morning stiffness in and around the joints lasting for at least 1 hour before maximal improvement; arthritis of three or more joint areas: at least three joint areas have simultaneously had soft tissue swelling or fluid (not bony overgrowth alone) observed by a physician; the 14 possible joint areas (right and left) are proximal interphalangeal (PIP), metacarpophalangeal (MCP), wrist, elbow, knee, ankle, and metatarsophalangeal (MTP) joints; arthritis of hand joints: at least one joint area swollen as above in wrist, MCP, or PIP joint; symmetric arthritis: simultaneous involvement of the same joint areas (as in arthritis of three or more joint areas, above) on both sides of the body (bilateral involvement of PIP, MCP, or MTP joints is acceptable without absolute symmetry); rheumatoid nodules: subcutaneous nodules over bony prominences or extensor surfaces or in juxta-articular regions that are observed by a physician; serum rheumatoid factor: demonstration of abnormal amounts of serum rheumatoid factor by any method that has been positive in fewer than five percent of normal control patients; radiographic changes: radiographic changes typical of rheumatoid arthritis on posteroanterior hand and wrist X-rays, which must include erosions or unequivocal bony decalcification localized to or most marked adjacent to the involved joints (osteoarthritis changes alone do not qualify). Diagnosis of RA is typically made if a patient satisfies at least four of the above criteria.

A number of published studies report the attempted identification of reliable biomarkers for diagnostic and prognostic purposes. (See e.g., Rioja et al., *Arthritis and Rheum.* 58(8):2257-2267 (2008); Pyrpasopoulou et al., *Mol. Diagn. Ther.* 14(1):43-48 (2010); US 2004/0009479; US 2007/0105133; WO 2007/038501; WO 2007/135568; WO 2008/104608; WO 2008/056198; WO 2008/132176; and WO 2008/154423). No clinically validated diagnostic markers, however, e.g., biomarkers, have been identified that enable clinicians or others to accurately define pathophysiological aspects of rheumatoid arthritis, clinical activity, response to therapy, prognosis, or risk of developing the disease. Accordingly, as RA patients seek treatment, there is considerable trial and error involved in the search for therapeutic agent(s) effective for a particular patient. Such trial and error often involves considerable risk and discomfort the patient in order to find the most effective therapy. Thus, there is a need for more effective means for determining which patients will respond to which treatment and for incorporating such determinations into more effective treatment regimens for RA patients.

It would therefore be highly advantageous to have additional diagnostic methods, including molecular-based diagnostic methods, that can be used to objectively identify the presence of and/or classify the disease in a patient, define pathophysiologic aspects of rheumatoid arthritis, clinical activity, response to therapy, including response to treatment with various RA therapeutic agents, prognosis, and/or risk of developing rheumatoid arthritis. In addition, it would be advantageous to have molecular-based diagnostic markers associated with various clinical and/or pathophysiological and/or other biological indicators of disease. Thus, there is a continuing need to identify new molecular biomarkers associated with rheumatoid arthritis as well as other autoimmune disorders. Such associations would greatly benefit the identification of the presence of rheumatoid arthritis in patients or the determination of susceptibility to develop the disease. Such associations would also benefit the identification of pathophysiologic aspects of RA, clinical activity, response to therapy, or prognosis. In addition, statistically and biologically significant and reproducible information regarding such associations could be utilized as an integral component in efforts to identify specific subsets of patients who would be expected to significantly benefit from treatment with a particular therapeutic agent, for example where the therapeutic agent is or has been shown in clinical studies to be of therapeutic benefit in such specific RA patient subpopulation.

The invention described herein meets the above-described needs and provides other benefits.

All references cited herein, including patent applications and publications, are incorporated by reference in their entirety for any purpose.

SUMMARY

The compositions and methods of the invention are based, at least in part, on the definition of four new and distinct molecular phenotypes (also referred to herein as molecular subtypes) of rheumatoid arthritis (RA). These four RA molecular subtypes described herein were defined based on differential gene expression between the subtypes and significant associations of each of the molecular subtypes with certain histology indicators of joint pathology as well as certain biological pathways. The terms "molecular phenotype" and "molecular subtype" are used interchangeably herein.

Accordingly, in one aspect, therapeutic targets for the treatment of a certain molecular subtype of RA, described herein as lymphoid-rich (L) subtype, are provided. In certain embodiments, a L subtype therapeutic target is selected from one or a combination of genes listed in Table 5. In certain embodiments, a L subtype therapeutic target is selected from one or a combination of genes listed in Table 1. In certain embodiments, a L subtype therapeutic target is selected from one or a combination of genes listed in Table 10. In certain embodiments, a L subtype therapeutic target is selected from one or a combination of proteins encoded by one or a combination of genes listed in Table 5. In certain embodiments, a L subtype therapeutic target is selected from one or a combination of proteins encoded by one or a combination of genes listed in Table 1. In certain embodiments, a L subtype therapeutic target is selected from one or a combination of proteins encoded by one or a combination of genes listed in Table 10. In certain embodiments, a therapeutic target of L subtype of RA is selected from one or more of CD20 (synonymous with MS4A1), CTLA4, CD3, CRTAM, IL2Rβ, IL2Rγ, CD19, HLAII, CD79a, CD79b, FcRH5 (synonymous with IRTA2), CD38, IL21R, IL12Rβ1, and IL12Rβ2.

In another aspect, methods of diagnosing a certain subtype of RA, described herein as L subtype, comprise measuring the gene expression of one or a combination of genes listed in Table 5, or measuring the amount of protein expressed by one or a combination of genes listed in Table 5. In certain embodiments, one or more of the genes identified in Table 5, or proteins encoded by said genes, are biomarkers of the L subtype. In certain embodiments, methods of diagnosing L subtype RA comprise measuring the gene expression of one or a combination of genes listed in Table 1, or measuring the amount of protein expressed by one or a combination of genes listed in Table 1. In certain embodiments, one or more of the genes identified in Table 1, or proteins encoded by said genes, are biomarkers of the L subtype. In certain embodiments, methods of diagnosing L subtype RA comprise measuring the gene expression of one or a combination of genes listed in Table 10, or measuring the amount of protein expressed by one or a combination of genes listed in Table 10. In certain embodiments, one or more of the genes identified in Table 10, or proteins encoded by said genes, are biomarkers of the L subtype. In certain embodiments, methods of diagnosing L subtype of RA comprise measuring the gene expression or protein expression of one or more of CXCL13, FcRH5 (synonymous with IRTA2), sFcRH5 (synonymous with sIRTA2), LTβ, ICAM3, IL18, PACAP, TNFRSF7, IgJ, IGM, IgG, and XBP1. In certain embodiments, methods of diagnosing L subtype of RA comprise measuring protein expression of CXCL13 and/or sFcRH5 and/or RF in serum. In certain embodiments, a patient is diagnosed with L subtype RA when the serum level of CXCL13 is greater than 116.6 pg/ml, or greater than 150 pg/ml, or greater than 200 pg/ml, or greater than 250 pg/ml, or greater than 300 pg/ml. In certain embodiments, a patient is diagnosed with L subtype RA when the serum level of sFcRH5 is greater than 126.7 ng/ml, or greater than 150 ng/ml, or greater than 200 ng/ml, or greater than 250 ng/ml, or greater than 300 ng/ml. In certain embodiments, a patient is diagnosed with L subtype RA when the serum is positive for RF and when the serum level of sFcRH5 is elevated compared to a control sample. In certain such embodiments, the serum level of sFcRH5 is greater than 126.7 ng/ml, or greater than 150 ng/ml, or greater than 200 ng/ml, or greater than 250 ng/ml, or greater than 300 ng/ml. In certain embodiments, a patient is diagnosed with L subtype RA when the serum is positive for RF and when the serum level of both sFcRH5 and CXCL13 are elevated compared to a control sample. In certain such embodiments, the serum level of sFcRH5 is greater than 126.7 ng/ml, or greater than 150 ng/ml, or greater than 200 ng/ml, or greater than 250 ng/ml, or greater than 300 ng/ml and the serum level of CXCL13 is greater than 116.6 pg/ml, or greater than 150 pg/ml, or greater than 200 pg/ml, or greater than 250 pg/ml, or greater than 300 pg/ml.

In another aspect, therapeutic targets for the treatment of a certain molecular subtype of RA, described herein as myeloid-rich (M) subtype, are provided. In certain embodiments, a M subtype therapeutic target is selected from one or a combination of genes listed in Table 6. In certain embodiments, a M subtype therapeutic target is selected from one or a combination of genes listed in Table 2. In certain embodiments, a M subtype therapeutic target is selected from one or a combination of genes listed in Table 11. In certain embodiments, a M subtype therapeutic target is selected from one or a combination of proteins encoded by one or a combination of genes listed in Table 6. In certain embodiments, a M subtype therapeutic target is selected from one or a combination of proteins encoded by one or a combination of genes listed in Table 2. In certain embodiments, a M subtype therapeutic target is selected from one or a combination of proteins encoded by one or a combination of genes listed in Table 11. In certain embodiments, a therapeutic target of M subtype of RA is selected from one or more of CLEC5A, CLEC7A, ALCAM, IL1RAP, IRAK1, NRP2, TREM1, and VEGF.

In another aspect, methods of diagnosing a certain subtype of RA, described herein as the M subtype, comprise measuring the gene expression of one or a combination of genes listed in Table 6, or measuring the amount of protein expressed by one or a combination of genes listed in Table 6. In certain embodiments, one or more of the genes identified in Table 6, or proteins encoded by said genes, are biomarkers of the M subtype. In certain embodiments, methods of diagnosing M subtype RA comprise measuring the gene expression of one or a combination of genes listed in Table 2, or measuring the protein expressed by one or a combination of genes listed in Table 2. In certain embodiments, one or more of the genes identified in Table 2, or proteins encoded by said genes, are biomarkers of the M subtype. In certain embodiments, methods of diagnosing M subtype RA comprise measuring the gene expression of one or a combination of genes listed in Table 11, or measuring the protein expressed by one or a combination of genes listed in Table 11. In certain embodiments, one or more of the genes identified in Table 11, or proteins encoded by said genes, are biomarkers of the M subtype. In certain embodiments, methods of diagnosing M subtype of RA comprise measuring the gene expression or protein expression of one or more of ADAM8, CTSB, CXCL3, ICAM1, IL18BP, IL1B, IL8, MMP12, CCL2, VEGFA, and S100A11.

In another aspect, therapeutic targets for the treatment of a certain molecular subtype of RA, described herein as fibroblast-rich type 2 (F2) subtype, are provided. In certain embodiments, a F2 subtype therapeutic target is selected from one or a combination of genes listed in Table 7. In certain embodiments, a F2 subtype therapeutic target is selected from one or a combination of genes listed in Table 3. In certain embodiments, a F2 subtype therapeutic target is selected from one or a combination of genes listed in Table 12. In certain embodiments, a F2 subtype therapeutic target is selected from one or a combination of proteins encoded by one or a combination of genes listed in Table 7. In certain embodiments, a F2 subtype therapeutic target is selected from one or a combination of proteins encoded by one or a combination of genes listed in Table 3. In certain embodiments, a F2 subtype therapeutic target is selected from one or a combination of proteins encoded by one or a combination of genes listed in Table 12. In certain embodiments, a therapeutic target of F2 subtype of RA is selected from one or more of IL17D, IL17RC, TIMP3, and TNFRSF11B.

In another aspect, methods of diagnosing a certain subtype of RA, described herein as the F2 subtype, comprise measuring the gene expression of one or a combination of genes listed in Table 7, or measuring the protein expressed by one or a combination of genes listed in Table 7. In certain embodiments, one or more of the genes identified in Table 7, or proteins encoded by said genes, are biomarkers of the F2 subtype. In certain embodiments, methods of diagnosing F2 subtype RA comprise measuring the gene expression of one or a combination of genes listed in Table 3, or measuring the protein expressed by one or a combination of genes listed in Table 3. In certain embodiments, one or more of the genes identified in Table 3, or proteins encoded by said genes, are biomarkers of the F2 subtype. In certain embodiments, methods of diagnosing F2 subtype RA comprise measuring the gene expression of one or a combination of genes listed in Table 12, or measuring the protein expressed by one or a combination of genes listed in Table 12. In certain embodiments, one or more of the genes identified in Table 12, or proteins encoded by said genes, are biomarkers of the F2 subtype. In certain embodiments, methods of diagnosing F2 subtype of RA comprise measuring the gene expression or protein expression of one or more of FGF10, FGF18, FGF2, LRP6, TGFβ2, WNT11, BMP6, BTC, CLU, CRLF1, TIMP3, FZD10, FZD7, FZD8, and IL17D.

In another aspect, therapeutic targets for the treatment of a certain molecular subtype of RA, described herein as fibroblast-rich type 1 (F1) subtype, are provided. In certain embodiments, a F1 subtype therapeutic target is selected from one or a combination of genes listed in Table 8. In certain embodiments, a F1 subtype therapeutic target is selected from one or a combination of genes listed in Table 4. In certain embodiments, a F1 subtype therapeutic target is selected from one or a combination of genes listed in Table 13. In certain embodiments, a F1 subtype therapeutic target is selected from one or a combination of proteins encoded by one or a combination of genes listed in Table 8. In certain embodiments, a F1 subtype therapeutic target is selected from one or a combination of proteins encoded by one or a combination of genes listed in Table 4. In certain embodiments, a F1 subtype therapeutic target is selected from one or a combination of proteins encoded by one or a combination of genes listed in Table 13. In certain embodiments, a therapeutic target of F1 subtype of RA is selected from one or more of CDH11, ITGA11, and CLEC11A.

In another aspect, methods of diagnosing a certain subtype of RA, described herein as the F1 subtype, comprise measuring the gene expression of one or a combination of genes listed in Table 8, or measuring the protein expressed by one or a combination of genes listed in Table 8. In certain embodiments, one or more of the genes identified in Table 8, or proteins encoded by said genes, are biomarkers of the F1 subtype. In certain embodiments, methods of diagnosing F1 subtype RA comprises measuring the gene expression of one or a combination of genes listed in Table 4, or measuring the protein expressed by one or a combination of genes listed in Table 4. In certain embodiments, one or more of the genes identified in Table 4, or proteins encoded by said genes, are biomarkers of the F1 subtype. In certain embodiments, methods of diagnosing F1 subtype RA comprises measuring the gene expression of one or a combination of genes listed in Table 13, or measuring the protein expressed by one or, a combination of genes listed in Table 13. In certain embodiments, one or more of the genes identified in Table 13, or proteins encoded by said genes, are biomarkers of the F1 subtype. In certain embodiments, methods of diagnosing F1 subtype of RA comprise measuring the gene expression or protein expression of one or more of ITGA11, MMP11, MMP13, MMP16, MMP28, ADAM12, ADAM22, CTSK, CTHRC1, ENPEP, POSTN, ANGPT2, SFRP2, TIE1, and VWF.

In one aspect, gene expression is measured by microarray. In another aspect gene expression is measured by real-time quantitative polymerase chain reaction (qPCR). In another aspect, gene expression is measured by multiplex-PCR. According to another embodiment, gene expression is measured by observing protein expression levels of an aforementioned gene. According to another embodiment, expression of a gene of interest is considered elevated when compared to a healthy control if the relative mRNA level of the gene of interest is greater than 2 fold of the level of a control gene mRNA. According to another embodiment, the relative mRNA level of the gene of interest is greater than 3 fold, fold, 10 fold, 15 fold, 20 fold, 25 fold, or 30 fold compared to a healthy control gene expression level. In one aspect, the gene expression level is measured by a method selected from a PCR method, a microarray method, or an immunoassay method. In one embodiment, the microarray method comprises the use of a microarray chip having one or more nucleic acid molecules that can hybridize under stringent conditions to a nucleic acid molecule encoding a gene mentioned above or having one or more polypeptides (such as peptides or antibodies) that can bind to one or more of the proteins encoded by the genes mentioned above. In one embodiment, the PCR method is qPCR. In one embodiment, the PCR method is multiplex-PCR. According to one embodiment, the immunoassay method comprises binding an antibody to protein expressed from a gene mentioned above in a patient sample and determining if the protein level from the patient sample is elevated. In certain embodiments, the immunoassay method is an enzyme-linked immunosorbent assay (ELISA). In certain embodiments, protein expression of CXCL13, sFcRH5, and/or RF are measured by ELISA.

In one aspect, a method of identifying a subtype of rheumatoid arthritis in a subject is provided, the method comprising measuring in a biological sample obtained from the subject the expression of one or more genes, or one or more proteins encoded by said genes, associated with a certain subtype. In one aspect, the subtype of RA is selected from L subtype, M subtype, F2 subtype, and F1 subtype as described herein. In certain embodiments, the subtype of RA is L subtype and the one or more genes, or one or more proteins encoded by said genes, are selected from one or a combination of genes listed in Table 1 or Table 5 or Table 10. In certain embodiments, the subtype of RA is L subtype and the one or more genes are selected from one or a combination of genes listed in Table 1 or Table 5 or Table 10 and the expression of the one or more genes is measured using the corresponding probes listed in Table 1 or Table 5 or Table 10, respectively. In certain embodiments, the subtype of RA is L subtype and the one or more genes, or one or more proteins encoded by said genes, are selected from CXCL13, FcRH5 (synonymous with IRTA2), sFcRH5 (synonymous with sIRTA2), LTβ, ICAM3, IL18, PACAP, TNFRSF7, IgJ, IGM, IgG, and XBP1. In certain embodiments, the biological sample is a serum sample, and the protein expression measured is selected from CXCL13 and sFcRH5. In certain embodiments, the biological sample is a serum sample, the serum sample is positive for RF, and the protein expression measured is selected from CXCL13 and sFcRH5. In certain embodiments, the biological sample is a serum sample, the serum sample is positive for RF, and the protein expression measured is CXCL13 and sFcRH5. In certain embodiments, the subtype of RA is identified as L subtype when the serum level of CXCL13 is greater than 116.6 pg/ml, or greater than 150 pg/ml, or greater than 200 pg/ml, or greater than 250 pg/ml, or greater than 300 pg/ml. In certain embodiments, the subtype of RA is identified as L subtype when the serum level of FcRH5 is greater than 126.7 ng/ml, or greater than 150 ng/ml, or greater than 200 ng/ml, or greater than 250 ng/ml, or greater than 300 ng/ml. In certain embodiments, the subtype of RA is M subtype and the one or more genes, or one or more proteins encoded by said genes, are selected from one or a combination of genes listed in Table 2 or Table 6 or Table 11. In certain embodiments, the subtype of RA is M subtype and the one or more genes are selected from one or a combination of genes listed in Table 2 or Table 6 or Table 11 and the expression of the one or more genes is measured using the corresponding probes listed in Table 2 or Table 6 or Table 11, respectively. In certain embodiments, the subtype of RA is M subtype and the one or more genes, or one or more proteins encoded by said genes, are selected from ADAM8, CTSB, CXCL3, ICAM1, IL18BP, IL1B, IL8, MMP12, CCL2, VEGFA, and S100A11. In certain embodiments, the subtype of RA is F2 subtype and the one or more genes, or one or more proteins encoded by said genes, are selected from one or a combination of genes listed in. Table 3 or Table 7 or Table 12. In certain embodiments, the subtype of RA is F2 subtype and the one or more genes are selected from one or a combination of genes listed in Table 3 or Table 7 or Table 12 and the expression of the one or more genes is measured using the corresponding probes listed in Table 3 or Table 7 or Table 12, respectively. In certain embodiments, the subtype of RA is F2 subtype and the one or more genes, or one or more proteins encoded by said genes, are selected from FGF10, FGF18, FGF2, LRP6, TGFβ2, WNT11, BMP6, BTC, CLU, CRLF1, TIMP3, FZD10, FZD7, FZD8, and IL17D. In certain embodiments, the subtype of RA is F1 subtype and the one or more genes, or one or more proteins encoded by said genes, are selected from one or a combination of genes listed in Table 4 or Table 8 or Table 13. In certain embodiments, the subtype of RA is F1 subtype and the one or more genes are selected from one or a combination of genes listed in Table 4 or Table 8 or Table 13 and the expression of the one or more genes is measured using the corresponding probes listed in Table 4 or Table 8 or Table 13, respectively. In certain embodiments, the subtype of RA is F1 subtype and the one or more genes, or one or more proteins encoded by said genes, are selected from ITGA11, MMP11, MMP13, MMP16, MMP28, ADAM12, ADAM22, CTSK, CTHRC1, ENPEP, POSTN, ANGPT2, SFRP2, TIE1, and VWF.

In another aspect, a method for predicting whether a subject with RA will respond to a RA therapeutic agent is provided, the method comprising measuring in a biological sample obtained from the subject the expression of one or more genes of a gene signature, or the expression of one or more proteins encoded by said genes (a protein signature), associated with a molecular subtype of RA. In one aspect, the gene signature or protein signature is associated with a molecular subtype of RA selected from L subtype, M subtype, F2 subtype, and F1 subtype as described herein. In certain embodiments, the gene signature or protein signature is associated with L subtype and the one or more genes, or one or more proteins encoded by said genes, are selected from one or a combination of genes listed in Table 1 or Table 5 or Table 10. In certain embodiments, the gene signature is associated with L subtype and the one or more genes are selected from one or a combination of genes listed in Table 1 or Table 5 or Table 10 and the expression of the one or more genes is measured using the corresponding probes listed in Table 1 or Table 5 or Table 10, respectively. In certain embodiments, gene signature or protein signature is associated with L subtype and the one or more genes, or one or more proteins encoded by said genes, are selected from CXCL13, FcRH5 (synonymous with IRTA2), sFcRH5 (synonymous with sIRTA2), LTβ, ICAM3, IL18, PACAP, TNFRSF7, IgJ, IGM, IgG, and XBP1. In certain embodiments, the protein signature is associated with L subtype and one or more proteins encoded by said genes are selected from CXCL13, sFcRH5 and RF. In certain embodiments, the biological sample is a serum sample. In certain embodiments, the RA therapeutic agent is a B-cell antagonist. In certain embodiments, the B-cell antagonist is selected from CD22 antibodies, CD20 antibodies, BR3 antibodies, and BR3-Fc immunoadhesins. In certain embodiments, the CD20 antibody is selected from rituximab, ibritumomab tiuxetan, tositumomab, 1F5, 2H7, and A20. In certain embodiments, methods for predicting whether a subject with RA will respond to rituximab are provided, comprising measuring serum levels of CXCL13, sFcRH5, and/or RF. In one embodiment, a subject with RA is predicted to respond to rituximab when the serum level of CXCL13 is greater than 116.6 pg/ml. In one embodiment, a subject with RA is predicted to respond to rituximab when the serum level of sFcRH5 is greater than 126.7 ng/ml. In one embodiment, a subject with RA is predicted to respond to rituximab when the serum level of CXCL13 is greater than 116.6 pg/ml and the serum level of sFcRH5 is greater than 126.7 ng/ml. In one embodiment, a subject with RA is predicted to respond to rituximab when the serum is positive for RF and the serum level of CXCL13 is greater than 116.6 pg/ml and the serum level of sFcRH5 is greater than 126.7 ng/ml.

In another aspect, the gene signature or protein signature mentioned above is associated with M subtype and the one or more genes, or one or more proteins encoded by said genes, are selected from one or a combination of genes listed in Table 2 or Table 6 or Table 11. In certain embodiments, the gene signature is associated with M subtype and the one or more genes are selected from one or a combination of genes listed in Table 2 or Table 6 or Table 11 and the expression of the one or more genes is measured using the corresponding probes listed in Table 2 or Table 6 or Table 11, respectively. In certain embodiments, the gene signature or protein signature is associated with M subtype and the one or more genes, or one or more proteins encoded by said genes, are selected from ADAM8, CTSB, CXCL3, ICAM1, IL18BP, IL1B, IL8, MMP12, CCL2, VEGFA, and S100A11.

In yet another aspect, the gene signature or protein signature mentioned above is associated with F2 subtype and the one or more genes, or one or more proteins encoded by said genes, are selected from one or a combination of genes listed in Table 3 or Table 7 or Table 12. In certain embodiments, the gene signature is associated with F2 subtype and the one or more genes are selected from one or a combination of genes listed in Table 3 or Table 7 or Table 12 and the expression of the one or more genes is measured using the corresponding probes listed in Table 3 or Table 7 or Table 12, respectively. In certain embodiments, the gene signature or protein signature is associated with F2 subtype and the one or more genes, or one or more proteins encoded by said genes, are selected from FGF10, FGF18, FGF2, LRP6, TGFβ2, WNT11, BMP6, BTC, CLU, CRLF1, TIMP3, FZD10, FZD7, FZD8, and IL17D.

In still another aspect, the gene signature or protein signature is associated with F1 subtype and the one or more genes, or one or more proteins encoded by said genes, are selected from one or a combination of genes listed in Table 4 or Table 8 or Table 13. In certain embodiments, the gene signature is associated with F1 subtype and the one or more genes are selected from one or a combination of genes listed in Table 4 or Table 8 or Table 13 and the expression of the one or more genes is measured using the corresponding probes listed in Table 4 or Table 8 or Table 13, respectively. In certain embodiments, the gene signature or protein signature is associated with F1 subtype and the one or more genes, or one or more proteins encoded by said genes, are selected from ITGA11, MMP11, MMP13, MMP16, MMP28, ADAM12, ADAM22, CTSK, CTHRC1, ENPEP, POSTN, ANGPT2, SFRP2, T1141, and VWF.

In certain embodiments, the RA therapeutic agent targets a biological pathway selected from cytokine/chemokine, lymphocyte, dendritic cell, macrophage, fibroblast, osteoblast and osteoclast. In certain embodiments, the RA therapeutic agent is selected from a TNFα inhibitor, a B-cell antagonist, an IL-17A/F binding agent, an IL-6 binding agent, an inhibitor of costimulation, e.g., an inhibitor of the CD28/B7 pathway, a CD4 binding agent. In certain embodiments, the inhibitor of the CD28/B7 pathway is CTLA4-Ig.

In yet another aspect, a method of diagnosing or prognosing RA in a subject is provided, the method comprising measuring in a biological sample obtained from the subject the expression of one or more genes, or one or more proteins encoded by said genes, associated with a certain subtype. In one aspect, the subtype of RA is selected from L subtype, M subtype, F2 subtype, and F1 subtype as described herein. In certain embodiments, the subtype of RA is L subtype and the one or more genes, or one or more proteins encoded by said genes, are selected from one or a combination of genes listed in Table 1 or Table 5 or Table 10. In certain embodiments, the subtype of RA is. L subtype and the one or more genes are selected from one or a combination of genes listed in Table 1 or Table 5 or Table 10 and the expression of the one or more genes is measured using the corresponding probes listed in Table 1 or Table 5 or Table 10, respectively. In certain embodiments, the subtype of RA is L subtype and the one or more genes, or one or more proteins encoded by said genes, are selected from CXCL13, FcRH5 (synonymous with IRTA2), sFcRH5 (synonymous with sIRTA2), LTβ, ICAM3, IL18, PACAP, TNFRSF7, IgJ, IGM, IgG, and XBP1. In certain embodiments, the methods comprise measuring in a serum sample obtained from the subject, the protein expression of CXCL13, sFcRH5, and/or RF. In certain embodiments, a patient is diagnosed or prognosed with L subtype RA when the serum level of CXCL13 is greater than 116.6 pg/ml, or greater than 150 pg/ml, or greater than 200 pg/ml, or greater than 250 pg/ml, or greater than 300 pg/ml. In certain embodiments, a patient is diagnosed or prognosed with L subtype RA when the serum level of FcRH5 is greater than 126.7 ng/ml, or greater than 150 ng/ml, or greater than 200 ng/ml, or greater than 250 ng/ml, or greater than 300 ng/ml. In certain embodiments, the biological sample is a serum sample, the serum sample is positive for RF, and the protein expression measured is selected from one of CXCL13 and sFcRH5. In certain embodiments, the biological sample is a serum sample, the serum sample is positive for RF, and the protein expression measured is both of CXCL13 and sFcRH5. In certain embodiments, the subtype of RA is M subtype and the one or more genes, or one or more proteins encoded by said genes, are selected from one or a combination of genes listed in Table 2 or Table 6 or Table 11. In certain embodiments, the subtype of RA is M subtype and the one or more genes are selected from one or a combination of genes listed in Table 2 or Table 6 or Table 11 and the expression of the one or more genes is measured using the corresponding probes listed in Table 2 or Table 6 or Table 11, respectively. In certain embodiments, the subtype of RA is M subtype and the one or more genes, or one or more proteins encoded by said genes, are selected from ADAM8, CTSB, CXCL3, ICAM1, IL18BP, IL1B, IL8, MMP12, CCL2, VEGFA, and S100A11. In certain embodiments, the subtype of RA is F2 subtype and the one or more genes, or one or more proteins encoded by said genes, are selected from one or a combination of genes listed in Table 3 or Table 7 or Table 12. In certain embodiments, the subtype of RA is F2 subtype and the one or more genes are selected from one or a combination of genes listed in Table 3 or Table 7 or Table 12 and the expression of the one or more genes is measured using the corresponding probes listed in Table 3 or Table 7 or Table 12, respectively. In certain embodiments, the subtype of RA is F2 subtype and the one or more genes, or one or more proteins encoded by said genes, are selected from FGF10, FGF18, FGF2, LRP6, TGFβ2, WNT11, BMP6, BTC, CLU, CRLF1, TIMP3, FZD10, FZD7, FZD8, and IL17D. In certain embodiments, the subtype of RA is F1 subtype and the one or more genes, or one or more proteins encoded by said genes, are selected from one or a combination of genes listed in Table 4 or Table 8 or Table 13. In certain embodiments, the subtype of RA is F1 subtype and the one or more genes are selected from one or a combination of genes listed in Table 4 or Table 8 or Table 13 and the expression of the one or more genes is measured using the corresponding probes listed in Table 4 or Table 8 or Table 13, respectively. In certain embodiments, the subtype of RA is F1 subtype and the one or more genes, or one or more proteins encoded by said genes, are selected from ITGA11, MMP11, MMP13, MMP16, MMP28, ADAM12, ADAM22, CTSK, CTHRC1, ENPEP, POSTN, ANGPT2, SFRP2, TIE1, and VWF.

In a still further aspect, a method of aiding in the diagnosis or prognosis of RA in a subject is provided, the method comprising measuring in a biological sample obtained from the subject the expression of one or more genes, or one or more proteins encoded by said genes, associated with a given subtype. In one aspect, the subtype of RA is selected from L subtype, M subtype, F2 subtype, and F1 subtype as described herein. In certain embodiments, the subtype of RA is L subtype and the one or more genes, or one or more proteins encoded by said genes, are selected from one or a combination of genes listed in Table 1 or Table 5 or Table 10. In certain embodiments, the subtype of RA is L subtype and the one or more genes are selected from one or a combination of genes listed in Table 1 or Table 5 or Table 10 and the expression of the one or more genes is measured using the corresponding probes listed in Table 1 or Table 5 or Table 10, respectively. In certain embodiments, the subtype of RA is L subtype and the one or more genes, or one or more proteins encoded by said genes, are selected from CXCL13, FcRH5 (synonymous with IRTA2), sFcRH5 (synonymous with sIRTA2), LTβ, ICAM3, IL18, PACAP, TNFRSF7, IgJ, IGM, IgG, and XBP1. In certain embodiments, the methods comprise measuring in a serum sample obtained from the subject, the protein expression of CXCL13, sFcRH5, and/or RF. In certain embodiments, diagnosis or prognosis of L subtype RA is aided when the serum level of CXCL13 is greater than 116.6 pg/ml, or greater than 150 pg/ml, or greater than 200 pg/ml, or greater than 250 pg/ml, or greater than 300 pg/ml. In certain embodiments, diagnosis or prognosis of L subtype RA is aided when the serum level of FcRH5 is greater than 126.7 ng/ml, or greater than 150 ng/ml, or greater than 200 ng/ml, or greater than 250 ng/ml, or greater than 300 ng/ml. In certain embodiments, the biological sample is a serum sample, the serum sample is positive for RF, and the protein expression measured is selected from one of CXCL13 and sFcRH5. In certain embodiments, the biological sample is a serum sample, the serum sample is positive for RF, and the protein expression measured is both of CXCL13 and sFcRH5. In certain embodiments, the subtype of RA is M subtype and the one or more genes, or one or more proteins encoded by said genes, are selected from one or a combination of genes listed in Table 2 or Table 6 or Table 11. In certain embodiments, the subtype of RA is M subtype and the one or more genes are selected from one or a combination of genes listed in Table 2 or Table 6 or Table 11 and the expression of the one or more genes is measured using the corresponding probes listed in Table 2 or Table 6 or Table 11, respectively. In certain embodiments, the subtype of RA is M subtype and the one or more genes, or one or more proteins encoded by said genes, are selected from ADAM8, CTSB, CXCL3, ICAM1, IL18BP, IL1B, IL8, MMP12, CCL2, VEGFA, and S100A11. In certain embodiments, the subtype of RA is F2 subtype and the one or more genes, or one or more proteins encoded by said genes, are selected from one or a combination of genes listed in Table 3 or Table 7 or Table 12. In certain embodiments, the subtype of RA is F2 subtype and the one or more genes are selected from one or a combination of genes listed in Table 3 or Table 7 or Table 12 and the expression of the one or more genes is measured using the corresponding probes listed in Table 3 or Table 7 or Table 12, respectively. In certain embodiments, the subtype of RA is F2 subtype and the one or more genes, or one or more proteins encoded by said genes, are selected from FGF10, FGF18, FGF2, LRP6, TGFβ2, WNT11, BMP6, BTC, CLU, CRLF1, TIMP3, FZD10, FZD7, FZD8, and IL17D. In certain embodiments, the subtype of RA is F1 subtype and the one or more genes, or one or more proteins encoded by said genes, are selected from one or a combination of genes listed in Table 4 or Table 8 or Table 13. In certain embodiments, the subtype of RA is F1 subtype and the one or more genes are selected from one or a combination of genes listed in Table 4 or Table 8 or Table 13 and the expression of the one or more genes is measured using the corresponding probes listed in Table 4 or Table 8 or Table 13, respectively. In certain embodiments, the subtype of RA is F1 subtype and the one or more genes, or one or more proteins encoded by said genes, are selected from ITGA11, MMP11, MMP13, MMP16, MMP28, ADAM12, ADAM22, CTSK, CTHRC1, ENPEP, POSTN, ANGPT2, SFRP2, TIE1, and VWF.

In one aspect, a method of treating RA in a subject in whom a gene signature or a protein signature associated with a molecular subtype of RA has been detected. In one aspect, the gene signature or protein signature is associated with a molecular subtype of RA selected from L subtype, M subtype, F2 subtype, and F1 subtype as described herein. In certain embodiments, the gene signature is associated with L subtype and the gene signature comprises one or a combination of genes listed in Table 1 or Table 5 or Table 10. In certain embodiments, the gene signature is associated with L subtype and the one or more genes are selected from one or a combination of genes listed in Table 1 or Table 5 or Table 10 and the expression of the one or more genes is measured using the corresponding probes listed in Table 1 or Table 5 or Table 10, respectively. In certain embodiments, the gene signature is associated with L subtype and the gene signature comprises one or a combination of genes selected from CXCL13, FcRH5 (synonymous with IRTA2), sFcRH5 (synonymous with sIRTA2), LTβ, ICAM3, IL18, PACAP, TNFRSF7, IgJ, IGM, IgG, and XBP1. In certain embodiments, a protein signature is associated with L subtype and the protein signature comprises one or a combination of proteins selected from CXCL13, sFcRH5 (synonymous with sIRTA2), LTβ, ICAM3, IL18, PACAP, TNFRSF7, IgJ, IGM, IgG, and XBP1. In certain embodiments, the protein signature comprises CXCL13, sFcRH5, and/or RF. In certain embodiments, the gene signature is associated with M subtype and the gene signature or protein signature comprises one or a combination of genes, or proteins encoded by said genes, listed in Table 2 or Table 6 or Table 11. In certain embodiments, the gene signature is associated with M subtype and the one or more genes are selected from one or a combination of genes listed in Table 2 or Table 6 or Table 11 and the expression of the one or more genes is measured using the corresponding probes listed in Table 2 or Table 6 or Table 11, respectively. In certain embodiments, the gene signature or protein signature is associated with M subtype and the gene signature or protein signature comprises one or a combination of genes, or proteins encoded by said genes, selected from ADAM8, CTSB, CXCL3, ICAM1, IL18BP, IL1B, IL8, MMP12, CCL2, VEGFA, and S100A11. In certain embodiments, the gene signature or protein signature is associated with F2 subtype and the gene signature or protein signature comprises one or a combination of genes, or proteins encoded by said genes, listed in Table 3 or Table 7 or Table 12. In certain embodiments, the gene signature is associated with F2 subtype and the one or more genes are selected from one or a combination of genes listed in Table 3 or Table 7 or Table 12 and the expression of the one or more genes is measured using the corresponding probes listed in Table 3 or Table 7 or Table 12, respectively. In certain embodiments, the gene signature or protein signature is associated with F2 subtype and the gene signature or protein signature comprises one or a combination of genes, or proteins encoded by said genes, selected from FGF10, FGF18, FGF2, LRP6, TGFβ2, WNT11, BMP6, BTC, CLU, CRLF1, TIMP3, FZD10, FZD7, FZD8, and IL17D. In certain embodiments, the gene signature or protein signature is associated with F1 subtype and the gene signature or protein signature comprises one or a combination of genes, or proteins encoded by said genes, listed in Table 4 or Table 8 or Table 13. In certain embodiments, the gene signature is associated with F1 subtype and the one or more genes are selected from one or a combination of genes listed in Table 4 or Table 8 or Table 13 and the expression of the one or more genes is measured using the corresponding probes listed in Table 4 or Table 8 or Table 13, respectively. In certain embodiments, the gene signature or protein signature is associated with F1 subtype and the gene signature or protein signature comprises one or a combination of genes, or proteins encoded by said genes, selected from ITGA11, MMP11, MMP13, MMP16, MMP28, ADAM12, ADAM22, CTSK, CTHRC1, ENPEP, POSTN, ANGPT2, SFRP2, TIE1, and VWF.

In another aspect, a method of treating a subject having a molecular subtype of RA is provided, the method comprising administering to the subject a therapeutic agent effective to treat the subtype in a subject in whom a gene signature or a protein signature associated with the molecular subtype of RA has been detected. In one aspect, the gene signature or protein signature is associated with a molecular subtype of RA selected from L subtype, M subtype, F2 subtype, and F1 subtype as described herein. In certain embodiments, the gene signature is associated with L subtype and the gene signature comprises one or a combination of genes listed in Table 1 or Table 5 or Table 10. In certain embodiments, the gene signature is associated with L subtype and the one or more genes are selected from one or a combination of genes listed in Table 1 or Table 5 or Table 10 and the expression of the one or more genes is measured using the corresponding probes listed in Table 1 or Table 5 or Table 10, respectively. In certain embodiments, the gene signature is associated with L subtype and the gene signature comprises one or a combination of genes selected from CXCL13, FcRH5 (synonymous with IRTA2), sFcRH5 (synonymous with sIRTA2), LTβ, ICAM3, IL18, PACAP, TNFRSF7, IgJ, IGM, IgG, and XBP1. In certain embodiments, a protein signature is associated with L subtype and the protein signature comprises one or a combination of proteins selected from CXCL13, sFcRH5 (synonymous with sIRTA2), LTβ, ICAM3, IL18, PACAP, TNFRSF7, IgJ, IGM, IgG, and XBP1. In certain embodiments, the protein signature comprises CXCL13, sFcRH5 and/or RF. In certain embodiments, the gene signature or protein signature is associated with M subtype and the gene signature or protein signature comprises one or a combination of genes, or proteins encoded by said genes, listed in Table 2 or Table 6 or Table 11. In certain embodiments, the gene signature is associated with M subtype and the one or more genes are selected from one or a combination of genes listed in Table 2 or Table 6 or Table 11 and the expression of the one or more genes is measured using the corresponding probes listed in Table 2 or Table 6 or Table 11, respectively. In certain embodiments, the gene signature or protein signature is associated with M subtype and the gene signature or protein signature comprises one or a combination of genes, or proteins encoded by said genes, selected from ADAM8, CTSB, CXCL3, ICAM1, IL18BP, IL1B, MMP12, CCL2, VEGFA, and S100A11. In certain embodiments, the gene signature or protein signature is associated with F2 subtype and the gene signature or protein signature comprises one or a combination of genes, or proteins encoded by said genes, listed in Table 3 or Table 7 or Table 12. In certain embodiments, the gene signature is associated with F2 subtype and the one or more genes are selected from one or a combination of genes listed in Table 3 or Table 7 or Table 12 and the expression of the one or more genes is measured using the corresponding probes listed in Table 3 or Table 7 or Table 12, respectively. In certain embodiments, the gene signature or protein signature is associated with F2 subtype and the gene signature or protein signature comprises one or a combination of genes, or proteins encoded by said genes, selected from FGF10, FGF18, FGF2, LRP6, TGFβ2, WNT11, BMP6, BTC, CLU, CRLF1, FZD10, FZD7, FZD8, and IL17D. In certain embodiments, the gene signature is associated with F1 subtype and the gene signature or protein signature comprises one or a combination of genes listed in Table 4 or Table 8 or Table 13. In certain embodiments, the gene signature is associated with F1 subtype and the one or more genes are selected from one or a combination of genes listed in Table 4 or Table 8 or Table 13 and the expression of the one or more genes is measured using the corresponding probes listed in Table 4 or Table 8 or Table 13, respectively. In certain embodiments, the gene signature or protein signature is associated with F1 subtype and the gene signature or protein signature comprises one or a combination of genes, or proteins encoded by said genes, selected from ITGA11, MMP11, MMP13, MMP16, MMP28, ADAM12, ADAM22, CTSK, CTHRC1, ENPEP, POSTN, ANGPT2, SFRP2, TIE1, and VWF.

In another aspect, a method comprising manufacturing a RA therapeutic agent is provided, which includes packaging the agent with instructions to administer the agent to a subject who has or is believed to have RA and in whom a gene signature or a protein signature associated with a molecular subtype of RA has been detected. In one aspect, the gene signature or protein signature is associated with a molecular subtype of RA selected from L subtype, M subtype, F2 subtype, and F1 subtype as described herein. In certain embodiments, the gene signature is associated with L subtype and the gene signature comprises one or a combination of genes listed in Table 1 or Table 5 or Table 10. In certain embodiments, the gene signature is associated with L subtype and the one or more genes are selected from one or a combination of genes listed in Table 1 or Table 5 or Table 10 and the expression of the one or more genes is measured using the corresponding probes listed in Table 1 or Table 5 or Table 10, respectively. In certain embodiments, gene signature is associated with L subtype and the gene signature comprises one or a combination of genes selected from CXCL13, FcRH5 (synonymous with IRTA2), sFcRH5 (synonymous with sIRTA2), LTβ, ICAM3, IL18, PACAP, TNFRSF7, IgJ, IGM, IgG, and XBP1. In certain embodiments, a protein signature is associated with L subtype and the protein signature comprises one or a combination of proteins selected from CXCL13, sFcRH5 (synonymous with sIRTA2), LTβ, ICAM3, IL18, PACAP, TNFRSF7, IgJ, IGM, IgG, and XBP1. In certain embodiments, the protein signature comprises CXCL13, sFcRH5 and/or RF. In certain embodiments, the gene signature or protein signature is associated with M subtype and the gene signature or protein signature comprises one or a combination of genes, or proteins encoded by said genes, listed in Table 2 or Table 6 or Table 11. In certain embodiments, the gene signature is associated with M subtype and the one or more genes are selected from one or a combination of genes listed in Table 2 or Table 6 or Table 11 and the expression of the one or more genes is measured using the corresponding probes listed in Table 2 or Table 6 or Table 11, respectively. In certain embodiments, the gene signature or protein signature is associated with M subtype and the gene signature or protein signature comprises one or a combination of genes, or proteins encoded by said genes, selected from ADAM8, CTSB, CXCL3, ICAM1, IL18BP, IL1B, IL8, MMP12, CCL2, VEGFA, and S100A11. In certain embodiments, the gene signature or protein signature is associated with F2 subtype and the gene signature or protein signature comprises one or a combination of genes, or proteins encoded by said genes, listed in Table 3 or Table 7 or Table 12. In certain embodiments, the gene signature is associated with F2 subtype and the one or more genes are selected from one or a combination of genes listed in Table 3 or Table 7 or Table 12 and the expression of the one or more genes is measured using the corresponding probes listed in Table 3 or Table 7 or Table 12, respectively. In certain embodiments, the gene signature or protein signature is associated with F2 subtype and the gene signature or protein signature comprises one or a combination of genes, or proteins encoded by said genes, selected from FGF10, FGF18, FGF2, LRP6, TGFβ2, WNT11, BMP6, BTC, CLU, CRLF1, TIMP3, FZD10, FZD7, FZD8, and IL17D. In certain embodiments, the gene signature or protein signature is associated with F1 subtype and the gene signature or protein signature comprises one or a combination of genes, or proteins encoded by said genes, listed in Table 4 or Table 8 or Table 13. In certain embodiments, the gene signature is associated with F1 subtype and the one or more genes are selected from one or a combination of genes listed in Table 4 or Table 8 or Table 13 and the expression of the one or more genes is measured using the corresponding probes listed in Table 4 or Table 8 or Table 13, respectively. In certain embodiments, the gene signature or protein signature is associated with F1 subtype and the gene signature or protein signature comprises one or a combination of genes, or proteins encoded by said genes, selected from ITGA11, MMP11, MMP13, MMP16, MMP28, ADAM12, ADAM22, CTSK, CTHRC1, ENPEP, POSTN, ANGPT2, SFRP2, TIE1, and VWF.

In one aspect, a method for selecting a patient suffering from RA for treatment with a RA therapeutic agent is provided, the method comprising detecting the presence of a gene signature or protein signature associated with a molecular subtype of RA. In certain embodiments, the gene signature is associated with L subtype and the gene signature comprises one or a combination of genes listed in Table 1 or Table 5 or Table 10. In certain embodiments, the gene signature is associated with L subtype and the one or more genes are selected from one or a combination of genes listed in Table 1 or Table 5 or Table 10 and the expression of the one or more genes is measured using the corresponding probes listed in Table 1 or Table 5 or Table 10, respectively. In certain embodiments, gene signature is associated with L subtype and the gene signature comprises one or a combination of genes selected from CXCL13, FcRH5 (synonymous with IRTA2), sFcRH5 (synonymous with sIRTA2), LTβ, ICAM3, IL18, PACAP, TNFRSF7, IgJ, IGM, IgG, and XBP1. In certain embodiments, a protein signature is associated with L subtype and the protein signature comprises one or a combination of proteins selected from CXCL13, sFcRH5 (synonymous with sIRTA2), LTβ, ICAM3, IL18, PACAP, TNFRSF7, IgJ, IGM, IgG, and XBP1. In certain embodiments, the protein signature comprises CXCL13, sFcRH5, and/or RF. In certain embodiments, the gene signature or protein signature is associated with M subtype and the gene signature or protein signature comprises one or a combination of genes, or proteins encoded by said genes, listed in Table 2 or Table 6 or Table 11. In certain embodiments, the gene signature is associated with M subtype and the one or more genes are selected from one or a combination of genes listed in Table 2 or Table 6 or Table 11 and the expression of the one or more genes is measured using the corresponding probes listed in Table 2 or Table 6 or Table 11, respectively. In certain embodiments, the gene signature or protein signature is associated with M subtype and the gene signature or protein signature comprises one or a combination of genes, or proteins encoded by said genes, selected from ADAM8, CTSB, CXCL3, ICAM1, IL18BP, IL1B, IL8, MMP12, CCL2, VEGFA, and S100A11. In certain embodiments, the gene signature or protein signature is associated with F2 subtype and the gene signature or protein signature comprises one or a combination of genes, or proteins encoded by said genes, listed in Table 3 or Table 7 or Table 12. In certain embodiments, the gene signature is associated with F2 subtype and the one or more genes are selected from one or a combination of genes listed in Table 3 or Table 7 or Table 12 and the expression of the one or more genes is measured using the corresponding probes listed in Table 3 or Table 7 or Table 12, respectively. In certain embodiments, the gene signature or protein signature is associated with F2 subtype and the gene signature or protein signature comprises one or a combination of genes, or proteins encoded by said genes, selected from FGF10, FGF18, FGF2, LRP6, TGFβ2, WNT11, BMP6, BTC, CLU, CRLF1, TIMP3, FZD10, FZD7, FZD8, and IL17D. In certain embodiments, the gene signature or protein signature is associated with F1 subtype and the gene signature or protein signature comprises one or a combination of genes, or proteins encoded by said genes, listed in Table 4 or Table 8 or Table 13. In certain embodiments, the gene signature is associated with F1 subtype and the one or more genes are selected from one or a combination of genes listed in Table 4 or Table 8 or Table 13 and the expression of the one or more genes is measured using the corresponding probes listed in Table 4 or Table 8 or Table 13, respectively. In certain embodiments, the gene signature or protein signature is associated with F1 subtype and the gene signature or protein signature comprises one or a combination of genes, or proteins encoded by said genes, selected from ITGA11, MMP11, MMP13, MMP16, MMP28, ADAM12, ADAM22, CTSK, CTHRC1, ENPEP, POSTN, ANGPT2, SFRP2, TIE1, and VWF.

In another aspect, a method of assessing a stage of RA in a subject or in a sample obtained from the subject is provided, the method comprising detecting in a biological sample obtained from the subject, the presence of a gene signature or protein signature associated with a molecular subtype of RA. In certain embodiments, the gene signature or protein signature is associated with L subtype and the gene signature comprises one or a combination of genes listed in Table 1 or Table 5. In certain embodiments, the gene signature is associated with L subtype and the one or more genes are selected from one or a combination of genes listed in Table 1 or Table 5 or Table 10 and the expression of the one or more genes is measured using the corresponding probes listed in Table 1 or Table 5 or Table 10, respectively. In certain embodiments, gene signature is associated with L subtype and the gene signature comprises one or a combination of genes selected from CXCL13, FcRH5 (synonymous with IRTA2), sFcRH5 (synonymous with sIRTA2), LTβ, ICAM3, IL18, PACAP, TNFRSF7, IgJ, IGM, IgG, and XBP1. In certain embodiments, a protein signature is associated with L subtype and the protein signature comprises one or a combination of proteins selected from CXCL13, sFcRH5 (synonymous with sIRTA2), LTβ, ICAM3, IL18, PACAP, TNFRSF7, IgJ, IGM, IgG, and XBP1. In certain embodiments, the protein signature comprises CXCL13, sFcRH5, and/or RF. In certain embodiments, the gene signature or protein signature is associated with M subtype and the gene signature or protein signature comprises one or a combination of genes, or proteins encoded by said genes, listed in Table 2 or Table 6 or Table 11. In certain embodiments, the gene signature is associated with M subtype and the one or more genes are selected from one or a combination of genes listed in Table 2 or Table 6 or Table 11 and the expression of the one or more genes is measured using the corresponding probes listed in Table 2 or Table 6 or Table 11, respectively. In certain embodiments, the gene signature or protein signature is associated with M subtype and the gene signature or protein signature comprises one or a combination of genes, or proteins encoded by said genes, selected from ADAM8, CTSB, CXCL3, ICAM1, IL18BP, IL1B, IL8, MMP12, CCL2, VEGFA, and S100A11. In certain embodiments, the gene signature or protein signature is associated with F2 subtype and the gene signature or protein signature comprises one or a combination of genes, or proteins encoded by said genes, listed in Table 3 or Table 7 or Table 12. In certain embodiments, the gene signature is associated with F2 subtype and the one or more genes are selected from one or a combination of genes listed in Table 3 or Table 7 or Table 12 and the expression of the one or more genes is measured using the corresponding probes listed in Table 3 or Table 7 or Table 12, respectively. In certain embodiments, the gene signature or protein signature is associated with F2 subtype and the gene signature or protein signature comprises one or a combination of genes, or proteins encoded by said genes, selected from FGF10, FGF18, FGF2, LRP6, TGFβ2, WNT11, BMP6, BTC, CLU, CRLF1, TIMP3, FZD10, FZD7, FZD8, and IL17D. In certain embodiments, the gene signature or protein signature is associated with F1 subtype and the gene signature or protein signature comprises one or a combination of genes, or proteins encoded by said genes, listed in Table 4 or Table 8 or Table 13. In certain embodiments, the gene signature is associated with F1 subtype and the one or more genes are selected from one or a combination of genes listed in Table 4 or Table 8 or Table 13 and the expression of the one or more genes is measured using the corresponding probes listed in Table 4 or Table 8 or Table 13, respectively. In certain embodiments, the gene signature or protein signature is associated with F1 subtype and the gene signature or protein signature comprises one or a combination of genes, or proteins encoded by said genes, selected from ITGA11, MMP11, MMP13, MMP16, MMP28, ADAM12, ADAM22, CTSK, CTHRC1, ENPEP, POSTN, ANGPT2, SFRP2, TIE1, and VWF.

In yet another aspect, kits for diagnosing a molecular subtype of RA in a patient comprising detecting a gene signature associated with the molecular subtype in a biological sample are provided. In certain embodiments, a kit for diagnosing L subtype is provided and comprises (1) one or more nucleic acid molecules that hybridize with a gene selected from CXCL13, FcRH5 (synonymous with IRTA2), sFcRH5 (synonymous with sIRTA2), LTβ, ICAM3, IL18, PACAP, TNFRSF7, IgJ, IGM, IgG, and XBP1; and (2) instructions for measuring the expression levels of the gene from a RA patient sample, wherein elevated expression levels of any one, combination or all of said genes is indicative of L subtype. In certain embodiments, a kit for diagnosing M subtype is provided and comprises (1) one or more nucleic acid molecules that hybridize with a gene selected from ADAM8, CTSB, CXCL3, ICAM1, IL18BP, IL1B, IL8, MMP12, CCL2, VEGFA, and S100A11; and (2) instructions for measuring the expression levels of the gene from a RA patient sample, wherein elevated expression levels of any one, combination or all of said genes is indicative of M subtype. In certain embodiments, a kit for diagnosing F2 subtype is provided and comprises (1) one or more nucleic acid molecules that hybridize with a gene selected from FGF10, FGF18, FGF2, LRP6, TGFβ2, WNT11, BMP6, BTC, CLU, CRLF1, TIMP3, FZD10, FZD7, FZD8, and IL17D; and (2) instructions for measuring the expression levels of the gene from a RA patient sample, wherein elevated expression levels of any one, combination or all of said genes is indicative of F2 subtype. In certain embodiments, a kit for diagnosing F1 subtype is provided and comprises (1) one or more nucleic acid molecules that hybridize with a gene selected from ITGA11, MMP11, MMP13, MMP16, MMP28, ADAM12, ADAM22, CTSK, CTHRC1, ENPEP, POSTN, ANGPT2, SFRP2, TIE1, and VWF; and (2) instructions for measuring the expression levels of the gene from a RA patient sample, wherein elevated expression levels of any one, combination or all of said genes is indicative of F1 subtype. In certain embodiments, the gene expression level is measured by assaying for mRNA levels. In certain embodiments, the assay comprises a PCR method and/or the use of a microarray chip. In one embodiment, the PCR method is qPCR. In one embodiment, the PCR method is multiplex-PCR. In certain embodiments, kits include at least one enzyme selected from a nuclease, a ligase, and a polymerase.

In a further aspect, kits for diagnosing a molecular subtype of RA in a patient comprising detecting expression of one or more proteins associated with the molecular subtype in a biological sample from the patient are provided. In certain embodiments, a kit for diagnosing L subtype is provided and comprises (1) one or more protein molecules, for example including, but not limited to, antibodies, that bind to a protein selected from CXCL13, sFcRH5 (synonymous with sIRTA2), LTβ, ICAM3, IL18, PACAP, TNFRSF7, IgJ, IGM, IgG, and XBP1; and (2) instructions for measuring the expression levels of the protein from a RA patient sample, wherein elevated expression levels of any one, combination or all of said proteins is indicative of L subtype. In certain embodiments, the proteins detected are selected from CXCL13, sFcRH5, RF and combinations thereof. In certain embodiments, a kit for diagnosing M subtype is provided and comprises (1) one or more protein molecules that bind to a protein selected from ADAM8, CTSB, CXCL3, ICAM1, IL18BP, IL1B, IL8, MMP12, CCL2, VEGFA, and S100A11; and (2) instructions for measuring the expression levels of the protein from a RA patient sample, wherein elevated expression levels of any one, combination or all of said proteins is indicative of M subtype. In certain embodiments, a kit for diagnosing F2 subtype is provided and comprises (1) one or more protein molecules that bind to a protein selected from FGF10, FGF18, FGF2, LRP6, TGFβ2, WNT11, BMP6, BTC, CLU, CRLF1, TIMP3, FZD10, FZD7, FZD8, and IL17D; and (2) instructions for measuring the expression levels of the protein from a RA patient sample, wherein elevated expression levels of any one, combination or all of said proteins is indicative of F2 subtype. In certain embodiments, a kit for diagnosing F1 subtype is provided and comprises (1) one or more protein molecules that bind to a protein selected from ITGA11, MMP11, MMP13, MMP16, MMP28, ADAM12, ADAM22, CTSK, CTHRC1, ENPEP, POSTN, ANGPT2, SFRP2, TIE1, and VWF; and (2) instructions for measuring the expression levels of the protein from a RA patient sample, wherein elevated expression levels of any one, combination or all of said proteins is indicative of F1 subtype. In certain embodiments, the protein molecule is an antibody, a peptide, or a peptibody. In a further embodiment, the kit comprises a microarray chip for detecting the protein molecule(s).

In one aspect, a method of treating rheumatoid arthritis in a patient comprising administering an effective amount of a RA therapeutic agent to the patient to treat the rheumatoid arthritis, provided that a serum sample from the patient contains an amount of CXCL13 greater than 116.6 pg/ml, or an amount of sFcRH5 greater than 126.7 ng/ml, or a combination thereof is provided. In a further embodiment, the serum sample is positive for RF. In certain embodiments, the RA therapeutic agent is a B-cell antagonist. In certain embodiments, the B-cell antagonist is selected from an antibody to CD22, an antibody to CD20, an antibody to BR3, and a BR3-Fc immunoadhesin. In certain embodiments, the B-cell antagonist is an antibody to CD20 and the antibody to CD20 is selected from rituximab, ibritumomab tiuxetan, tositumomab, 1F5, 2H7, and A20.

In another aspect, a method of treating rheumatoid arthritis in a patient comprising administering to the patient an effective amount of a B-cell antagonist, wherein before the administration a serum sample from the patient was determined to contain an amount of CXCL13 greater than 116.6 pg/ml, or an amount of sFcRH5 greater than 126.7 ng/ml, or a combination thereof, whereby the amount or amounts of CXCL13, sFcRH5, or a combination thereof indicates that the patient will respond to treatment with the antagonist is provided. In a further embodiment, the serum sample is positive for RF. In certain embodiments, the RA therapeutic agent is a B-cell antagonist. In certain embodiments, the B-cell antagonist is selected from an antibody to CD22, an antibody to CD20, an antibody to BR3, and a BR3-Fc immunoadhesin. In certain embodiments, the B-cell antagonist is an antibody to CD20 and the antibody to CD20 is selected from rituximab, ibritumomab tiuxetan, tositumomab, 1F5, 2H7, and A20.

In yet another aspect, a method of treating rheumatoid arthritis in a patient comprising administering to the patient an effective amount of a B-cell antagonist, wherein before the administration a serum sample from the patient was determined to contain an amount of CXCL13 greater than 116.6 pg/ml, or an amount of sFcRH5 greater than 126.7 ng/ml, or a combination thereof, whereby the amount or amounts of CXCL13, sFcRH5, or a combination thereof indicates that the patient is likely to respond favorably to treatment with the antagonist is provided. In a further embodiment, the serum sample is positive for RF. In certain embodiments, the RA therapeutic agent is a B-cell antagonist. In certain embodiments, the B-cell antagonist is selected from an antibody to CD22, an antibody to CD20, an antibody to BR3, and a BR3-Fc immunoadhesin. In certain embodiments, the B-cell antagonist is an antibody to CD20 and the antibody to CD20 is selected from rituximab, ibritumomab tiuxetan, tositumomab, 1F5, 2H7, and A20.

In still another aspect, a method for advertising a B-cell antagonist or a pharmaceutically acceptable composition thereof comprising promoting, to a target audience, the use of that antagonist or pharmaceutical composition thereof for treating a patient or patient population with rheumatoid arthritis from which a serum sample has been obtained showing an amount of CXCL13 greater than 116.6 pg/ml, or an amount of sFcRH5 greater than 126.7 ng/ml, or a combination of these amounts is provided. In a further embodiment, the serum sample is positive for RF.

In one aspect, an article of manufacture comprising, packaged together, a pharmaceutical composition comprising a B-cell antagonist and a pharmaceutically acceptable carrier and a label stating that the antagonist or pharmaceutical composition is indicated for treating patients with rheumatoid arthritis which a serum sample has been obtained showing an amount of CXCL13 greater than 116.6 pg/ml, or an amount of sFcRH5 greater than 126.7 ng/ml, or a combination of these amounts is provided. In a further embodiment, the serum sample is positive for RF.

In another aspect, a method for manufacturing a B-cell antagonist or a pharmaceutical composition thereof comprising combining in a package the antagonist or pharmaceutical composition and a label stating that the antagonist or pharmaceutical composition is indicated for treating patients with rheumatoid arthritis from which a serum sample has been obtained showing an amount of CXCL13 greater than 116.6 pg/ml, or an amount of sFcRH5 greater than 126.7 ng/ml, or a combination of these amounts is provided. In a further embodiment, the serum sample is positive for RF.

In yet another aspect, a method of providing a treatment option for patients with rheumatoid arthritis comprising packaging a B-cell antagonist in a vial with a package insert containing instructions to treat patients with rheumatoid arthritis from whom a sample has been obtained that contains an amount of CXCL13 greater than 116.6 pg/ml, or an amount of sFcRH5 greater than 126.7 ng/ml, or a combination of these amounts is provided. In a further embodiment, the sample is positive for RF.

In still another aspect, a method of specifying a B-cell antagonist for use in a rheumatoid arthritis patient subpopulation, the method comprising providing instruction to administer the B-cell antagonist to a patient subpopulation characterized by the presence in a serum sample from said subpopulation of an amount of CXCL13 greater than 116.6 pg/ml, or an amount of sFcRH5 greater than 126.7 ng/ml, or a combination of these amounts is provided. In a further embodiment, the serum sample is positive for RF.

In one aspect, a method for marketing a B-cell antagonist for use in a rheumatoid arthritis patient subpopulation, the method comprising informing a target audience about the use of the antagonist for treating the patient subpopulation characterized by the presence, in serum samples from patients of such subpopulation, of an amount of CXCL13 greater than 116.6 pg/ml, or an amount of sFcRH5 greater than 126.7 ng/ml, or a combination of these amounts is provided. In a further embodiment, the serum samples from patients of such subpopulation are positive for RF.

In another aspect, a method is provided for selecting a therapy for a patient or a patient subpopulation with rheumatoid arthritis comprising: (a) determining in a serum sample from the patient the amount of CXCL13, sFcRH5, or both of these amounts; (b) determining whether the serum sample is RF positive or RF negative; and (c) selecting a B-cell antagonist as the therapy if the patient's sample is RF positive and has an amount of CXCL13 greater than 116.6 pg/ml, or an amount of sFcRH5 greater than 126.7 ng/ml, or a combination of these amounts in the sample.

Figure 1:
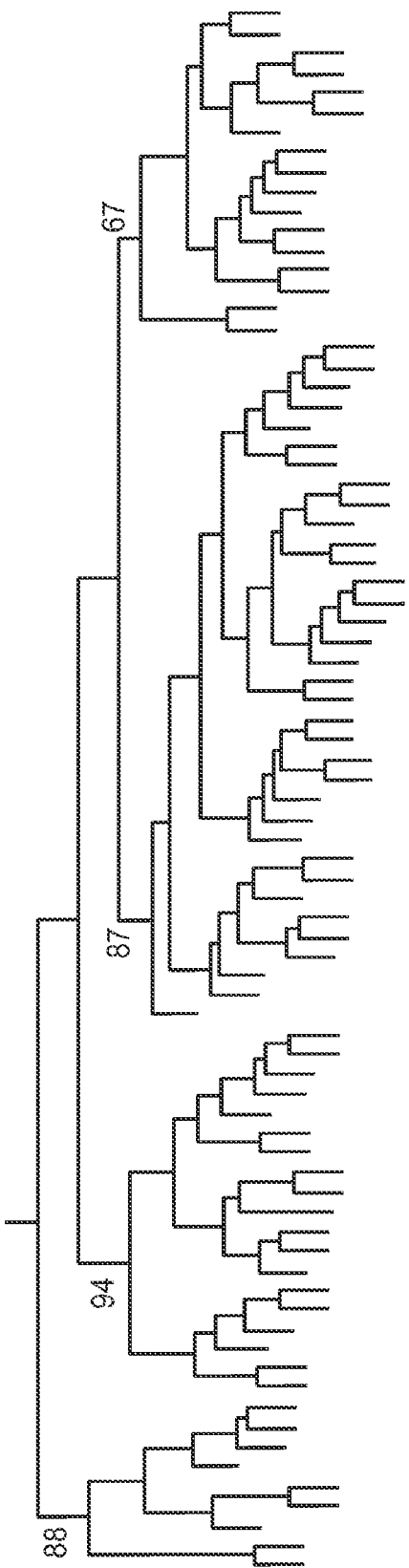
FIG. 1 shows a dendrogram depicting sample clusters and branch support values (88, 94, 87, and 67) following microarray analysis of synovial tissues from RA patients as described in Example 1.

L=lymphoid-rich subtype; M=myeloid-rich subtype. Each molecular phenotype is indicated at the top of the figure above the bootstrapped dendrogram; corresponding boxes around gene expression within the heatmap are indicated and highlight specific areas of coregulated signature genes. Expression data was z-score normalized for visualization (bar at bottom of figure).

FIG. 3 shows molecular, clinical, histological, and immunohistochemical characteristics of L subtype synovial tissue samples as described in Example 1. (A) Expression of XBP1 transcription factor in L subtype samples (L) compared to non-L subtype samples (NL); (B) Expression of XBP1 transcription factor in synovial samples containing lymphoid aggregates (+) compared to synovial samples lacking lymphoid aggregates (−); (C) Graphical plot of erythroid sedimentation rate (ESR) ("Sed Rate") compared to XBP1 expression level in all RA samples tested; (D) Graphical plot of C-reactive protein compared to XBP1 expression level in all RA samples tested; (E) hematoxylin and eosin staining of a representative synovial sample of the L subtype; (F) immunohistochemical staining for the T cell marker CD3 of a representative synovial sample of the L subtype; (G) immunohistochemical staining for the activated leukocyte marker CD68 of a representative synovial sample of the L subtype; (H) immunohistochemical staining for the B cell marker CD20 of a representative sample of the L subtype.

FIG. 4 shows molecular, histological, and immunohistochemical characteristics of M subtype synovial tissue samples as described in Example 1. (A) Expression of ICAM1 in M subtype samples (M) compared to the expression in the other subtypes (F1, F2, L); (B) Graphical plot of IL1β gene expression compared to TNF gene expression in M subtype samples; (C) hematoxylin and eosin staining of a representative synovial sample of the M subtype; (D) immunohistochemical staining for the T cell marker CD3 of a representative synovial sample of the M subtype; (E) immunohistochemical staining for the activated leukocyte marker CD68 of a representative synovial sample of the M subtype; (F) immunohistochemical staining for the B cell marker CD20 of a representative synovial sample of the M subtype.

FIG. 5 shows molecular, histological, and immunohistochemical characteristics of F2 subtype synovial tissue samples as described in Example 1. (A) Expression of IL17D in F2 subtype samples (F2) compared to the expression in the other subtypes (F1, L, and M); (B) hematoxylin and eosin staining of a representative synovial sample of the F2 subtype; (C) immunohistochemical staining for the T cell marker CD3 of a representative synovial sample of the F2 subtype; (D) immunohistochemical staining for the activated leukocyte marker CD68 of a representative synovial sample of the F2 subtype; (E) immunohistochemical staining for the B cell marker CD20 of a representative synovial sample of the F2 subtype.

FIG. 6 shows molecular, histological, and immunohistochemical characteristics of F1 subtype synovial tissue samples as described in Example 1. (A) Expression of ITGA11 in F1 subtype samples (F1) compared to the expression in the other subtypes (F2, L, and M); (B) hematoxylin and eosin staining of a representative synovial sample of the F1 subtype; (C) immunohistochemical staining for the T cell marker CD3 of a representative synovial sample of the F1 subtype; (D) immunohistochemical staining for the activated leukocyte marker CD68 of a representative synovial sample of the F1 subtype; (E) immunohistochemical staining for the B cell marker CD20 of a representative synovial sample of the F1 subtype.

Figure 7:
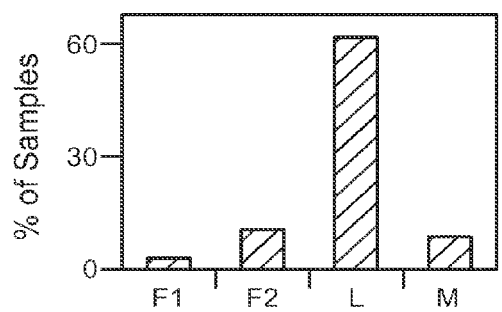

FIG. 7 shows the percentage of samples with lymphoid clusters according to molecular subtype as described in Example 1. F1, F2, L, and M molecular subtypes are indicated along the bottom axis.

FIG. 8 shows, within each indicated molecular subtype, the value of certain samples for certain classical markers of RA as described in Example 1. (A) erythroid sedimentation rate (ESR) in mm/hr; (B) C-reactive protein (CRP) in mg/dL; (C) radiographic progression by stage. F1, F2, L, and M molecular subtypes are indicated in each of (A)-(C) along the bottom axis; each dot represents the value for one individual sample.

Figure 9:
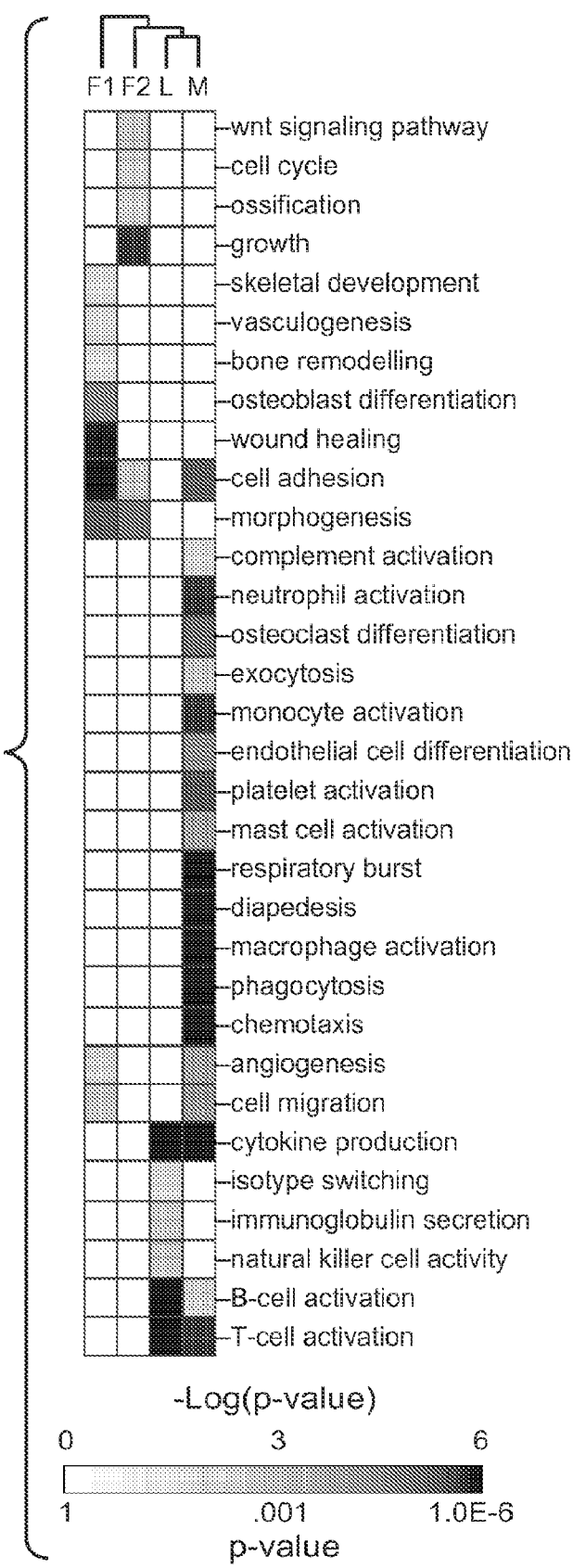

FIG. 9 shows biological pathways within each molecular subtype identified by statistical analysis of gene signatures specific to each subtype as described in Example 1. The heatmap depicts the results of the analysis. Each of the subtypes F1, F2, L, and M is listed across the top of the heatmap; biological pathways are indicated along the right side of the heatmap; grey shading within the heatmap corresponds to the p-values for statistically enriched pathways within each subtype according to the scale shown at the bottom of the figure.

FIG. 10 shows the validation of selected genes found to be differentially expressed by microarray analysis as described in Example 2, (A) F1-specific transcripts; (B) F2-specific transcripts; (C) L-specific transcripts; (D) M-specific transcripts. In each of (A)-(D), the name of the gene transcript is indicated at the top of the graph; each of the subtypes F1, F2, L, and M, along with normal (Nrml) and osteoarthritis (OA) individuals, is indicated along the horizontal axis of each graph; transcript abundance relative to the house keeping gene, HPRT1, is indicated along the vertical axis of each graph.

FIG. 11 shows a graphical plot of (A) serum sFcRH5 levels and (B) serum CXCL13 levels in RA patients in the REFLEX trial prior to dosing with rituximab as compared to healthy controls as described in Example 3. Serum sFcRH5 levels are plotted on the vertical axis in ng/ml in (A); serum CXCL13 levels are plotted on the vertical axis in pg/ml in (B); healthy controls and RA patients are indicated on the horizontal axis in (A) and (B).

Figure 12:
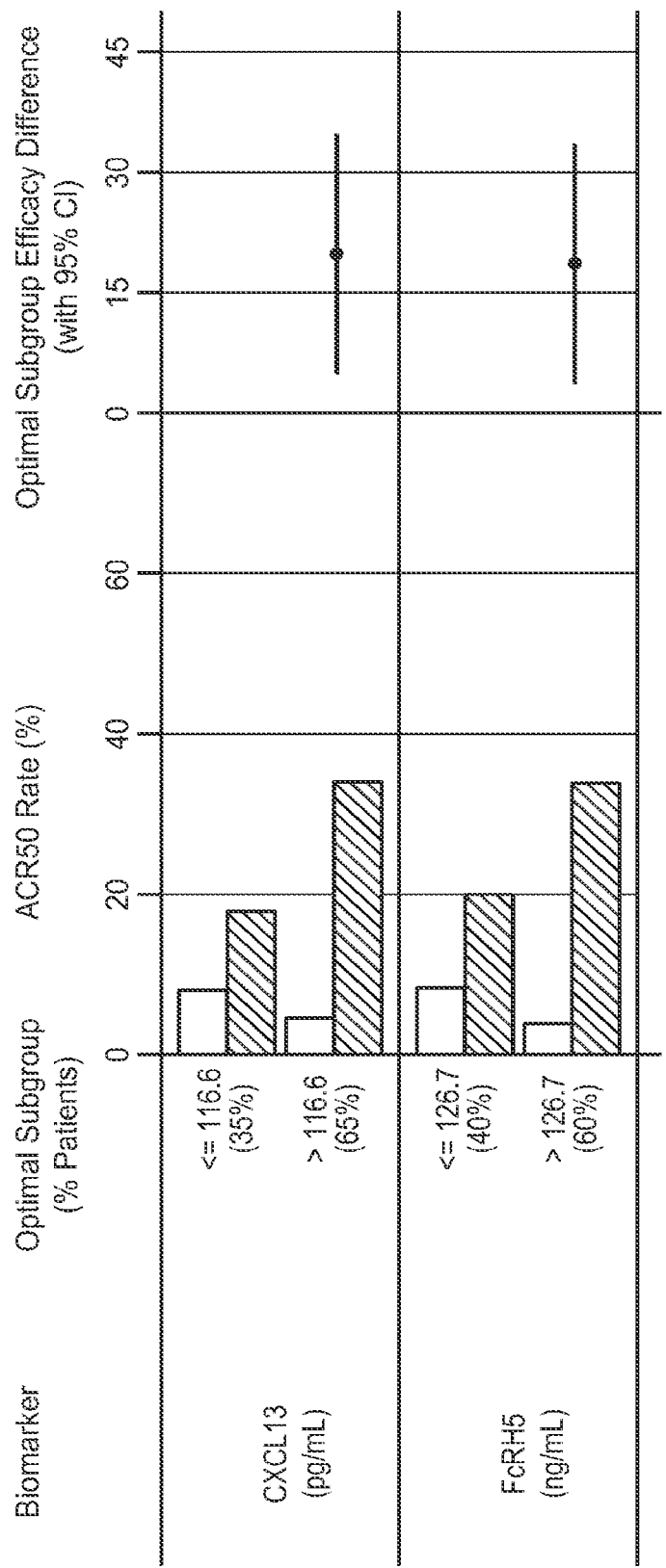

FIG. 12 shows the results of the threshold sensitivity analysis of CXCL13 and sFcRH5 data as described in Example 3. Striped bars: rituximab-treated patients; open bars: placebo-treated patients; the width of the bars reflect the number of patients in the group; the right side of the figure shows the placebo-corrected optimal subgroup efficacy difference between the biomarker-high group and the biomarker-low group with 95% confidence intervals (CI).

FIG. 13 shows placebo-controlled 24 week ACR50 response rates in patient subsets defined by sFcRH5 level and RF seropositivity in the REFLEX trial (A) and in the SERENE trial (B) as described in Example 3. Striped bars, rituximab-treated patients; open bars, placebo-treated patients. The patient subsets are indicated along the horizontal axis (all patients, FcRH5 or hi, RF negative or positive); the number of patients in each subset showing an ACR50 response compared to the total number of patients in that subset is indicated above each bar. The placebo-controlled ACR50 response rate (ΔACR50) is also indicated for each subset at the top of the graph.

FIG. 14 shows placebo-controlled 24 week ACR50 response rates in patient subsets defined by sFcRH5 level, CXCL13 level and RF seropositivity in the REFLEX trial as described in Example 3. Striped bars, rituximab-treated patients; open bars, placebo-treated patients. The patient subsets are indicated along the horizontal axis (all patients, FcRH5 lo or hi, CXCL13 lo or hi, RF negative or positive); the number of patients in each subset showing an ACR50 response compared to the total number of patients in that subset is indicated above each bar. The placebo-controlled ACR50 response rate (ΔACR50) is also indicated for each subset at the top of the graph.

DETAILED DESCRIPTION

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Certain Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

"Rheumatoid arthritis," (RA) refers to a chronic systemic autoimmune inflammatory disease that mainly involves the synovial membrane of multiple joints with resultant injury to the articular cartilage, resulting in joint destruction. The main presenting symptoms in RA are pain, stiffness, swelling, and/or loss of function of one or more joints.

The term "polynucleotide" or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O— allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR 2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, refers to short, single stranded polynucleotides that are at least about seven nucleotides in length and less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single stranded polynucleotide that is capable of hybridizing to a nucleic acid and allowing the polymerization of a complementary nucleic acid, generally by providing a free 3'-OH group.

The term "array" or "microarray" refers to an ordered arrangement of hybridizable array elements, preferably polynucleotide probes (e.g., oligonucleotides), on a substrate. The substrate can be a solid substrate, such as a glass slide, or a semi-solid substrate, such as nitrocellulose membrane.

The term "amplification" refers to the process of producing one or more copies of a reference nucleic acid sequence or its complement. Amplification may be linear or exponential (e.g., PCR). A "copy" does not necessarily mean perfect sequence complementarity or identity relative to the template sequence. For example, copies can include nucleotide analogs such as deoxyinosine, intentional sequence alterations (such as sequence alterations introduced through a primer comprising a sequence that is hybridizable, but not fully complementary, to the template), and/or sequence errors that occur during amplification.

The term "detection" includes any means of detecting, including direct and indirect detection.

"Elevated expression" or "elevated levels" refers to an increased expression of a mRNA or a protein in a patient relative to a control, such as an individual or individuals who are not suffering from RA.

The term "molecular subtype," used interchangeably with "molecular phenotype," refers to a subtype or phenotype of RA characterized by the expression of one or more particular genes or one or more particular proteins, or a particular pattern of expression of a combination of genes or a combination of proteins. The expression of particular genes, proteins or combinations of genes or proteins may be further associated with certain pathological, histological, and/or clinical features of RA.

The term "multiplex-PCR" refers to a single PCR reaction carried out on nucleic acid obtained from a single source (e.g., a patient) using more than one primer set for the purpose of amplifying two or more DNA sequences in a single reaction.

As used herein, "rheumatoid factor," or "RF," refers to IgM, IgG, or IgA isotypes, singly or in any combination, of antibodies detected in patient serum and directed to antigenic determinants present on human and animal IgG.

The term "positive for RF" refers to a result of an assay for RF, e.g., an ELISA assay, where the result is above a threshold or cutoff value for that assay for samples that are considered to reproducibly contain detectable levels of RF.

The term "negative for RF" refers to a result of an assay for RF, e.g., an ELISA assay, where the result is at or below a threshold or cutoff value for that assay for samples that are considered to reproducibly contain undetectable levels of RF.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, can be identified by those that: (1) employ low ionic strength and high temperature for washing, for example 0.015 M sodium chloride/0.0015 M sodium citrate/ 0.1% sodium dodecyl sulfate at 50 C; (2) employ during hybridization a denaturing agent, such as formamide, for example, 50% (v/v) formamide with 0.1% bovine serum albumin/0.1% Ficoll/0.1% polyvinylpynolidone/50 mM sodium phosphate buffer at pH 6.5 with 750 mM sodium chloride, 75 mM sodium citrate at 42 C; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42 C, with a 10 minute wash at 42 C in 0.2×SSC (sodium chloride/ sodium citrate) followed by a 10 minute high-stringency wash consisting of 0.1×SSC containing EDTA at 55 C.

"Moderately stringent conditions" can be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50 C. The skilled artisan will recognize how to adjust the temperature, ionic strength, etc. as necessary to accommodate factors such as probe length and the like.

The term "biomarker" as used herein refers to an indicator of e.g., a pathological state of a patient, which can be detected in a biological sample of the patient. Biomarkers include, but are not limited to, DNA, RNA, protein, carbohydrate, or glycolipid-based molecular markers.

The term "diagnosis" is used herein to refer to the identification or classification of a molecular or pathological state, disease or condition. For example, "diagnosis" may refer to identification of a particular type of RA. "Diagnosis" may also refer to the classification of a particular subtype of RA, e.g., by histopathological criteria (e.g., lymphoid infiltration or follicle-like lymphoid cluster), or by molecular features (e.g., a subtype characterized by expression of one or a combination of particular genes or proteins encoded by said genes).

The term "aiding diagnosis" is used herein to refer to methods that assist in making a clinical determination regarding the presence, or nature, of a particular type of symptom or condition of RA. For example, a method of aiding diagnosis of RA can comprise measuring the expression of certain genes in a biological sample from an individual.

The term "prognosis" is used herein to refer to the prediction of the likelihood of autoimmune disorder-attributable disease symptoms of an autoimmune disease such as RA. The term "prediction" is used herein to refer to the likelihood that a patient will respond either favorably or unfavorably to a drug or set of drugs. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely.

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the invention are useful in attempts to delay development of a disease or disorder.

An "effective amount" refers to an amount effective, at dosages and for periods of time necessary, to achieve the desired therapeutic or prophylactic result. A "therapeutically effective amount" of a therapeutic agent may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

An "individual," "subject" or "patient" is a vertebrate. In certain embodiments, the vertebrate is a mammal. Mammals include, but are not limited to, primates (including human and non-human primates) and rodents (e.g., mice and rats). In certain embodiments, a mammal is a human.

A "control subject" refers to a healthy subject who has not been diagnosed as having RA and who does not suffer from any sign or symptom associated with RA.

The term "sample," as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized.

By "tissue" or "cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like. A "reference sample", "reference cell", "reference tissue", "control sample", "control cell", or "control tissue", as used herein, refers to a sample, cell or tissue obtained from a source known, or believed, not to be afflicted with the disease or condition for which a method or composition of the invention is being used to identify. In one embodiment, a reference sample, reference cell, reference tissue, control sample, control cell, or control tissue is obtained from a healthy part of the body of the same subject or patient in whom a disease or condition is being identified using a composition or method of the invention. In one embodiment, a reference sample, reference cell, reference tissue, control sample, control cell, or control tissue is obtained from a healthy part of the body of an individual who is not the subject or patient in whom a disease or condition is being identified using a composition or method of the invention.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to both protein and nucleic acid.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

A "medicament" is an active drug to treat a disease, disorder, and/or condition. In one embodiment, the disease, disorder, and/or condition is RA or its symptoms or side effects.

The term "increased resistance" to a particular therapeutic agent or treatment option, when used in accordance with the invention, means decreased response to a standard dose of the drug or to a standard treatment protocol.

The term "decreased sensitivity" to a particular therapeutic agent or treatment option, when used in accordance with the invention, means decreased response to a standard dose of the agent or to a standard treatment protocol, where decreased response can be compensated for (at least partially) by increasing the dose of agent, or the intensity of treatment.

"Patient response" or "response" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) decrease of autoimmune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment.

The term "gene signature" is used interchangeably with "gene expression signature" and refers to one or a combination of genes whose expression is indicative of a particular subtype of RA characterized by certain molecular, pathological, histological, and/or clinical features. In certain embodiments, the expression of one or more genes comprising the gene signature is elevated compared to that in control subjects.

The term "protein signature" is used interchangeably with "protein expression signature" and refers to one or a combination of proteins whose expression is indicative of a particular subtype of RA characterized by certain molecular, pathological, histological, and/or clinical features. In certain embodiments, the expression of one or more proteins comprising the protein signature is elevated compared to that in control subjects.

A "RA therapeutic agent," a "therapeutic agent effective to treat RA," and grammatical variations thereof, as used herein, refer to an agent that when provided in an effective amount is known, clinically shown, or expected by clinicians to provide a therapeutic benefit in a subject who has RA.

A "B-cell surface marker" or "B-cell surface antigen" herein is an antigen expressed on the surface of a B cell that can be targeted with an antagonist that binds thereto. Exemplary B-cell surface markers include the CD10, CD19, CD20 (MS4A1), CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CMS, and CD86 leukocyte surface markers (for descriptions, see The Leukocyte Antigen Facts Book, 2nd Edition. 1997, ed. Barclay et al. Academic Press, Harcourt Brace & Co., New York). Other B-cell surface markers include RP105, FcRH2, B-cell CR2, CCR6, P2×5, HLA-DOB, CXCR5, FCER2, BR3, Btig, NAG14, SLGC16270, FcRH1, IRTA2, ATWD578, FcRH3, IRTA1, FcRH6, BCMA, and 239287. The B-cell surface marker of particular interest is preferentially expressed on B cells compared to other non-B-cell tissues of a mammal and may be expressed on both precursor B cells and mature B cells.

An "antibody that binds to a B-cell surface marker" is a molecule that, upon binding to a B-cell surface marker, destroys or depletes B cells in a mammal and/or interferes with one or more B-cell functions, e.g. by reducing or preventing a humoral response elicited by the B cell. The antibody in certain instances is able to deplete B cells (i.e, reduce circulating B-cell levels) in a mammal treated therewith. Such depletion may be achieved via various mechanisms such as antibody-dependent cell-mediated cytotoxicity (ADCC) and/or complement-dependent cytotoxicity (CDC), inhibition of B-cell proliferation, and/or induction of B-cell death (e.g. via apoptosis).

An "antagonist" refers to a molecule capable of neutralizing, blocking, inhibiting, abrogating, reducing or interfering with the activities of a particular or specified protein, including its binding to one or more receptors in the case of a ligand or binding to one or more ligands in case of a receptor. Antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of the protein, and fusion proteins, receptor molecules and derivatives which bind specifically to the protein thereby sequestering its binding to its target, antagonist variants of the protein, antisense molecules directed to the protein, RNA aptamers, and ribozymes against the protein.

A "B-cell antagonist" is a molecule that, upon binding to a B-cell surface marker, destroys or depletes B cells in a mammal and/or interferes with one or more B-cell functions, e.g. by reducing or preventing a humoral response elicited by the B cell. The antagonist in certain instances is able to deplete B cells (i.e. reduce circulating B-cell levels) in a mammal treated therewith. Such depletion may be achieved via various mechanisms such as ADCC and/or CDC, inhibition of B-cell proliferation, and/or induction of B-cell death (e.g. via apoptosis). Exemplary antagonists include synthetic or native-sequence peptides, fusion proteins, and small-molecule antagonists that bind to the B-cell marker, optionally conjugated with or fused to a cytotoxic agent. Examples include but are not limited to, e.g., CD22 antibodies, CD20 antibodies, BR3 antibodies (e.g., WO0224909), and BR3-Fc immunoadhesin.

Examples of CD20 antibodies include: "C2B8," which is now called "rituximab" ("RITUXAN®") (U.S. Pat. No. 5,736,137); the yttrium-[90]-labeled 2B8 murine antibody designated "Y2B8" or "ibritumomab tiuxetan" (ZEVALIN®) commercially available from IDEC Pharmaceuticals, Inc. (U.S. Pat. No. 5,736,137; 2B8 deposited with ATCC under accession no. HB11388 on Jun. 22, 1993); murine IgG2a "B1," also called "tositumomab," optionally labeled with $^{131}$I to generate the "$^{13}$I—B1" or "iodine I$^{131}$ tositumomab" antibody (BEXXAR™) commercially available from Corixa (see, also, U.S. Pat. No. 5,595,721); murine monoclonal antibody "1F5" (Press et al. Blood 69(2):584-591 (1987) and variants thereof including "framework-patched" or humanized 1F5 (WO 2003/002607, Leung, S.; ATCC deposit HB-96450); murine 2H7 and chimeric 2H7 antibody (U.S. Pat. No. 5,677,180); humanized 2H7 (see, e.g., WO04/056312; US20060024295); HUMAX-CD20™ antibodies (Genmab, Denmark); the human monoclonal antibodies set forth in WO 2004/035607 (Teeling et al.); AME-133™ antibodies (Applied Molecular Evolution); A20 antibody or variants thereof such as chimeric or humanized A20 antibody (cA20, hA20, respectively) (US 2003/0219433, Immunomedics); and monoclonal antibodies L27, G28-2, 93-1 B3, B-C1 or NU-B2 available from the International Leukocyte Typing Workshop (Valentine et al., In: Leukocyte Typing III (McMichael, Ed., p. 440, Oxford University Press (1987)).

The terms "BAFF," "BAFF polypeptide," "TALL-1" or "TALL-1 polypeptide," "BLyS", and "THANK" when used herein encompass "native-sequence BAFF polypeptides" and "BAFF variants." "BAFF" is a designation given to those polypeptides that have the human BAFF sequence as set forth in, for example, U.S. Pat. Pub. No. 2006/0110387, and homologs and fragments and variants thereof, which have the biological activity of the native-sequence BAFF. A biological activity of BAFF can be selected from the group consisting of promoting B-cell survival, promoting B-cell maturation, and binding to BR3. The term "BAFF" includes those polypeptides described in Shu et al., *J. Leukocyte Biol.*, 65:680 (1999); GenBank Accession No. AF136293; WO 1998/18921; EP 869,180; WO 1998/27114; WO 1999/12964; WO 1999/33980; Moore et al., *Science*, 285:260-263 (1999); Schneider et al., *J. Exp. Med.*, 189:1747-1756 (1999); and Mukhopadhyay et al., *J. Biol. Chem.*, 274: 15978-15981 (1999).

The term "BAFF antagonist" as used herein is used in the broadest sense, and includes any molecule that (1) binds a native-sequence BAFF polypeptide or binds a native-sequence BR3 polypeptide to block, partially or fully, BR3 interaction with BAFF polypeptide, and (2) partially or fully blocks, inhibits, or neutralizes native-sequence BAFF signaling. Native-sequence BAFF polypeptide signaling promotes, among other things, B-cell survival and B-cell maturation. The inhibition, blockage, or neutralization of BAFF signaling results in, inter alia, a reduction in the number of B cells. A BAFF antagonist as defined herein will partially or fully block, inhibit, or neutralize one or more biological activities of a BAFF polypeptide, in vitro or in vivo. In one embodiment, a biologically active BAFF potentiates any one or a combination of the following events in vitro or in vivo: an increased survival of B cells, an increased level of IgG and/or IgM, an increased numbers of plasma cells, and processing of NF-κb2/100 to p52 NF-κβ in splenic B cells (e.g., Batten et al., *J. Exp. Med.* 192:1453-1465 (2000); Moore et al., *Science* 285:260-263 (1999); and Kayagaki et al., *Immunity*, 10:515-524 (2002)).

In some embodiments, a BAFF antagonist as defined herein includes anti-BAFF antibodies, BAFF-binding polypeptides (including immunoadhesins and peptides), and BAFF-binding small molecules. BAFF antagonists include, for example, the BAFF-binding antibodies described in WO 2002/02641 (e.g., antibodies comprising the amino acid sequence of any of SEQ ID NOS:1-46, 321-329, 834-872, 1563-1595, 1881-1905 of Table 1 thereof). In a further embodiment, the immunoadhesin comprises a BAFF-binding region of a BAFF receptor (e.g., an extracellular domain of BR3, BCMA, or TACI). In a still further embodiment, the immunoadhesin is BR3-Fc. Other examples of BAFF-binding Fc proteins can be found in WO 2002/66516, WO 2000/40716, WO 2001/87979, WO 2003/024991, WO 2002/16412, WO 2002/38766, WO 2002/092620, and WO 2001/12812. Methods of making BAFF antagonists are described, for example, in US 2005/0095243 and US 2005/0163775.

The terms "BR3", "BR3 polypeptide" or "BR3 receptor" when used herein encompass native-sequence BR3 polypeptides and BR3 variants, as defined hereinbelow. "BR3" is a designation given to those polypeptides comprising, for example, the human BR3 sequence set forth in WO 2003/14294 and US 2005/0070689. BR3 polypeptides can be isolated from a variety of sources, such as from human tissue types or from another source, or prepared by recombinant and/or synthetic methods. The term BR3 includes the BR3 polypeptides described in WO 2002/24909, WO 2003/14294, and US 2005/0070689. Anti-BR3 antibodies can be prepared in accordance with methods set for in, for example, WO 2003/14294 and US 2005/0070689.

A "native-sequence" BR3 polypeptide or "native BR3" comprises a polypeptide having the same amino acid sequence as the corresponding BR3 polypeptide derived from nature. Such native-sequence BR3 polypeptides can be isolated from nature or can be produced by recombinant and/or synthetic means. The term "native-sequence BR3 polypeptide" specifically encompasses naturally occurring truncated, soluble or secreted forms (e.g., an extracellular domain sequence), naturally occurring variant forms (e.g., alternatively spliced forms) and naturally occurring allelic variants of the polypeptide. The BR3 polypeptides of the invention include the BR3 polypeptide comprising or consisting of the contiguous sequence of amino acid residues 1 to 184 of a human BR3 (see WO 2003/14294 and US 2005/0070689).

A BR3 "extracellular domain" or "ECD" refers to a form of the BR3 polypeptide that is essentially free of the transmembrane and cytoplasmic domains. ECD forms of BR3 include a polypeptide comprising any one of the amino acid sequences selected from the group consisting of amino acids 1-77, 2-62, 2-71, 1-61, 7-71, 23-38 and 2-63 of human BR3. In certain embodiments, BAFF antagonists are polypeptides comprising any one of the above-mentioned ECD forms of human BR3 and variants and fragments thereof that bind a native BAFF.

"BR3 variant" means a BR3 polypeptide having at least about 80% amino acid sequence identity with the amino acid sequence of a native-sequence, full-length BR3 or BR3 ECD and binds a native-sequence BAFF polypeptide. Optionally, the BR3 variant includes a single cysteine-rich domain. Such BR3 variant polypeptides include, for instance, BR3 polypeptides wherein one or more amino acid residues are added, or deleted, at the N- and/or C-terminus, as well as within one or more internal domains, of the full-length amino acid sequence. Fragments of the BR3ECD that bind a native sequence BAFF polypeptide are also contemplated.

The term "APRIL antagonist" as used herein is used in the broadest sense, and includes any molecule that (1) binds a native-sequence APRIL polypeptide or binds a native-sequence ligand to APRIL to block, partially or fully, the ligand's interaction with APRIL polypeptide, and (2) partially or fully blocks, inhibits, or neutralizes native-sequence APRIL signaling. Native-sequence APRIL polypeptide signaling promotes, among other things, B-cell survival and B-cell maturation. APRIL (a proliferation-inducing ligand) is a TNF family member with a shared receptor to BAFF. Examples of APRIL antagonists include but are not limited to atacicept (same as TACI-Ig immunoadhesin) and a BAFF/APRIL antagonist (soluble BCMA-Fc).

The term "cytokine" is a generic term for proteins released by one cell population that act on another cell as intercellular mediators. Examples of such cytokines are lymphokines, monokines; interleukins (ILs) such as IL-1, IL-1a, IL-2, IL-3, IL-4, IL-5, IL-6, IL-7, IL-8, IL-9, IL-11, IL-12, IL-15, IL-17A, IL-17F, IL-17A/F; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native-sequence cytokines, including synthetically produced small-molecule entities and pharmaceutically acceptable derivatives and salts thereof.

For the purposes herein, "tumor necrosis factor-alpha (TNF-alpha)" refers to a human TNF-alpha molecule comprising the amino acid sequence as described in Pennica et al., Nature, 312:724 (1984) or Aggarwal et al., JBC, 260:2345 (1985).

A "TNF-alpha inhibitor" herein is an agent that inhibits, to some extent, a biological function of TNF-alpha, generally through binding to TNF-alpha and neutralizing its activity. Examples of TNF inhibitors specifically contemplated herein are etanercept (ENBREL®), infliximab (REMICADE®), adalimumab (HUMIRA®), golimumab (SIMPONI™), and certolizumab pegol)(CIMZIA®).

An "IL-17A/F binding agent" is an agent, e.g., an antibody, that binds to the cytokine IL-17A/F or an agent that is cross-reactive with TL-17A and IL-17F.

An "IL-6 binding agent" is an agent, e.g., an antibody, that binds to the cytokine IL-6.

A "CD4 binding agent" is an agent, e.g., an antibody, that binds to the surface glycoprotein CD4 expressed on cells of the T lymphocyte lineage.

Examples of "disease-modifying anti-rheumatic drugs" or "DMARDs" include hydroxycloroquine, sulfasalazine, methotrexate (plus oral and subcutaneous methotrexate), leflunomide, azathioprine, D-penicillamine, Gold (oral), Gold (intramuscular), minocycline, cyclosporine, Staphylococcal protein A immunoadsorption, including salts and derivatives thereof, etc.

"CTLA4" is expressed on activated T lymphocytes and is involved in down-regulation of the immune response. Other names for CTLA4 in the literature include cytotoxic T-lymphocyte-associated antigen 4, cytotoxic T-lymphocyte-associated protein 4, cell differentiation antigen CD152, and cytotoxic T-lymphocyte-associated granule serine protease 4.

A therapeutic agent that has "marketing approval," or that has been "approved as a therapeutic agent," or grammatical variations thereof of these phrases, as used herein, refer to an agent (e.g., in the form of a drug formulation, medicament) that is approved, licensed, registered or authorized by a relevant governmental entity (e.g., federal, state or local regulatory agency, department, bureau) to be sold by and/or through and/or on behalf of a commercial entity (e.g., a for-profit entity) for the treatment of a particular disorder (e.g., RA) or a patient subpopulation (e.g., patients of a particular ethnicity, gender, lifestyle, disease risk profile, etc.). A relevant governmental entity includes, for example, the Food and Drug Administration (FDA), European Medicines Evaluation Agency (EMEA), and equivalents thereof.

"Antibodies" (Abs) and "immunoglobulins" (Igs) refer to glycoproteins having similar structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is a minimum antibody fragment which contains a complete antigen-binding site. In one embodiment, a two-chain Fv species consists of a dimer of one heavy- and one light-chain variable domain in tight, non-covalent association. Collectively, the six CDRs of an Fv confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature*, 256: 495 (1975); Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633, 425; 5,661,016; Marks et al., *Bio. Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996) and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6855-9855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which comprises an amino acid sequence corresponding to that of an antibody produced by a human and/or has been made using any of the techniques for making human antibodies as disclosed herein. Such techniques include screening human-derived combinatorial libraries, such as phage display libraries (see, e.g., Marks et al., *J. Mol. Biol.*, 222: 581-597 (1991) and Hoogenboom et al., *Nucl. Acids Res.*, 19: 4133-4137 (1991)); using human myeloma and mouse-human heteromyeloma cell lines for the production of human monoclonal antibodies (see, e.g., Kozbor *J. Immunol.*, 133: 3001 (1984); Brodeur et al., *Monoclonal Antibody Production Techniques and Applications*, pp. 55-93 (Marcel Dekker, Inc., New York, 1987); and Boerner et al., *J. Immunol.*, 147: 86 (1991)); and generating monoclonal antibodies in transgenic animals (e.g., mice) that are capable of producing a full repertoire of human antibodies in the absence of endogenous immunoglobulin production (see, e.g., Jakobovits et al., *Proc. Natl. Acad. Sci. USA*, 90: 2551 (1993); Jakobovits et al., *Nature*, 362: 255 (1993); Bruggermann et al., *Year in Immunol.*, 7: 33 (1993)). This definition of a human antibody specifically excludes a humanized antibody comprising antigen-binding residues from a non-human animal.

An "affinity matured" antibody is one with one or more alterations in one or more CDRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of HVR and/or framework residues is described by: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking antibody" or an "antagonist antibody" is one which inhibits or reduces a biological activity of the antigen it binds. Certain blocking antibodies or antagonist antibodies partially or completely inhibit the biological activity of the antigen.

As used herein, "growth-inhibitory" antibodies are those that prevent or reduce proliferation of a cell expressing an antigen to which the antibody binds. For example, the antibody may prevent or reduce proliferation of B cells in vitro and/or in vivo.

Antibodies that "induce apoptosis" refer to antibodies that induce programmed cell death, e.g. of a B cell, as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

Antibody "effector functions" refer to those biological activities attributable to the Fc region (a native-sequence Fc region or amino-acid-sequence-variant Fc region) of an antibody, and vary with the antibody isotype. Examples of antibody effector functions include but are not limited to: C1q binding and complement-dependent cytotoxicity (CDC); Fc-receptor binding; antibody-dependent cell-mediated cytotoxicity (ADCC); phagocytosis; down-regulation of cell-surface receptors (e.g. B-cell receptor); and B-cell activation.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is typically defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise herein, the numbering of the residues in an immunoglobulin heavy chain is that of the EU index as in Kabat (Kabat et al., *Sequences of Proteins of Immunological Interest*, Ed. 5 (Public Health Service, National Institutes of Health, Bethesda, Md., 1991)). The "EU index as in Kabat" refers to the residue numbering of the human IgG1 EU antibody.

A "functional Fc region" possesses an "effector function" of a native-sequence Fc region. Exemplary "effector functions" include but are not limited to C1q binding; CDC; Fc-receptor binding; ADCC; phagocytosis; down-regulation of cell-surface receptors (e.g. B-cell receptor; BCR), etc. Such effector functions generally require the Fc region to be combined with a binding domain (e.g. an antibody-variable domain) and can be assessed using various assays as disclosed, for example, herein.

A "native-sequence Fc region" comprises an amino acid sequence identical to the amino acid sequence of an Fc region found in nature. Native-sequence human Fc regions include a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence which differs from that of a native-sequence Fc region by virtue of at least one amino acid modification, typically one or more amino acid substitution(s).

The term "Fe-region-comprising antibody" refers to an antibody that comprises an Fc region. The C-terminal lysine (residue 447 according to the EU numbering system) of the Fc region may be removed, for example, during purification of the antibody or by recombinant engineering the nucleic acid encoding the antibody. Accordingly, a composition comprising an antibody having an Fc region can comprise an antibody with K447, with all K447 removed, or a mixture of antibodies with and without the K447 residue.

"Fc receptor" or "FcR" describes a receptor that binds to the Fc region of an antibody. In some embodiments, an FcR is a native-human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIII (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daëron, *Anna. Rev. Immunol.* 15:203-234 (1997)). FcRs are reviewed, for example, in Ravetch and Kinet, *Anna. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward, *Immunology Today,* 18 (12):592-8 (1997); Ghetie et al., *Nature Biotechnology,* 15 (7):637-40 (1997); Hinton et al., *J. Biol. Chem.,* 279(8):6213-6 (2004); WO 2004/92219 (Hinton et al.).

Binding to human FcRn in vivo and serum half-life of human FcRn high-affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See, also, for example, Shields et al., *J. Biol. Chem.,* 9(2): 6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural-killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g., NK cells, neutrophils, and macrophages) enables these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol.,* 9:457-492 (1991). To assess ADCC activity of a molecule of interest, an in vitro ADCC assay, such as that described in U.S. Pat. No. 5,500,362 or 5,821,337 or 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al., *Proc. Natl. Acad. Sci.* (USA), 95:652-656 (1998).

"Complement-dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g. as described in Gazzano-Santoro et al., *J. Immunol. Methods,* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 and WO 1999/51642. See, also, e.g., Idusogie et al., *J. Immunol.* 164:4178-4184 (2000).

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

A "small molecule" or "small organic molecule" is defined herein as an organic molecule having a molecular weight below about 500 Daltons.

The word "label" when used herein refers to a detectable compound or composition. The label is typically conjugated or fused directly or indirectly to a reagent, such as a nucleic acid probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which results in a detectable product.

An "isolated" biological molecule, such as a nucleic acid, polypeptide, or antibody, is one which has been identified and separated and/or recovered from at least one component of its natural environment.

Reference to "about" a value or parameter herein includes (and describes) embodiments that are directed to that value or parameter per se. For example, description referring to "about X" includes description of "X."

The term "pharmaceutical formulation" refers to a sterile preparation that is in such form as to permit the biological activity of the medicament to be effective, and which contains no additional components that are unacceptably toxic to a subject to which the formulation would be administered.

A "sterile" formulation is aseptic or free from all living microorganisms and their spores.

A "package insert" is used to refer to instructions customarily included in commercial packages of therapeutic products or medicaments, that contain information about the indications, usage, dosage, administration, contraindications, other therapeutic products to be combined with the packaged product, and/or warnings concerning the use of such therapeutic products or medicaments and the like.

A "kit" is any manufacture (e.g a package or container) comprising at least one reagent, e.g., a medicament for treatment of RA or joint damage, or a probe for specifically detecting a biomarker gene or protein of the invention. In certain embodiments, the manufacture is promoted, distributed, or sold as a unit for performing the methods of the present invention.

A "target audience" is a group of people or an institution to whom or to which a particular medicament is being promoted or intended to be promoted, as by marketing or advertising, especially for particular uses, treatments, or indications, such as individual patients, patient populations, readers of newspapers, medical literature, and magazines, television or internet viewers, radio or internet listeners, physicians, drug companies, etc.

The term "serum sample" refers to any serum sample obtained from an individual. Methods for obtaining sera from mammals are well known in the art.

The expression "not responsive to," as it relates to the reaction of subjects or patients to one or more of the medicaments that were previously administered to them, describes those subjects or patients who, upon administration of such medicament(s), did not exhibit any or adequate signs of treatment of the disorder for which they were being treated, or they exhibited a clinically unacceptably high degree of toxicity to the medicament(s), or they did not maintain the signs of treatment after first being administered such medicament(s), with the word treatment being used in this context as defined herein. The phrase "not responsive" includes a description of those subjects who are resistant and/or refractory to the previously administered medication(s), and includes the situations in which a subject or patient has progressed while receiving the medicament(s) that he or she is being given, and in which a subject or patient has progressed within 12 months (for example, within six months) after completing a regimen involving the medicament(s) to which he or she is no longer responsive. The non-responsiveness to one or more medicaments thus includes subjects who continue to have active disease following previous or current treatment therewith. For instance, a patient may have active disease activity after about one to three months of therapy with the medicament(s) to which they are non-responsive. Such responsiveness may be assessed by a clinician skilled in treating the disorder in question.

For purposes of non-response to medicament(s), a subject who experiences "a clinically unacceptably high level of toxicity" from previous or current treatment with one or more medicaments experiences one or more negative side-effects or adverse events associated therewith that are considered by an experienced clinician to be significant, such as, for example, serious infections, congestive heart failure, demyelination (leading to multiple sclerosis), significant hypersensitivity, neuropathological events, high degrees of autoimmunity, a cancer such as endometrial cancer, non-Hodgkin's lymphoma, breast cancer, prostate cancer, lung cancer, ovarian cancer, or melanoma, tuberculosis (TB), and the like.

By "reducing the risk of a negative side effect" is meant reducing the risk of a side effect resulting from treatment with the antagonist herein to a lower extent than the risk observed resulting from treatment of the same patient or another patient with a previously administered medicament. Such side effects include those set forth above regarding toxicity, and are preferably infection, cancer, heart failure, or demyelination.

The "amount" or "level" of a biomarker associated with an increased clinical benefit to a RA patient or patient with joint damage is a detectable level in a biological sample. These can be measured by methods known to one skilled in the art and also disclosed herein. The expression level or amount of biomarker assessed can be used to determine the response to the treatment.

The terms "level of expression" or "expression level" in general are used interchangeably and generally refer to the amount of a polynucleotide or an amino acid product or protein in a biological sample. "Expression" generally refers to the process by which gene-encoded information is converted into the structures present and operating in the cell. Therefore, as used herein, "expression" of a gene may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. "Expressed genes" include those that are transcribed into a polynucleotide as mRNA and then translated into a protein, and also those that are transcribed into RNA but not translated into a protein (for example, transfer and ribosomal RNAs).

Rheumatoid Arthritis

Autoimmune diseases remain clinically important diseases in humans. As the name implies, autoimmune diseases act through the body's own immune system. While the pathological mechanisms differ among individual types of autoimmune diseases, one general mechanism involves the generation of antibodies (referred to herein as self-reactive antibodies or autoantibodies) directed against specific endogenous proteins. Physicians and scientists have identified more than 70 clinically distinct autoimmune diseases, including RA, multiple sclerosis (MS), vasculitis, immune-mediated diabetes, and lupus such as systemic lupus erythematosus (SLE). While many autoimmune diseases are rare—affecting fewer than 200,000 individuals—collectively, these diseases afflict millions of Americans, an estimated five percent of the population, with women disproportionately affected by most diseases. The chronic nature of these diseases leads to an immense social and financial burden.

Inflammatory arthritis is a prominent clinical manifestation in diverse autoimmune disorders including RA, psoriatic arthritis (PsA), SLE, Sjögren's syndrome, and polymyositis. Most of these patients develop joint deformities on physical examination but typically only RA and PsA patients manifest bone erosions on imaging studies.

RA is a chronic inflammatory disease that affects approximately 0.5 to 1% of the adult population in northern Europe and North America, and a slightly lower proportion in other parts of the world. Alamanos and Drosos, *Autoimmun. Rev.*, 4: 130-136 (2005). It is a systemic inflammatory disease characterized by chronic inflammation in the synovial membrane of affected joints, which ultimately leads to loss of daily function due to chronic pain and fatigue. The majority of patients also experience progressive deterioration of cartilage and bone in the affected joints, which may eventually lead to permanent disability. The long-term prognosis of RA is poor, with approximately 50% of patients experiencing significant functional disability within 10 years from the time of diagnosis. Keystone, *Rheumatology*, 44 (Suppl. 2): ii8-ii12 (2005). Life expectancy is reduced by an average of 3-10 years. Alamanos and Drosos, supra. Patients with a high titer of rheumatoid factor (RF) (approximately 80% of patients) have more aggressive disease (Bukhari et al., *Arthritis Rheum.*, 46: 906-912 (2002)), with a worse long-term outcome and increased mortality over those who are RF negative. Heliovaara et al., *Ann. Rheum. Dis.*, 54: 811-814 (1995)).

The pathogenesis of chronic inflammatory bone diseases, such as RA, is not fully elucidated. Such diseases are accompanied by bone loss around affected joints due to increased osteoclastic resorption. This process is mediated largely by increased local production of pro-inflammatory cytokines. Teitelbaum, *Science*, 289:1504-1508 (2000); Goldring and Gravallese, *Arthritis Res.*, 2(1):33-37 (2000). These cytokines can act directly on cells in the osteoclast lineage or indirectly by affecting the production of the essential osteoclast differentiation factor, receptor activator of NFκB ligand (RANKL), and/or its soluble decoy receptor, osteoprotegerin (OPG), by osteoblast/stromal cells. Hofbauer et al., *J. Bone Min. Res.*, 15(1):2-12 (2000). Tumor necrosis factor-alpha (TNF-α) is a major mediator of inflammation. Its importance in the pathogenesis of various forms of bone loss is supported by several lines of experimental and clinical evidence. Feldmann et al., *Cell*, 85(3):307-310 (1996). However, TNF-α is not essential for osteoclastogenesis (Douni et al., *J. Inflamm.*, 47:27-38 (1996)), erosive arthritis (Campbell et al., *J. Clin. Invest.*, 107(12):1519-1527 (2001)), or osteolysis (Childs et al., *J. Bon. Min. Res.*, 16:338-347 (2001)), as these can occur in the absence of TNF-α.

In RA specifically, an immune response is thought to be initiated/perpetuated by one or several antigens presenting in the synovial compartment, producing an influx of acute inflammatory cells and lymphocytes into the joint. Successive waves of inflammation lead to the formation of an invasive and erosive tissue called pannus. This contains proliferating fibroblast-like synoviocytes and macrophages that produce proinflammatory cytokines such as TNF-α and interleukin-1 (IL-1). Local release of proteolytic enzymes, various inflammatory mediators, and osteoclast activation contributes to much of the tissue damage. There is loss of articular cartilage and the formation of bony erosions. Surrounding tendons and bursa may become affected by the inflammatory process. Ultimately, the integrity of the joint structure is compromised, producing disability.

The precise contributions of B cells to the immunopathogenesis of RA are not completely characterized. However, there are several possible mechanisms by which B cells may participate in the disease process. Silverman and Carson, *Arthritis Res. Ther.*, 5 Suppl. 4: S1-6 (2003).

Historically, B cells were thought to contribute to the disease process in RA predominantly by serving as the precursors of autoantibody-producing cells. A number of autoantibody specificities have been identified including antibodies to Type II collagen, and proteoglycans, as well as RFs. The generation of large quantities of antibody leads to immune complex formation and the activation of the complement cascade. This in turn amplifies the immune response and may culminate in local cell lysis. Increased RF synthesis and complement consumption has been correlated with disease activity. The presence of RF itself is associated with a more severe form of RA and the presence of extra-articular features.

Evidence exists (Janeway et al., *J. Immunol.*, 138:1051 (1998); Rivera et al., *Int. Immunol.*, 13: 1583-1593 (2001)) showing that B cells are highly efficient antigen-presenting cells (APC). RF-positive B cells may be particularly potent APCs, since their surface immunoglobulin would readily allow capture of any immune complexes regardless of the antigens present within them. Many antigens may thus be processed for presentation to T cells. In addition, it has been recently suggested that this may also allow RF-positive B cells to self-perpetuate. Edwards et al., *Immunology*, 97: 188-196 (1999).

For activation of T cells, two signals need to be delivered to the cell; one via the T-cell receptor (TCR), which recognizes the processed peptide in the presence of major histocompatibility complex (MHC) antigen, and a second, via co-stimulatory molecules. When activated, B cells express co-stimulatory molecules on their surface and can thus provide the second signal for T-cell activation and the generation of effector cells.

B cells may promote their own function as well as that of other cells by producing cytokines. Harris et al., *Nat. Immunol.*, 1: 475-482 (2000). TNF-α, IL-1, lymphotoxin-α, and IL-10 are amongst some of the cytokines that B cells may produce in the RA synovium.

Although T-cell activation is considered to be a key component in the pathogenesis of RA, recent work using human synovium explants in severe combined immunodeficiency disorders (SCID) mice has demonstrated that T-cell activation and retention within the joint is critically dependent on the presence of B cells. Takemura et al., *J. Immunol.*, 167: 4710-4718 (2001). The precise role of B cells in this is unclear, since other APCs did not appear to have the same effect on T cells.

Structural damage to joints is an important consequence of chronic synovial inflammation. Between 60% and 95% of patients with RA develop at least one radiographic erosion within 3-8 years of disease onset. Paulus et al., *J. Rheumatol.*, 23: 801-805 (1996); Hulsmans et al., *Arthritis Rheum.*, 43: 1927-1940 (2000). In early RA, the correlation between radiographic damage scores and functional capacity is weak, but after 8 years of disease, correlation coefficients can reach as high as 0.68. Scott et al., *Rheumatology*, 39:122-132 (2000). In 1,007 patients younger than age 60 years who had RA for at least four years, Wolfe et al. (*Arthritis Rheum*, 43 Suppl. 9:S403 (2000)) found a significant association among the rate of progression of the Larsen radiographic damage score (Larsen et al., *Acta Radiol. Diagn.* 18:481-491 (1977)), increasing Social Security disability status, and decreasing family income.

Diagnosis of RA may be according to current American College of Rheumatology (ACR) criteria and may include morning stiffness in and around the joints lasting for at least 1 hour before maximal improvement; arthritis of three or more joint areas: at least three joint areas have simultaneously had soft tissue swelling or fluid (not bony overgrowth alone) observed by a physician; the 14 possible joint areas (right and left) are proximal interphalangeal (PIP), metacarpophalangeal (MCP), wrist, elbow, knee, ankle, and metatarsophalangeal (MTP) joints; arthritis of hand joints: at least one joint area swollen as above in wrist, MCP, or PIP joint; symmetric arthritis: simultaneous involvement of the same joint areas (as in arthritis of three or more joint areas, above) on both sides of the body (bilateral involvement of PIP, MCP, or MTP joints is acceptable without absolute symmetry); rheumatoid nodules: subcutaneous nodules over bony prominences or extensor surfaces or in juxta-articular regions that are observed by a physician; serum rheumatoid factor: demonstration of abnormal amounts of serum rheumatoid factor by any method that has been positive in fewer than five percent of normal control patients; radiographic changes: radiographic changes typical of rheumatoid arthritis on posteroanterior hand and wrist X-rays, which must include erosions or unequivocal bony decalcification localized to or most marked adjacent to the involved joints (osteoarthritis changes alone do not qualify). Diagnosis of RA is typically made if a patient satisfies at least four of the above criteria.

Prevention or retardation of radiographic damage is one of the goals of RA treatment. Edmonds et al., *Arthritis Rheum.*, 36:336-340 (1993). Controlled clinical trials of 6 or 12 months' duration have documented that the progression of radiographic damage scores was more rapid in the placebo group than in groups that received methotrexate (MTX) (Sharp et al., *Arthritis Rheum.*, 43: 495-505 (2000)), leflunomide (Sharp et al., supra), sulfasalazine (SSZ) (Sharp et al., supra), prednisolone (Kirwan et al., *N. Engl. J. Med.*, 333:142-146 (1995); Wassenberg et al., *Arthritis Rheum*, 42: Suppl 9:S243 (1999)), interleukin-1 receptor antagonist (Bresnihan et al., *Arthritis Rheum*, 41: 2196-2204 (1998)), or an infliximab/MTX combination. Lipsky et al., *N. Eng. J. Med.*, 343: 1594-1604 (2000). Clinical trials have also documented that radiographic progression following treatment with etanercept was less rapid than that following treatment with MTX. Bathon et al., *N. Engl. J. Med.*, 343:1586-1593 (2000). Other studies have evaluated radiographic progression in patients treated with corticosteroids (Joint Committee of the Medical Research Council and Nuffield Foundation, *Ann Rheum. Dis.*, 19:331-337 (1960); Van Everdingen et al., *Ann. Intern. Med.*, 136:1-12 (2002)), cyclosporin A (Priolo et al., *J. Rheumatol.*, 24:2113-2118 (1997); Forre, *Arthritis Rheum.*, 37:1506-1512 (1994)), MTX versus azathioprine (Jeurissen et al., *Ann. Intern. Med.*, 114:999-1004 (1991)), MTX versus auranofin (Weinblatt et al., *Arthritis Rheum.*, 36:613-619 (1993)), MTX (meta-analysis) (Alarcon et al., *J. Rheumatol.*, 19:1868-1873 (1992)), hydroxychloroquine (HCQ) versus SSZ (Van der Heijde et al., *Lancet*, 1:1036-1038 (1989)), SSZ (Hannonen et al., *Arthritis Rheum.*, 36:1501-1509 (1993)), the COBRA (Combinatietherapei Bij Reumatoide Artritis) combination of prednisolone, MTX, and SSZ (Boers et al., *Lancet*, 350:309-318 (1997); Landewe et al., *Arthritis Rheum.*, 46: 347-356 (2002)), combinations of MTX, SSZ, and HCQ (O'Dell et al., *N. Engl. J. Med.*, 334:1287-1291 (1996); Mottonen et al., *Lancet*, 353:1568-1573 (1999)), the combination of cyclophosphamide, azathioprine, and HCQ (Csuka et al., *JAMA*, 255:2315-2319 (1986)), and the combination of adalimumab with MTX. Keystone et al., *Arthritis Rheum.*, 46 Suppl. 9:S205 (2002).

The FDA has now approved labeling claims that certain medications, e.g., leflunomide, etanercept, and infliximab, slow the progression of radiographic joint damage. These claims are based on the statistically significant differences in progression rates observed between randomly assigned treatment groups and control groups. However, the progression rates in individuals within the treatment and control groups overlap to a considerable extent. Therefore, despite significant differences between treatment groups, these data cannot be used to estimate the probability that a patient who is starting a treatment will have a favorable outcome with respect to progression of radiographic damage. Various methods have been suggested to categorize paired radiographs from individual patients as not progressive, e.g., damage scores of 0 at both time points, no increase in damage scores, no new joints with erosions, and a change in score not exceeding the smallest detectable difference (i.e., 95% confidence interval for the difference between repeated readings of the same radiograph). Lassere et al., *J. Rheumatol.*, 26: 731-739 (1999).

Determining whether there has been increased structural damage in an individual patient during the interval between paired radiographs obtained at the beginning and end of a 6- or 12-month clinical trial has been difficult, for several reasons. The rate of radiographic damage is not uniform within a population of RA patients; a few patients may have rapidly progressing damage, but many may have little or no progression, especially if the tie interval is relatively short. The methods for scoring radiographic damage, e.g., Sharp (Sharp et al., *Arthritis Rheum.*, 14: 706-720 (1971); Sharp et al., *Arthritis Rheum.*, 28: 1326-1335 (1985)), Larsen (Larsen et al., *Acta Radiol. Diagn.*, 18: 481-491 (1977)), and modifications of these methods (Van der Heijde, *J. Rheumatol.*, 27: 261-263 (2000)), depend on the judgment and the interpretation of the reader as to what is real. Factors to determine are whether an apparent interruption of the subchondral cortical plate is real, or whether a decrease in the distance between the cortices on opposite sides of a joint is real, or is due to a slight change in the position of the joint relative to the film and the radiographic beam, to a change in radiographic exposure, or to some other technical factor.

Therefore, the recorded score is an approximation of the true damage, and for many subjects, the smallest detectable difference between repeat scores of the same radiographs is larger than the actual change that has occurred during the interval between the baseline and final radiographs. If the reader is blinded to the temporal sequence of the films, these unavoidable scoring errors may be in either direction, leading to apparent "healing" when the score decreases or to apparent rapid progression when reading error increases the difference between films. When the study involves a sufficiently large population of patients who have been randomly assigned to receive an effective treatment as compared with placebo, the positive and negative reading errors offset each other, and small but real differences between treatment groups can be detected.

The imprecision of the clinical measures that are used to quantitate RA disease activity has caused a similar problem. Statistically significant differences between certain outcome measures from clinical trials were not useful for estimating the probability of improvement for an individual who was starting the treatment. Paulus et al., *Arthritis Rheum.*, 33:477-484 (1990). Attribution of individual improvement became practical with the creation of the American College of Rheumatology (ACR) 20% composite criteria for improvement (ACR20), which designated a patient as improved if there was 20% improvement in the tender and swollen joint counts and 20% improvement in at least three of five additional measures (pain, physical function, patient global health assessment, physician global health assessment, and acute-phase reactant levels). Felson et al., *Arthritis Rheum.*, 38:727-735 (1995). All of these measures have large values for the smallest detectable difference, but by requiring simultaneous improvement in five of the seven aspects of the same process (disease activity), the randomness of the seven measurement errors is constrained, and it is easier to attribute real improvement to the individual.

In RA, joint damage is a prominent feature. Radiologic parameters of joint destruction are seen as a key outcome measure in descriptions of disease outcome. In the recent OMERACT (Outcome Measures in Rheumatology Clinical Trials) consensus meeting, radiology was chosen as part of the core set of outcome measures for longitudinal observational studies. Wolfe et al., *Arthritis Rheum.*, 41 Supp 9: 5204 (1998) abstract. Radiology is also part of the WHO/ILAR (World Health Organization/International League of Associations for Rheumatology) required core set of measures for long-term clinical trials. Tugwell and Boers, *J. Rheumatol.*, 20:528-530 (1993).

Available data on the outcome of radiologic damage in RA have been obtained in both short-term and long-term studies. In short-term studies of RA patients with recent-onset disease, radiographs obtained every six months showed that after an initial rapid progression, there was diminution of the progression rate of radiologic damage in the hands and feet after two to three years. Van der Heijde et al., *Arthritis Rheum.*, 35: 26-34 (1992); Fex et al., *Br. J. Rheumatol.*, 35: 1106-1115 (1996). In long-term studies with radiographs taken less frequently, a constant rate of progression was found, with relentless deterioration of damage up to 25 years of disease duration. Wolfe and Sharp, *Arthritis Rheum.*, 41:1571-1582 (1998); Graudal et al., *Arthritis Rheum.*, 41:1470-1480 (1998); Plant et al., *J. Rheumatol.*, 25:417-426 (1998); Kaarela and Kautiainen, *J. Rheumatol.*, 24:1285-1287 (1997). Whether these differences in radiographic progression pattern are due to differences in the scoring techniques is not clear.

The scoring systems used differ in the number of joints being scored, the presence of independent scores for erosions (ERO) and joint space narrowing (JSN), the maximum score per joint, and the weighing of a radiologic abnormality. As yet, there is no consensus on the scoring method of preference. During the first three years of follow-up in a cohort study of patients with early arthritis, JSN and ERO were found to differ in their contribution to the measured progression in radiologic damage of the hands and feet. Van der Heijde et al., *Arthritis Rheum.*, 35:26-34 (1992). Furthermore, methods that independently score ERO and JSN, such as the Sharp and Kellgren scores, were found to be more sensitive to change in early RA than methods using an overall measure, such as the Larsen score. Plant et al., *J. Rheumatol.*, 21:1808-1813 (1994); Cuchacovich et al., *Arthritis Rheum.*, 35:736-739 (1992). The Sharp score is a very labor-intensive method. Van der Heijde, *Baillieres Clin. Rheumatol.*, 10:435-453 (1996). In late or destructive RA, the Sharp and the Larsen methods were found to provide similar information. However, the sensitivity to change of the various scoring methods late in the disease has not yet been investigated, and it can be argued that the scoring methods that independently measure ERO and JSN provide useful information. Pincus et al., *J. Rheumatol.*, 24:2106-2112 (1997). See also Drossaers-Bakker et al., *Arthritis Rheum.*, 43:1465-1472 (2000), which compared the three radiologic scoring systems for the long-term assessment of RA.

Paulus et al., *Arthritis Rheum.*, 50: 1083-1096 (2004) categorized radiographic joint damage as progressive or non-progressive in individuals with RA participating in clinical trials, and concluded that RA joint damage in an observational cohort can be classified as progressive or non-progressive with the use of a composite definition that includes a number of imprecise and related, but distinct, measures of structural joint damage. It appears that in day-to-day clinical management of an RA patient, an interval change between a pair of radiographs of at least five Sharp radiographic damage score units should be present before one considers the structural change to be real and uses it as the basis for a treatment decision.

Certain RA Therapeutic Agents

Initial therapy of RA typically involves administration of one or more of the following drugs: nonsteroidal antiinflammatory drugs (NSAIDs), e.g., acetylsalicylic acid (e.g., aspirin), ibuprofen (Motrin), naproxen (Naprosyn), indomethacin (Indocin), nabumetone (Relafen), tolmetin (Tolectin); glucocorticoid (via joint injection); and low-dose prednisone. See "Guidelines for the management of rheumatoid arthritis," Arthritis & Rheumatism 46(2): 328-346 (February, 2002). The majority of patients with newly diagnosed RA are started with disease-modifying antirheumatic drug (DMARD) therapy within 3 months of diagnosis. DMARDs commonly used in RA are hydroxychloroquine, sulfasalazine, methotrexate (plus oral and subcutaneous methotrexate), leflunomide, azathioprine, D-penicillamine, Gold (oral), Gold (intramuscular), minocycline, cyclosporine, Staphylococcal protein A immunoadsorption. In certain instances, patients are treated with immunomodulating agents such as azathioprine or cyclophosphamide. Additional RA therapeutic agents include an anti-cytokine agent (e.g., anti-tumor necrosis factor α, anti-interleukin-1-receptor (e.g., anakinra), anti-interleukin 10, anti-interleukin 6 receptor, anti-interleukin 6, anti-interferon alpha, anti-B-lymphocyte stimulator), an inhibitor of costimulation (e.g., anti-CD154, CTLA4-Ig (e.g., abatacept)).

In certain instances, TNFα inhibitors have been used for therapy of RA. Exemplary TNFα inhibitors include etanercept (sold under the trade name ENBREL®), infliximab (sold under the trade name REMICADE®), adalimumab (sold under the trade name HUMIRA®), golimumab (sold under the trade name SIMPONI™) and certolizumab pegol (sold under the trade name CIMZIA®).

Etanercept (sold under the trade name ENBREL®) is an injectable drug approved in the U.S. for therapy of active RA. Etanercept binds to TNFα and serves to remove most TNFα from joints and blood, thereby preventing TNFα from promoting inflammation and other symptoms of rheumatoid arthritis. Etanercept is an "immunoadhesin" fusion protein consisting of the extracellular ligand binding portion of the human 75 kD (p75) tumor necrosis factor receptor (TNFR) linked to the Fc portion of a human IgG1. The drug has been associated with negative side effects including serious infections and sepsis, and nervous system disorders such as multiple sclerosis (MS). See, e.g., www.remicade-infliximab.com/pages/enbrel_embrel.html.

Infliximab, sold under the trade name REMICADE®, is an immune-suppressing drug prescribed to treat RA and Crohn's disease. Infliximab is a chimeric monoclonal antibody that binds to TNFα and reduces inflammation in the body by targeting and binding to TNFα which produces inflammation. Infliximab has been linked to certain fatal reactions such as heart failure and infections including tuberculosis as well as demyelination resulting in MS. See, e.g., www.remicade-infliximab.com.

In 2002, Abbott Laboratories received FDA approval to market adalimumab (sold under the trade name HUMIRA®), previously known as D2E7. Adalimumab is a human monoclonal antibody that binds to TNFα and is approved for reducing the signs and symptoms and inhibiting the progression of structural damage in adults with moderately to severely active RA who have had insufficient response to one or more traditional disease modifying DMARDs.

In April 2009, Centocor Ortho Biotech Inc. received FDA approval to market golimumab (sold under the trade name SIMPONI™) for patients with moderate to severe RA, psoriatic arthritis, and ankylosing spondylitis. Golimumab is a human IgG1κ monoclonal antibody specific for human TNFα and which is self-administered by patients subcutaneously once every month. Golimumab binds to both soluble and transmembrane bioactive forms of TNFα. Similar to other agents that inhibit TNFα, golimumab has been associated with certain adverse events such as risk of infection, including serious and life-threatening fungal infections.

In May 2009, certolizumab pegol (sold under the trade name CIMZIA®) was approved by the FDA for treatment of patients with RA. It is administered by a healthcare professional by subcutaneous injection every two weeks during induction and then every four weeks during maintenance. Certolizumab pegol is a recombinant, humanized antibody Fab' fragment, with specificity for human TNFα, conjugated to an approximately 40 kDa polyethylene glycol (PEG2MAL40K). Certolizumab pegol has also been associated with certain safety risks such as increased risk of serious infection, similar to other TNFα inhibitors.

In certain instances, the rituximab antibody (sold under the trade name RITUXAN®) has been used as a therapy for RA. Rituximab is a genetically engineered chimeric murine/human monoclonal antibody directed against the CD20 antigen. Rituximab is the antibody called "C2B8" in U.S. Pat. No. 5,736,137 issued Apr. 7, 1998 (Anderson et al.).

Another anti-CD20 antibody is ocrelizumab. Ocrelizumab is a humanized variant of an anti-CD20 antibody, 2H7. Such humanized 2H7 variants are described, for example, in International Publication No. WO 2004/056312 (International Application No. PCT/US2003/040426).

RA therapeutic agents having B-cell antagonist activity can be identified, for example, by screening compounds for certain biological properties. For example, a method of screening can be employed as described in Sundberg et al., *Cancer Research* 66, 1775-1782 (2006) wherein a compound was screened for inhibition of B-cell proliferation by targeting c-myc protein for rapid and specific degradation. See also Mackay et al., *Annual Review of Immunology*, 21: 231-264 (2003) regarding BAFF, APRIL, and a tutorial on B-cell survival and screening, and Thangarajh et al., *Scandinavian J. Immunol.*, 65(1):92 (2007) on B-cell proliferation and APRIL. In addition, Sakurai et al., *European J. Immunol.*, 37(1):110 (2007) discloses that TACT attenuates antibody production co-stimulated by BAFF-R and CD40. Further, Acosta-Rodriguez et al., *European J. Immunol.*, 37(4):990 (2007) discloses that BAFF and LPS cooperate to induce B cells to become susceptible to CD95/Fas-mediated cell death. Further screening methods can be found in Martin and Chan, "B Cell Immunobiology in Disease: Evolving Concepts from the Clinic Annual Review of Immunology," 24:467-496 (2006), Pillai et al., "Marginal Zone B Cells" *Annual Review of Immunology*, 23:161-196 (2005), and Hardy and Hayakawa, "B Cell Development Pathways," *Annual Review of Immunology*, 19:595-621 (2001). From these and other references the skilled artisan can screen for the appropriate antagonists. Microarrays can be used for this purpose (Hagmann, *Science,* 290:82-83 (2000)), as well as RNA interference (RNAi) (Ngo et al., *Nature,* 441:106-110 (2006)).

B-cell antagonists included within the scope of the present invention include antibodies, synthetic or native-sequence peptides, immunoadhesins, and small-molecule antagonists that bind to a B-cell surface marker or a B-cell specific survival or proliferation factor, optionally conjugated with or fused to another molecule. In certain embodiments, the antagonist comprises an antibody or immunoadhesin. It includes BLyS antagonists such as immunoadhesins, including, but not limited to, anti-CD23 (e.g., lumiliximab), anti-CD20, anti-CD22, or anti-BR3 antibodies, APRIL antagonists, and/or BLyS immunoadhesins. In certain embodiments, the BLyS immunoadhesin is selected from BR3 immunoadhesin comprising the extracellular domain of BR3, TACI immunoadhesin comprising the extracellular domain of TACI, and BCMA immunoadhesin comprising the extracellular domain of BCMA. Certain embodiments of BR3 immunoadhesin include hBR3-Fc as described in WO 2005/00351, U.S. Pat. Pub. No. 2005/0095243, U.S. Pat. Pub. No. 2005/0163775 and WO 2006/068867. In certain embodiments, the BLyS antagonist is an anti-BLyS antibody, wherein the anti-BLyS antibody binds BLyS within a region of BLyS comprising residues 162-275, or an anti-BR3 antibody, wherein the anti-BR3 antibody binds BR3 in a region comprising residues 23-38 of human BR3. In certain embodiments, the immunoadhesins are selected from TACI-Ig (atacicept) and BR3-Ig. In certain embodiments, the B-cell antagonist is to CD20, CD22, BAFF, or APRIL. In certain such embodiments, the antagonist is an antibody or TACI-Ig.

The CD22 antigen, or CD22, also known as BL-CAM or Lyb8, is a type 1 integral membrane glycoprotein with molecular weight of about 130 (reduced) to 140 kD (unreduced). It is expressed in both the cytoplasm and cell membrane of B-lymphocytes. CD22 antigen appears early in B-cell lymphocyte differentiation at approximately the same stage as the CD19 antigen. Unlike certain other B-cell markers, CD22 membrane expression is limited to the late differentiation stages comprised between mature B cells (CD22+) and plasma cells (CD22−). The CD22 antigen is described, for example, in Wilson et al., *J. Exp. Med.,* 173:137 (1991) and Wilson et al., *J. Immunol.,* 150:5013 (1993).

Certain exemplary anti-CD22 antibodies include those described in EP 1,476,120 (Tedder and Tuscano), EP 1,485, 130 (Tedder), and EP 1,504,035 (Popplewell et al.), as well as those described in U.S. Pat. Pub. No. 2004/0258682 (Leung et al.), U.S. Pat. No. 5,484,892 (Dana-Farber), U.S.

Pat. No. 6,183,744 (Immunomedics, epratuzumab), and U.S. Pat. No. 7,074,403 (Goldenberg and Hansen).

BLyS (also known as BAFF, TALL-1, THANK, TNFSF13B, or zTNF4) is a member of the TNF1 ligand superfamily that is essential for B-cell survival and maturation. BAFF overexpression in transgenic mice leads to B-cell hyperplasia and development of severe autoimmune disease (Mackay et al., *J. Exp. Med.,* 190:1697-1710 (1999); Gross et al., *Nature,* 404:995-999 (2000); Khare et al., *Proc. Natl. Acad. Sci. U.S.A,* 97:3370-3375 (2000)). BAFF levels are elevated in human patients with a variety of autoimmune disorders, such as SLE, RA, and Sjögren's syndrome (Cheema et al., *Arthritis Rheum.,* 44:1313-1319 (2001); Groom et al, *J. Clin. Invest.,* 109:59-68 (2002); Zhang et al., *J. Immunol.,* 166:6-10 (2001)). Furthermore, BAFF levels correlate with disease severity, suggesting that BAFF can play a direct role in the pathogenesis of these illnesses. BAFF acts on B cells by binding to three members of the TNF receptor superfamily, TACI, BCMA, and BR3 (also known as BAFF-R) (Gross et al., supra; Thompson et al., *Science,* 293:2108-2111 (2001); Yan et al., *Curr. Biol.* 11:1547-1552 (2001); Yan et al., *Nat. Immunol.,* 1:37-41 (2000); Schiemann et al., *Science,* 293:2111-2114 (2001)).

Of the three, only BR3 is specific for BAFF; the other two also bind the related TNF family member, A proliferation-inducing ligand (APRIL). Comparison of the phenotypes of BAFF and receptor knockout or mutant mice indicates that signaling through BR3 mediates the B-cell survival functions of BAFF (Thompson et al., supra; Yan et al., supra, 2001; Schiemann et al., supra). In contrast, TACI ap-pears to act as an inhibitory receptor (Yan, *Nat. Immunol.,* 2:638-643 (2001)), while the role of BCMA is unclear (Schiemann et al., supra). US 2007/0071760 discloses treating B-cell malignancies using a TACI-Ig fusion molecule in an amount sufficient to suppress proliferation-inducing functions of BlyS and APRIL.

BR3 is a 184-residue type III transmembrane protein expressed on the surface of B cells (Thompson et al., supra; Yan, *Nat. Immun.,* supra). The intracellular region bears no sequence similarity to known structural domains or protein-protein interaction motifs. Nevertheless, BAFF-induced signaling through BR3 results in processing of the transcription factor NF-B2/p100 to p52 (Claudio et al., *Nat. Immunol.,* 3:958-965 (2002); Kayagaki et al., *Immunity,* 10:515-524 (2002)). The extracellular domain (ECD) of BR3 is also divergent. TNFR family members are usually characterized by the presence of multiple cysteine-rich domains (CRDs) in their extracellular region; each CRD is typically composed of about 40 residues stabilized by six cysteines in three disulfide bonds. Conventional members of this family make contacts with ligand through two CRDs interacting with two distinct patches on the ligand surface (Bodmer et al., *Trends Biochem. Sci.,* 27:19-26 (2002)). However, the BR3 ECD contains only four cysteine residues, capable of forming a partial CRD at most, raising the question of how such a small receptor imparts high-affinity ligand binding.

It has been shown that the BAFF-binding domain of BR3 resides within a 26-residue core region (Kayagaki et al., supra). Six BR3 residues, when structured within a β-hairpin peptide (bhpBR3), were sufficient to confer BAFF binding and block BR3-mediated signaling. Others have reported polypeptides purported to interact with BAFF (e.g., WO 2002/24909, WO 2003/035846, WO 2002/16312, and WO 2002/02641).

Loss of function and radiographic change occur early in the course of the disease. These changes can be delayed or prevented with the use of certain DMARDs. Although several DMARDs are initially clinically effective and well tolerated, many of these drugs become less effective or exhibit increased toxicity over time. Based on its efficacy and tolerability, MTX has become the standard therapy by which other treatments are measured. Bathon et al., *N. Eng. J. Med.,* 343:1586-1593 (2000); Albert et al., *J. Rheumatol.,* 27:644-652 (2000).

Recent studies have examined radiographic progression in patients with late-stage RA who have taken leflunomide, MTX, or placebo (Strand et al., *Arch. Intern. Med.,* 159: 2542-2550 (1999)) as well as patients who have taken infliximab plus MTX or placebo plus MTX following a partial response to MTX. Lipsky et al., *N. Engl. J. Med.,* 343:1594-1602 (2000); Maini et al., *Lancet,* 354:1932-1939 (1999). In the first year of the ENBREL™ ERA (early RA) trial, etanercept was shown to be significantly more effective than MTX in improving signs and symptoms of disease and in inhibiting radiographic progression. Bathon et al., *N. Eng. J. Med.,* 343:1586-1593 (2000). Genovese et al., *Arthritis Rheum.* 46:1443-1450 (2002) reports results from the second year of the study, concluding that etanercept as monotherapy was safe and superior to MTX in reducing disease activity, arresting structural damage, and decreasing disability over two years in patients with early aggressive RA. Also studied was the safety and clinical activity of ocrelizumab (a humanized antibody targeting C D20+B cells) in combination with MTX in moderate-to-severe RA patients (Ph I/II ACTION study). Genovese et al., *Arthritis Rheum.,* 54(9): S66-S67 (September 2006).

Further, reduction in radiographic progression in the hands and feet was observed in patients with early RA after receiving infliximab in combination with MTX. Van der Heijde et al., *Annals Rheumatic Diseases,* 64:417 (2005). Patients with early RA achieved a clinically meaningful and sustained improvement in physical function after treatment with infliximab. Smolen et al., *Annals Rheumatic Diseases,* 64:418-419 (2005).

The effect of infliximab therapy on bone mineral density in patients with ankylosing spondylitis (AS) resulting from a randomized, placebo-controlled trial named ASSERT) is reported by Van der Heijde et al., *Annals Rheumatic Diseases,* 64:319 (2005). The ASSERT trial showed that infliximab improved fatigue and pain in patients with AS. Van der Heijde et al., *Annals Rheumatic Diseases,* 64:318-319 (2005). The efficacy and safety of infliximab in AS patients treated according to ASSERT are described by van der Heijde et al., *Arthritis Rheum.,* 52:582-591 (2005). The authors conclude that infliximab was well tolerated and effective in a large cohort of patients with AS during a 24-week study period. In addition, the effect of infliximab therapy on spinal inflammation was assessed by magnetic resonance imaging in a randomized, placebo-controlled trial of 279 patients with AS. Van der Heijde et al., *Annals Rheumatic Diseases,* 64:317 (2005). The manner in which the treatment effect on spinal radiographic progression in patients with AS should be measured is addressed by van der Heijde et al., *Arthritis Rheum.* 52:1979-1985 (2005).

The results of radiographic analyses of the infliximab multinational PsA controlled trial (IMPACT) after one year are reported by Antoni et al., Annals *Rheumatic Diseases* 64:107 (2005). Evidence of radiographic benefit of treatment with infliximab plus MTX in RA patients who had no clinical improvement, with a detailed subanalysis of data from the anti-TNF trial in RA with concomitant therapy study, is reported by Smolen et al., *Arthritis Rheum.* 52:1020-1030 (2005). Radiographic progression (as measured by mean change in modified Sharp/van der Heijde score) was much greater in patients receiving MTX plus placebo than in patients receiving infliximab plus MTX. The authors conclude that even in patients without clinical improvement, treatment with infliximab plus MTX provided significant benefit with regard to the destructive process, suggesting that in such patients these two measures of disease are dissociated. The association between baseline radiographic damage and improvement in physical function after treatment of patients having RA with infliximab is described by Breedveld et al., *Annals Rheumatic Diseases*, 64:52-55 (2005). Structural damage was assessed using the van der Heijde modification of the Sharp score. The authors conclude that greater joint damage at baseline was associated with poorer physical function at baseline and less improvement in physical function after treatment, underlining the importance of early intervention to slow the progression of joint destruction.

Rheumatoid Arthritis Molecular Biomarkers

A number of investigators have carried out microarray gene expression profiling studies of synovial tissue isolated from RA patients. The published studies include van der Pouw Kraan T C et al., Discovery of distinctive gene expression profiles in rheumatoid synovium using cDNA microarray technology: evidence for the existence of multiple pathways of tissue destruction and repair, *Genes Immun* April; 4(3):187-96 (2003); van der Pouw Kraan T C, et al., Rheumatoid arthritis is a heterogeneous disease: evidence for differences in the activation of the STAT-1 pathway between rheumatoid tissues, *Arthritis Rheum* August;48(8): 2132-45 (2003); Finis K et al., Analysis of pigmented villonodular synovitis with genome-wide complementary DNA microarray and tissue array technology reveals insight into potential novel therapeutic approaches, *Arthritis Rheum* March; 54(3):1009-19 (2006); Lindberg J, et al., Effect of infliximab on mRNA expression profiles in synovial tissue of rheumatoid arthritis patients, *Arthritis Res Ther.* 8(6): R179 (2006); van der Pouw Kraan T C et al., Responsiveness to anti-tumour necrosis factor alpha therapy is related to pre-treatment tissue inflammation levels in rheumatoid arthritis patients, *Ann Rheum Dis. April;* 67(4):563-6 (2008); Huber R et al., Identification of intra-group, inter-individual, and gene-specific variances in mRNA expression profiles in the rheumatoid arthritis synovial membrane, *Arthritis Res Ther* 10(4):R98 (2008); Badot V et al., Gene expression profiling in the synovium identifies a predictive signature of absence of response to adalimumab therapy in rheumatoid arthritis, *Arthritis Res Ther.* 11(2):R57 (2009), Epub 2009 Apr. 23.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the present invention can be generated using standard techniques known in the art.

Gene expression signatures associated with RA and certain subtypes of RA are provided herein. These signatures constitute biomarkers for RA and/or subtypes of RA, and/or predispose or contribute to development, persistence and/or progression of RA. Accordingly, the invention disclosed herein is useful in a variety of settings, e.g., in methods and compositions related to RA diagnosis and therapy.

Detection of Gene Expression Levels

Nucleic acid, according to any of the methods described herein may be RNA transcribed from genomic DNA or cDNA generated from RNA. Nucleic acid may be derived from a vertebrate, e.g., a mammal. A nucleic acid is said to be "derived from" a particular source if it is obtained directly from that source or if it is a copy of a nucleic acid found in that source.

Nucleic acid includes copies of the nucleic acid, e.g., copies that result from amplification. Amplification may be desirable in certain instances, e.g., in order to obtain a desired amount of material for detecting variations. The amplicons may then be subjected to a variation detection method, such as those described below, to determine expression of certain genes.

A microarray is a multiplex technology that typically uses an arrayed series of thousands of nucleic acid probes to hybridize with, e.g, a cDNA or cRNA sample under high-stringency conditions. Probe-target hybridization is typically detected and quantified by detection of fluorophore-, silver-, or chemiluminescence-labeled targets to determine relative abundance of nucleic acid sequences in the target. In typical microarrays, the probes are attached to a solid surface by a covalent bond to a chemical matrix (via epoxy-silane, amino-silane, lysine, polyacrylamide or others). The solid surface is for example, glass, a silicon chip, or microscopic beads. Various microarrays are commercially available, including those manufactured, for example, by Affymetrix, Inc. and Illumina, Inc.

A biological sample may be obtained using certain methods known to those skilled in the art. Biological samples may be obtained from vertebrate animals, and in particular, mammals. In certain instances, a biological sample is synovial tissue, serum or peripheral blood mononuclear cells (PBMC). By screening such body samples, a simple early diagnosis can be achieved for diseases such as RA. In addition, the progress of therapy can be monitored more easily by testing such body samples for variations in expression levels of target nucleic acids (or encoded polypeptides).

Subsequent to the determination that a subject, or the tissue or cell sample comprises a gene expression signature disclosed herein, it is contemplated that an effective amount of an appropriate RA therapeutic agent may be administered to the subject to treat the RA in the subject. Clinical diagnosis in mammals of the various pathological conditions described herein can be made by the skilled practitioner. Clinical diagnostic techniques are available in the art which allow, e.g., for the diagnosis or detection of RA in a mammal.

A RA therapeutic agent can be administered in accordance with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Optionally, administration may be performed through mini-pump infusion using various commercially available devices.

Kits

For use in the applications described or suggested herein, kits or articles of manufacture are also provided. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be a polynucleotide specific for a polynucleotide comprising one or more genes of a gene expression signature. Where the kit utilizes nucleic acid hybridization to detect the target nucleic acid, the kit may also have containers containing nucleotide(s) for amplification of the target nucleic acid sequence and/or a container comprising a reporter means, such as a biotin-binding protein, such as avidin or streptavidin, bound to a reporter molecule, such as an enzymatic, florescent, or radioisotope label.

Kits will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above. Other optional components in the kit include one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc.

Methods of Marketing

The invention herein also encompasses a method for marketing a RA therapeutic agent or a pharmaceutically acceptable composition thereof comprising promoting to, instructing, and/or specifying to a target audience, the use of the agent or pharmaceutical composition thereof for treating a patient or patient population with RA from which a sample has been obtained showing the presence of a genetic variation as disclosed herein.

Marketing is generally paid communication through a non-personal medium in which the sponsor is identified and the message is controlled. Marketing for purposes herein includes publicity, public relations, product placement, sponsorship, underwriting, and sales promotion. This term also includes sponsored informational public notices appearing in any of the print communications media designed to appeal to a mass audience to persuade, inform, promote, motivate, or otherwise modify behavior toward a favorable pattern of purchasing, supporting, or approving the invention herein.

The marketing of the diagnostic method herein may be accomplished by any means. Examples of marketing media used to deliver these messages include television, radio, movies, magazines, newspapers, the internet, and billboards, including commercials, which are messages appearing in the broadcast media.

The type of marketing used will depend on many factors, for example, on the nature of the target audience to be reached, e.g., hospitals, insurance companies, clinics, doctors, nurses, and patients, as well as cost considerations and the relevant jurisdictional laws and regulations governing marketing of medicaments and diagnostics. The marketing may be individualized or customized based on user characterizations defined by service interaction and/or other data such as user demographics and geographical location.

EXAMPLES

The following are examples of the methods and compositions of the invention. It is understood that various other embodiments may be practiced, given the general description provided above.

Example 1

Methods and Subjects

Subjects and Synovial Biopsies

All procedures involving specimens obtained from human subjects were performed under a protocol approved by the University of Michigan Institutional Review Board. Human synovial tissues were obtained by synovectomy from affected joints in patients diagnosed with RA based upon the presence of at least four of the seven criteria developed by the American College of Rheumatology for RA (Arnett, F. C., et al., *Arthritis Rheum.*, 31: 315-324 (1988)). Excised tissues were immediately snap-frozen in liquid nitrogen and stored at −80° C. For matched histology sections, samples were brought briefly to −20° C., cryostat sectioned and immediately brought back to −80° C. Frozen samples were homogenized in Qiagen brand RLT and RNA was isolated according to the manufacturers recommended protocol (Qiagen, Valencia, Calif.)

Methods

Microarray Hybridization

The methods for preparation of cRNA and for array hybridization were provided by Affymetrix, Inc. (Santa Clara, Calif.). Briefly, 3 μg of total RNA was converted into double-stranded cDNA using a cDNA synthesis kit, SuperScript Choice (Invitrogen, Carlsbad, Calif.) and a T7-(dT)$_{24}$ oligomer primer (Biosearch Technologies, Inc., Novato, Calif.). Double-stranded cDNA was purified using affinity resin Sample Cleanup Module Kit (Affymetrix, Inc.) and then ethanol precipitated. Labeled cRNA was generated from the cDNA by using a T7 RNA polymerase and biotin-labeled nucleotide in an in vitro transcription reagents (Enzo Diagnostics, Inc., Farmingdale, N.Y.). The labeled cRNA was purified using Affymetrix Sample Cleanup Module Kit. The amount of labeled cRNA was determined by measuring absorbance at 260 nm and using the convention that 1 OD at 260 nm corresponds to 40 μg/ml of RNA. Fifteen micrograms of labeled cRNA was fragmented by incubating at 94° C. for 30 min in 40 mM Tris-acetate pH 8.1, 100 mM potassium acetate and 30 mM magnesium acetate. Samples were then hybridized to GeneChip® Human Genome U133 Plus 2.0 Arrays (Affymetrix, Inc.) at 45° C. for 19 hours in a rotisserie oven set at 60 rpm. Arrays were washed and stained in the Affymetrix Fluidics station and scanned on GeneChip® scanner 3000. Data analysis was performed using the Affymetrix GeneChip® operating system and analysis software.

Histopathology and Immunohistochemistry

Stains were performed on 5-μm-thick frozen sections of human synovial tissue fixed in acetone. Some sections were stained with hematoxylin and eosin for histologic evaluation. Other sections were blocked in 10% serum for 30 minutes and stained for the detection of cells expressing the following lineage markers (CD20—mouse anti-human clone L26, 5 μg/ml, Dako; CD3—rabbit anti-human antibody SP7, 1:200 dilution, NeoMarkers; and CD68—mouse anti-human clone KP-1, 2.5 μg/ml Dako). All immunohistochemical stains were detected with species specific, biotinylated secondary antibodies and 3,3'-diaminobenzidine (DAB).

Statistical Analyses

Statistical analyses of microarray data was performed with the open-source tools available in the statistical programming environment, R (available at the URL: cran(dot)r-project(dot)org) and the commercially available Spotfire Decision Site (TIBCO Software Inc, Palo Alto, Calif.). Identification of molecular subytpes was performed by multi-scale bootstrap resampling using the open-source R package, Pvclust (Suzuki, R. and Shimodaira, H., Bioinformatics, 22(12), 1540-1542 (2006)). Heatmap visualizations and identification of differentially expressed genes was performed using analysis of variance provided by Spotfire. Identification of pathways significantly over-represented within each subtype was performed using CoPub, following the developers' recommended protocol (Frijters, R. et al., Nucleic Acids Res. 36:W406-W410 (Web server issue doi: 10.1093/nar/gkn215) (2008)); available at the URL: services(dot)nbic(dot)nl(slash)cgi-bin(slash)copub(slash)microarray_analysis(dot)pl. Briefly, Affymetrix probeset identifiers that were specifically upregulated within each subtype (~1000 top ranked probesets) were uploaded to the webserver. The GeneChip® Human Genome U133A Plus 2.0 Array (Affymetrix, Inc.) was selected as the background data set, the search category was limited to biological processes and all calculation settings were left at their defaults. The resulting data was saved to a personal computer and formatted for comparative heatmap visualization in Spotfire.

Identification of Classifiers: Molecular Phenotype Training and Testing

Using the filtered expression data set consisting of 20,776 probes and the class labels we sought to build a series of two-class and multiclass classification models which could distinguish (i) each putative patient subclass from the other three subtypes or (ii) mutually distinguish all four subclasses from each other, respectively. We refer to such classification models herein as "classifiers." In the case where multiple samples were available from the same patient, one sample from that patient was selected at random to enter into the model. Variable (probe) selection and model training was performed using the CMA package (Slawski et al., BMC Bioinformatics 9:439 (2008)). In the case of the two-class models, variable selection was performed by ranking each probe's association with a given class label according to either the absolute value of its two-sample t-statistic or its robust Wilcoxon statistic. For the multiclass model, each probe was ranked by the values of its one-way F-statistic or its robust Kruskall-Wallis test statistic across all four putative classes. The values of the test statistics were recorded over N=48 rounds of leave-one-out cross-validation (LOOCV), or, when the class sizes were deemed large enough, i.e., for the F2, L and M two-class models, over 100 repeated rounds of 5-fold cross-validation. For each model and choice of test statistic, and at each round of cross-validation, a list of the top 20 probes with the largest, most significant values of their test statistic was retained. A probe-specific voting-based variable importance measure was created in which the number (or fraction) of rounds of cross-validation a probe appeared in the list of the top 20 most strongly associated probes was calculated.

Performing linear discriminant analysis (LDA) in the CMA package, an estimated class label, obtained from using these specific 48 patient samples, could be compared to the original estimated labels of the clustering results. As a sanity check, the variable selection and LDA steps were repeated using permuted class labels, resulting in increased rates of misclassification.

Publicly available independent test data on a two-color microarray platform (Lindberg et al., PLoS One 5(6):e11310 (2010)) were used to assess the robustness of the models constructed from the training data. For each RA patient two-two-way model and for the multiclass model, the set of unique probes, aggregated over choice of parametric or robust test statistic, which ever appeared in a given round of cross-validation's list of top 20 probes, was applied to a LDA model on the training data using the MASS package in R (Venables, W. N. & Ripley, B. D. (2002) Modern Applied Statistics with S. Fourth Edition. Springer, New York. ISBN 0-387-95457-0). Using LOOCV, new, predicted class labels were obtained by applying the LDA model built on the training data to the new test set data. Probes between the two data sets were linked by their unique Entrez Gene identification number. In the case where multiple probes in either data set mapped to a given Entrez Gene number, a unique probe was selected to represent a given gene. In the original Affymetrix training data, the probe with the highest variable importance score over rounds of LOOCV was selected. In the case of ties, one probe was chosen at random. Unique representative probes in the test data were also selected at random. Missing data in the test data set were imputed using the median expression value for that probe. Prior to performing LDA, both the training and test data were centered and scaled to place them on more equal footing. The classifiers for each of the four molecular phenotypes are provided below.

Identification of Molecular Phenotypes (Subtypes)

Gene expression microarray experiments on synovial tissues isolated from patients with RA were carried out, for example, to assess gene expression patterns as a basis to advance understanding of the molecular pathways important in RA pathogenesis and progression as well as to identify potential therapeutic targets and biomarkers for diagnostic and prognostic purposes. Gene expression microarray experiments on 81 synovial tissue samples, excised from 50 RA patients, were carried out using a whole genome expression array, the GeneChip® Human Genome U133 Plus 2.0 Array (Affymetrix, Inc.). Expression data was normalized using manufacturer provided software, MAS5, standardized to 500, log transformed and z-scored. A probe was included in the analysis if it had a minimum expression of at least 100 and it varied by 1.5 standard deviations in at least 5 samples relative to probe's mean expression level across all samples. This assessment yielded 20,776 probes, which were randomly sampled with replacement for 10,000 iterations and clustered using correlation as the distance metric and average linkage for agglomeration. The resulting dendogam shown in FIG. 1 depicts the sample clustering and the resulting bootstrapped branch support values.

Figure 2:
FIG. 2 shows a heatmap and bootstrapped dendrogram (vertical lines) revealing four molecular phenotypes (subtypes) of RA as described in Example 1. F1=fibroblast-rich type 1 subtype; F2=fibroblast-rich type 2 subtype.
Figure 3A:
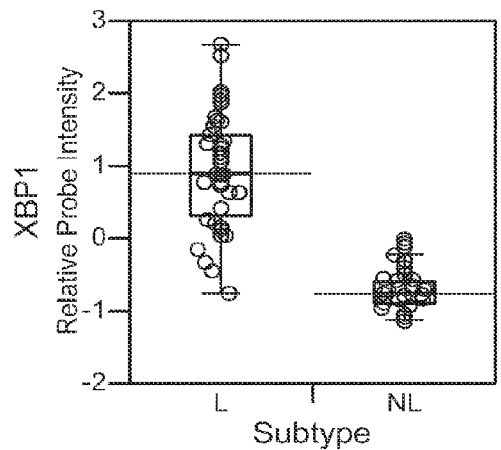
Figure 3B:
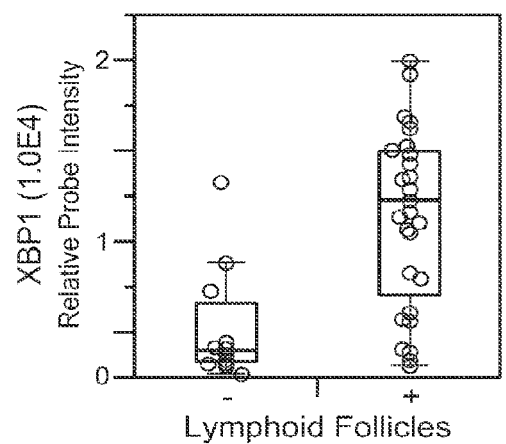
Figure 3C:
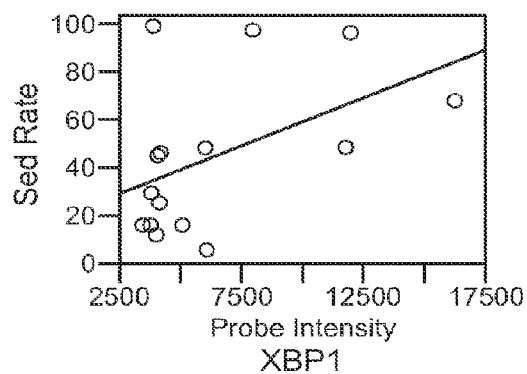
Figure 3D:
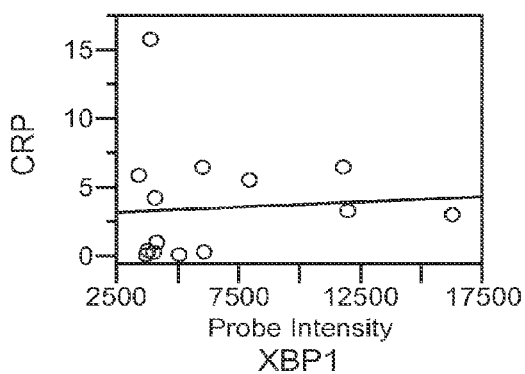
Figure 3E:
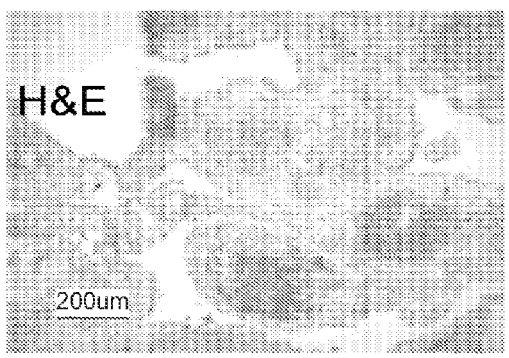
Figure 3F:
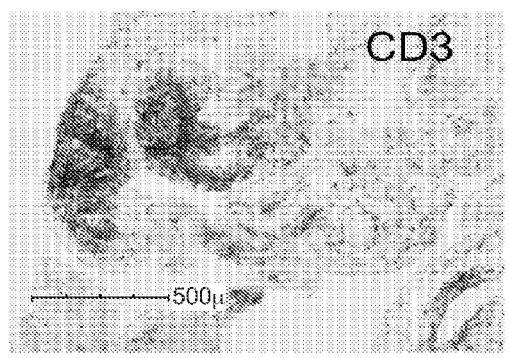
Figure 3G:
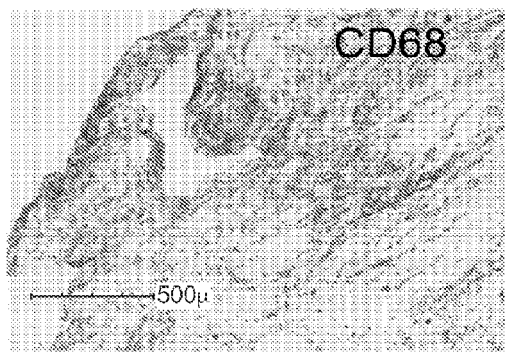
Figure 3H:
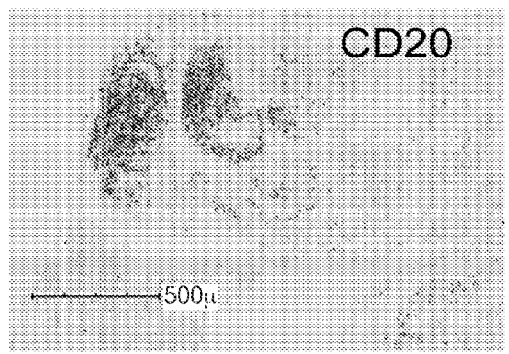
Figure 4A:
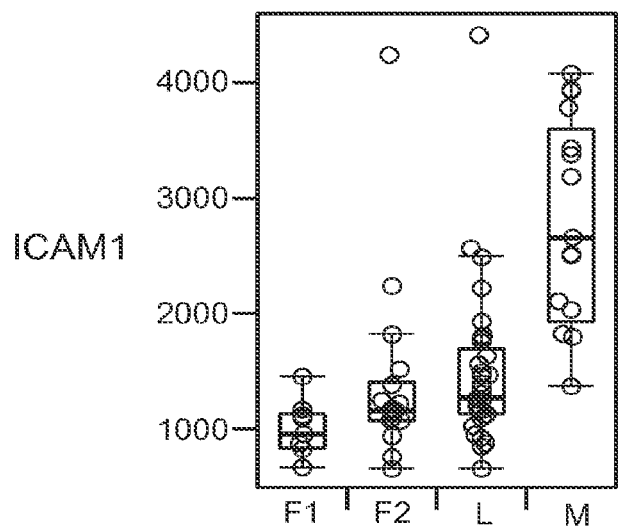
Figure 4B:
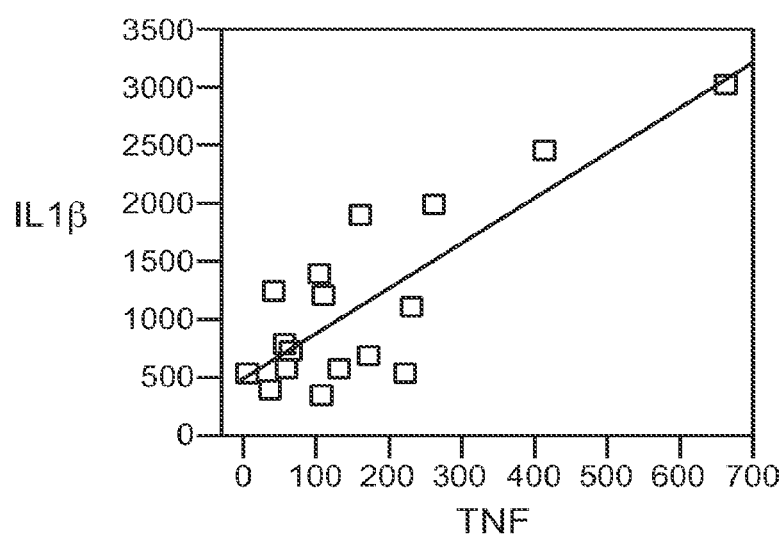
Figure 4C:
Figure 4D:
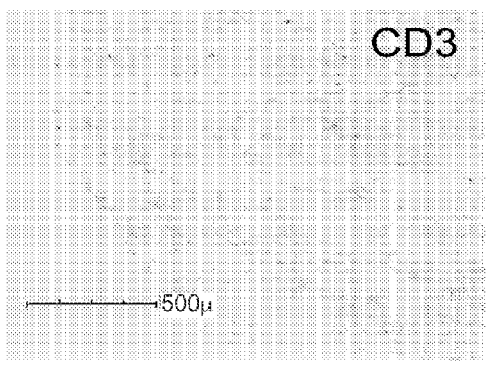
Figure 4E:
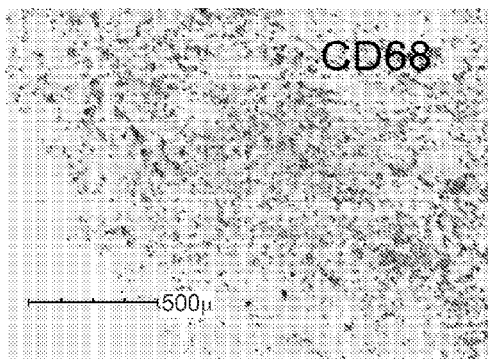
Figure 4F:
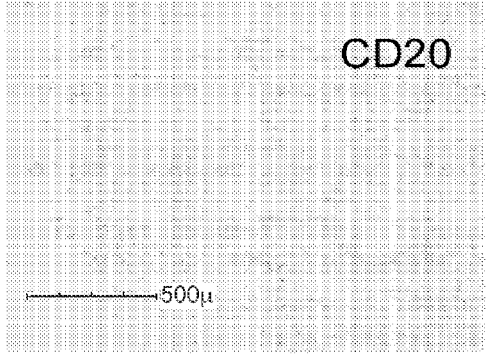
Figure 5A:
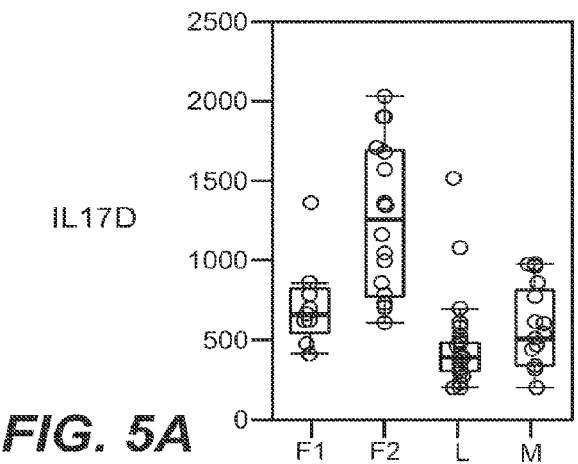
Figure 5B:
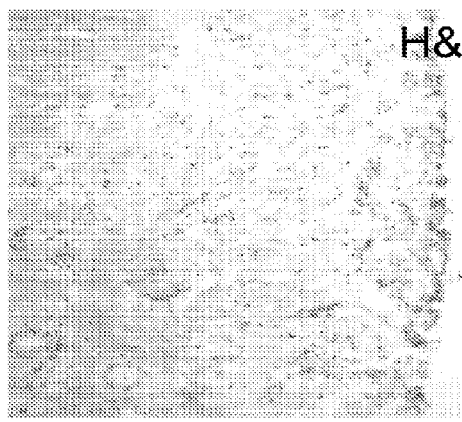
Figure 5C:
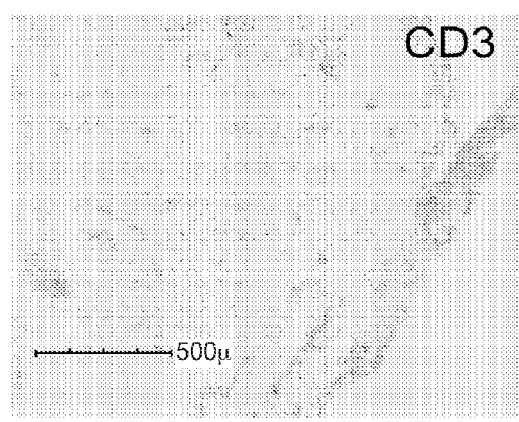
Figure 5D:
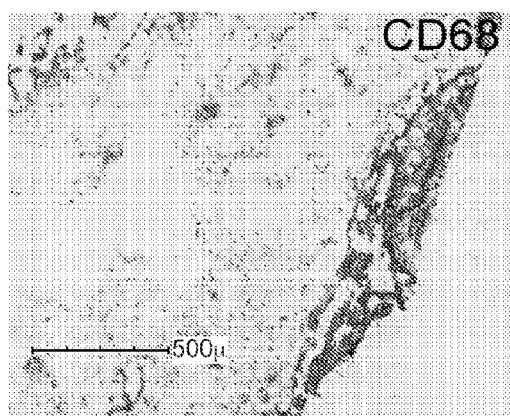
Figure 5E:
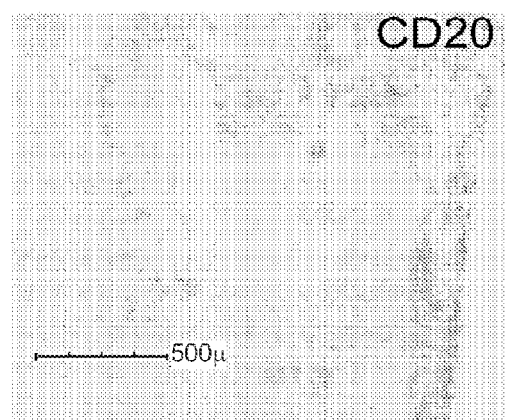

We analyzed the heatmap resulting from the microarray experiment (FIG. 2) and identified four molecular subtypes of RA based on relative expression levels of genes differentially expressed between the different RA molecular subtypes. We assigned samples to four distinct groups inferred from the bootstrapped dendrogram (FIG. 2). Analysis of variance on log transformed expression data identified differentially expressed genes within each group. Hierarchical clustering was performed on statistically significant probes (5501 probes with p<1.0E-6). Expression data was z-score normalized for visualization.

As shown in FIG. 2, the largest grouping of samples (45%) defined the molecular subtype described herein as lymphoid-rich (L) (FIG. 2, the branches at the top of the dendrogram labeled "L" at the top of figure and corresponding box shown within the heatmap, 87% bootstrap support). These samples shared extensive lymphoid infiltration and follicle-like lymphoid clusters (each p<0.01). The gene expression signature of this group of samples revealed a pattern characteristic of B cells, plasma cells, T cells, and macrophages and implicated certain pathways including B and T cell activation, isotype switching, Ig secretion and cytokine production. Table 5 provides a list of probe sets (and associated genes) that are associated with L subtype. These were identified from the microarray data using the following criteria: (1) Fold change≥1.5 within the L subtype; (2) t-test p-value≥0.0001; and (3) annotated as belonging to at least one of the following molecular categories of proteins: secreted, plasma membrane, kinase, G-coupled protein receptor, phosphatase, nuclear receptor, ion channel, E3-ligase, de-ubiquitinating enzyme.

Table 1 below shows a subset of certain of these probe sets (and associated genes) from Table 5 that have been identified as therapeutic targets and biomarkers of the L subtype. The genes identified in Table 1 encode proteins that share the properties of surface expression and secretion. Proteins having those properties can, in certain instances, be targeted with, for example, monoclonal antibodies and in that case are considered therapeutic targets. Secreted proteins and products cleaved from the cell membrane can, in certain cases, be measured and in that case are considered biomarkers.

TABLE 1

Certain L subtype therapeutic targets and biomarkers.

| ProbeID | NETAFFX: GeneTitle | NETAFFX: GeneSymbol | Unison: Protcomp | Fold Change | p-value |
|---|---|---|---|---|---|
| 210356_x_at | membrane-spanning 4-domains, subfamily A, member 1 | MS4A1 | Plasma membrane | 5.182001696 | 1.07E−13 |
| 217418_x_at | membrane-spanning 4-domains, subfamily A, member 1 | MS4A1 | Plasma membrane | 5.708081511 | 6.62E−13 |
| 228592_at | Membrane-spanning 4-domains, subfamily A, member 1 | MS4A1 | Plasma membrane | 8.475244795 | 1.06E−12 |
| 228599_at | Membrane-spanning 4-domains, subfamily A, member 1 | MS4A1 | Plasma membrane | 4.628458246 | 4.08E−13 |
| 221331_x_at | cytotoxic T-lymphocyte-associated protein 4 | CTLA4 | Plasma membrane | 2.342826855 | 7.67E−11 |
| 231794_at | cytotoxic T-lymphocyte-associated protein 4 | CTLA4 | Plasma membrane | 1.785965453 | 7.40E−08 |
| 234362_s_at | cytotoxic T-lymphocyte-associated protein 4 | CTLA4 | Plasma membrane | 1.971205062 | 2.69E−12 |
| 236341_at | cytotoxic T-lymphocyte-associated protein 4 | CTLA4 | Plasma membrane | 2.398839174 | 6.75E−09 |
| 213539_at | CD3D antigen, delta polypeptide (TiT3 complex) | CD3D | Plasma membrane | 2.45243047 | 1.43E−08 |
| 205456_at | CD3E antigen, epsilon polypeptide (TiT3 complex) | CD3E | Plasma membrane | 1.915380475 | 2.79E−10 |
| 206804_at | CD3G antigen, gamma polypeptide (TiT3 complex) | CD3G | Plasma membrane | 3.056708104 | 6.56E−06 |
| 210031_at | CD3Z antigen, zeta polypeptide (TiT3 complex) | CD3Z | Plasma membrane | 2.14803062 | 1.60E−11 |
| 206914_at | class-I MHC-restricted T cell associated molecule | CRTAM | Plasma membrane | 1.697660887 | 9.47E−10 |
| 205291_at | interleukin 2 receptor, beta \| interleukin 2 receptor, beta | IL2RB | Plasma membrane | 1.700032107 | 1.14E−10 |
| 204116_at | interleukin 2 receptor, gamma (severe combined immunodeficiency) | IL2RG | Plasma membrane | 2.261825374 | 4.95E−11 |
| 206398_s_at | CD19 antigen | CD19 | Plasma membrane | 2.872617474 | 3.29E−16 |
| 217001_x_at | major histocompatibility complex, class II, DO alpha | HLA-DOA | Plasma membrane | 1.589617654 | 1.39E−08 |
| 226878_at | Major histocompatibility | HLA-DOA | Plasma membrane | 1.561941309 | 3.01E−06 |

TABLE 1-continued

Certain L subtype therapeutic targets and biomarkers.

| ProbeID | NETAFFX: GeneTitle | NETAFFX: GeneSymbol | Unison: Protcomp | Fold Change | p-value |
|---|---|---|---|---|---|
| 205671_s_at | complex, class II, DO alpha major histocompatibility complex, class II, DO beta | HLA-DOB | Plasma membrane | 4.102368289 | 4.62E−17 |
| 205049_s_at | CD79A antigen (immunoglobulin-associated alpha) \| CD79A antigen (immunoglobulin-associated alpha) | CD79A | Plasma membrane | 6.214381039 | 7.29E−15 |
| 1555779_a_at | CD79A antigen (immunoglobulin-associated alpha) | CD79A | Plasma membrane | 3.486445366 | 1.47E−17 |
| 205297_s_at | CD79B antigen (immunoglobulin-associated beta) | CD79B | Plasma membrane | 2.131525118 | 6.42E−15 |
| 224404_s_at | immunoglobulin superfamily receptor translocation associated 2 \| immunoglobulin superfamily receptor translocation associated 2 | IRTA2 | Plasma membrane | 7.598702121 | 6.29E−20 |
| 224405_at | immunoglobulin superfamily receptor translocation associated 2 \| immunoglobulin superfamily receptor translocation associated 2 | IRTA2 | Plasma membrane | 4.857349464 | 1.42E−19 |
| 224406_s_at | immunoglobulin superfamily receptor translocation associated 2 \| immunoglobulin superfamily receptor translocation associated 2 | IRTA2 | Plasma membrane | 3.753764961 | 2.57E−20 |
| 231647_s_at | immunoglobulin superfamily receptor translocation associated 2 | IRTA2 | Plasma membrane | 11.05597709 | 9.47E−21 |
| 205692_s_at | CD38 antigen (p45) | CD38 | Plasma membrane | 3.802517688 | 9.27E−20 |
| 236191_at | CD38 antigen (p45) | CD38 | Plasma membrane | 2.235267342 | 6.23E−08 |
| 1552584_at | interleukin 12 receptor, beta 1 | IL12RB1 | Plasma membrane | 1.551031389 | 2.43E−05 |
| 206999_at | interleukin 12 receptor, beta 2 | IL12RB2 | Plasma membrane | 1.75915602 | 1.04E−05 |
| 219971_at | interleukin 21 receptor | IL21R | Plasma membrane | 2.933140561 | 1.33E−09 |
| 221658_s_at | interleukin 21 receptor | IL21R | Plasma membrane | 1.915118011 | 7.74E−08 |
| 205242_at | chemokine (C-X-C motif) ligand 13 (B-cell chemoattractant) | CXCL13 | Extracellular (Secreted) | 5.900697331 | 4.68E−05 |
| 207339_s_at | lymphotoxin beta (TNF superfamily, member 3) | LTB | Plasma membrane | 2.807618909 | 1.70E−09 |
| 204949_at | intercellular adhesion molecule 3 | ICAM3 | Plasma membrane | 2.650287454 | 3.47E−17 |
| 206295_at | interleukin 18 (interferon-gamma-inducing factor) | IL18 | Extracellular (Secreted) | 1.607893049 | 2.43E−07 |
| 211633_x_at | Immunoglobulin heavy constant gamma 1 (G1m marker) \| Immunoglobulin heavy constant gamma 1 (G1m marker) | IGHG1 | Extracellular (Secreted) | 9.72344799 | 1.95E−13 |

TABLE 1-continued

Certain L subtype therapeutic targets and biomarkers.

| ProbeID | NETAFFX: GeneTitle | NETAFFX: GeneSymbol | Unison: Protcomp | Fold Change | p-value |
|---|---|---|---|---|---|
| 209374_s_at | immunoglobulin heavy constant mu | IGHM | Extracellular (Secreted) | 3.479239038 | 2.11E−12 |
| 221286_s_at | proapoptotic caspase adaptor protein | PACAP | Extracellular (Secreted) | 22.71584082 | 1.30E−15 |
| 223565_at | proapoptotic caspase adaptor protein | PACAP | Extracellular (Secreted) | 14.28785156 | 4.53E−18 |

Using the molecular phenotype training and testing statistical methods described above, an L phenotype classifier was identified, as indicated in Table 10 below.

TABLE 10

L phenotype (subtype) classifier genes and probes

| ProbeID | NETAFFX: GeneTitle | NETAFFX: GeneSymbol |
|---|---|---|
| 234366_x_at | 28396&3493&3500 (Entrez Gene Identifiers) | NA |
| 217235_x_at | 28396&3493&3500 (Entrez Gene Identifiers) | NA |
| 236401_at | 170575&26157 (Entrez Gene Identifiers) | NA |
| 200670_at | Xbox binding protein 1 | XBP1 |
| 1554050_at | sphingomyelin phosphodiesterase acidlike 3B | SMPDL3B |
| 1556180_at | hypothetical protein LOC255458 | LOC255458 |
| 217480_x_at | similar to Ig kappa chain | LOC339562 |
| 204269_at | pim2 oncogene | PIM2 |
| 232167_at | Solute carrier family 2 facilitated glucose transporter member 11 | SLC2A11 |
| 226811_at | family with sequence similarity 46 member C | FAM46C |
| 238560_at | nuclear domain 10 protein | NDP52 |
| 1555779_a_at | CD79A antigen immunoglobulinassociated alpha | CD79A |
| 218237_s_at | solute carrier family 38 member 1 | SLC38A1 |
| 226773_at | MRNA clone ICRFp507I1077 | NA |
| 215946_x_at | immunoglobulin lambdalike polypeptide 1 & similar to bK246H31 immunoglobulin lambdalike polypeptide 1 preBcell specific | IGLL1 & LOC91316 |
| 204613_at | phospholipase C gamma 2 phosphatidylinositolspecific | PLCG2 |
| 217369_at | similar to immunoglobulin M chain | LOC440361 |
| 216542_x_at | hypothetical protein MGC27165 | MGC27165 |
| 216207_x_at | immunoglobulin kappa variable 1D13 | IGKV1D13 |
| 201998_at | ST6 betagalactosamide alpha26sialyltranferase 1 | ST6GAL1 |
| 217168_s_at | homocysteineinducible endoplasmic reticulum stressinducible ubiquitinlike domain member 1 | HERPUD1 |
| 212204_at | DKFZP564G2022 protein | DKFZP564G2022 |
| 64064_at | GTPase IMAP family member 5 | GIMAP5 |
| 229721_x_at | Der1like domain family member 3 | DERL3 |
| 219435_at | hypothetical protein FLJ22170 | FLJ22170 |
| 203335_at | phytanoylCoA hydroxylase Refsum disease | PHYH |
| 231611_at | NA | NA |
| 214268_s_at | myotubularin related protein 4 | MTMR4 |
| 208093_s_at | nudE nuclear distribution gene E homolog like 1 A nidulans & nudE nuclear distribution gene E homolog like 1 A nidulans | NDEL1 |
| 226075_at | SPRY domaincontaining SOCS box protein SSB1 | SSB1 |
| 213118_at | NA | NA |
| 218318_s_at | nemo like kinase | NLK |
| 227326_at | Transmembrane anchor protein 1 | TMAP1 |
| 223917_s_at | solute carrier family 39 zinc transporter member 3 | SLC39A3 |
| 208056_s_at | corebinding factor runt domain alpha subunit 2; translocated to 3 | CBFA2T3 |
| 231016_s_at | NA | NA |
| 202916_s_at | family with sequence similarity 20 member B | FAM20B |
| 217390_x_at | NA | NA |
| 219118_at | FK506 binding protein 11 19 kDa | FKBP11 |
| 229686_at | purinergic receptor P2Y Gprotein coupled 8 | P2RY8 |
| 212311_at | KIAA0746 protein | KIAA0746 |
| 212699_at | secretory carrier membrane protein 5 | SCAMP5 |
| 219631_at | low density lipoproteinrelated protein 12 | LRP12 |
| 202089_s_at | solute carrier family 39 zinc transporter member 6 | SLC39A6 |
| 1555981_at | hypothetical protein DKFZp762C2414 | DKFZp762C2414 |
| 220647_s_at | E2IG2 protein | E2IG2 |
| 237383_at | NA | NA |
| 230337_at | son of sevenless homolog 1 Drosophila | SOS1 |
| 1559820_at | APG10 autophagy 10like S cerevisiae | APG10L |

Another grouping of samples shown in FIG. 2 (21%) defined the molecular subtype described herein as myeloid-rich (M) (FIG. 2, the branches at the top of the dendrogram labeled "M" at the top of figure and corresponding box shown within the heatmap, 67% branch support). The gene expression signature of this group of samples revealed a pattern characteristic of monocytes, macrophages, neutrophils, and lymphocytes and implicated certain pathways including macrophage activation, phagocytosis, respiratory burst, T cell activation and cytokine production. In addition, this subtype was inversely associated with joint vascularity ($p<0.05$). Table 6 provides a list of probe sets (and associated genes) that are associated with the M subtype. These were identified from the microarray data using the following criteria: (1) Fold change≥1.5 within the M subtype; (2) t-test p-value≤0.0001; and (3) annotated as belonging to at least one of the following molecular categories of proteins: secreted, plasma membrane, kinase, G-coupled protein receptor, phosphatase, nuclear receptor, ion channel, E3-ligase, de-ubiquitinating enzyme.

Table 2 below shows a subset of certain of these probe sets (and associated genes) from Table 6 that have been identified as therapeutic targets and biomarkers of the M subtype. The genes identified in Table 2 encode proteins that share the properties of surface expression and secretion. Proteins having those properties can, in certain instances, be targeted with, for example, monoclonal antibodies and in that case are considered therapeutic targets. Secreted proteins and products cleaved from the cell membrane can, in certain cases, be measured and in that case are considered biomarkers.

TABLE 2

Certain M subtype therapeutic targets and biomarkers.

| ProbeID | NETAFFX: GeneTitle | NETAFFX: GeneSymbol | Unison: Protcomp | Fold Change | p-value |
|---|---|---|---|---|---|
| 219890_at | C-type lectin domain family 5, member A | CLEC5A | Extracellular (Secreted) | 7.362977 | 2.42E−07 |
| 221698_s_at | C-type lectin domain family 7, member A \| C-type lectin domain family 7, member A | CLEC7A | Plasma membrane | 2.051059 | 5.18E−09 |
| 1555214_a_at | C-type lectin domain family 7, member A | CLEC7A | Plasma membrane | 2.246684 | 0.000198 |
| 1554406_a_at | C-type lectin domain family 7, member A | CLEC7A | Plasma membrane | 1.581093 | 1.30E−07 |
| 1555756_a_at | C-type lectin domain family 7, member A | CLEC7A | Plasma membrane | 1.893079 | 1.41E−06 |
| 201951_at | Activated leukocyte cell adhesion molecule | ALCAM | Plasma membrane | 2.174859 | 7.52E−10 |
| 210233_at | interleukin 1 receptor accessory protein | IL1RAP | Plasma membrane | 2.13583 | 8.45E−10 |
| 201587_s_at | interleukin-1 receptor-associated kinase 1 | IRAK1 | Nuclear | 1.523179 | 3.11E−09 |
| 210842_at | neuropilin 2 | NRP2 | Plasma membrane | 3.63583 | 1.52E−05 |
| 232701_at | Neuropilin 2 | NRP2 | Plasma membrane | 1.892335 | 2.23E−05 |
| 219434_at | triggering receptor expressed on myeloid cells 1 | TREM1 | Extracellular (Secreted) | 2.054149 | 2.84E−08 |
| 210512_s_at | vascular endothelial growth factor | VEGF | Extracellular (Secreted) | 2.563299 | 4.62E−11 |
| 210513_s_at | vascular endothelial growth factor | VEGF | Extracellular (Secreted) | 1.635665 | 1.97E−09 |
| 211527_x_at | vascular endothelial growth factor | VEGF | Extracellular (Secreted) | 3.030532 | 2.35E−13 |
| 212171_x_at | vascular endothelial growth factor | VEGF | Extracellular (Secreted) | 2.323697 | 2.23E−14 |
| 205179_s_at | a disintegrin and metalloproteinase domain 8 \| a disintegrin and metalloproteinase domain 8 | ADAM8 | Plasma membrane | 2.429618 | 3.40E−06 |
| 205180_s_at | a disintegrin and metalloproteinase domain 8 \| a disintegrin and metalloproteinase domain 8 | ADAM8 | Plasma membrane | 2.620813 | 1.03E−07 |
| 213274_s_at | cathepsin B | CTSB | Lysosomal | 1.656338 | 2.02E−09 |
| 207850_at | chemokine (C-X-C motif) ligand 3 | CXCL3 | Extracellular (Secreted) | 2.692214 | 2.61E−07 |
| 202637_s_at | intercellular adhesion molecule 1 (CD54), human rhinovirus receptor | ICAM1 | Plasma membrane | 2.12742 | 8.01E−14 |
| 202638_s_at | intercellular adhesion molecule 1 (CD54), human rhinovirus receptor | ICAM1 | Plasma membrane | 2.297289 | 1.58E−17 |
| 215485_s_at | intercellular adhesion molecule 1 (CD54), human rhinovirus receptor | ICAM1 | Plasma membrane | 2.070317 | 1.48E−12 |
| 222868_s_at | interleukin 18 binding protein | IL18BP | Extracellular (Secreted) | 1.523947 | 5.91E−06 |
| 205067_at | interleukin 1, beta | IL1B | Extracellular (Secreted) | 1.680015 | 0.000269 |
| 39402_at | interleukin 1, beta | IL1B | Extracellular (Secreted) | 2.550957 | 2.81E−06 |
| 202859_x_at | interleukin 8 | IL8 | Extracellular (Secreted) | 3.188671 | 1.62E−05 |
| 211506_s_at | interleukin 8 | IL8 | Extracellular (Secreted) | 4.223337 | 1.08E−06 |
| 204580_at | matrix metalloproteinase 12 (macrophage elastase) | MMP12 | Extracellular (Secreted) | 8.298394 | 5.23E−07 |

TABLE 2-continued

Certain M subtype therapeutic targets and biomarkers.

| ProbeID | NETAFFX: GeneTitle | NETAFFX: GeneSymbol | Unison: Protcomp | Fold Change | p-value |
|---|---|---|---|---|---|
| 200660_at | S100 calcium binding protein A11 (calgizzarin) | S100A11 | NO_LOCALIZATION | 1.574125 | 3.46E−11 |

Using the molecular phenotype training and testing statistical methods described above, an M phenotype classifier was identified, as indicated in Table 11 below.

TABLE 11

M phenotype (subtype) classifier genes and probes

| ProbeID | NETAFFX: GeneTitle | NETAFFX: GeneSymbol |
|---|---|---|
| 224374_s_at | elastin microfibril interfacer 2 & elastin microfibril interfacer 2 | EMILIN2 |
| 203175_at | ras homolog gene family member G rho G | RHOG |
| 212715_s_at | flavoprotein oxidoreductase MICAL3 | MICAL3 |
| 202944_at | Nacetylgalactosaminidase alpha | NAGA |
| 212268_at | serine or cysteine proteinase inhibitor clade B ovalbumin member 1 | SERPINB1 |
| 202638_s_at | intercellular adhesion molecule 1 CD54 human rhinovirus receptor | ICAM1 |
| 200808_s_at | zyxin | ZYX |
| 226587_at | Ubiquitin protein ligase E3A human papilloma virus E6associated protein Angelman syndrome | UBE3A |
| 214785_at | vacuolar protein sorting 13A yeast | VPS13A |
| 218627_at | hypothetical protein FLJ11259 | FLJ11259 |
| 216598_s_at | chemokine CC motif ligand 2 | CCL2 |
| 1557915_s_at | glutathione Stransferase omega 1 | GSTO1 |
| 207697_x_at | leukocyte immunoglobulinlike receptor subfamily B with TM and ITIM domains member 2 | LILRB2 |
| 214752_x_at | filamin A alpha actin binding protein 280 | FLNA |
| 210225_x_at | leukocyte immunoglobulinlike receptor subfamily B with TM and ITIM domains member 3 & leukocyte immunoglobulinlike receptor subfamily B with TM and ITIM domains member 3 | LILRB3 |
| 204088_at | purinergic receptor P2X ligandgated ion channel 4 | P2RX4 |
| 211133_x_at | leukocyte immunoglobulinlike receptor subfamily B with TM and ITIM domains member 3 | LILRB3 |
| 227026_at | Mphase phosphoprotein mpp8 | HSMPP8 |
| 208018_s_at | hemopoietic cell kinase | HCK |
| 208691_at | NA | NA |
| 207850_at | chemokine CXC motif ligand 3 | CXCL3 |
| 210784_x_at | leukocyte immunoglobulinlike receptor subfamily B with TM and ITIM domains member 3 | LILRB3 |
| 209344_at | tropomyosin 4 | TPM4 |
| 201950_x_at | capping protein actin filament muscle Zline beta | CAPZB |
| 201118_at | phosphogluconate dehydrogenase & phosphogluconate dehydrogenase | PGD |
| 227961_at | Cathepsin B | CTSB |
| 212041_at | ATPase H+ transporting lysosomal 38 kDa V0 subunit d isoform 1 | ATP6V0D1 |
| 202856_s_at | solute carrier family 16 monocarboxylic acid transporters member 3 | SLC16A3 |
| 210042_s_at | cathepsin Z | CTSZ |
| 220088_at | complement component 5 receptor 1 C5a ligand | C5R1 |
| 219053_s_at | Hypothetical protein FLJ20847 | FLJ20847 |
| 214683_s_at | CDClike kinase 1 | CLK1 |
| 212171_x_at | vascular endothelial growth factor | VEGF |
| 223019_at | chromosome 9 open reading frame 88 | C9orf88 |
| 212481_s_at | tropomyosin 4 | TPM4 |
| 202206_at | ADPribosylation factorlike 7 | ARL7 |
| 226389_s_at | Rap guanine nucleotide exchange factor GEF 1 | RAPGEF1 |
| 207332_s_at | transferrin receptor p90 CD71 | TFRC |
| 202637_s_at | intercellular adhesion molecule 1 CD54 human rhinovirus receptor | ICAM1 |
| 201972_at | ATPase H+ transporting lysosomal 70 kDa V1 subunit A | ATP6V1A |
| 215706_x_at | zyxin | ZYX |
| 222877_at | Neuropilin 2 | NRP2 |
| 205098_at | chemokine CC motif receptor 1 | CCR1 |
| 202679_at | NiemannPick disease type C1 | NPC1 |
| 241684_at | Transcribed locus weakly similar to NP_0603121 hypothetical protein FLJ20489 [Homo sapiens] | NA |
| 216035_x_at | transcription factor 7like 2 Tcell specific HMGbox | TCF7L2 |
| 242824_at | KIAA0485 protein | KIAA0485 |
| 202207_at | ADPribosylation factorlike 7 | ARL7 |
| 204137_at | transmembrane 7 superfamily member 1 upregulated in kidney | TM7SF1 |

TABLE 11-continued

M phenotype (subtype) classifier genes and probes

| ProbeID | NETAFFX: GeneTitle | NETAFFX: GeneSymbol |
|---|---|---|
| 205479_s_at | plasminogen activator urokinase | PLAU |
| 202087_s_at | cathepsin L | CTSL |
| 218665_at | frizzled homolog 4 Drosophila | FZD4 |
| 226354_at | lactamase beta | LACTB |
| 212675_s_at | KIAA0582 | KIAA0582 |
| 213457_at | malignant fibrous histiocytoma amplified sequence 1 | MFHAS1 |
| 211135_x_at | leukocyte immunoglobulinlike receptor subfamily B with TM and ITIM domains member 3 | LILRB3 |
| 213313_at | RAB GTPase activating protein 1 | RABGAP1 |
| 215485_s_at | intercellular adhesion molecule 1 CD54 human rhinovirus receptor | ICAM1 |
| 205775_at | family with sequence similarity 50 member B | FAM50B |
| 210512_s_at | vascular endothelial growth factor | VEGF |
| 202484_s_at | methylCpG binding domain protein 2 | MBD2 |
| 1560060_s_at | vacuolar protein sorting 37C yeast | VPS37C |
| 211160_x_at | actinin alpha 1 | ACTN1 |
| 230528_s_at | hypothetical protein MGC2752 | MGC2752 |
| 210845_s_at | plasminogen activator urokinase receptor | PLAUR |
| 213571_s_at | eukaryotic translation initiation factor 4E member 2 | EIF4E2 |

As shown in FIG. 2, two non-inflammatory molecular subtypes were identified. The first grouping (22%) defined the molecular subtype described herein as fibroblast-rich type 2 (F2) (FIG. 2, the branches at the top of the dendrogram labeled "F2" at the top of figure and corresponding box shown within the heatmap, 94% branch support). The gene expression signature of this group of samples revealed a pattern characteristic of fibroblasts and osteoblasts and implicated certain pathways including bone formation, growth and differentiation, wnt-signaling and tumorigenesis. The F2 gene expression signature was inversely associated with lymphocyte and CD15+ cell infiltration (each p<0.01). The second non-inflammatory grouping (11%) defined the molecular subtype described herein as fibroblast-rich type 1 (F1) (FIG. 2, the branches at the top of the dendrogram labeled "F1" at the top of figure and corresponding box shown within the heatmap, 88% branch support). The gene expression signature of this group of samples revealed a pattern characteristic of fibroblasts, osteoclasts, and osteoblasts and implicated certain pathways including bone destruction and vasculogenesis. In addition, the F1 subtype was associated with a higher degree of synovial lining hyperplasia compared to the other subtypes. Tables 7 and 8 provide a list of probe sets (and associated genes) that are associated with F2 and F1 subtypes, respectively. These were identified from the microarray data using the following criteria: (1) Fold change≥1.5 within the L subtype; (2) t-test p-value≤0.0001; and (3) annotated as belonging to at least one of the following molecular categories of proteins: secreted, plasma membrane, kinase, G-coupled protein receptor, phosphatase, nuclear receptor, ion channel, E3-ligase, de-ubiquitinating enzyme.

Table 3 below shows a subset of certain of these probe sets (and associated genes) from Table 7 that have been identified as therapeutic targets and biomarkers of the F2 subtype. Table 4 below shows a subset of certain of these probe sets (and associated genes) from Table 8 that have been identified as therapeutic targets and biomarkers of the F1 subtype. The genes identified in Tables 3 and 4 encode proteins that share the properties of surface expression and secretion. Proteins having those properties can, in certain instances, be targeted with, for example, monoclonal antibodies and in that case are considered therapeutic targets. Secreted proteins and products cleaved from the cell membrane can, in certain cases, be measured and in that case are considered biomarkers.

TABLE 3

Certain F2 subtype therapeutic targets and biomarkers.

| ProbeID | NETAFFX: GeneTitle | NETAFFX: GeneSymbol | Unison: Protcomp | Fold Change | p-value |
|---|---|---|---|---|---|
| 227401_at | interleukin 17D | IL17D | Extracellular (Secreted) | 2.453105 | 2.26E−12 |
| 228977_at | Interleukin 17D | IL17D | NA | 1.999348 | 1.75E−11 |
| 221926_s_at | interleukin 17 receptor C | IL17RC | NO_LOCALIZATION | 2.406789 | 8.12E−09 |
| 201147_s_at | tissue inhibitor of metalloproteinase 3 (Sorsby fundus dystrophy, pseudoinflammatory) | TIMP3 | Extracellular (Secreted) | 1.872803 | 9.91E−13 |
| 201148_s_at | tissue inhibitor of metalloproteinase 3 (Sorsby fundus dystrophy, pseudoinflammatory) | TIMP3 | Extracellular (Secreted) | 1.915979 | 4.22E−12 |

TABLE 3-continued

Certain F2 subtype therapeutic targets and biomarkers.

| ProbeID | NETAFFX: GeneTitle | NETAFFX: GeneSymbol | Unison: Protcomp | Fold Change | p-value |
|---|---|---|---|---|---|
| 201149_s_at | tissue inhibitor of metalloproteinase 3 (Sorsby fundus dystrophy, pseudoinflammatory) | TIMP3 | Extracellular (Secreted) | 2.064168 | 1.45E−11 |
| 240135_x_at | Tissue inhibitor of metalloproteinase 3 (Sorsby fundus dystrophy, pseudoinflammatory) | TIMP3 | Extracellular (Secreted) | 2.474079 | 4.55E−07 |
| 204932_at | tumor necrosis factor receptor superfamily, member 11b (osteoprotegerin) | TNFRSF11B | Extracellular (Secreted) | 3.094446 | 1.47E−07 |
| 204933_s_at | tumor necrosis factor receptor superfamily, member 11b (osteoprotegerin) | TNFRSF11B | Extracellular (Secreted) | 3.791135 | 8.36E−08 |
| 231762_at | fibroblast growth factor 10 | FGF10 | Extracellular (Secreted) | 2.530553 | 4.25E−06 |
| 206987_x_at | fibroblast growth factor 18 | FGF18 | Extracellular (Secreted) | 2.36539 | 1.98E−05 |
| 211029_x_at | fibroblast growth factor 18 | fibroblast growth factor 18 | FGF18 | Extracellular (Secreted) | 2.332917 | 2.81E−05 |
| 211485_s_at | fibroblast growth factor 18 | FGF18 | Extracellular (Secreted) | 2.955372 | 1.03E−05 |
| 231382_at | Fibroblast growth factor 18 | FGF18 | Extracellular (Secreted) | 2.766924 | 1.55E−07 |
| 204421_s_at | fibroblast growth factor 2 (basic) | FGF2 | NO_LOCALIZATION | 1.56491 | 3.28E−07 |
| 204422_s_at | fibroblast growth factor 2 (basic) | FGF2 | NO_LOCALIZATION | 2.144299 | 1.38E−07 |
| 205606_at | low density lipoprotein receptor-related protein 6 | LRP6 | Plasma membrane | 1.935109 | 4.17E−05 |
| 209909_s_at | transforming growth factor, beta 2 | TGFB2 | Extracellular (Secreted) | 2.066203 | 4.94E−15 |
| 220407_s_at | transforming growth factor, beta 2 | TGFB2 | Extracellular (Secreted) | 1.711286 | 8.48E−10 |
| 228121_at | Transforming growth factor, beta 2 | TGFB2 | Extracellular (Secreted) | 1.699841 | 3.07E−13 |
| 206737_at | wingless-type MMTV integration site family, member 11 | WNT11 | Extracellular (Secreted) | 3.235511 | 3.83E−07 |
| 206176_at | bone morphogenetic protein 6 | BMP6 | Extracellular (Secreted) | 1.617235 | 2.14E−06 |
| 207326_at | betacellulin | BTC | Plasma membrane | 4.484959 | 6.59E−11 |
| 241412_at | betacellulin | BTC | Plasma membrane | 5.748075 | 1.57E−12 |
| 219764_at | frizzled homolog 10 (*Drosophila*) | FZD10 | Plasma membrane | 1.886755 | 9.08E−10 |
| 203705_s_at | frizzled homolog 7 (*Drosophila*) | FZD7 | Plasma membrane | 1.977168 | 1.12E−13 |
| 203706_s_at | frizzled homolog 7 (*Drosophila*) | FZD7 | Plasma membrane | 2.148229 | 7.07E−15 |
| 224325_at | frizzled homolog 8 (*Drosophila*) | frizzled homolog 8 (*Drosophila*) | FZD8 | Plasma membrane | 2.039929 | 2.47E−13 |
| 227405_s_at | frizzled homolog 8 (*Drosophila*) | FZD8 | Plasma membrane | 2.033817 | 1.11E−13 |

TABLE 4

Certain F1 subtype therapeutic targets and biomarkers.

| ProbeID | NETAFFX: GeneTitle | NETAFFX: GeneSymbol | Unison: Protcomp | Fold Change | p-value |
|---|---|---|---|---|---|
| 236179_at | Cadherin 11, type 2, OB-cadherin (osteoblast) | CDH11 | Plasma membrane | 2.478118072 | 1.48E−13 |

TABLE 4-continued

Certain F1 subtype therapeutic targets and biomarkers.

| ProbeID | NETAFFX: GeneTitle | NETAFFX: GeneSymbol | Unison: Protcomp | Fold Change | p-value |
|---|---|---|---|---|---|
| 239286_at | Cadherin 11, type 2, OB-cadherin (osteoblast) | CDH11 | Plasma membrane | 2.003613835 | 1.78E−09 |
| 241780_at | Cadherin 11, type 2, OB-cadherin (osteoblast) | CDH11 | Plasma membrane | 1.991499524 | 5.56E−06 |
| 207173_x_at | cadherin 11, type 2, OB-cadherin (osteoblast) | CDH11 | Plasma membrane | 1.848606565 | 1.15E−11 |
| 207172_s_at | cadherin 11, type 2, OB-cadherin (osteoblast) | CDH11 | Plasma membrane | 1.803978278 | 1.00E−10 |
| 222899_at | integrin, alpha 11 | ITGA11 | Plasma membrane | 2.22681306 | 1.32E−08 |
| 205131_x_at | C-type lectin domain family 11, member A | CLEC11A | Cytoplasmic | 2.751077434 | 1.15E−12 |
| 211709_s_at | C-type lectin domain family 11, member A \| C-type lectin domain family 11, member A | CLEC11A | Cytoplasmic | 2.09446091 | 3.80E−11 |
| 210783_x_at | C-type lectin domain family 11, member A | CLEC11A | Cytoplasmic | 2.078646468 | 3.56E−06 |
| 203876_s_at | matrix metalloproteinase 11 (stromelysin 3) | MMP11 | Plasma membrane | 2.200173425 | 8.85E−06 |
| 235908_at | matrix metalloproteinase 11 (stromelysin 3) | MMP11 | Plasma membrane | 1.952831042 | 1.58E−10 |
| 205959_at | matrix metalloproteinase 13 (collagenase 3) \| matrix metalloproteinase 13 (collagenase 3) | MMP13 | Extracellular (Secreted) | 8.887243061 | 2.09E−09 |
| 207012_at | matrix metalloproteinase 16 (membrane-inserted) | MMP16 | Plasma membrane | 1.749078693 | 2.81E−08 |
| 224207_x_at | matrix metalloproteinase 28 | MMP28 | Extracellular (Secreted) | 2.533723399 | 3.21E−09 |
| 222937_s_at | matrix metalloproteinase 28 | MMP28 | Extracellular (Secreted) | 1.616679576 | 9.53E−07 |
| 213790_at | A disintegrin and metalloproteinase domain 12 (meltrin alpha) | ADAM12 | Plasma membrane | 6.765178528 | 3.70E−12 |
| 226777_at | A disintegrin and metalloproteinase domain 12 (meltrin alpha) | ADAM12 | Plasma membrane | 5.054380937 | 1.32E−12 |
| 202952_s_at | a disintegrin and metalloproteinase domain 12 (meltrin alpha) | ADAM12 | Plasma membrane | 4.582308224 | 1.37E−11 |
| 241026_at | A disintegrin and metalloproteinase domain 12 (meltrin alpha) | ADAM12 | Plasma membrane | 3.111313526 | 1.10E−05 |
| 215613_at | A disintegrin and metalloproteinase domain 12 (meltrin alpha) | ADAM12 | Plasma membrane | 2.348274812 | 3.16E−07 |
| 208227_x_at | a disintegrin and metalloproteinase domain 22 | ADAM22 | Plasma membrane | 3.465935261 | 1.11E−09 |
| 202450_s_at | cathepsin K (pycnodysostosis) | CTSK | Lysosomal | 1.746776635 | 4.32E−14 |
| 211148_s_at | angiopoietin 2 | ANGPT2 | Extracellular (Secreted) | 1.961743434 | 3.09E−10 |
| 205572_at | angiopoietin 2 | ANGPT2 | Extracellular (Secreted) | 1.858241241 | 5.95E−08 |

TABLE 4-continued

Certain F1 subtype therapeutic targets and biomarkers.

| ProbeID | NETAFFX: GeneTitle | NETAFFX: GeneSymbol | Unison: Protcomp | Fold Change | p-value |
|---|---|---|---|---|---|
| 236034_at | Angiopoietin 2 | ANGPT2 | Extracellular (Secreted) | 1.74308462 | 8.68E−08 |
| 223121_s_at | secreted frizzled-related protein 2 | SFRP2 | Extracellular (Secreted) | 3.420031277 | 5.12E−07 |
| 223122_s_at | secreted frizzled-related protein 2 | SFRP2 | Extracellular (Secreted) | 2.45294325 | 4.10E−07 |
| 204051_s_at | secreted frizzled-related protein 4 | SFRP4 | Extracellular (Secreted) | 2.115342409 | 8.29E−05 |
| 204468_s_at | tyrosine kinase with immunoglobulin-like and EGF-like domains 1 | TIE1 | Plasma membrane | 2.020004455 | 2.91E−07 |
| 202112_at | von Willebrand factor | VWF | Extracellular (Secreted) | 1.858748797 | 1.03E−08 |

Using the molecular phenotype training and testing statistical methods described above, an F2 phenotype classifier was identified, as indicated in Table 12 below.

TABLE 12

F2 phenotype (subtype) classifier genes and probes

| ProbeID | NETAFFX: GeneTitle | NETAFFX: GeneSymbol |
|---|---|---|
| 201802_at | solute carrier family 29 nucleoside transporters member 1 | SLC29A1 |
| 227405_s_at | frizzled homolog 8 Drosophila | FZD8 |
| 204237_at | GULP engulfment adaptor PTB domain containing 1 | GULP1 |
| 205158_at | ribonuclease RNase A family 4 | RNASE4 |
| 227526_at | Full length insert cDNA clone ZD42A08 | NA |
| 204235_s_at | GULP engulfment adaptor PTB domain containing 1 | GULP1 |
| 203554_x_at | pituitary tumortransforming 1 | PTTG1 |
| 201801_s_at | solute carrier family 29 nucleoside transporters member 1 | SLC29A1 |
| 206002_at | G proteincoupled receptor 64 | GPR64 |
| 212914_at | chromobox homolog 7 | CBX7 |
| 228084_at | Fulllength cDNA clone CS0DF027YF17 of Fetal brain of Homo sapiens human | NA |
| 222043_at | clusterin complement lysis inhibitor SP4040 sulfated glycoprotein 2 testosteronerepressed prostate message 2 apolipoprotein J | CLU |
| 229310_at | kelch repeat and BTB POZ domain containing 9 | KBTBD9 |
| 225728_at | importin 9 | IPO9 |
| 226247_at | pleckstrin homology domain containing family A phosphoinositide binding specific member 1 | PLEKHA1 |
| 205794_s_at | neurooncological ventral antigen 1 | NOVA1 |
| 213497_at | ankyrin repeat and BTB POZ domain containing 2 | ABTB2 |
| 207551_s_at | malespecific lethal 3like 1 Drosophila | MSL3L1 |
| 227554_at | Hypothetical LOC402560 | NA |
| 223315_at | netrin 4 | NTN4 |
| 208868_s_at | GABAA receptorassociated protein like 1 | GABARAPL1 |
| 210046_s_at | isocitrate dehydrogenase 2 NADP+ mitochondrial | IDH2 |
| 219295_s_at | procollagen Cendopeptidase enhancer 2 | PCOLCE2 |
| 221796_at | neurotrophic tyrosine kinase receptor type 2 | NTRK2 |
| 208869_s_at | GABAA receptorassociated protein like 1 | GABARAPL1 |
| 225950_at | Transcribed locus moderately similar to NP_0553011 neuronal thread protein AD7cNTP [Homo sapiens] | NA |
| 204288_s_at | ArgAblinteracting protein ArgBP2 | ARGBP2 |
| 223842_s_at | scavenger receptor class A member 3 | SCARA3 |
| 203306_s_at | solute carrier family 35 CMPsialic acid transporter member A1 | SLC35A1 |
| 208792_s_at | clusterin complement lysis inhibitor SP4040 sulfated glycoprotein 2 testosteronerepressed prostate message 2 apolipoprotein J | CLU |
| 203744_at | highmobility group box 3 | HMGB3 |
| 1555778_a_at | periostin osteoblast specific factor | POSTN |
| 227308_x_at | latent transforming growth factor beta binding protein 3 | LTBP3 |
| 229969_at | Transcribed locus weakly similar to NP_0790122 gasdermin domain containing 1 [Homo sapiens] | NA |
| 224989_at | Hypothetical protein LOC201895 | LOC201895 |
| 222423_at | Nedd4 family interacting protein 1 | NDFIP1 |
| 227052_at | Hypothetical protein LOC201895 | LOC201895 |
| 230351_at | hypothetical protein LOC283481 | LOC283481 |
| 219230_at | hypothetical protein FLJ10970 | FLJ10970 |
| 226197_at | Transcribed locus strongly similar to XP_4960551 similar to p40 [Homo sapiens] | NA |
| 212599_at | autism susceptibility candidate 2 | AUTS2 |
| 203805_s_at | Fanconi anemia complementation group A & Fanconi anemia complementation group A | FANCA |
| 202429_s_at | protein phosphatase 3 formerly 2B catalytic subunit alpha isoform calcineurin A alpha | PPP3CA |
| 218471_s_at | BardetBiedl syndrome 1 | BBS1 |
| 227290_at | CDNA FLJ13598 fis clone PLACE1009921 | NA |
| 1552790_a_at | hypothetical protein FLJ32803 | FLJ32803 |
| 212616_at | chromodomain helicase DNA binding protein 9 | CHD9 |

Using the molecular phenotype training and testing statistical methods described above, an F1 phenotype classifier was identified, as indicated in Table 13 below.

TABLE 13

F1 phenotype (subtype) classifier genes and probes

| ProbeID | NETAFFX: GeneTitle | NETAFFX: GeneSymbol |
| --- | --- | --- |
| 213059_at | cAMP responsive element binding protein 3like 1 | CREB3L1 |
| 204385_at | kynureninase Lkynurenine hydrolase | KYNU |
| 207172_s_at | cadherin 11 type 2 OBcadherin osteoblast | CDH11 |
| 212771_at | chromosome 10 open reading frame 38 | C10orf38 |
| 218454_at | hypothetical protein FLJ22662 | FLJ22662 |
| 203010_at | signal transducer and activator of transcription 5A | STAT5A |
| 210992_x_at | Fc fragment of IgG low affinity IIc receptor for CD32 | FCGR2C |
| 203903_s_at | hephaestin | HEPH |
| 227307_at | Tetraspanin similiar to uroplakin 1 | LOC90139 |
| 201307_at | septin 11 | SEPT11 |
| 202902_s_at | cathepsin S | CTSS |
| 202897_at | protein tyrosine phosphatase nonreceptor type substrate 1 | PTPNS1 |
| 226098_at | KIAA1374 protein | KIAA1374 |
| 206116_s_at | tropomyosin 1 alpha | TPM1 |
| 204787_at | Vset and immunoglobulin domain containing 4 | VSIG4 |
| 230264_s_at | adaptorrelated protein complex 1 sigma 2 subunit | AP1S2 |
| 227618_at | FLJ44635 protein | FLJ44635 |
| 206571_s_at | mitogenactivated protein kinase kinase kinase kinase 4 | MAP4K4 |
| 217984_at | ribonuclease T2 | RNASET2 |
| 212276_at | lipin 1 | LPIN1 |
| 203417_at | microfibrillarassociated protein 2 | MFAP2 |
| 223614_at | NA | NA |
| 211981_at | collagen type IV alpha 1 | COL4A1 |
| 226828_s_at | hairyenhancerofsplit related with YRPW motiflike | HEYL |
| 209081_s_at | collagen type XVIII alpha 1 | COL18A1 |
| 228396_at | NA | NA |
| 224759_s_at | hypothetical protein MGC17943 | MGC17943 |
| 212951_at | G proteincoupled receptor 116 | GPR116 |
| 222664_at | potassium channel tetramerisation domain containing 15 | KCTD15 |
| 221942_s_at | guanylate cyclase 1 soluble alpha 3 | GUCY1A3 |
| 205819_at | macrophage receptor with collagenous structure & macrophage receptor with collagenous structure | MARCO |
| 204677_at | cadherin 5 type 2 VEcadherin vascular epithelium | CDH5 |
| 228339_at | Transcribed locus strongly similar to XP_5308421 LOC462106 [*Pan troglodytes*] | NA |
| 227235_at | *Homo sapiens* clone IMAGE: 5302158 mRNA | NA |
| 219489_s_at | nucleoredoxin | NXN |
| 203299_s_at | adaptorrelated protein complex 1 sigma 2 subunit | AP1S2 |
| 203300_x_at | adaptorrelated protein complex 1 sigma 2 subunit | AP1S2 |
| 224749_at | chromosome 16 open reading frame 9 | C16orf9 |
| 210663_s_at | kynureninase Lkynurenine hydrolase | KYNU |
| 227333_at | Hypothetical protein MGC48972 | MGC48972 |
| 209696_at | fructose16bisphosphatase 1 | FBP1 |
| 212985_at | Fulllength cDNA clone CS0DC015YK09 of Neuroblastoma Cot 25normalized of *Homo sapiens* human | NA |
| 226575_at | zinc finger protein 462 | ZNF462 |
| 229121_at | CDNA FLJ44441 fis clone UTERU2020242 | NA |
| 214770_at | macrophage scavenger receptor 1 | MSR1 |
| 201401_s_at | adrenergic beta receptor kinase 1 | ADRBK1 |
| 227627_at | serumglucocorticoid regulated kinaselike | SGKL |
| 218041_x_at | solute carrier family 38 member 2 | SLC38A2 |
| 217846_at | glutaminyltRNA synthetase | QARS |
| 203507_at | CD68 antigen | CD68 |
| 203505_at | ATPbinding cassette subfamily A ABC1 member 1 | ABCA1 |
| 202418_at | Yip1 interacting factor homolog *S cerevisiae* | YIF1 |
| 221685_s_at | hypothetical protein FLJ20364 | FLJ20364 |
| 230422_at | formyl peptide receptorlike 2 | FPRL2 |
| 226084_at | microtubuleassociated protein 1B | MAP1B |
| 203923_s_at | cytochrome b245 beta polypeptide chronic granulomatous disease | CYBB |
| 211208_s_at | calciumcalmodulindependent serine protein kinase MAGUK family | CASK |
| 219694_at | hypothetical protein FLJ11127 | FLJ11127 |
| 217388_s_at | kynureninase Lkynurenine hydrolase | KYNU |
| 1555778_a_at | periostin osteoblast specific factor | POSTN |
| 1554285_at | hepatitis A virus cellular receptor 2 | HAVCR2 |
| 204834_at | fibrinogenlike 2 | FGL2 |
| 203148_s_at | tripartite motifcontaining 14 | TRIM14 |
| 207857_at | leukocyte immunoglobulinlike receptor subfamily A with TM domain member 2 & leukocyte immunoglobulinlike receptor subfamily A with TM domain member 2 | LILRA2 |
| 238668_at | Transcribed locus | NA |
| 232617_at | cathepsin S | CTSS |
| 217983_s_at | ribonuclease T2 | RNASET2 |

TABLE 13-continued

F1 phenotype (subtype) classifier genes and probes

| ProbeID | NETAFFX: GeneTitle | NETAFFX: GeneSymbol |
|---|---|---|
| 1555349_a_at | integrin beta 2 antigen CD18 p95 lymphocyte functionassociated antigen 1; macrophage antigen 1 mac1 beta subunit | ITGB2 |
| 211395_x_at | Fc fragment of IgG low affinity IIc receptor for CD32 | FCGR2C |
| 204006_s_at | Fc fragment of IgG low affinity IIIa receptor CD16a & Fc fragment of IgG low affinity IIIb receptor CD16b | FCGR3A & FCGR3B |
| 210629_x_at | leukocyte specific transcript 1 | LST1 |
| 218961_s_at | polynucleotide kinase 3phosphatase | PNKP |
| 203922_s_at | cytochrome b245 beta polypeptide chronic granulomatous disease | CYBB |
| 202803_s_at | integrin beta 2 antigen CD18 p95 lymphocyte functionassociated antigen 1; macrophage antigen 1 mac1 beta subunit | ITGB2 |
| 209083_at | coronin actin binding protein 1A | CORO1A |

To further characterize each of the molecular subtypes and find associations between the gene expression signature of each molecular subtype and clinical and histological features of RA, samples of the each of the molecular subtypes were analyzed for expression of one or more particular genes predominantly expressed in that subtype. Certain samples were also assessed for associations with systemic measure of inflammation, the erythroid sedimentation rate (ESR) and C-reactive protein (CRP) levels. Also, associations with radiographic progression were assessed. In addition, the samples were subjected to histological and immunohistochemical analyses.

FIG. 3 shows the results of these studies for the L subtype samples. FIG. 3A shows that the transcription factor XBP1 is upregulated in the L subtype samples (L) compared to samples of other subtypes (NL). Accordingly, expression of XBP1 is an L subtype-specific surrogate marker. Furthermore, FIG. 3B shows that XBP1 expression is significantly upregulated in synovial samples containing lymphoid aggregates (+) compared to samples lacking lymphoid aggregates (−). Box and whisker plots for FIGS. 3A and 3B represent each sample as an open circle. The box represents the 25th to 75th percentile and contains the median value (horizontal line within the box). The whiskers extend from the box to represent values up to 1.5 times above and below the interquartile range. FIG. 3 also shows that XBP1 expression is not associated with ESR (FIG. 3C) or CRP levels (FIG. 3D). FIGS. 3E-H show the results of histological and immunohistochemical staining of representative samples of the L subtype. FIG. 3E shows staining with hematoxylin and eosin; FIG. 3F shows immunohistochemical staining for the T cell marker CD3; FIG. 3G shows immunohistochemical staining for the activated leukocyte marker CD68; FIG. 3H shows immunohistochemical staining for the B cell marker CD20.

FIG. 4 shows the characterization of the M subtype samples. FIG. 4A shows that the gene ICAM1 is upregulated in the M subtype samples (M) compared to samples of the other subtypes (F1, F2, and L). In FIG. 4A, a box and whisker plot represents each sample as an open circle. The box represents the 25th to 75th percentile and contains the median value (horizontal line within the box). The whiskers extend from the box to represent values up to 1.5 times above and below the interquartile range. Accordingly, expression of ICAM1 is an M subtype-specific surrogate marker. FIG. 4B is a graphical plot of IL1β gene expression compared to TNF gene expression in M subtype samples. The plot shows that IL1β gene expression and TNF gene expression in synovial samples of the M subtype are correlated. This correlation was not observed in the other three molecular subtypes (data not shown). FIGS. 4C-F show the results of histological and immunohistochemical staining of representative samples of the M subtype. FIG. 4C shows staining with hematoxylin and eosin; FIG. 4D shows immunohistochemical staining for the T cell marker CD3; FIG. 4E shows immunohistochemical staining for the activated leukocyte marker CD68; FIG. 4F shows immunohistochemical staining for the B cell marker CD20.

FIG. 5 shows the characterization of the F2 subtype samples. FIG. 5A shows that the gene IL17D is upregulated in the F2 subtype samples (M) compared to samples of the other subtypes (F1, L, and M). In FIG. 5A, a box and whisker plot represents each sample as an open circle. The box represents the 25th to 75th percentile and contains the median value (horizontal line within the box). The whiskers extend from the box to represent values up to 1.5 times above and below the interquartile range. Accordingly, expression of IL17D is an F2 subtype-specific surrogate marker. FIGS. 5B-E show the results of histological and immunohistochemical staining of representative samples of the F2 subtype. FIG. 5B shows staining with hematoxylin and eosin; FIG. 5C shows immunohistochemical staining for the T cell marker CD3; FIG. 5D shows immunohistochemical staining for the activated leukocyte marker CD68; FIG. 5E shows immunohistochemical staining for the B cell marker CD20.

FIG. 6 shows the characterization of the F1 subtype samples. FIG. 6A shows that the gene ITGA11 is upregulated in the F1 subtype samples (M) compared to samples of the other subtypes (F2, L, and M). In FIG. 6A, a box and whisker plot represents each sample as an open circle. The box represents the 25th to 75th percentile and contains the median value (horizontal line within the box). The whiskers extend from the box to represent values up to 1.5 times above and below the interquartile range. Accordingly, expression of ITGA11 is an F1 subtype-specific surrogate marker. FIGS. 6B-E show the results of histological and immunohistochemical staining of representative samples of the F1 subtype. FIG. 6B shows staining with hematoxylin and eosin; FIG. 6C shows immunohistochemical staining for the T cell marker CD3; FIG. 6D shows immunohistochemical staining for the activated leukocyte marker CD68; FIG. 6E shows immunohistochemical staining for the B cell marker CD20.

For each of the subtypes, we determined the number of samples that were obtained from particular joints. This data is presented in Table 9 below.

TABLE 9

Distribution of joints by molecular subtype.

| Joint | Molecular Subtype | | | |
|---|---|---|---|---|
| | F1 | F2 | L | M |
| Elbow | 0 | 0 | 0 | 1 |
| Foot | 0 | 1 | 0 | 0 |
| Hand | 0 | 2 | 4 | 10 |
| Hip | 2 | 1 | 2 | 0 |
| Knee | 1 | 4 | 5 | 1 |
| Wrist | 1 | 1 | 1 | 0 |

As indicated above, we observed follicle-like lymphoid clusters in the L subtype. We also analyzed histological sections of samples from each of the other three subtypes in addition to the L subtype and quantitated the percentage of samples within each subtype showing lymphoid clusters (or aggregates). The results are shown in FIG. 7. As shown in FIG. 7, approximately 60% of the L subtype samples had lymphoid clusters, whereas a much smaller percentage (<10%) of the F2 and M subtype samples had lymphoid clusters. An even smaller percentage of the F1 subtype samples (2%-3%) had lymphoid clusters. These results indicate that the L-subtype gene expression signature is associated with the presence of organized lymphoid structures within the joint.

Figure 8A:
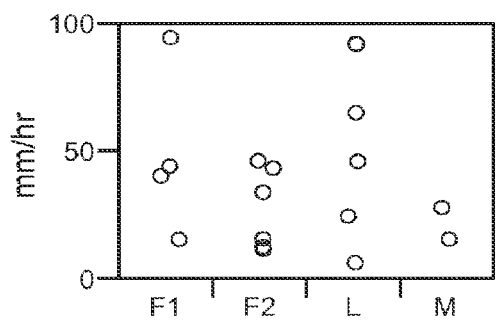
Figure 8B:
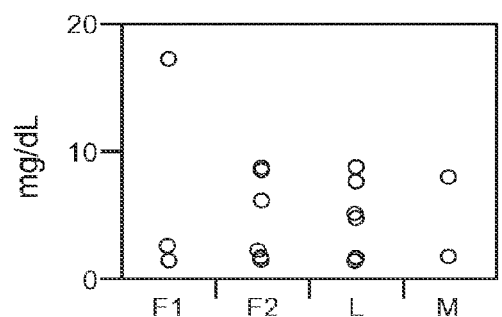
Figure 8C:
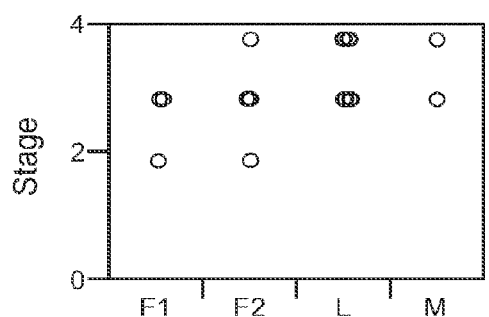

The associations of each of the subtypes with systemic measures of inflammation, the erythroid sedimentation rate (ESR) and C-reactive protein (CRP) levels, were assessed, as well as associations of each of the subtypes with radiographic progression. ESR, CRP, and radiographic assessments were performed according to standard procedures well known to those skilled in the art. These associations are shown graphically in FIGS. 8A-C. As shown in FIGS. 8A-C, none of the subtypes is clearly associated with ESR, CRP and/or radiographic progression. As discussed above, ESR, CRP levels and radiographic progression have been employed as diagnostic markers in RA, each having certain limitations. See also Pinals, R. S., et. al., Arthritis Rheum 24:1308 (1981) and Felson, D. T., et al., Arthritis Rheum 38: 727-35 (1995). Accordingly, the gene expression signatures described here provide, for example but not limited to, new diagnostic compositions which can be employed using methods as described herein and which augment or circumvent limitations of prior diagnostic markers or methods.

To identify biological pathways implicated in each of the molecular subtypes, statistical analysis (pathway analysis) of the gene signatures specific to each subtype was performed. The results of this analysis are depicted in the heatmap shown in FIG. 9. Each molecular subtype is listed at the top of the heatmap and biological pathways are provided along the right side of the heatmap. The heatmap is shaded to represent the –log of the p-values for statistically enriched pathways within each subtype according to the scale shown at the bottom of the figure. Statistically enriched pathways were identified using a publicly available web-service, CoPub, following the developers' recommended protocol (Frijters, R. et al., Nucleic Acids Res. 36:W406-W410 (Web server issue doi:10.1093/nar/gkn215) (2008)); available at the URL: services(dot)nbic(dot)nl (slash)cgi-bin(slash)copub(slash)microarray_analysis(dot) pl. Briefly, Affymetrix probeset identifiers that were specifically upregulated within each subtype (~1000 top ranked probesets) were uploaded to the web-server. The GeneChip® Human Genome U133A Plus 2.0 Array (Affymetrix, Inc.) was selected as the background data set, the search category was limited to biological processes and all calculation settings were left at their defaults. The resulting data was saved to a personal computer and formatted for comparative visualization. As indicated in FIG. 9, the biological pathways showing the highest statistical enrichment in the L subtype include, for example, B and T cell activation and cytokine production; the biological pathways showing the highest statistical enrichment in the M subtype include, for example, macrophage activation, phagocytosis, respiratory burst, and cytokine production; the biological pathways showing the highest statistical enrichment in the F2 subtype include, for example, bone formation, growth and differentiation, wnt-signaling and cell cycle; and the biological pathways showing the highest statistical enrichment in the F1 subtype include, for example, osteoblast differentiation, bone remodeling and vasculogenesis.

Example 2

To further characterize the molecular four phenotypes (subtypes) identified in Example 1, select genes representing the specific cellularities and biological processes of each phenotype were tested for specificity using real-time quantitative polymerase chain reaction (qPCR). As non-RA controls we used a set of synovial samples obtained from osteoarthritis patients (OA) and a set of synovial samples obtained from patients suffering from joint trauma but not from RA (Normal [Nrml]). Real-time qPCR was carried out as follows.

cDNA synthesis was performed using the iScript™ cDNA synthesis kit and protocol (Biorad, Hercules, Calif.). Two hundred ng of total RNA was added to a 20 μl cDNA reaction mixture containing 4 μl 5× iScript™ reaction mixture, 1 μl iScript™ reverse transcriptase and nuclease-free water. The reverse transcription reaction mixture was incubated at 25° C. for 5 minutes, 42° C. for 30 minutes and 85° C. for 5 minutes.

A gene specific pre-amplification of cDNA samples was performed using the TaqMan® PreAmp Master Mix (Applied Biosystems, Foster City, Calif.). One μl of a total of 77 20× TaqMan® Gene Expression Assays (all assays contained FAM™ dye-labeled MGB probes, Applied Biosystems, Foster City, Calif.) were pooled and diluted with 1×TE buffer for a final concentration of 0.2× per assay. Per sample, 1.25 μl of cDNA, 1.25 μl of the pooled assay mix and 2.5 μl of 2× TaqMan® PreAmp Master Mix (Applied Biosystems) were mixed. The pre-amplification reactions were done in a GeneAmp® PCR System 9700 (Applied Biosystems, Foster City, Calif.) using the protocol, 95° C. for 10 minutes, and 14 cycles of 95° C. for 15 seconds and 60° C. for 4 minutes. After thermal cycling, the pre-amplified samples were diluted five times with 1×TE buffer.

Semi-quantitative real-time RT-PCR validation of microarray data for 45 genes and three housekeeping genes (HPRT1, GAPDH and B-Actin) was performed using the BioMark™ 48.48 Dynamic Arrays (Fluidigm Corporation, South San Francisco, Calif.). A sample mix, containing 2.5 μl of pre-amplified cDNA, 2.5 μl of TaqMan® Universal PCR Master Mix (Applied Biosystems, Foster City, Calif.) and 0.25 μl of DA Sample Loading Reagent (Fluidigm Corporation, South San Francisco, Calif.) and an assay mix containing 2.5 μl 20× TaqMan® Gene Expression Assay (Applied Biosystems, Foster City, Calif.) and 2.5 μl DA Assay Loading reagent (Fluidigm Corporation, South San Francisco, Calif.) were prepared. Following priming of the 48.48 Dynamic Array with control line fluid in an IFC controller (Fluidigm Corporation, South San Francisco, Calif.), 5 µl sample mix was loaded into each sample inlet and 5 µl assay mix into the detector inlet of the chip. All samples were loaded in duplicate. The chip was subsequently placed in the IFC Controller for loading and mixing of the samples and assays and then transferred to the BioMark™ Real-Time PCR System. The cycling program consisted of 10 minutes at 95° C. followed by 40 cycles of 95° C. for 15 seconds and 1 minute at 60° C.

Data was analyzed using the Fluidigm Gene Expression Data Analysis software (version 2.1.1, Fluidigm Corporation, South San Francisco, Calif.) to obtain CT values. The relative abundance was calculated according to the formula: 2^(average CT gene A–average CT HPRT1). HPRT1 was the most stable house keeping gene. Results are shown in FIGS. 10A-D.

In each of FIGS. 10A-D, box-plots for each gene in each sample are shown grouped by the molecular phenotypes, F1, F2, L, and M. Five healthy controls (Nrml) and 41 uninflamed osteoarthritis (OA) samples were included for reference. Boxes within each plot represent the 25th to 75th percentiles, horizontal lines represent medians, whiskers represent estimates of the 95% confidence intervals and individual dots correspond to each observation.

Figure 10A:
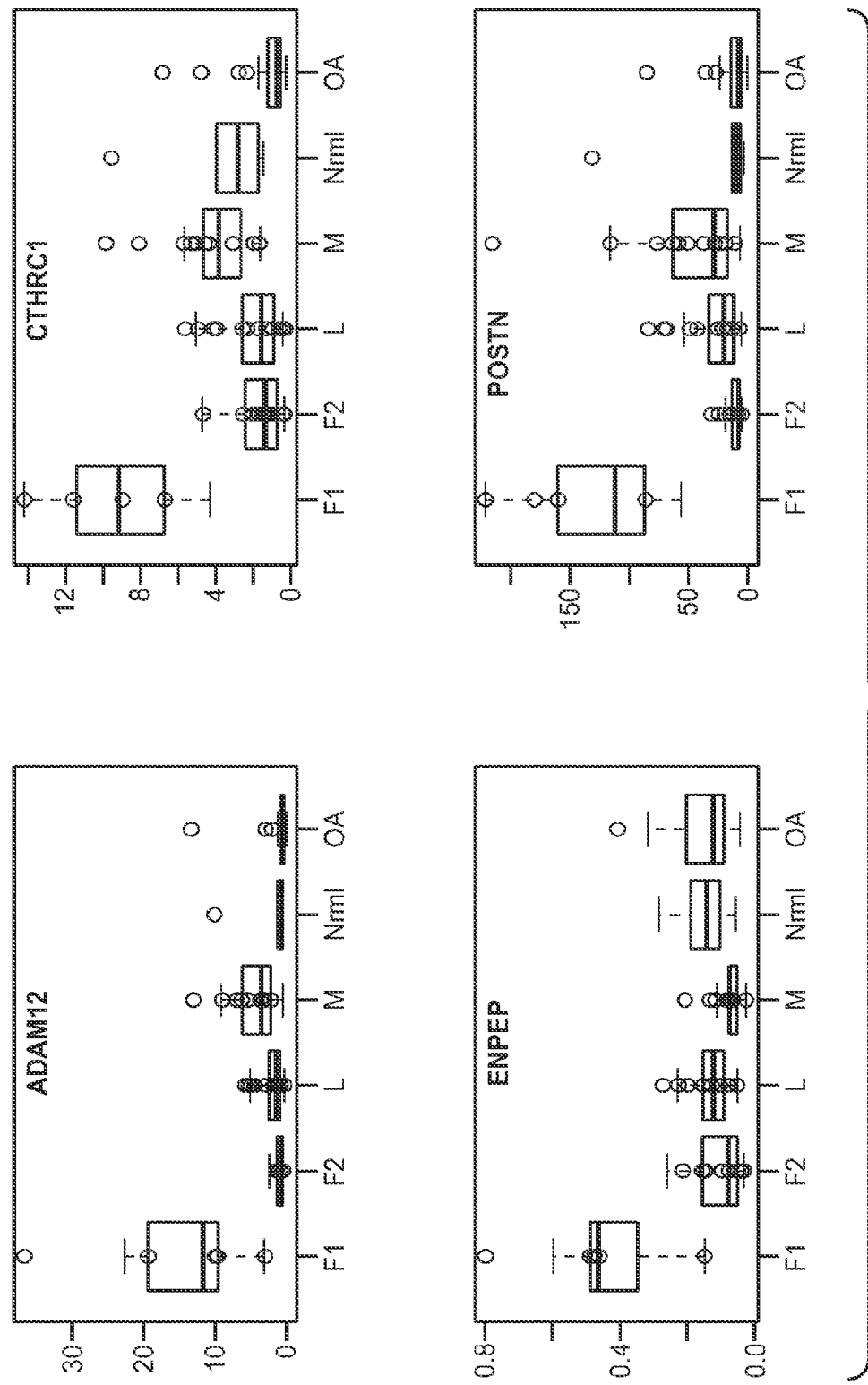

The results for the F1 phenotype are shown in FIG. 10A. Periostin (POSTN) was validated as an F1-specific transcript (FIG. 10A). Others have shown that POSTN is expressed predominantly in collagen-rich fibrous connective tissues that are subjected to constant mechanical stresses (Oku et al., *Int J Hematol.* 88(1):57-63 (2008)). POSTN expression is induced by TGFB and has been shown to be a component of bone marrow fibrosis. Additional validated F1-specific transcripts included ADAM12, CTHRC1, and ENPEP (FIG. 10A)

Figure 10B:
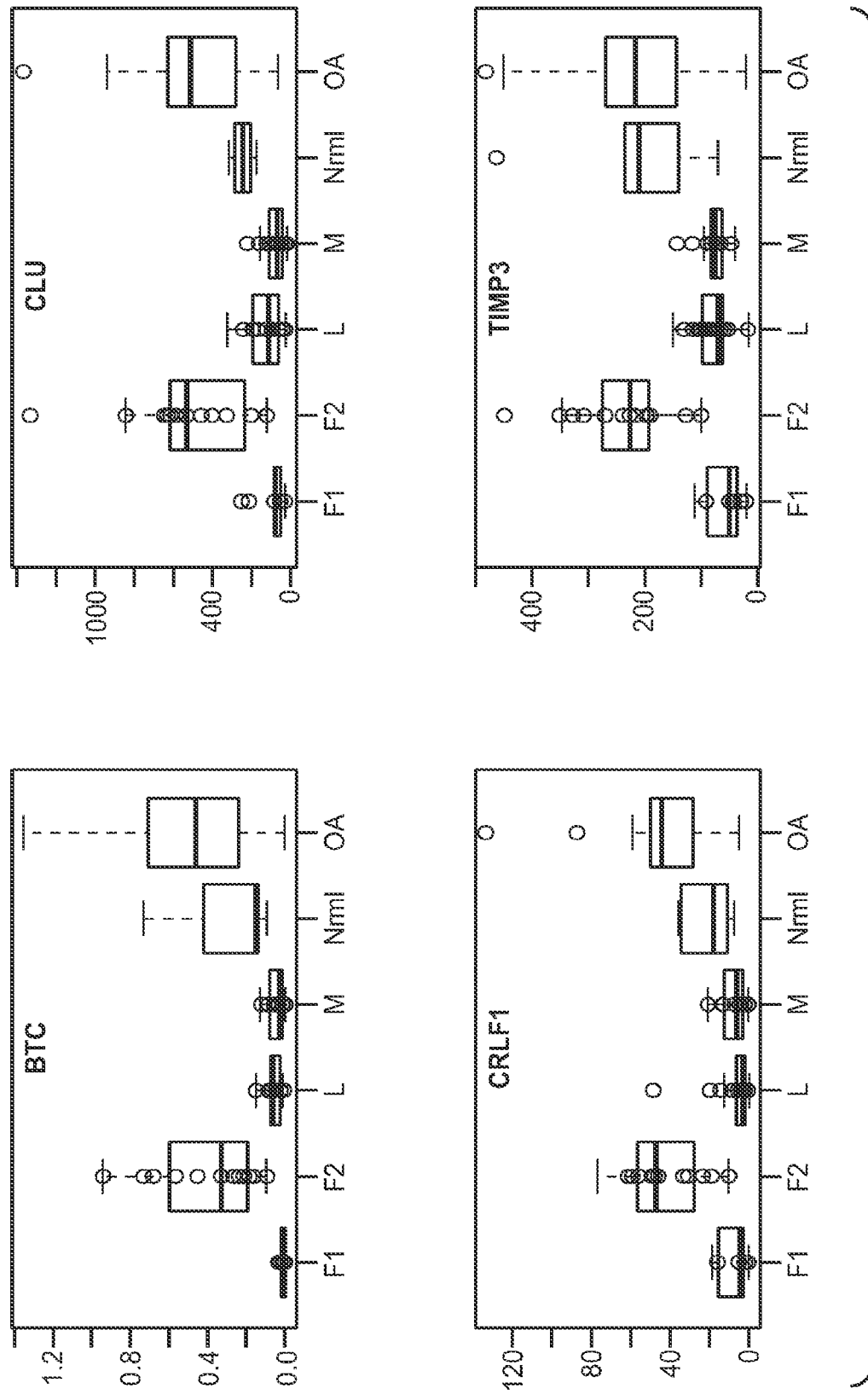

As shown in FIG. 10B, the F2-specific transcripts BTC, CLU, CRLF1 and TIMP3 were all upregulated in patient samples identified as F2, however, the levels of these transcripts in F2 tissues were not significantly different from the levels found in OA tissues.

Figure 10C:
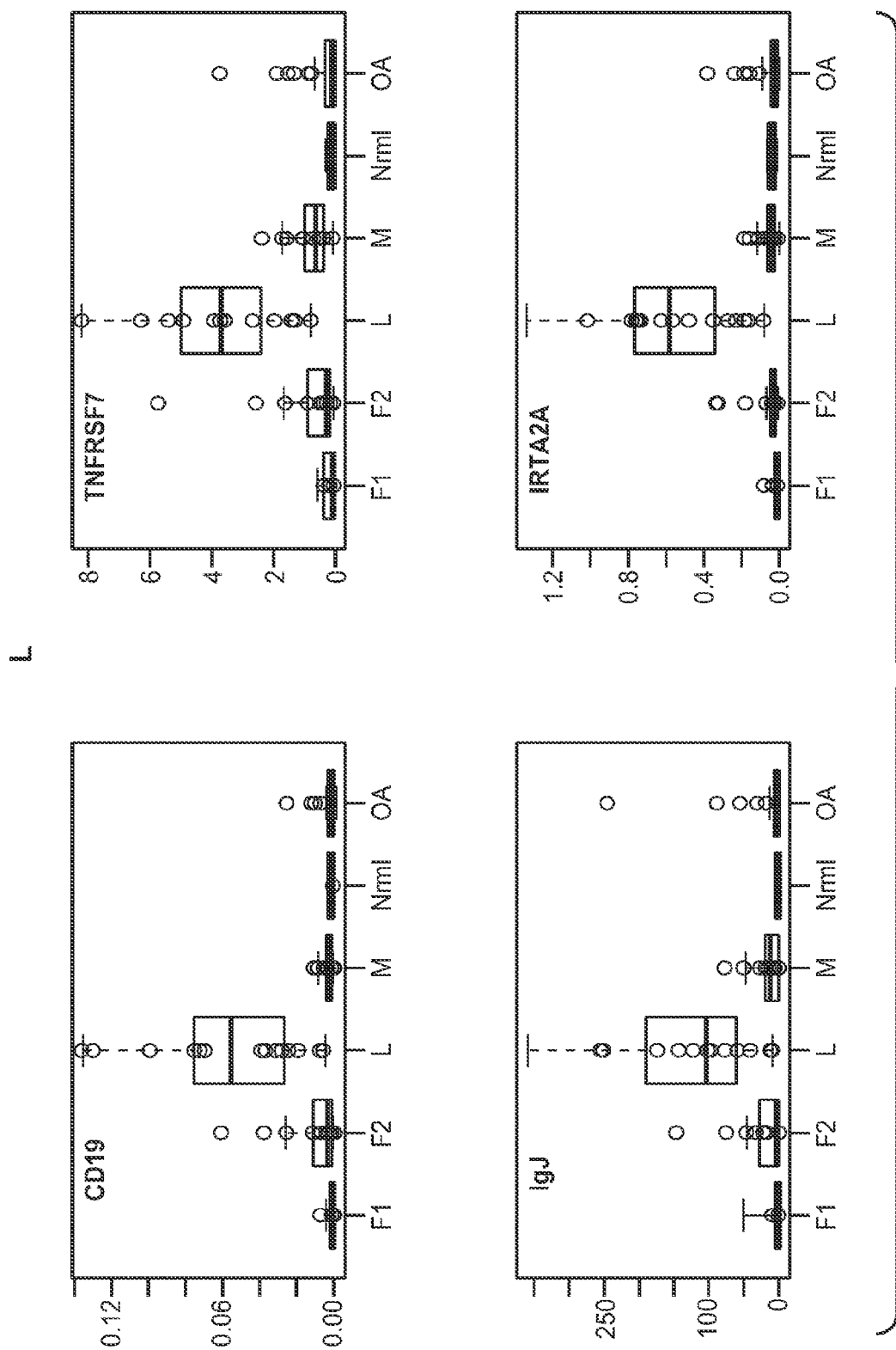

As indicated in FIG. 10C, the B cell transcripts CD19, TNFRSF7, IgJ and IRTA2 demonstrated specificity for the L phenotype. Expression of each of these transcripts in L tissues was significantly higher than in normal and OA tissues.

Figure 10D:
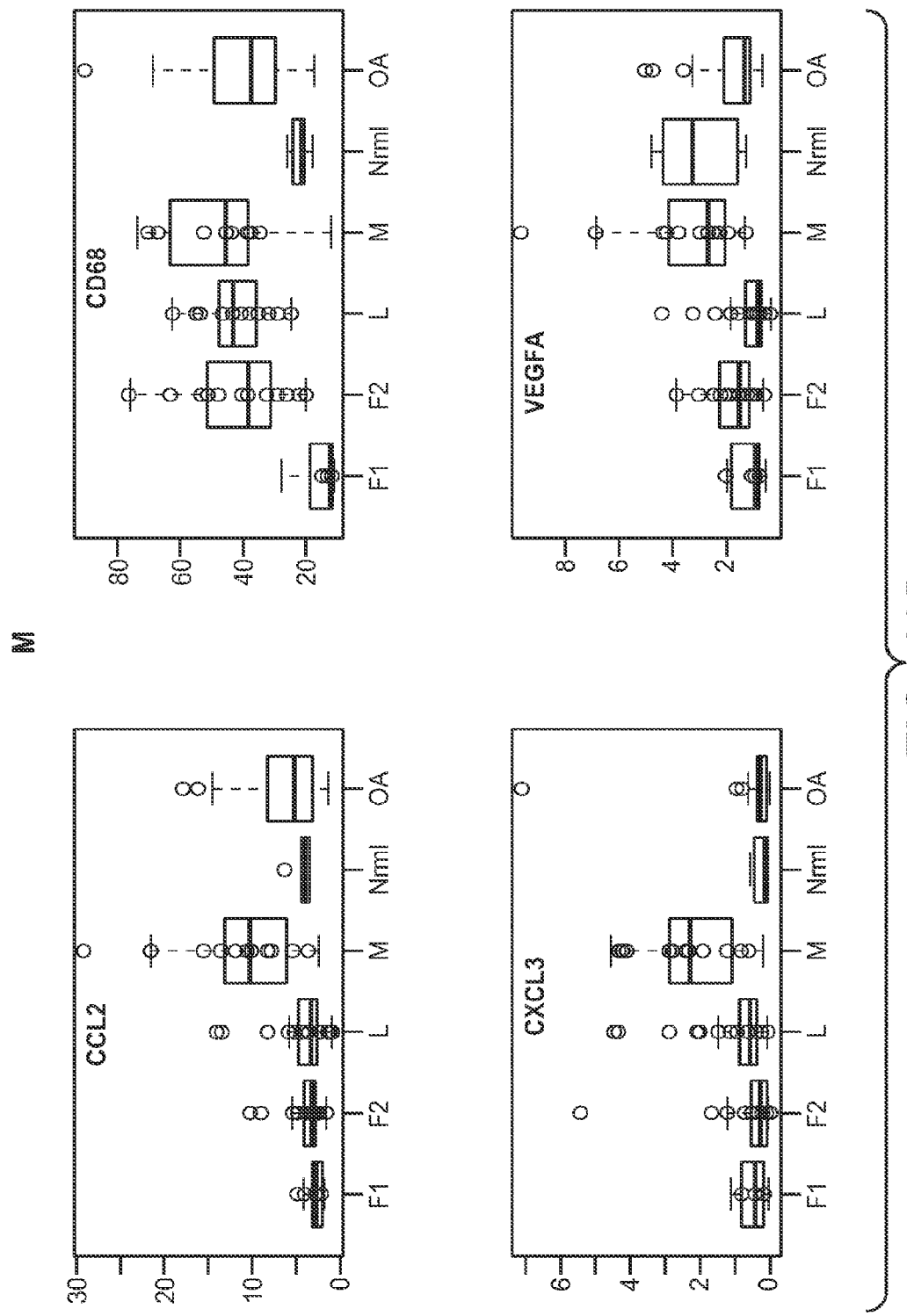

As shown in FIG. 10D, CCL2, CXCL3 and VEGFA were all specific to the M phenotype, whereas the macrophage activation marker CD68 showed similar levels in all phenotypes except F1 which had similar low levels with normal controls. Also noteworthy were the levels of VEGFA, which was unique to the M phenotype among RA and OA samples, but did not differ from normal samples.

These findings provide platform-independent validation of phenotype-specific differential gene expression. Importantly, all of the analytes tested here encode for cell surface and/or soluble proteins and could therefore serve as phenotype-specific biomarkers that may be measurable systemically or in synovial fluid. In addition, because these analytes were easily detectable by qPCR, the possibility of direct synovial tissue assessment could be feasible using minimally invasive biopsy techniques.

Example 3

As described above, the L subtype was associated with the presence of organized lymphoid structures in histological sections of synovial tissue. These lymphoid clusters were also shown to contain large numbers of B cells (see, e.g., FIG. 3H). Furthermore, it is likely that the lymphoid clusters contain antibody secreting plasma cells based on the morphology of the clusters which resemble germinal centers. In addition, as described above, the L subtype was associated with the expression of genes characteristic of B cells, plasma cells, and other cells. Such genes include, as indicated in Table 1, IRTA2 (FcRH5) and CXCL13. While CXCL13 is a soluble chemokine that can be detected systemically, full length FcRH5 is a B-cell-restricted membrane bound protein. It is also, however, expressed as a truncated soluble protein due to alternate splicing of the primary mRNA (Hatzivassiliou, G., et al., *Immunity* 14:277-289, doi:S1074-7613(01)00109-1 [pii] (2001); Ise, T., et al., *Leukemia* 21:169-174, doi:2404445 [pii] 10.1038/sj.leu.2404445 (2007)). Accordingly, we hypothesized that sFcRH5 and CXCL13 might be measurable in the serum of RA patients and if so, could prove useful as serum biomarkers of the L subtype. Moreover, because a number of therapeutic agents target B cells, including anti-CD20 therapeutic antibodies, such as rituximab, we sought to determine whether serum sFcRH5 and/or CXCL13 could be useful as biomarkers for predicting patient responsiveness to such therapeutic agents.

We thus conducted the following experiments to ascertain whether serum sFcRH5 and CXCL13 levels could be used as biomarkers of the L subtype of RA and/or to predict patient responsiveness to anti-B cell therapeutic agents. As an exemplary anti-B cell therapeutic agent, we chose rituximab. Serum from 339 RA patients in a double blind, placebo-controlled phase III randomized controlled trial known as REFLEX (Randomized Evaluation of Long-Term Efficacy of Rituximab in RA) was collected and analyzed as described further below. The REFLEX trial was conducted by Genentech, Inc., Biogen-Idec, Inc. and Roche, the topline clinical findings of which were published by Cohen, S. B., et al., *Arthritis Rheum* 54:2793-2806 (2006).

First, we assayed levels of sFcRH5 in the patient sera at baseline (one day prior to dosing with rituximab) and compared that to levels in healthy control samples. To assay sFcRH5, we used an anti-FcRH5 monoclonal antibody, 6H1, (ATCC No. PTA-7211) that recognizes the extracellular domain of the FcRH5 molecule. This antibody is also described in International Patent Application No. PCT/US2010/029516. ELISA wells (384/plate) were coated with ms6H1 mAb at 0.5 µg/mL in 0.05M Carbonate/Bicarbonate buffer (pH 9.6) at 2-8° C. overnight. After removal of coat solution, nonspecific binding sites were blocked by incubating for at least 1 hr with blocking solution (PBS/0.5% BSA/0.05% Tween20/15 ppm Proclin, 50 µl/well). After washing the plates with 100 µl wash buffer (PBS/0.05% Tween), standard (20-0.156 ng/ml) or sample diluted in assay buffer (PBS/0.5% BSA/0.05% Tween-20/15 ppm Proclin 300/0.25% CHAPS/0.35M NaCl/5 mM EDTA, pH 7.4, 5% Fetal bovine serum) was added (25 pd/well) and incubated for 2 hrs at RT then moved to 2-8° C. for overnight incubation. After an overnight incubation, the plates were allowed to shake at room temperature (RT) for 1 hr. Then the plates were washed and 70 ng/mL of biotinylated pAb from R&D Systems was added (25 µl/well) and incubated for an additional 1 hr. Following washing, streptavidin-horseradish peroxidase (Amdex) diluted 1:10,000 was added to the plate, and incubated for 30 min. Following another wash, tetramethyl benzidine substrate (Moss TMB) was added (25 µL/well), color was allowed to develop for 15 min, and the reaction was stopped by the addition of 1 M phosphoric acid (25 µl/well). The plates were read at a wavelength of 450 nm, with reference at 630 nm, using a microplate reader (Thermo Labsystems, Finland). The concentration of soluble FcRH5 in the samples was extrapolated from a 4-parameter fit of the standard curve.

Figure 11A:
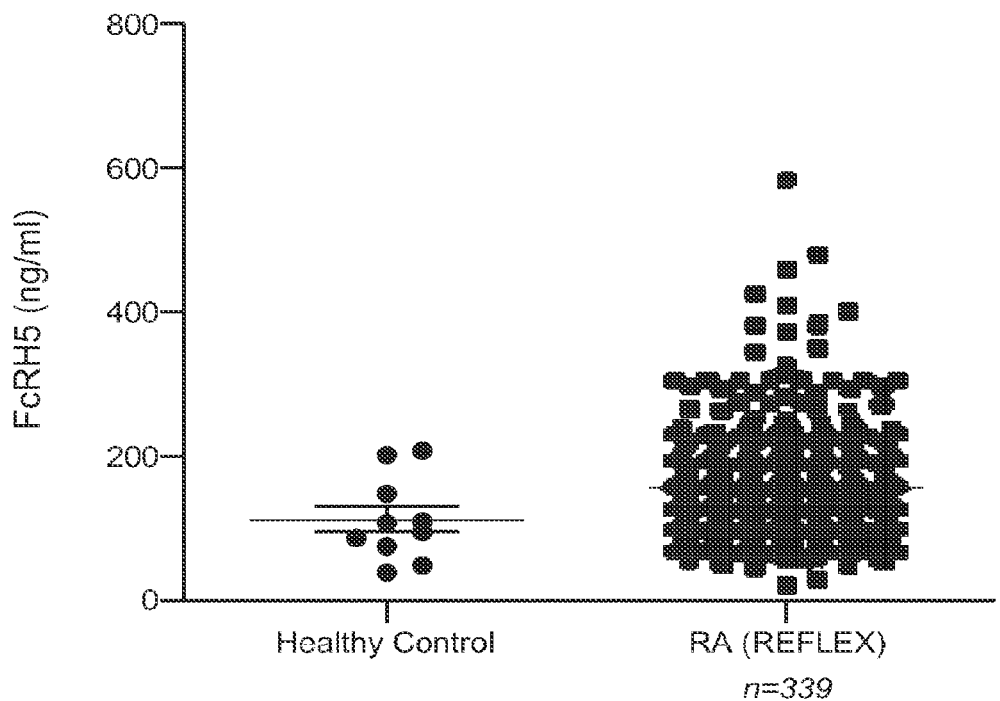

As shown in FIG. 11A, the serum level of sFcRH5 was clearly elevated in some RA patients compared to healthy controls. Accordingly, these results support the hypothesis that sFcRH5 serum levels can be used as a serum biomarker of RA, including L subtype of RA.

Figure 11B:
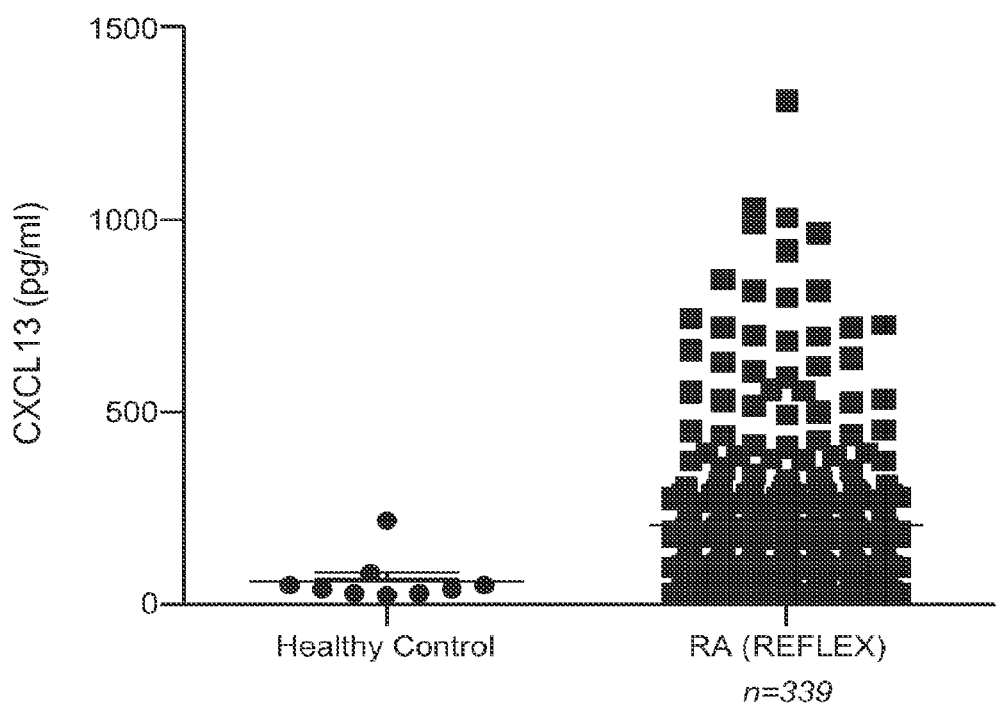

In addition, we determined the serum levels of CXCL13 in the same patient samples and healthy controls using the human CXCL13/BLC/BCA-1 Quantikine ELISA Kit from R&D Systems (Cat. No. DCX130). The data are shown in FIG. 11B. Similar to the results with sFcRH5, FIG. 11B shows that serum levels of CXCL13 were elevated in some RA patients compared to healthy controls. Thus, these results support the hypothesis that CXCL13 serum levels can be used as a serum biomarker of RA, including L subtype of RA.

Next, we conducted a threshold sensitivity analysis of the sFcRH5 and CXCL13 data to identify patient subgroups within the REFLEX trial with greater clinical benefit to rituximab as defined by ACR50 response at 24 weeks. The threshold sensitivity analysis was conducted as follows. The objective was to identify candidate biomarker subgroups that represented at least 20% of patients from the REFLEX trial and enriched for placebo-corrected ACR50 responses (ACR50 for the rituximab plus methotrexate group minus ACR50 for the placebo plus methotrexate group) at week 24 after the first course of rituximab. To identify subgroups with increased clinical benefit, the study population from REFLEX was stratified using baseline clinical characteristics and serological biomarkers measured in patients for whom serum samples were available. The baseline characteristics for the patient subgroups that had matching biomarker serum samples were comparable with the overall patient group in the clinical trial. For surveys of each continuous biomarker (where a range of discrete values was possible) and outcome measure ACR50 at week 24, a plot was generated presenting subgroup efficacy differentials versus a range of potential threshold values (20th-80$^{th}$ biomarker percentiles in 5-percentile increments) to control bias. The threshold giving the largest efficacy differential (Δhigh−Δlow) was then identified. For this threshold, a permutation test was used to address statistical significance. For each permutation, biomarker values were permuted and both treatment assignment and the outcome measure were fixed. The largest efficacy differential was computed for the permutated data set, which was compared to the largest efficacy differential observed from the original data. Permutation p-values were based on 2000 permutations. A 95% confidence interval on the largest efficacy differential was calculated.

FIG. 12 shows that a subgroup of patients with sFcRH5 levels greater than 126.7 ng/ml, and a subgroup of patients with CXCL13 levels greater than 116.6 pg/ml, demonstrated significantly higher ACR50 response rates compared with patients with lower levels of these biomarkers. The striped bars in FIG. 12 are rituximab-treated patients. FIG. 12 also shows that the placebo response rates (open bars) for these biomarker-defined subgroups did not behave in a similar manner. The right side of FIG. 12 shows the optimal subgroup efficacy difference (with 95% CI); i.e., the placebo-corrected efficacy difference between the biomarker-high and biomarker-low subgroups. Because the biomarker levels of both CXCL13 and sFcRH5 were associated with improved ACR50 rates in rituximab-treated patients, but not in placebo-treated patients, these results suggest that CXCL13 and sFcRH5 serum levels are predictive of enhanced responsiveness to rituximab and not, for example, simply prognostic for disease severity and/or progression.

We next assessed the level of the putative lymphoid signature serum marker Rheumatoid Factor (RF), a prototypical RA autoantibody, in combination with sFcRH5 in serum of patients in the REFLEX trial (described above) or a second trial known as SERENE. SERENE (Study Evaluating Rituximab's Efficacy in MTX iNadequate rEsponders) was also a pivotal placebo-controlled clinical trial of rituximab, but in DMARD-IR RA patients, the topline clinical findings of which were published by Emery et al., *Ann Rheum Dis.* 69(9):1629-35 (2010). In these experiments, sFcRH5 was assayed as described above. RF was assayed using a commercially available ELISA kit that measures IgM, IgG, and IgA isotypes of RF (Catalog #303-305, TheraTest Labs, Lombard, Ill.).

Figure 13A:
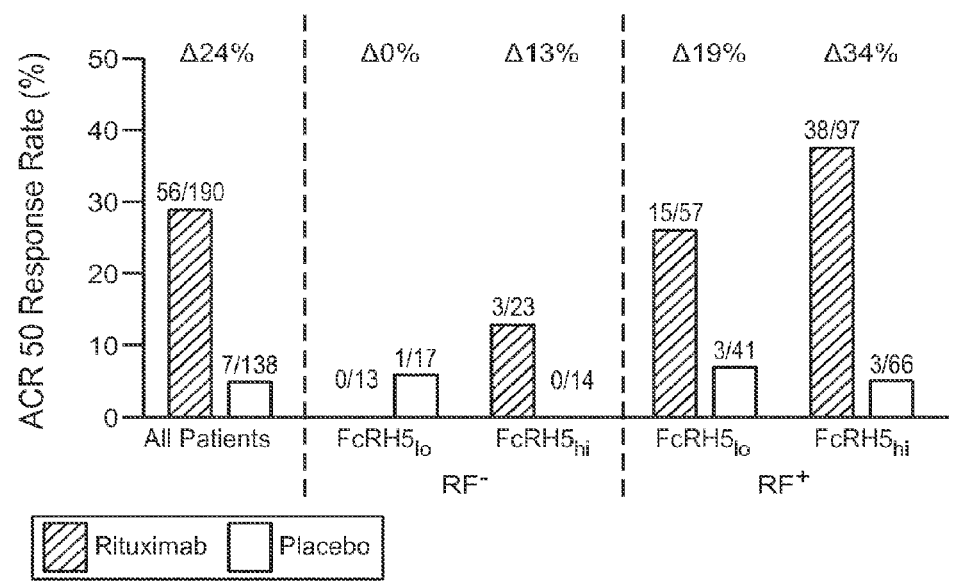
Figure 13B:
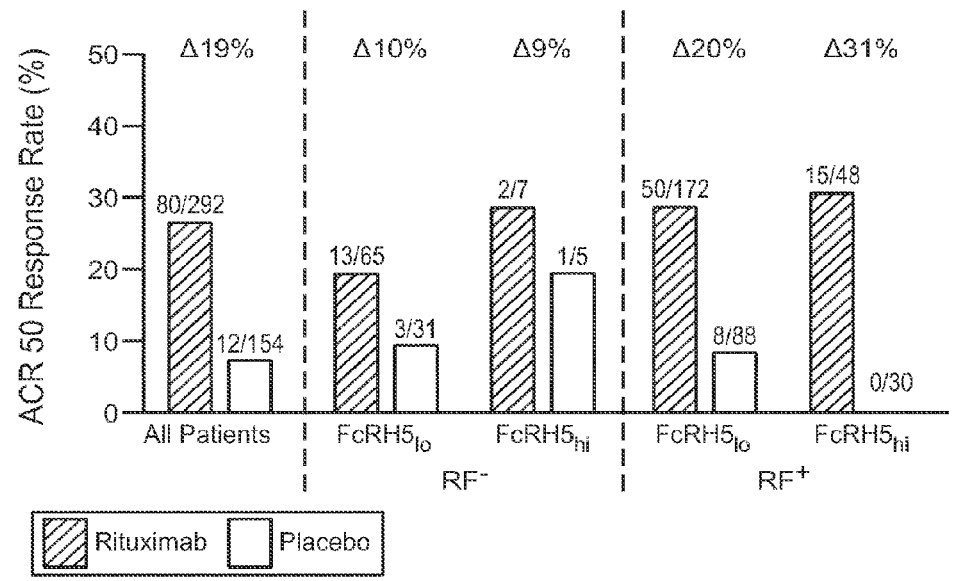

FIG. 13 shows the results of the assessment of placebo-controlled 24 week ACR50 response rates in lymphoid biomarker-defined patient subsets in both the REFLEX (FIG. 13A) and SERENE (FIG. 13B) trials. ACR50 response rates are shown for all patients in each study as well as patient subsets defined by sFcRH5 level and/or seropositivity for RF. The concentration cutoffs for sFcRH5 high vs sFcRH5 low subsets were 126.7 ng/ml for REFLEX and 165 ng/ml for SERENE as determined by a threshold sensitivity analysis for each study. The threshold sensitivity analysis was conducted as described above. The numbers of patients treated with rituximab or placebo, as well as the numbers of patients that subsequently met the ACR50 response criteria, are shown in FIGS. 13A-B for each subset. The placebo-controlled ACR50 response rate (ΔACR50) is indicated for each subset. As can be seen in FIGS. 13A and 13B, patient subsets with elevated sFcRH5 and also seropositive for RF had enhanced placebo-controlled ACR50 response rates compared with the unselected trial population. In contrast, the patient subsets defined by low sFcRH5 levels and/or seronegative status for RF had diminished placebo-controlled ACR50 rates.

In addition, in the REFLEX study we examined at baseline the soluble FcRH5 and RF biomarkers in combination with serum levels of CXCL13 for which an optimal cutpoint (116.6 pg/ml) had been determined using the threshold sensitivity method (see above). RF, sFcRH5 and CXCL13 were assayed as described above. FIG. 14 shows that patients with low baseline levels of all three biomarkers have no ACR50 response to rituximab treatment, while patients with high levels of all three biomarkers have enriched response to rituximab treatment. These data suggest that activity of the B cell pathway, a hallmark of the lymphoid subset, influences subsequent clinical response to B cell depletion therapy.

In summary, these data support the hypothesis that patients with RA characterized by a lymphoid infiltrate in their tissues, and with elevated serum levels of biomarkers specifically and significantly expressed in the L subtype gene expression signature, i.e., sFcRH5, CXCL13, and RF have a more robust clinical response to a B cell-depleting agent such as rituximab.

TABLE 5

Gene expression associated with the L subtype of RA.

| ProbeID | NETAFFX: GeneTitle | NETAFFX: GeneSymbol | Fold Change | p-value |
|---|---|---|---|---|
| 221286_s_at | proapoptotic caspase adaptor protein | PACAP | 22.72 | 1E−15 |
| 223565_at | proapoptotic caspase adaptor protein | PACAP | 14.29 | 5E−18 |
| 204698_at | interferon stimulated gene 20 kDa | ISG20 | 9.35 | 2E−09 |
| 1552623_at | hematopoietic SH2 domain containing | HSH2D | 9.32 | 1E−13 |
| 205267_at | "POU domain, class 2, associating factor 1" | POU2AF1 | 8.99 | 6E−21 |
| 228592_at | "Membrane-spanning 4-domains, subfamily A, member 1" | MS4A1 | 8.48 | 1E−12 |
| 206641_at | "tumor necrosis factor receptor superfamily, member 17" | TNFRSF17 | 6.79 | 4E−22 |
| 221602_s_at | regulator of Fas-induced apoptosis | regulator of Fas-induced apoptosis | TOSO | 6.43 | 5E−11 |
| 215946_x_at | "immunoglobulin lambda-like polypeptide 1 | similar to bK246H3.1 (immunoglobulin lambda-like polypeptide 1, pre-B-cell specific)" | IGLL1 | LOC91316 | 6.37 | 2E−18 |
| 204269_at | pim-2 oncogene | PIM2 | 6.27 | 1E−18 |
| 235401_s_at | Fc receptor homolog expressed in B cells | FREB | 6.21 | 2E−14 |
| 230673_at | polycystic kidney and hepatic disease 1 (autosomal recessive)-like 1 | PKHD1L1 | 6.16 | 2E−12 |
| 219463_at | chromosome 20 open reading frame 103 | C20orf103 | 6.14 | 3E−11 |
| 219159_s_at | SLAM family member 7 | SLAMF7 | 6.07 | 2E−18 |
| 217231_s_at | microtubule associated serine/threonine kinase 1 | MAST1 | 5.85 | 5E−12 |
| 217418_x_at | "membrane-spanning 4-domains, subfamily A, member 1" | MS4A1 | 5.71 | 7E−13 |
| 229971_at | G protein-coupled receptor 114 | GPR114 | 5.38 | 4E−19 |
| 230075_at | "RAB39B, member RAS oncogene family" | RAB39B | 5.34 | 9E−15 |
| 1552999_a_at | WAP four-disulfide core domain 10B | WFDC10B | 5.28 | 7E−12 |
| 210356_x_at | "membrane-spanning 4-domains, subfamily A, member 1" | MS4A1 | 5.18 | 1E−13 |
| 205544_s_at | complement component (3d/Epstein Barr virus) receptor 2 | CR2 | 5.12 | 3E−09 |
| 222838_at | SLAM family member 7 | SLAMF7 | 4.99 | 3E−20 |
| 234306_s_at | SLAM family member 7 | SLAMF7 | 4.80 | 9E−15 |
| 238695_s_at | "RAB39B, member RAS oncogene family" | RAB39B | 4.78 | 3E−13 |
| 235400_at | Fc receptor homolog expressed in B cells | FREB | 4.65 | 4E−12 |
| 228599_at | "Membrane-spanning 4-domains, subfamily A, member 1" | MS4A1 | 4.63 | 4E−13 |
| 210370_s_at | lymphocyte antigen 9 | LY9 | 4.51 | 1E−15 |
| 206866_at | "cadherin 4, type 1, R-cadherin (retinal)" | CDH4 | 4.50 | 4E−09 |
| 232112_at | Ral GEF with PH domain and SH3 binding motif 2 | RALGPS2 | 4.43 | 4E−14 |
| 220338_at | Ral GEF with PH domain and SH3 binding motif 2 | RALGPS2 | 4.40 | 7E−17 |
| 237759_at | CD48 antigen (B-cell membrane protein) | CD48 | 4.30 | 2E−13 |
| 241844_x_at | hypothetical protein FLJ23235 | FLJ23235 | 4.29 | 7E−15 |
| 201689_s_at | tumor protein D52 | TPD52 | 4.27 | 2E−16 |
| 236280_at | Transcribed locus | NA | 4.26 | 2E−17 |
| 226147_s_at | polymeric immunoglobulin receptor | PIGR | 4.21 | 2E−06 |
| 1553039_a_at | ankyrin repeat and SOCS box-containing 10 | ASB10 | 4.19 | 2E−12 |
| 201688_s_at | tumor protein D52 | TPD52 | 4.16 | 9E−15 |
| 206296_x_at | mitogen-activated protein kinase kinase kinase kinase 1 | MAP4K1 | 4.12 | 4E−08 |
| 212311_at | KIAA0746 protein | KIAA0746 | 4.10 | 8E−22 |
| 229152_at | chromosome 4 open reading frame 7 | C4orf7 | 4.08 | 6E−06 |
| 1555613_a_at | zeta-chain (TCR) associated protein kinase 70 kDa | ZAP70 | 4.06 | 1E−12 |
| 215967_s_at | lymphocyte antigen 9 | LY9 | 4.06 | 8E−11 |
| 215779_s_at | "histone 1, H2bg" | HIST1H2BG | 4.06 | 6E−11 |
| 219888_at | sperm associated antigen 4 | SPAG4 | 3.90 | 6E−17 |
| 204960_at | "protein tyrosine phosphatase, receptor type, C-associated protein" | PTPRCAP | 3.87 | 2E−14 |
| 205753_at | "C-reactive protein, pentraxin-related" | CRP | 3.86 | 1E−16 |
| 223750_s_at | toll-like receptor 10 | TLR10 | 3.86 | 2E−08 |
| 211517_s_at | "interleukin 5 receptor, alpha" | IL5RA | 3.82 | 5E−10 |
| 235863_at | homolog of mouse skeletal muscle sarcoplasmic reticulum protein JP-45 | FLJ32416 | 3.75 | 4E−09 |
| 214469_at | "histone 1, H2ae" | HIST1H2AE | 3.64 | 2E−08 |
| 227189_at | copine V | CPNE5 | 3.62 | 3E−21 |
| 229721_x_at | "Der1-like domain family, member 3" | DERL3 | 3.61 | 1E−19 |
| 201691_s_at | tumor protein D52 | TPD52 | 3.56 | 8E−14 |
| 220059_at | BCR downstream signaling 1 | BRDG1 | 3.54 | 3E−14 |
| 211789_s_at | Mlx interactor | MONDOA | 3.50 | 4E−08 |
| 201690_s_at | tumor protein D52 | TPD52 | 3.49 | 5E−18 |
| 210279_at | G protein-coupled receptor 18 | GPR18 | 3.49 | 2E−12 |
| 206686_at | "pyruvate dehydrogenase kinase, isoenzyme 1" | PDK1 | 3.42 | 5E−13 |
| 207245_at | "UDP glycosyltransferase 2 family, polypeptide B17" | UGT2B17 | 3.41 | 4E−06 |
| 1557770_at | "phosphatidylinositol-3-phosphate/phosphatidylinositol 5-kinase, type III" | PIP5K3 | 3.35 | 1E−22 |
| 220035_at | nucleoporin 210 kDa | NUP210 | 3.34 | 4E−13 |
| 221601_s_at | regulator of Fas-induced apoptosis | regulator of Fas-induced apoptosis | TOSO | 3.32 | 7E−11 |
| 214615_at | "purinergic receptor P2Y, G-protein coupled, 10" | P2RY10 | 3.27 | 1E−14 |
| 225792_at | Hook homolog 1 (*Drosophila*) | HOOK1 | 3.24 | 4E−16 |
| 234383_x_at | NA | NA | 3.23 | 2E−12 |
| 205903_s_at | "potassium intermediate/small conductance calcium-activated channel, subfamily N, member 3" | KCNN3 | 3.22 | 2E−08 |
| 240070_at | Hypothetical protein FLJ39873 | FLJ39873 | 3.21 | 9E−13 |
| 1555342_a_at | unc-5 homolog C (*C. elegans*) | UNC5C | 3.20 | 8E−15 |
| 206121_at | adenosine monophosphate deaminase 1 (isoform M) | AMPD1 | 3.20 | 1E−12 |
| 229629_at | Transcribed locus | NA | 3.17 | 4E−12 |
| 223246_s_at | spermatid perinuclear RNA binding protein | STRBP | 3.15 | 2E−11 |
| 242458_at | Ral GEF with PH domain and SH3 binding motif 2 | RALGPS2 | 3.14 | 5E−13 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 240098_at | RAP1 interacting factor homolog (yeast) | RIF1 | 3.12 | 5E−10 |
| 210448_s_at | "purinergic receptor P2X, ligand-gated ion channel, 5" | P2RX5 | 3.06 | 9E−12 |
| 204891_s_at | lymphocyte-specific protein tyrosine kinase | LCK | 3.03 | 2E−09 |
| 240265_at | TRAF3-interacting Jun N-terminal kinase (JNK)-activating modulator | T3JAM | 3.01 | 9E−11 |
| 228705_at | calpain 12 | CAPN12 | 2.99 | 2E−09 |
| 215243_s_at | "gap junction protein, beta 3, 31 kDa (connexin 31)" | GJB3 | 2.99 | 1E−13 |
| 207237_at | "potassium voltage-gated channel, shaker-related subfamily, member 3" | KCNA3 | 2.98 | 8E−11 |
| 228897_at | "Der1-like domain family, member 3" | DERL3 | 2.95 | 2E−16 |
| 213888_s_at | TRAF3-interacting Jun N-terminal kinase (JNK)-activating modulator | T3JAM | 2.90 | 1E−13 |
| 243969_at | "solute carrier family 24 (sodium/potassium/calcium exchanger), member 4" | SLC24A4 | 2.90 | 3E−10 |
| 209602_s_at | GATA binding protein 3 | GATA3 | 2.89 | 9E−08 |
| 206398_s_at | CD19 antigen | CD19 | 2.87 | 3E−16 |
| 220169_at | hypothetical protein FLJ23235 | FLJ23235 | 2.86 | 9E−14 |
| 237251_at | hypothetical protein FLJ32884 | FLJ32884 | 2.85 | 2E−08 |
| 223751_x_at | toll-like receptor 10 | TLR10 | 2.83 | 1E−14 |
| 235165_at | par-6 partitioning defective 6 homolog beta (*C. elegans*) | PARD6B | 2.83 | 8E−08 |
| 227134_at | synaptotagmin-like 1 | SYTL1 | 2.82 | 2E−20 |
| 208553_at | "histone 1, H1e" | HIST1H1E | 2.82 | 9E−05 |
| 206780_at | "glutamate decarboxylase 2 (pancreatic islets and brain, 65 kDa)" | GAD2 | 2.82 | 2E−05 |
| 206048_at | zinc finger protein 339 | ZNF339 | 2.82 | 1E−08 |
| 200670_at | X-box binding protein 1 | XBP1 | 2.81 | 7E−22 |
| 220507_s_at | "ureidopropionase, beta" | UPB1 | 2.81 | 5E−13 |
| 231124_x_at | Lymphocyte antigen 9 | LY9 | 2.81 | 6E−13 |
| 209829_at | chromosome 6 open reading frame 32 | C6orf32 | 2.80 | 1E−08 |
| 224102_at | "purinergic receptor P2Y, G-protein coupled, 12" | P2RY12 | 2.80 | 2E−05 |
| 222067_x_at | "histone 1, H2bd" | HIST1H2BD | 2.78 | 8E−15 |
| 233500_x_at | "C-type lectin superfamily 2, member D" | CLEC2D | 2.77 | 5E−08 |
| 1561820_at | "sodium channel, voltage gated, type VIII, alpha" | SCN8A | 2.76 | 6E−15 |
| 241914_s_at | hypothetical protein LOC123876 \| xenobiotic/medium-chain fatty acid: CoA ligase | LOC123876 \| HXMA | 2.76 | 5E−13 |
| 219014_at | placenta-specific 8 | PLAC8 | 2.76 | 2E−11 |
| 228167_at | kelch-like 6 (*Drosophila*) | KLHL6 | 2.75 | 2E−19 |
| 206896_s_at | "guanine nucleotide binding protein (G protein), gamma 7" | GNG7 | 2.74 | 4E−16 |
| 216277_at | BUB1 budding uninhibited by benzimidazoles 1 homolog (yeast) | BUB1 | 2.74 | 1E−12 |
| 228258_at | FLJ00332 protein | FLJ00332 | 2.72 | 2E−11 |
| 1553237_x_at | "protocadherin alpha subfamily C, 1" | PCDHAC1 | 2.72 | 4E−10 |
| 214470_at | "killer cell lectin-like receptor subfamily B, member 1 \| killer cell lectin-like receptor subfamily B, member 1" | KLRB1 | 2.71 | 4E−12 |
| 220126_at | testes-specific protease 50 | TSP50 | 2.71 | 1E−07 |
| 204563_at | selectin L (lymphocyte adhesion molecule 1) | SELL | 2.70 | 1E−09 |
| 1560219_at | "CDNA FLJ34490 fis, clone HLUNG2004707" | NA | 2.67 | 4E−13 |
| 210538_s_at | baculoviral IAP repeat-containing 3 | BIRC3 | 2.67 | 1E−10 |
| 237323_at | hypothetical protein FLJ22761 | FLJ22761 | 2.66 | 2E−10 |
| 204949_at | intercellular adhesion molecule 3 | ICAM3 | 2.65 | 3E−17 |
| 212314_at | KIAA0746 protein | KIAA0746 | 2.65 | 3E−18 |
| 224520_s_at | hypothetical protein MGC13168 \| hypothetical protein MGC13168 | MGC13168 | 2.65 | 1E−10 |
| 228320_x_at | hypothetical protein LOC92558 | LOC92558 | 2.65 | 1E−09 |
| 206255_at | B lymphoid tyrosine kinase | BLK | 2.64 | 2E−08 |
| 1558972_s_at | chromosome 6 open reading frame 190 | C6orf190 | 2.64 | 2E−09 |
| 1555086_at | signal transducer and activator of transcription 5B | STAT5B | 2.63 | 9E−08 |
| 237159_x_at | "Transcribed locus, weakly similar to XP_517655.1 similar to KIAA0825 protein [*Pan troglodytes*]" | NA | 2.62 | 2E−08 |
| 206337_at | chemokine (C-C motif) receptor 7 \| chemokine (C-C motif) receptor 7 | CCR7 | 2.62 | 5E−11 |
| 1552596_at | growth arrest-specific 2 like 2 | GAS2L2 | 2.61 | 2E−12 |
| 230011_at | similar to mouse meiosis defective 1 gene | MGC40042 | 2.60 | 9E−17 |
| 226452_at | "pyruvate dehydrogenase kinase, isoenzyme 1" | PDK1 | 2.59 | 7E−16 |
| 229686_at | "purinergic receptor P2Y, G-protein coupled, 8" | P2RY8 | 2.59 | 6E−19 |
| 214540_at | "histone 1, H2bo" | HIST1H2BO | 2.58 | 4E−09 |
| 205890_s_at | ubiquitin D | UBD | 2.58 | 2E−07 |
| 223299_at | SEC11-like 3 (*S. cerevisiae*) | SEC11L3 | 2.58 | 3E−16 |
| 239088_at | Transcribed locus | NA | 2.58 | 2E−10 |
| 1552940_at | putative membrane protein HE9 | HE9 | 2.58 | 2E−06 |
| 230863_at | Low density lipoprotein-related protein 2 | LRP2 | 2.58 | 2E−06 |
| 1563290_at | "dynein, axonemal, heavy polypeptide 3" | DNAH3 | 2.57 | 7E−11 |
| 213915_at | natural killer cell group 7 sequence | NKG7 | 2.55 | 7E−09 |
| 208515_at | "histone 1, H2bm" | HIST1H2BM | 2.55 | 3E−10 |
| 209813_x_at | T cell receptor gamma variable 9 \| T cell receptor gamma variable 9 \| TCR gamma alternate reading frame protein \| TCR gamma alternate reading frame protein | TRGV9 \| TARP | 2.55 | 2E−12 |
| 219551_at | ELL associated factor 2 | EAF2 | 2.54 | 2E−18 |
| 216901_s_at | "zinc finger protein, subfamily 1A, 1 (Ikaros)" | ZNFN1A1 | 2.54 | 3E−07 |
| 1554069_at | EPH receptor A8 | EPHA8 | 2.53 | 7E−07 |
| 237230_at | glycoprotein hormone alpha 2 | GPHA2 | 2.53 | 1E−05 |
| 1558971_at | chromosome 6 open reading frame 190 | C6orf190 | 2.52 | 3E−12 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 232352_at | "ISL2 transcription factor, LIM/homeodomain, (islet-2)" | ISL2 | 2.52 | 9E−07 |
| 214032_at | zeta-chain (TCR) associated protein kinase 70 kDa | ZAP70 | 2.51 | 2E−09 |
| 1565836_at | NA | NA | 2.48 | 1E−10 |
| 231746_at | Mix1 homeobox-like 1 (*Xenopus laevis*) | MIXL1 | 2.48 | 2E−11 |
| 241860_at | Serine/threonine kinase 17b (apoptosis-inducing) | STK17B | 2.48 | 4E−11 |
| 221271_at | interleukin 21 | IL21 | 2.47 | 2E−07 |
| 244780_at | sphingosine-1-phosphate phosphatase 2 | SGPP2 | 2.46 | 1E−06 |
| 231021_at | "Solute carrier family 6 (neurotransmitter transporter), member 19" | SLC6A19 | 2.46 | 2E−08 |
| 1554240_a_at | "integrin, alpha L (antigen CD11A (p180), lymphocyte function-associated antigen 1; alpha polypeptide)" | ITGAL | 2.45 | 4E−12 |
| 1555687_a_at | "C-type lectin domain family 4, member C" | CLEC4C | 2.44 | 4E−09 |
| 217073_x_at | apolipoprotein A-I | APOA1 | 2.43 | 7E−05 |
| 243797_at | serine/threonine kinase 17b (apoptosis-inducing) | STK17B | 2.42 | 2E−11 |
| 215960_at | "solute carrier family 5 (low affinity glucose cotransporter), member 4" | SLC5A4 | 2.42 | 2E−07 |
| 204536_s_at | NA | NA | 2.42 | 2E−07 |
| 1553279_at | butyrophilin-like 9 | BTNL9 | 2.41 | 2E−05 |
| 1553856_s_at | "purinergic receptor P2Y, G-protein coupled, 10" | P2RY10 | 2.40 | 6E−14 |
| 236341_at | cytotoxic T-lymphocyte-associated protein 4 | CTLA4 | 2.40 | 7E−09 |
| 211181_x_at | runt-related transcription factor 1 (acute myeloid leukemia 1; aml1 oncogene) | RUNX1 | 2.39 | 3E−08 |
| 213534_s_at | PAS domain containing serine/threonine kinase | PASK | 2.39 | 2E−11 |
| 208546_x_at | "histone 1, H2bh" | HIST1H2BH | 2.38 | 6E−07 |
| 222897_s_at | zinc finger protein 64 homolog (mouse) | ZFP64 | 2.38 | 3E−09 |
| 235372_at | Fc receptor homolog expressed in B cells | FREB | 2.37 | 9E−16 |
| 224538_s_at | par-6 partitioning defective 6 homolog gamma (*C. elegans*) \| par-6 partitioning defective 6 homolog gamma (*C. elegans*) | PARD6G | 2.37 | 6E−12 |
| 205804_s_at | TRAF3-interacting Jun N-terminal kinase (JNK)-activating modulator | T3JAM | 2.37 | 1E−09 |
| 229360_at | suppressor of hairy wing homolog 2 (*Drosophila*) | SUHW2 | 2.36 | 3E−11 |
| 1554343_a_at | BCR downstream signaling 1 | BRDG1 | 2.36 | 1E−10 |
| 1552386_at | hypothetical protein FLJ33641 | FLJ33641 | 2.36 | 6E−10 |
| 237162_at | ankyrin repeat domain 15 | ANKRD15 | 2.35 | 1E−05 |
| 1552839_at | chromosome 14 open reading frame 54 | C14orf54 | 2.35 | 5E−07 |
| 221331_x_at | cytotoxic T-lymphocyte-associated protein 4 | CTLA4 | 2.34 | 8E−11 |
| 233252_s_at | spermatid perinuclear RNA binding protein | STRBP | 2.34 | 3E−18 |
| 210769_at | cyclic nucleotide gated channel beta 1 | CNGB1 | 2.33 | 2E−07 |
| 204470_at | "chemokine (C-X-C motif) ligand 1 (melanoma growth stimulating activity, alpha)" | CXCL1 | 2.33 | 2E−06 |
| 204475_at | matrix metalloproteinase 1 (interstitial collagenase) | MMP1 | 2.33 | 8E−06 |
| 205884_at | "integrin, alpha 4 (antigen CD49D, alpha 4 subunit of VLA-4 receptor)" | ITGA4 | 2.31 | 9E−11 |
| 223953_s_at | zinc finger and BTB domain containing 37 | ZBTB37 | 2.30 | 3E−05 |
| 207635_s_at | "potassium voltage-gated channel, subfamily H (eag-related), member 1" | KCNH1 | 2.30 | 1E−06 |
| 1553890_s_at | hypothetical protein BC018697 | LOC126147 | 2.30 | 6E−12 |
| 211469_s_at | chemokine (C-X-C motif) receptor 6 | CXCR6 | 2.29 | 6E−09 |
| 220286_at | hypothetical protein FLJ20313 | FLJ20313 | 2.29 | 2E−05 |
| 204890_s_at | lymphocyte-specific protein tyrosine kinase | LCK | 2.29 | 2E−09 |
| 228298_at | hypothetical protein MGC16044 | MGC16044 | 2.29 | 2E−17 |
| 216920_s_at | T cell receptor gamma variable 9 \| TCR gamma alternate reading frame protein | TRGV9 \| TARP | 2.29 | 1E−16 |
| 214595_at | "potassium voltage-gated channel, subfamily G, member 1" | KCNG1 | 2.28 | 5E−07 |
| 228236_at | chromosome 20 open reading frame 54 | C20orf54 | 2.28 | 3E−07 |
| 221690_s_at | "NACHT, leucine rich repeat and PYD containing 2" | NALP2 | 2.28 | 1E−12 |
| 208523_x_at | "histone 1, H2bi" | HIST1H2BI | 2.27 | 1E−05 |
| 221442_at | melanocortin 3 receptor | MC3R | 2.26 | 4E−13 |
| 233504_at | chromosome 9 open reading frame 84 | C9orf84 | 2.26 | 4E−05 |
| 1553675_at | kinesin-like 8 | KNSL8 | 2.26 | 3E−07 |
| 205309_at | "sphingomyelin phosphodiesterase, acid-like 3B" | SMPDL3B | 2.25 | 1E−10 |
| 211339_s_at | IL2-inducible T-cell kinase | ITK | 2.25 | 1E−08 |
| 206367_at | renin | REN | 2.25 | 2E−07 |
| 244033_at | NA | NA | 2.25 | 3E−18 |
| 232635_at | chromosome 14 open reading frame 145 | C14orf145 | 2.24 | 1E−14 |
| 227353_at | Epidermodysplasia verruciformis 2 | EVER2 | 2.24 | 3E−12 |
| 1552806_a_at | sialic acid binding Ig-like lectin 10 | SIGLEC10 | 2.23 | 1E−06 |
| 33304_at | interferon stimulated gene 20 kDa | ISG20 | 2.23 | 7E−14 |
| 206369_s_at | "phosphoinositide-3-kinase, catalytic, gamma polypeptide" | PIK3CG | 2.22 | 3E−06 |
| 238629_x_at | NA | NA | 2.22 | 4E−06 |
| 205254_x_at | "transcription factor 7 (T-cell specific, HMG-box)" | TCF7 | 2.22 | 4E−10 |
| 1553804_a_at | hypothetical protein FLJ25414 | FLJ25414 | 2.21 | 4E−11 |
| 204118_at | CD48 antigen (B-cell membrane protein) \| CD48 antigen (B-cell membrane protein) | CD48 | 2.20 | 3E−15 |
| 211885_x_at | "fucosyltransferase 6 (alpha (1,3) fucosyltransferase)" | FUT6 | 2.20 | 3E−07 |
| 1569980_x_at | GLI-Kruppel family member HKR1 | HKR1 | 2.20 | 3E−05 |
| 1552682_a_at | AF15q14 protein | AF15Q14 | 2.20 | 2E−07 |
| 215806_x_at | T cell receptor gamma variable 9 \| TCR gamma alternate reading frame protein | TRGV9 \| TARP | 2.20 | 8E−15 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 223903_at | toll-like receptor 9 | TLR9 | 2.20 | 5E−16 |
| 206785_s_at | "killer cell lectin-like receptor subfamily C, member 1 \| killer cell lectin-like receptor subfamily C, member 2" | KLRC1 \| KLRC2 | 2.20 | 4E−11 |
| 217552_x_at | "complement component (3b/4b) receptor 1, including Knops blood group system" | CR1 | 2.20 | 1E−07 |
| 216945_x_at | PAS domain containing serine/threonine kinase | PASK | 2.19 | 2E−10 |
| 211182_x_at | runt-related transcription factor 1 (acute myeloid leukemia 1; aml1 oncogene) | RUNX1 | 2.19 | 2E−07 |
| 1556149_at | armadillo repeat gene deletes in velocardiofacial syndrome | ARVCF | 2.19 | 9E−13 |
| 210265_x_at | NA | NA | 2.19 | 1E−05 |
| 227182_at | sushi domain containing 3 | SUSD3 | 2.18 | 1E−09 |
| 228795_at | "Protein kinase C, beta 1" | PRKCB1 | 2.18 | 4E−08 |
| 1570200_at | helicase (DNA) B | HELB | 2.17 | 8E−07 |
| 206324_s_at | death-associated protein kinase 2 | DAPK2 | 2.17 | 3E−09 |
| 236554_x_at | epidermodysplasia verruciformis 2 | EVER2 | 2.16 | 3E−13 |
| 233094_at | "Ubiquitin-conjugating enzyme E2D 1 (UBC4/5 homolog, yeast)" | UBE2D1 | 2.16 | 5E−07 |
| 228865_at | specifically androgen-regulated protein | SARG | 2.16 | 7E−08 |
| 225619_at | hypothetical protein FLJ30046 | FLJ30046 | 2.15 | 9E−10 |
| 210031_at | "CD3Z antigen, zeta polypeptide (TiT3 complex)" | CD3Z | 2.15 | 2E−11 |
| 205885_s_at | "integrin, alpha 4 (antigen CD49D, alpha 4 subunit of VLA-4 receptor)" | ITGA4 | 2.15 | 1E−09 |
| 219852_s_at | hypothetical protein FLJ13941 | FLJ13941 | 2.15 | 7E−07 |
| 209398_at | "histone 1, H1c" | HIST1H1C | 2.15 | 1E−11 |
| 209353_s_at | hypothetical protein MGC16664 | MGC16664 | 2.14 | 4E−06 |
| 228360_at | hypothetical protein LOC130576 | LOC130576 | 2.14 | 8E−09 |
| 215925_s_at | CD72 antigen | CD72 | 2.14 | 2E−09 |
| 207849_at | interleukin 2 | IL2 | 2.14 | 6E−05 |
| 213475_s_at | "integrin, alpha L (antigen CD11A (p180), lymphocyte function-associated antigen 1; alpha polypeptide)" | ITGAL | 2.14 | 6E−10 |
| 227641_at | F-box and leucine-rich repeat protein 16 | FBXL16 | 2.14 | 6E−15 |
| 236995_x_at | Transcription factor EC | TFEC | 2.13 | 4E−10 |
| 1553057_at | "serine (or cysteine) proteinase inhibitor, clade B (ovalbumin), member 12" | SERPINB12 | 2.13 | 1E−07 |
| 208574_at | SRY (sex determining region Y)-box 14 | SOX14 | 2.13 | 2E−06 |
| 214567_s_at | chemokine (C motif) ligand 1 \| chemokine (C motif) ligand 2 | XCL1 \| XCL2 | 2.12 | 7E−06 |
| 238531_x_at | NA | NA | 2.12 | 5E−08 |
| 231966_at | "protein phosphatase 1, regulatory (inhibitor) subunit 9A" | PPP1R9A | 2.12 | 1E−05 |
| 244578_at | lymphocyte cytosolic protein 2 (SH2 domain containing leukocyte protein of 76 kDa) | LCP2 | 2.12 | 6E−06 |
| 244781_x_at | IBR domain containing 2 | IBRDC2 | 2.12 | 6E−06 |
| 223709_s_at | "wingless-type MMTV integration site family, member 10A" | WNT10A | 2.12 | 7E−14 |
| 236655_at | Tumor protein D52 | TPD52 | 2.11 | 4E−11 |
| 211232_x_at | glucagon-like peptide 1 receptor | GLP1R | 2.11 | 2E−08 |
| 207226_at | "histone 1, H2bn" | HIST1H2BN | 2.11 | 7E−05 |
| 204852_s_at | "protein tyrosine phosphatase, non-receptor type 7" | PTPN7 | 2.11 | 7E−10 |
| 206437_at | "endothelial differentiation, G-protein-coupled receptor 6" | EDG6 | 2.11 | 3E−09 |
| 1552552_s_at | "C-type lectin domain family 4, member C" | CLEC4C | 2.10 | 2E−11 |
| 1560225_at | "Homo sapiens, clone IMAGE: 5244076, mRNA" | NA | 2.10 | 9E−08 |
| 231776_at | eomesodermin homolog (Xenopus laevis) | EOMES | 2.09 | 2E−08 |
| 212316_at | nucleoporin 210 kDa | NUP210 | 2.09 | 8E−15 |
| 206244_at | "complement component (3b/4b) receptor 1, including Knops blood group system" | CR1 | 2.09 | 8E−08 |
| 209695_at | "protein tyrosine phosphatase type IVA, member 3" | PTP4A3 | 2.09 | 2E−08 |
| 224273_at | chromosome 3 open reading frame 20 | C3orf20 | 2.09 | 1E−11 |
| 201287_s_at | syndecan 1 | SDC1 | 2.08 | 2E−09 |
| 240254_at | TRAF2 and NCK interacting kinase | TNIK | 2.08 | 2E−08 |
| 209603_at | GATA binding protein 3 | GATA3 | 2.08 | 6E−05 |
| 222859_s_at | dual adaptor of phosphotyrosine and 3-phosphoinositides | DAPP1 | 2.07 | 6E−12 |
| 1552807_a_at | sialic acid binding Ig-like lectin 10 | SIGLEC10 | 2.06 | 1E−05 |
| 1553132_a_at | membrane targeting (tandem) C2 domain containing 1 | MTAC2D1 | 2.06 | 3E−08 |
| 208060_at | paired box gene 7 | PAX7 | 2.06 | 7E−07 |
| 223732_at | "solute carrier family 23 (nucleobase transporters), member 1" | SLC23A1 | 2.06 | 2E−06 |
| 235229_at | "PREDICTED: Homo sapiens similar to Olfactory receptor 2I2 (LOC442197), mRNA" | NA | 2.05 | 4E−05 |
| 210313_at | "leukocyte immunoglobulin-like receptor, subfamily A (without TM domain), member 4" | ILT7 | 2.05 | 2E−06 |
| 206761_at | CD96 antigen | CD96 | 2.05 | 3E−13 |
| 241871_at | calcium/calmodulin-dependent protein kinase IV | CAMK4 | 2.05 | 5E−08 |
| 214157_at | GNAS complex locus | GNAS | 2.05 | 4E−17 |
| 41577_at | "protein phosphatase 1, regulatory (inhibitor) subunit 16B" | PPP1R16B | 2.05 | 3E−09 |
| 236852_at | NA | NA | 2.03 | 7E−06 |
| 207651_at | G protein-coupled receptor 171 | GPR171 | 2.03 | 4E−06 |
| 212315_s_at | nucleoporin 210 kDa | NUP210 | 2.03 | 1E−12 |
| 219812_at | Stromal antigen 3 | STAG3 | 2.03 | 3E−12 |
| 207655_s_at | B-cell linker | BLNK | 2.02 | 2E−17 |
| 206574_s_at | "protein tyrosine phosphatase type IVA, member 3" | PTP4A3 | 2.02 | 1E−08 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 206534_at | "glutamate receptor, ionotropic, N-methyl D-aspartate 2A" | GRIN2A | 2.02 | 4E−07 |
| 211384_s_at | "calcium-sensing receptor (hypocalciuric hypercalcemia 1, severe neonatal hyperparathyroidism)" | CASR | 2.02 | 1E−06 |
| 226659_at | differentially expressed in FDCP 6 homolog (mouse) | DEF6 | 2.02 | 2E−13 |
| 224289_s_at | FKSG83 | FKSG83 | 2.01 | 5E−05 |
| 208401_s_at | glucagon-like peptide 1 receptor | GLP1R | 2.01 | 5E−05 |
| 208888_s_at | nuclear receptor co-repressor 2 | NCOR2 | 2.01 | 3E−05 |
| 206897_at | "P antigen family, member 1 (prostate associated)" | PAGE1 | 2.01 | 2E−08 |
| 206978_at | chemokine (C-C motif) receptor 2 \| chemokine (C-C motif) receptor 2 | CCR2 | 2.01 | 3E−10 |
| 205828_at | "matrix metalloproteinase 3 (stromelysin 1, progelatinase)" | MMP3 | 2.00 | 2E−06 |
| 206449_s_at | mannan-binding lectin serine protease 1 (C4/C2 activating component of Ra-reactive factor) | MASP1 | 2.00 | 7E−10 |
| 217489_s_at | interleukin 6 receptor | IL6R | 1.99 | 2E−09 |
| 215509_s_at | BUB1 budding uninhibited by benzimidazoles 1 homolog (yeast) | BUB1 | 1.99 | 7E−06 |
| 220279_at | tripartite motif-containing 17 | TRIM17 | 1.99 | 4E−05 |
| 207902_at | "interleukin 5 receptor, alpha" | IL5RA | 1.99 | 2E−09 |
| 242375_x_at | NA | NA | 1.98 | 7E−06 |
| 1561336_at | deoxyribonuclease I-like 3 | DNASE1L3 | 1.98 | 2E−07 |
| 1564713_a_at | forkhead box N4 | FOXN4 | 1.98 | 3E−15 |
| 235522_at | NA | NA | 1.98 | 9E−12 |
| 202064_s_at | sel-1 suppressor of lin-12-like (C. elegans) | SEL1L | 1.98 | 5E−10 |
| 1560397_s_at | kelch-like 6 (Drosophila) | KLHL6 | 1.97 | 8E−07 |
| 203399_x_at | pregnancy specific beta-1-glycoprotein 3 | PSG3 | 1.97 | 8E−05 |
| 234362_s_at | cytotoxic T-lymphocyte-associated protein 4 | CTLA4 | 1.97 | 3E−12 |
| 236454_at | NA | NA | 1.97 | 1E−06 |
| 214446_at | "elongation factor, RNA polymerase II, 2" | ELL2 | 1.97 | 4E−05 |
| 207634_at | programmed cell death 1 | PDCD1 | 1.97 | 2E−07 |
| 206828_at | TXK tyrosine kinase | TXK | 1.97 | 3E−07 |
| 1559051_s_at | chromosome 6 open reading frame 150 | C6orf150 | 1.96 | 5E−11 |
| 223536_at | pleckstrin and Sec7 domain containing 2 | PSD2 | 1.96 | 3E−10 |
| 229526_at | aquaporin 11 | AQP11 | 1.96 | 1E−05 |
| 206366_x_at | chemokine (C motif) ligand 2 | XCL2 | 1.96 | 7E−05 |
| 229065_at | "solute carrier family 35, member F3" | SLC35F3 | 1.95 | 3E−07 |
| 1553486_a_at | hypothetical protein FLJ39647 | FLJ39647 | 1.95 | 8E−05 |
| 204769_s_at | "transporter 2, ATP-binding cassette, sub-family B (MDR/TAP)" | TAP2 | 1.95 | 3E−06 |
| 211670_x_at | "synovial sarcoma, X breakpoint 3 \| synovial sarcoma, X breakpoint 3" | SSX3 | 1.95 | 2E−05 |
| 1553176_at | SH2 domain-containing molecule EAT2 | EAT2 | 1.95 | 4E−08 |
| 206800_at | "5,10-methylenetetrahydrofolate reductase (NADPH)" | MTHFR | 1.95 | 2E−11 |
| 220563_s_at | SH3 and multiple ankyrin repeat domains 1 | SHANK1 | 1.94 | 2E−06 |
| 244195_at | Tubby like protein 4 | TULP4 | 1.94 | 8E−05 |
| 1556653_at | hypothetical protein FLJ25415 | FLJ25415 | 1.94 | 9E−07 |
| 228427_at | F-box protein 16 | FBXO16 | 1.94 | 3E−09 |
| 235116_at | TNF receptor-associated factor 1 | TRAF1 | 1.93 | 1E−10 |
| 226226_at | transmembrane protein 45B | TMEM45B | 1.93 | 6E−06 |
| 1559474_at | aortic preferentially expressed protein 1 | APEG1 | 1.93 | 3E−09 |
| 1559438_at | chromosome 21 open reading frame 58 | C21orf58 | 1.93 | 8E−06 |
| 1568822_at | GTP binding protein 5 (putative) | GTPBP5 | 1.93 | 7E−06 |
| 235117_at | similar to RIKEN cDNA 2510006C20 gene | LOC494143 | 1.92 | 3E−13 |
| 208490_x_at | "histone 1, H2bf" | HIST1H2BF | 1.92 | 1E−12 |
| 1552787_at | helicase (DNA) B | HELB | 1.92 | 1E−11 |
| 214481_at | "histone 1, H2am" | HIST1H2AM | 1.92 | 9E−05 |
| 1554050_at | "sphingomyelin phosphodiesterase, acid-like 3B" | SMPDL3B | 1.92 | 3E−15 |
| 240997_at | Hypothetical protein LOC131873 | LOC131873 | 1.92 | 1E−07 |
| 220132_s_at | "C-type lectin superfamily 2, member D" | CLEC2D | 1.92 | 4E−09 |
| 241723_at | IQ motif containing GTPase activating protein 2 | IQGAP2 | 1.92 | 8E−05 |
| 215551_at | estrogen receptor 1 | ESR1 | 1.92 | 8E−06 |
| 215071_s_at | NA | NA | 1.92 | 2E−08 |
| 213820_s_at | START domain containing 5 | STARD5 | 1.92 | 1E−05 |
| 218614_at | hypothetical protein FLJ10652 | FLJ10652 | 1.91 | 1E−13 |
| 219144_at | hypothetical protein MGC1136 | MGC1136 | 1.91 | 1E−05 |
| 220030_at | serine/threonine/tyrosine kinase 1 | STYK1 | 1.91 | 4E−06 |
| 243981_at | serine/threonine kinase 4 | STK4 | 1.91 | 8E−10 |
| 1557720_s_at | myosin heavy chain Myr 8 | MYR8 | 1.91 | 4E−07 |
| 229391_s_at | similar to RIKEN cDNA A630077B13 gene; RIKEN cDNA 2810048G17 | LOC441168 | 1.91 | 2E−05 |
| 227346_at | "Zinc finger protein, subfamily 1A, 1 (Ikaros)" | ZNFN1A1 | 1.90 | 6E−11 |
| 1553641_a_at | "testis specific, 13" | TSGA13 | 1.90 | 1E−05 |
| 226150_at | HTPAP protein | HTPAP | 1.90 | 3E−15 |
| 220144_s_at | ankyrin repeat domain 5 | ANKRD5 | 1.90 | 1E−06 |
| 207770_x_at | chorionic somatomammotropin hormone 2 | CSH2 | 1.90 | 1E−05 |
| 202063_at | sel-1 suppressor of lin-12-like (C. elegans) | SEL1L | 1.90 | 5E−15 |
| 209083_at | "coronin, actin binding protein, 1A" | CORO1A | 1.89 | 1E−07 |
| 221023_s_at | "potassium voltage-gated channel, subfamily H (eag-related), member 6 \| potassium voltage-gated channel, subfamily H (eag-related), member 6" | KCNH6 | 1.89 | 2E−08 |
| 234037_s_at | Hypothetical protein FLJ11996 | FLJ11996 | 1.89 | 2E−06 |
| 214617_at | perforin 1 (pore forming protein) \| perforin 1 (pore forming protein) | PRF1 | 1.89 | 7E−11 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 231338_at | nuclear protein in testis | NUT | 1.89 | 7E−06 |
| 222782_s_at | GEM interacting protein | GMIP | 1.89 | 5E−08 |
| 205038_at | "Zinc finger protein, subfamily 1A, 1 (Ikaros)" | ZNFN1A1 | 1.89 | 8E−09 |
| 216610_at | "solute carrier family 6 (neurotransmitter transporter, noradrenalin), member 2" | SLC6A2 | 1.89 | 7E−05 |
| 220428_at | "CD207 antigen, langerin" | CD207 | 1.88 | 7E−11 |
| 1559607_s_at | "Guanylate binding protein family, member 6" | GBP6 | 1.88 | 1E−07 |
| 217594_at | "zinc finger, CCHC domain containing 11" | ZCCHC11 | 1.88 | 1E−11 |
| 1553208_s_at | ADP-ribosylation factor-like 10A | ARL10A | 1.88 | 4E−05 |
| 224551_s_at | "spectrin, beta, non-erythrocytic 4 | spectrin, beta, non-erythrocytic 4" | SPTBN4 | 1.88 | 1E−05 |
| 202062_s_at | sel-1 suppressor of lin-12-like (*C. elegans*) | SEL1L | 1.87 | 3E−14 |
| 212699_at | secretory carrier membrane protein 5 | SCAMP5 | 1.87 | 5E−19 |
| 208364_at | "inositol polyphosphate-4-phosphatase, type I, 107 kDa" | INPP4A | 1.87 | 3E−09 |
| 215923_s_at | pleckstrin and Sec7 domain containing 4 | PSD4 | 1.87 | 3E−06 |
| 242601_at | hypothetical protein LOC253012 | LOC253012 | 1.87 | 4E−05 |
| 230050_at | BTB (POZ) domain containing 14A | BTBD14A | 1.87 | 2E−08 |
| 223634_at | "RASD family, member 2" | RASD2 | 1.87 | 6E−09 |
| 215085_x_at | deleted in lung and esophageal cancer 1 | DLEC1 | 1.87 | 1E−15 |
| 242242_at | ubiquitin specific protease 6 (Tre-2 oncogene) | USP6 | 1.87 | 4E−14 |
| 244029_at | Copine V | CPNE5 | 1.87 | 3E−14 |
| 238567_at | sphingosine-1-phosphate phosphotase 2 | SGPP2 | 1.86 | 4E−06 |
| 208273_at | NA | NA | 1.86 | 4E−06 |
| 208604_s_at | homeo box A3 | homeo box A3 | HOXA3 | 1.86 | 1E−09 |
| 219976_at | hook homolog 1 (*Drosophila*) | HOOK1 | 1.86 | 1E−05 |
| 203397_s_at | UDP-N-acetyl-alpha-D-galactosamine: polypeptide N-acetylgalactosaminyltransferase 3 (GalNAc-T3) | GALNT3 | 1.86 | 6E−08 |
| 1564237_at | "CDNA FLJ23858 fis, clone LNG07565" | NA | 1.86 | 3E−05 |
| 210140_at | cystatin F (leukocystatin) | CST7 | 1.86 | 2E−06 |
| 1555834_at | Ubiquitin carboxyl-terminal esterase L1 (ubiquitin thiolesterase) | UCHL1 | 1.86 | 1E−05 |
| 221377_s_at | recombining binding protein suppressor of hairless (*Drosophila*)-like | RBPSUHL | 1.85 | 1E−07 |
| 208536_s_at | BCL2-like 11 (apoptosis facilitator) | BCL2L11 | 1.85 | 9E−06 |
| 1552701_a_at | CARD only protein | COP1 | 1.85 | 1E−10 |
| 1553387_at | "ataxia telangiectasia mutated (includes complementation groups A, C and D)" | ATM | 1.85 | 8E−10 |
| 208488_s_at | "complement component (3b/4b) receptor 1, including Knops blood group system" | CR1 | 1.85 | 3E−09 |
| 220883_at | NA | NA | 1.85 | 7E−07 |
| 1555275_a_at | kelch-like 6 (*Drosophila*) | KLHL6 | 1.84 | 9E−12 |
| 207681_at | chemokine (C-X-C motif) receptor 3 | CXCR3 | 1.84 | 3E−11 |
| 1553857_at | hypothetical protein FLJ37794 | FLJ37794 | 1.84 | 5E−07 |
| 207238_s_at | "protein tyrosine phosphatase, receptor type, C" | PTPRC | 1.84 | 1E−07 |
| 1554601_at | T-cell lymphoma breakpoint associated target 1 | TCBA1 | 1.84 | 2E−05 |
| 1556849_at | Ring finger protein 38 | RNF38 | 1.84 | 3E−07 |
| 213416_at | NA | NA | 1.84 | 6E−10 |
| 1552497_a_at | SLAM family member 6 | SLAMF6 | 1.84 | 1E−14 |
| 1555120_at | CD96 antigen | CD96 | 1.84 | 4E−09 |
| 236838_at | hypothetical gene supported by BC019717 | LOC440360 | 1.84 | 3E−07 |
| 236337_at | hypothetical protein LOC221711 | LOC221711 | 1.84 | 2E−06 |
| 220384_at | thioredoxin domain containing 3 (spermatozoa) | TXNDC3 | 1.84 | 3E−08 |
| 201004_at | "signal sequence receptor, delta (translocon-associated protein delta)" | SSR4 | 1.84 | 8E−15 |
| 239588_s_at | Hypothetical protein FLJ20315 | FLJ20315 | 1.83 | 2E−08 |
| 211532_x_at | "killer cell immunoglobulin-like receptor, two domains, short cytoplasmic tail, 2" | KIR2DS2 | 1.83 | 4E−05 |
| 210708_x_at | "caspase 10, apoptosis-related cysteine protease" | CASP10 | 1.83 | 1E−08 |
| 241328_at | "zinc finger, matrin type 1" | ZMAT1 | 1.83 | 1E−05 |
| 228377_at | kelch-like 14 (*Drosophila*) | KLHL14 | 1.82 | 1E−08 |
| 213920_at | cut-like 2 (*Drosophila*) | CUTL2 | 1.81 | 4E−06 |
| 214907_at | carcinoembryonic antigen-related cell adhesion molecule | R29124_1 | 1.81 | 1E−12 |
| 1555981_at | hypothetical protein DKFZp762C2414 | DKFZp762C2414 | 1.81 | 4E−19 |
| 1555662_s_at | D-amino acid oxidase activator | DAOA | 1.81 | 3E−09 |
| 241927_x_at | NA | NA | 1.81 | 4E−08 |
| 1558698_at | zinc finger protein 264 | ZNF264 | 1.81 | 4E−06 |
| 203331_s_at | NA | NA | 1.81 | 4E−07 |
| 38149_at | NA | NA | 1.81 | 1E−15 |
| 221441_at | goosecoid-like | GSCL | 1.81 | 2E−05 |
| 215586_at | "Protein phosphatase 3 (formerly 2B), catalytic subunit, beta isoform (calcineurin A beta)" | PPP3CB | 1.81 | 1E−07 |
| 226099_at | "elongation factor, RNA polymerase II, 2" | ELL2 | 1.81 | 1E−08 |
| 206566_at | "solute carrier family 7 (cationic amino acid transporter, y+ system), member 1" | SLC7A1 | 1.80 | 2E−08 |
| 236134_at | WD-repeat protein | HAN11 | 1.80 | 1E−07 |
| 1556655_s_at | "CDNA FLJ38740 fis, clone KIDNE2011782" | NA | 1.80 | 2E−05 |
| 242752_at | MRNA (clone ICRFp507I1077) | NA | 1.80 | 4E−12 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 211620_x_at | runt-related transcription factor 1 (acute myeloid leukemia 1; aml1 oncogene) | runt-related transcription factor 1 (acute myeloid leukemia 1; aml1 oncogene) | RUNX1 | 1.80 | 5E−10 |
| 244313_at | Transcribed locus | NA | 1.80 | 8E−06 |
| 212750_at | "protein phosphatase 1, regulatory (inhibitor) subunit 16B" | PPP1R16B | 1.80 | 7E−08 |
| 224285_at | G protein-coupled receptor 174 | GPR174 | 1.80 | 2E−07 |
| 1554834_a_at | Ras association (RaIGDS/AF-6) domain family 5 | RASSF5 | 1.79 | 1E−07 |
| 231549_at | hypothetical protein MGC35194 | MGC35194 | 1.79 | 2E−05 |
| 210712_at | lactate dehydrogenase A-like 6B | LDHAL6B | 1.79 | 1E−06 |
| 219290_x_at | dual adaptor of phosphotyrosine and 3-phosphoinositides | DAPP1 | 1.79 | 3E−10 |
| 215315_at | zinc finger protein 549 | ZNF549 | 1.79 | 5E−05 |
| 242517_at | G protein-coupled receptor 54 | GPR54 | 1.79 | 8E−13 |
| 224062_x_at | "kallikrein 4 (prostase, enamel matrix, prostate)" | KLK4 | 1.79 | 1E−05 |
| 207686_s_at | "caspase 8, apoptosis-related cysteine protease" | CASP8 | 1.79 | 5E−08 |
| 231794_at | cytotoxic T-lymphocyte-associated protein 4 | CTLA4 | 1.79 | 7E−08 |
| 1560686_at | "integrin, alpha D" | ITGAD | 1.78 | 5E−11 |
| 1562338_at | Membrane-associated RING-CH protein I | MARCH-I | 1.78 | 2E−05 |
| 227690_at | "Gamma-aminobutyric acid (GABA) A receptor, beta 3" | GABRB3 | 1.78 | 2E−05 |
| 224360_s_at | protein kinase C and casein kinase substrate in neurons 1 | protein kinase C and casein kinase substrate in neurons 1 | PACSIN1 | 1.78 | 2E−05 |
| 213834_at | IQ motif and Sec7 domain 3 | IQSEC3 | 1.78 | 2E−06 |
| 205699_at | mitogen-activated protein kinase kinase 6 | MAP2K6 | 1.78 | 5E−08 |
| 221558_s_at | lymphoid enhancer-binding factor 1 | LEF1 | 1.78 | 2E−07 |
| 235768_at | SH3 domain containing ring finger 2 | SH3RF2 | 1.77 | 3E−05 |
| 224367_at | brain expressed X-linked 2 | brain expressed X-linked 2 | BEX2 | 1.77 | 6E−08 |
| 220369_at | KIAA2010 | KIAA2010 | 1.77 | 8E−06 |
| 224204_x_at | aryl hydrocarbon receptor nuclear translocator-like 2 | ARNTL2 | 1.77 | 9E−07 |
| 209911_x_at | "histone 1, H2bd" | HIST1H2BD | 1.77 | 3E−13 |
| 211085_s_at | serine/threonine kinase 4 | serine/threonine kinase 4 | STK4 | 1.77 | 3E−12 |
| 215332_s_at | "CD8 antigen, beta polypeptide 1 (p37)" | CD8B1 | 1.77 | 7E−05 |
| 222927_s_at | "lectin, mannose-binding, 1 like" | LMAN1L | 1.77 | 3E−05 |
| 206316_s_at | kinetochore associated 1 | KNTC1 | 1.77 | 7E−14 |
| 1555638_a_at | "SAM domain, SH3 domain and nuclear localisation signals, 1" | SAMSN1 | 1.77 | 1E−11 |
| 232372_at | Tubby like protein 4 | TULP4 | 1.77 | 2E−06 |
| 211003_x_at | "transglutaminase 2 (C polypeptide, protein-glutamine-gamma-glutamyltransferase)" | TGM2 | 1.77 | 1E−06 |
| 214217_at | "Glutamate receptor, metabotropic 5" | GRM5 | 1.77 | 3E−06 |
| 221251_x_at | high mobility group AT-hook 1-like 4 | high mobility group AT-hook 1-like 4 | HMGA1L4 | 1.77 | 4E−06 |
| 222943_at | "glucosidase, beta, acid 3 (cytosolic)" | GBA3 | 1.77 | 2E−09 |
| 235104_at | leukocyte-derived arginine aminopeptidase | LRAP | 1.77 | 1E−05 |
| 208261_x_at | "interferon, alpha 10" | IFNA10 | 1.76 | 1E−06 |
| 204205_at | "apolipoprotein B mRNA editing enzyme, catalytic polypeptide-like 3G" | APOBEC3G | 1.76 | 4E−09 |
| 1565483_at | "epidermal growth factor receptor (erythroblastic leukemia viral (v-erb-b) oncogene homolog, avian)" | EGFR | 1.76 | 8E−05 |
| 1557924_s_at | "alkaline phosphatase, liver/bone/kidney" | ALPL | 1.76 | 2E−05 |
| 206999_at | "interleukin 12 receptor, beta 2" | IL12RB2 | 1.76 | 1E−05 |
| 215573_at | Catalase | CAT | 1.76 | 5E−08 |
| 208537_at | "endothelial differentiation, sphingolipid G-protein-coupled receptor, 5" | EDG5 | 1.76 | 4E−08 |
| 214539_at | "serine (or cysteine) proteinase inhibitor, clade B (ovalbumin), member 10" | SERPINB10 | 1.76 | 1E−06 |
| 1569909_at | keratin 6L | KRT6L | 1.75 | 3E−09 |
| 206720_at | "mannosyl (alpha-1,6-)-glycoprotein beta-1,6-N-acetyl-glucosaminyltransferase" | MGAT5 | 1.75 | 3E−05 |
| 241049_at | "glutamate receptor, metabotropic 7" | GRM7 | 1.75 | 6E−09 |
| 1553552_at | trace amine receptor 5 | TRAR5 | 1.75 | 4E−07 |
| 222774_s_at | neuropilin (NRP) and tolloid (TLL)-like 2 | NETO2 | 1.75 | 8E−06 |
| 217407_x_at | peptidylprolyl isomerase (cyclophilin)-like 2 | PPIL2 | 1.75 | 2E−05 |
| 204935_at | "protein tyrosine phosphatase, non-receptor type 2" | PTPN2 | 1.75 | 7E−10 |
| 230717_at | lipocalcin 12 | LCN12 | 1.75 | 1E−05 |
| 1565935_at | prematurely terminated mRNA decay factor-like | LOC91431 | 1.75 | 4E−05 |
| 1555048_a_at | chromosome 21 open reading frame 29 | C21orf29 | 1.75 | 7E−05 |
| 233362_at | zinc finger protein 341 | ZNF341 | 1.75 | 2E−06 |
| 227677_at | "Janus kinase 3 (a protein tyrosine kinase, leukocyte)" | JAK3 | 1.74 | 1E−08 |
| 1556282_at | FGFR1 oncogene partner 2 | FGFR1OP2 | 1.74 | 3E−06 |
| 206901_at | hypothetical protein MGC11271 | MGC11271 | 1.74 | 5E−05 |
| 1562590_at | hypothetical protein FLJ25756 | FLJ25756 | 1.74 | 6E−06 |
| 220330_s_at | "SAM domain, SH3 domain and nuclear localisation signals, 1" | SAMSN1 | 1.74 | 3E−12 |
| 1555277_a_at | "solute carrier family 4, sodium bicarbonate cotransporter, member 5" | SLC4A5 | 1.74 | 6E−06 |
| 1554300_a_at | hypothetical protein LOC136306 | LOC136306 | 1.74 | 5E−05 |
| 222257_s_at | angiotensin I converting enzyme (peptidyl-dipeptidase A) 2 | ACE2 | 1.74 | 1E−05 |
| 1570516_s_at | "olfactory receptor, family 51, subfamily B, member 5" | OR51B5 | 1.74 | 5E−07 |
| 231332_at | Hypothetical protein LOC196394 | LOC196394 | 1.73 | 6E−08 |
| 208259_x_at | "interferon, alpha 7" | IFNA7 | 1.73 | 2E−06 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 211424_x_at | NA | NA | 1.73 | 9E−06 |
| 205552_s_at | "2',5'-oligoadenylate synthetase 1, 40/46 kDa" | OAS1 | 1.73 | 5E−05 |
| 204056_s_at | mevalonate kinase (mevalonic aciduria) | MVK | 1.73 | 2E−06 |
| 232562_at | "CDNA FLJ11554 fis, clone HEMBA1003037" | NA | 1.73 | 3E−05 |
| 239419_at | "Protein tyrosine phosphatase, receptor type, A" | VPS16 | 1.73 | 1E−07 |
| 1552504_a_at | BR serine/threonine kinase 1 | BRSK1 | 1.73 | 4E−10 |
| 213472_at | heterogeneous nuclear ribonucleoprotein H1 (H) | HNRPH1 | 1.73 | 4E−06 |
| 207854_at | glycophorin E | GYPE | 1.73 | 3E−06 |
| 224555_x_at | "interleukin 1 family, member 7 (zeta)" | IL1F7 | 1.73 | 5E−09 |
| 215442_s_at | thyroid stimulating hormone receptor | TSHR | 1.73 | 8E−05 |
| 206429_at | coagulation factor II (thrombin) receptor-like 1 | F2RL1 | 1.73 | 4E−05 |
| 207441_at | submaxillary gland androgen regulated protein 3 homolog B (mouse) | SMR3B | 1.73 | 4E−05 |
| 239646_at | KIAA1961 protein | RAPGEF6 | 1.73 | 7E−07 |
| 1552506_at | crumbs homolog 2 (*Drosophila*) | CRB2 | 1.73 | 1E−05 |
| 219259_at | "sema domain, immunoglobulin domain (Ig), transmembrane domain (TM) and short cytoplasmic domain, (semaphorin) 4A" | SEMA4A | 1.73 | 8E−10 |
| 232722_at | ribonuclease T2 | RNASET2 | 1.73 | 4E−08 |
| 207957_s_at | "Protein kinase C, beta 1" | PRKCB1 | 1.72 | 2E−05 |
| 1569830_at | "Protein tyrosine phosphatase, receptor type, C" | PTPRC | 1.72 | 9E−06 |
| 1554208_at | similar to mouse meiosis defective 1 gene | MGC40042 | 1.72 | 2E−15 |
| 238474_at | nucleoporin 43 kDa | NUP43 | 1.72 | 3E−07 |
| 220315_at | "poly (ADP-ribose) polymerase family, member 11" | PARP11 | 1.72 | 9E−07 |
| 216407_at | Vac14 homolog (*S. cerevisiae*) | VAC14 | 1.72 | 1E−06 |
| 238853_at | Glioma amplified sequence 64 | NA | 1.72 | 9E−06 |
| 211360_s_at | "inositol 1,4,5-triphosphate receptor, type 2" | ITPR2 | 1.71 | 1E−08 |
| 1561578_s_at | Similar to mitochondrial carrier triple repeat 1 | NA | 1.71 | 4E−06 |
| 238699_s_at | calcium/calmodulin-dependent serine protein kinase (MAGUK family) | CASK | 1.71 | 3E−06 |
| 235650_at | hypothetical protein FLJ23834 | FLJ23834 | 1.71 | 9E−09 |
| 240703_s_at | hect (homologous to the E6-AP (UBE3A) carboxyl terminus) domain and RCC1 (CHC1)-like domain (RLD) 1 | HERC1 | 1.71 | 4E−05 |
| 221696_s_at | serine/threonine/tyrosine kinase 1 \| serine/threonine/tyrosine kinase 1 | STYK1 | 1.71 | 3E−08 |
| 1552742_at | "potassium voltage-gated channel, subfamily H (eag-related), member 8" | KCNH8 | 1.71 | 4E−05 |
| 223809_at | regulator of G-protein signalling 18 | RGS18 | 1.71 | 2E−11 |
| 241737_x_at | Vaccinia related kinase 1 | VRK1 | 1.71 | 3E−07 |
| 242077_x_at | chromosome 6 open reading frame 150 | C6orf150 | 1.71 | 6E−09 |
| 221004_s_at | integral membrane protein 2C \| integral membrane protein 2C | ITM2C | 1.71 | 3E−06 |
| 1552343_s_at | phosphodiesterase 7A | PDE7A | 1.71 | 6E−07 |
| 1552801_at | calpain 13 | CAPN13 | 1.70 | 4E−06 |
| 206618_at | interleukin 18 receptor 1 | IL18R1 | 1.70 | 1E−04 |
| 205291_at | "interleukin 2 receptor, beta \| interleukin 2 receptor, beta" | IL2RB | 1.70 | 1E−10 |
| 207976_at | kelch-like 18 (*Drosophila*) | KLHL18 | 1.70 | 7E−09 |
| 1556412_at | KIAA0478 gene product | KIAA0478 | 1.70 | 1E−06 |
| 205269_at | lymphocyte cytosolic protein 2 (SH2 domain containing leukocyte protein of 76 kDa) | LCP2 | 1.70 | 1E−09 |
| 205016_at | "transforming growth factor, alpha" | TGFA | 1.70 | 8E−09 |
| 1560803_at | "dynein, axonemal, heavy polypeptide 3" | DNAH3 | 1.70 | 1E−05 |
| 235061_at | protein phosphatase 1K (PP2C domain containing) | PPM1K | 1.70 | 3E−12 |
| 1552857_a_at | 5-hydroxytryptamine (serotonin) receptor 6 | HTR6 | 1.70 | 2E−05 |
| 1563744_a_at | Disrupted in schizophrenia 1 | DISC1 | 1.69 | 4E−05 |
| 241357_at | extracellular signal-regulated kinase 8 | ERK8 | 1.69 | 3E−06 |
| 237036_at | F-box protein 10 | FBXO10 | 1.69 | 4E−05 |
| 221293_s_at | differentially expressed in FDCP 6 homolog (mouse) | DEF6 | 1.69 | 2E−10 |
| 235169_at | F-box protein 27 | FBXO27 | 1.69 | 2E−05 |
| 211207_s_at | acyl-CoA synthetase long-chain family member 6 | ACSL6 | 1.69 | 8E−06 |
| 1559425_at | "Protein kinase C, eta" | PRKCH | 1.69 | 8E−07 |
| 205668_at | lymphocyte antigen 75 | LY75 | 1.69 | 1E−07 |
| 1566963_at | NA | NA | 1.69 | 2E−05 |
| 208267_at | "transient receptor potential cation channel, subfamily V, member 5" | TRPV5 | 1.69 | 2E−08 |
| 210670_at | pancreatic polypeptide | PPY | 1.69 | 3E−09 |
| 220422_at | ubiquilin 3 | UBQLN3 | 1.69 | 7E−09 |
| 1555671_at | "amyotrophic lateral sclerosis 2 (juvenile) chromosome region, candidate 14" | ALS2CR14 | 1.69 | 9E−08 |
| 244692_at | hypothetical protein FLJ39501 | FLJ39501 | 1.69 | 8E−05 |
| 1559159_at | KIAA0582 | KIAA0582 | 1.69 | 5E−10 |
| 209006_s_at | NPD014 protein | NPD014 | 1.68 | 2E−08 |
| 219391_at | "3'(2'),5'-bisphosphate nucleotidase 1" | BPNT1 | 1.68 | 6E−09 |
| 215470_at | "CDNA FLJ36630 fis, clone TRACH2018278" | NA | 1.68 | 2E−05 |
| 208481_at | ankyrin repeat and SOCS box-containing 4 | ASB4 | 1.68 | 2E−05 |
| 240770_at | hypothetical protein LOC134285 | LOC134285 | 1.68 | 5E−05 |
| 219285_s_at | ninein (GSK3B interacting protein) | NIN | 1.68 | 1E−05 |
| 227152_at | hypothetical protein FLJ20696 | FLJ20696 | 1.68 | 4E−12 |
| 211080_s_at | NIMA (never in mitosis gene a)-related kinase 2 \| NIMA (never in mitosis gene a)-related kinase 2 | NEK2 | 1.68 | 2E−06 |
| 207735_at | ring finger protein 125 | RNF125 | 1.68 | 6E−10 |
| 228288_at | NA | NA | 1.68 | 2E−07 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 223605_at | "solute carrier family 25 (mitochondrial carrier), member 18" | SLC25A18 | 1.67 | 6E−06 |
| 230036_at | chromosome 7 open reading frame 6 | C7orf6 | 1.67 | 1E−10 |
| 1553177_at | SH2 domain-containing molecule EAT2 | EAT2 | 1.67 | 9E−09 |
| 237407_at | HS1-binding protein 3 | FLJ14249 | 1.67 | 5E−05 |
| 207509_s_at | leukocyte-associated Ig-like receptor 2 | LAIR2 | 1.67 | 7E−05 |
| 227811_at | "FGD1 family, member 3" | FGD3 | 1.67 | 2E−09 |
| 240843_at | "Protein tyrosine phosphatase, non-receptor type 2" | PTPN2 | 1.67 | 6E−06 |
| 217495_x_at | "calcitonin/calcitonin-related polypeptide, alpha" | CALCA | 1.67 | 1E−05 |
| 241988_x_at | Slingshot homolog 2 (*Drosophila*) | SSH2 | 1.67 | 2E−07 |
| 207162_s_at | "calcium channel, voltage-dependent, L type, alpha 1B subunit" | CACNA1B | 1.67 | 3E−09 |
| 220214_at | zinc finger protein 215 | ZNF215 | 1.67 | 2E−05 |
| 1563590_at | "Protein tyrosine phosphatase, receptor type, E" | PTPRE | 1.67 | 1E−06 |
| 207106_s_at | leukocyte tyrosine kinase | LTK | 1.66 | 1E−07 |
| 207114_at | "lymphocyte antigen 6 complex, locus G6C" | LY6G6C | 1.66 | 1E−07 |
| 219734_at | "SID1 transmembrane family, member 1" | SIDT1 | 1.66 | 2E−10 |
| 205255_x_at | "transcription factor 7 (T-cell specific, HMG-box)" | TCF7 | 1.66 | 2E−08 |
| 206916_x_at | tyrosine aminotransferase | TAT | 1.66 | 8E−06 |
| 222746_s_at | B-box and SPRY domain containing | BSPRY | 1.66 | 1E−13 |
| 220420_at | "lectin, mannose-binding, 1 like" | LMAN1L | 1.66 | 7E−06 |
| 234092_s_at | transmembrane 6 superfamily member 2 | TM6SF2 | 1.66 | 6E−08 |
| 222940_at | "sulfotransferase family 1E, estrogen-preferring, member 1" | SULT1E1 | 1.66 | 7E−05 |
| 226906_s_at | Rho GTPase activating protein 9 | ARHGAP9 | 1.66 | 2E−09 |
| 224290_at | NA | NA | 1.66 | 6E−06 |
| 219695_at | "sphingomyelin phosphodiesterase 3, neutral membrane (neutral sphingomyelinase II)" | SMPD3 | 1.66 | 3E−08 |
| 244011_at | protein phosphatase 1K (PP2C domain containing) | PPM1K | 1.66 | 6E−10 |
| 227609_at | epithelial stromal interaction 1 (breast) | EPSTI1 | 1.66 | 9E−07 |
| 1552703_s_at | "caspase 1, apoptosis-related cysteine protease (interleukin 1, beta, convertase) | CARD only protein" | CASP1 | COPI | 1.66 | 4E−12 |
| 232383_at | Transcription factor EC | TFEC | 1.66 | 3E−07 |
| 1553823_a_at | receptor transporting protein 1 | RTP1 | 1.66 | 3E−05 |
| 221340_at | caudal type homeo box transcription factor 4 | CDX4 | 1.65 | 7E−06 |
| 227344_at | "Zinc finger protein, subfamily 1A, 1 (Ikaros)" | ZNFN1A1 | 1.65 | 2E−11 |
| 229312_s_at | G kinase anchoring protein 1 | GKAP1 | 1.65 | 2E−09 |
| 203148_s_at | tripartite motif-containing 14 | TRIM14 | 1.65 | 4E−07 |
| 227552_at | septin 1 | 1-Sep | 1.65 | 4E−08 |
| 227462_at | Leukocyte-derived arginine aminopeptidase | LRAP | 1.65 | 2E−05 |
| 1553666_at | NY-REN-41 antigen | NY-REN-41 | 1.65 | 8E−05 |
| 239885_at | Transcribed locus | NA | 1.65 | 2E−09 |
| 235720_at | cysteine-rich protein 3 | CRIP3 | 1.65 | 1E−05 |
| 208286_x_at | "POU domain, class 5, transcription factor 1" | POU5F1 | 1.65 | 1E−07 |
| 213109_at | NA | NA | 1.65 | 8E−11 |
| 205299_s_at | "butyrophilin, subfamily 2, member A2" | BTN2A2 | 1.65 | 5E−10 |
| 236002_at | TAO kinase 3 | TAOK3 | 1.64 | 8E−09 |
| 1565818_s_at | "zinc finger protein, subfamily 1A, 1 (Ikaros)" | ZNFN1A1 | 1.64 | 1E−05 |
| 203110_at | PTK2B protein tyrosine kinase 2 beta | PTK2B | 1.64 | 2E−08 |
| 207592_s_at | hyperpolarization activated cyclic nucleotide-gated potassium channel 2 | HCN2 | 1.64 | 3E−06 |
| 223746_at | serine/threonine kinase 4 | STK4 | 1.64 | 9E−08 |
| 239438_at | Rap guanine nucleotide exchange factor (GEF) 6 | RAPGEF6 | 1.64 | 6E−05 |
| 240189_at | Transcribed locus | NA | 1.64 | 9E−08 |
| 220440_at | "lectin, galactoside-binding, soluble, 13 (galectin 13)" | LGALS13 | 1.64 | 2E−05 |
| 205538_at | "coronin, actin binding protein, 2A" | CORO2A | 1.64 | 1E−08 |
| 216997_x_at | "transducin-like enhancer of split 4 (E(sp1) homolog, *Drosophila*)" | TLE4 | 1.64 | 5E−09 |
| 236305_at | LOC317671 | LOC317671 | 1.64 | 3E−09 |
| 209685_s_at | "protein kinase C, beta 1" | PRKCB1 | 1.64 | 5E−06 |
| 1564231_at | KIAA1374 protein | KIAA1374 | 1.64 | 5E−10 |
| 236236_at | "CDNA FLJ30437 fis, clone BRACE2009045" | NA | 1.64 | 8E−05 |
| 206974_at | chemokine (C-X-C motif) receptor 6 | CXCR6 | 1.64 | 4E−07 |
| 242175_at | X-ray radiation resistance associated 1 | XRRA1 | 1.64 | 3E−05 |
| 207990_x_at | acrosomal vesicle protein 1 | ACRV1 | 1.64 | 8E−11 |
| 216877_x_at | "alkaline phosphatase, placental-like 2" | ALPPL2 | 1.63 | 2E−06 |
| 243410_at | "Protein tyrosine phosphatase, non-receptor type 2" | PTPN2 | 1.63 | 9E−08 |
| 214624_at | uroplakin 1A | UPK1A | 1.63 | 1E−07 |
| 206248_at | "protein kinase C, epsilon" | PRKCE | 1.63 | 4E−07 |
| 216112_at | Protein kinase N2 | PKN2 | 1.63 | 2E−06 |
| 208203_x_at | "killer cell immunoglobulin-like receptor, two domains, short cytoplasmic tail, 5" | KIR2DS5 | 1.63 | 2E−08 |
| 210969_at | protein kinase N2 | PKN2 | 1.63 | 4E−08 |
| 207838_x_at | pre-B-cell leukemia transcription factor interacting protein 1 | PBXIP1 | 1.63 | 1E−07 |
| 209569_x_at | DNA segment on chromosome 4 (unique) 234 expressed sequence | D4S234E | 1.63 | 8E−10 |
| 238054_at | ADP-ribosylhydrolase like 1 | ADPRHL1 | 1.63 | 4E−06 |
| 207382_at | tumor protein p73-like | TP73L | 1.63 | 6E−05 |
| 216624_s_at | "myeloid/lymphoid or mixed-lineage leukemia (trithorax homolog, *Drosophila*)" | MLL | 1.63 | 3E−05 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 217566_s_at | transglutaminase 4 (prostate) | TGM4 | 1.63 | 8E−05 |
| 223423_at | G protein-coupled receptor 160 | GPR160 | 1.63 | 8E−09 |
| 213017_at | abhydrolase domain containing 3 | ABHD3 | 1.63 | 4E−11 |
| 227736_at | chromosome 10 open reading frame 99 | C10orf99 | 1.63 | 7E−05 |
| 1555581_a_at | tumor protein p73-like | TP73L | 1.62 | 6E−05 |
| 219411_at | "engulfment and cell motility 3 (ced-12 homolog, C. elegans)" | ELMO3 | 1.62 | 2E−09 |
| 206830_at | "solute carrier family 4, sodium bicarbonate transporter-like, member 10" | SLC4A10 | 1.62 | 3E−05 |
| 211598_x_at | vasoactive intestinal peptide receptor 2 | vasoactive intestinal peptide receptor 2 | similar to vasoactive intestinal peptide receptor 2 | similar to vasoactive intestinal peptide receptor 2 | VIPR2 | LOC441305 | 1.62 | 9E−06 |
| 210743_s_at | CDC14 cell division cycle 14 homolog A (S. cerevisiae) | CDC14A | 1.62 | 6E−11 |
| 232995_at | DNA-damage inducible protein 1 | PDGFD | 1.62 | 2E−05 |
| 231230_at | Clone 23786 mRNA sequence | NA | 1.62 | 8E−05 |
| 244394_at | B lymphoid tyrosine kinase | BLK | 1.62 | 8E−05 |
| 211888_x_at | "caspase 10, apoptosis-related cysteine protease" | CASP10 | 1.62 | 1E−04 |
| 216522_at | "olfactory receptor, family 2, subfamily B, member 6" | OR2B6 | 1.62 | 2E−08 |
| 241913_at | Hypothetical gene supported by AK123781 | NA | 1.62 | 1E−06 |
| 204044_at | quinolinate phosphoribosyltransferase (nicotinate-nucleotide pyrophosphorylase (carboxylating)) | QPRT | 1.62 | 1E−08 |
| 206835_at | statherin | STATH | 1.62 | 5E−05 |
| 234775_at | "olfactory receptor, family 51, subfamily B, member 5" | OR51B5 | 1.62 | 7E−10 |
| 211005_at | linker for activation of T cells | LAT | 1.62 | 3E−08 |
| 204882_at | NA | NA | 1.62 | 1E−07 |
| 205639_at | acyloxyacyl hydrolase (neutrophil) | AOAH | 1.62 | 2E−06 |
| 1553102_a_at | DKFZP434C171 protein | DKFZP434C171 | 1.62 | 1E−12 |
| 223607_x_at | "zinc finger, SWIM domain containing 1" | ZSWIM1 | 1.62 | 2E−08 |
| 226313_at | chromosome 10 open reading frame 35 | C10orf35 | 1.61 | 3E−09 |
| 217711_at | "TEK tyrosine kinase, endothelial (venous malformations, multiple cutaneous and mucosal)" | TEK | 1.61 | 6E−05 |
| 225931_s_at | chromosome 17 open reading frame 27 | C17orf27 | 1.61 | 9E−11 |
| 204798_at | v-myb myeloblastosis viral oncogene homolog (avian) | MYB | 1.61 | 2E−06 |
| 204994_at | myxovirus (influenza virus) resistance 2 (mouse) | MX2 | 1.61 | 7E−06 |
| 49049_at | deltex 3 homolog (Drosophila) | DTX3 | 1.61 | 1E−06 |
| 215170_s_at | KIAA0912 protein | Cep152 | 1.61 | 7E−08 |
| 216288_at | cysteinyl leukotriene receptor 1 | CYSLTR1 | 1.61 | 4E−06 |
| 1552915_at | "interleukin 28A (interferon, lambda 2)" | IL28A | 1.61 | 4E−09 |
| 242976_at | "Homo sapiens, clone IMAGE: 5286757, mRNA" | NA | 1.61 | 2E−05 |
| 210629_x_at | leukocyte specific transcript 1 | LST1 | 1.61 | 4E−08 |
| 228551_at | hypothetical protein MGC24039 | MGC24039 | 1.61 | 2E−09 |
| 205509_at | carboxypeptidase B1 (tissue) | CPB1 | 1.61 | 3E−08 |
| 206295_at | interleukin 18 (interferon-gamma-inducing factor) | IL18 | 1.61 | 2E−07 |
| 1557193_at | "Protein tyrosine phosphatase, non-receptor type 2" | PTPN2 | 1.61 | 1E−09 |
| 219045_at | "ras homolog gene family, member F (in filopodia)" | RHOF | 1.61 | 6E−07 |
| 213990_s_at | p21(CDKN1A)-activated kinase 7 | PAK7 | 1.61 | 4E−07 |
| 234637_at | keratin associated protein 4-5 | KRTAP4-5 | 1.60 | 7E−05 |
| 206663_at | Sp4 transcription factor | SP4 | 1.60 | 2E−06 |
| 221578_at | Ras association (RaIGDS/AF-6) domain family 4 | RASSF4 | 1.60 | 6E−05 |
| 232721_at | tripartite motif-containing 55 | TRIM55 | 1.60 | 7E−05 |
| 1552796_a_at | single-minded homolog 1 (Drosophila) | SIM1 | 1.60 | 1E−05 |
| 210742_at | CDC14 cell division cycle 14 homolog A (S. cerevisiae) | CDC14A | 1.60 | 9E−07 |
| 1569257_at | formin-like 1 | FMNL1 | 1.60 | 5E−06 |
| 207217_s_at | NADPH oxidase 1 | NOX1 | 1.60 | 1E−06 |
| 1562238_at | Chromosome 13 open reading frame 22 | C13orf22 | 1.60 | 8E−07 |
| 1555248_a_at | WNK lysine deficient protein kinase 3 | WNK3 | 1.60 | 2E−05 |
| 216341_s_at | gonadotropin-releasing hormone receptor | GNRHR | 1.60 | 4E−07 |
| 1553556_at | "taste receptor, type 2, member 40" | TAS2R40 | 1.60 | 1E−05 |
| 1565635_at | NA | NA | 1.60 | 2E−05 |
| 240446_at | Mindbomb homolog 1 (Drosophila) | MIB1 | 1.60 | 3E−05 |
| 242549_at | protein kinase D3 | PRKD3 | 1.60 | 3E−09 |
| 205411_at | serine/threonine kinase 4 | STK4 | 1.60 | 1E−09 |
| 217701_x_at | NA | NA | 1.60 | 6E−05 |
| 239529_at | dendritic cell nuclear protein 1 | DCNP1 | 1.60 | 9E−05 |
| 215275_at | TRAF3-interacting Jun N-terminal kinase (JNK)-activating modulator | T3JAM | 1.60 | 2E−07 |
| 1565674_at | "Fc fragment of IgG, low affinity IIa, receptor (CD32)" | FCGR2A | 1.60 | 1E−04 |
| 234329_at | chloride intracellular channel 5 | CLIC5 | 1.60 | 1E−05 |
| 213778_x_at | zinc finger protein 276 homolog (mouse) | ZFP276 | 1.60 | 1E−10 |
| 211834_s_at | tumor protein p73-like | TP73L | 1.60 | 9E−05 |
| 220252_x_at | chromosome X open reading frame 21 | CXorf21 | 1.59 | 8E−10 |
| 1555423_at | slingshot homolog 2 (Drosophila) | SSH2 | 1.59 | 8E−05 |
| 219977_at | aryl hydrocarbon receptor interacting protein-like 1 | AIPL1 | 1.59 | 3E−07 |
| 203317_at | pleckstrin and Sec7 domain containing 4 | PSD4 | 1.59 | 9E−09 |
| 206280_at | "cadherin 18, type 2" | CDH18 | 1.59 | 2E−05 |
| 213953_at | keratin 20 | KRT20 | 1.59 | 9E−05 |
| 1556925_at | Chondroitin sulfate proteoglycan 6 (bamacan) | CSPG6 | 1.59 | 4E−09 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 220374_at | BTB (POZ) domain containing 5 | BTBD5 | 1.59 | 3E−07 |
| 227496_at | hypothetical protein LOC253842 | LOC253842 | 1.59 | 4E−07 |
| 227817_at | "Protein kinase C, beta 1" | PRKCB1 | 1.59 | 1E−05 |
| 211117_x_at | estrogen receptor 2 (ER beta) | ESR2 | 1.59 | 3E−05 |
| 203930_s_at | microtubule-associated protein tau | MAPT | 1.59 | 7E−05 |
| 236296_x_at | NA | NA | 1.59 | 9E−05 |
| 1553426_at | hypothetical protein FLJ37543 | FLJ37543 | 1.59 | 3E−07 |
| 235971_at | TRAF-interacting protein with a forkhead-associated domain | TIFA | 1.59 | 3E−09 |
| 241736_at | F-box and WD-40 domain protein 2 | FBXW2 | 1.59 | 6E−08 |
| 210359_at | metastasis suppressor 1 | MTSS1 | 1.58 | 1E−07 |
| 205599_at | TNF receptor-associated factor 1 | TRAF1 | 1.58 | 1E−11 |
| 221999_at | vaccinia related kinase 3 | VRK3 | 1.58 | 8E−13 |
| 220702_at | NA | NA | 1.58 | 3E−08 |
| 1555651_at | "olfactory receptor, family 10, subfamily A, member 5" | OR10A5 | 1.58 | 7E−05 |
| 216621_at | NA | NA | 1.58 | 4E−06 |
| 214339_s_at | mitogen-activated protein kinase kinase kinase kinase 1 | MAP4K1 | 1.58 | 2E−06 |
| 234455_at | zinc finger protein 1 homolog (mouse) | ZFP1 | 1.58 | 9E−05 |
| 212588_at | "protein tyrosine phosphatase, receptor type, C" | PTPRC | 1.58 | 1E−06 |
| 1567008_at | NA | NA | 1.58 | 3E−05 |
| 231874_at | NA | NA | 1.58 | 3E−10 |
| 231263_at | chromosome 6 open reading frame 81 | C6orf81 | 1.58 | 2E−05 |
| 211778_s_at | zinc finger protein 339 | zinc finger protein 339 | ZNF339 | 1.58 | 7E−07 |
| 206372_at | myogenic factor 6 (herculin) | MYF6 | 1.58 | 6E−05 |
| 1564029_at | ubiquitin specific protease 49 | MGC20741 | 1.58 | 5E−05 |
| 219233_s_at | gasdermin-like | GSDML | 1.58 | 3E−05 |
| 1553373_at | NA | NA | 1.58 | 1E−05 |
| 227607_at | associated molecule with the SH3 domain of STAM (AMSH) like protein | AMSH-LP | 1.58 | 1E−10 |
| 1562307_at | Ring finger protein 24 | RNF24 | 1.58 | 7E−06 |
| 221551_x_at | "ST6 (alpha-N-acetyl-neuraminyl-2,3-beta-galactosyl-1,3)-N-acetylgalactosaminide alpha-2,6-sialyltransferase 4" | ST6GALNAC4 | 1.58 | 1E−08 |
| 206674_at | fms-related tyrosine kinase 3 | FLT3 | 1.58 | 1E−05 |
| 207725_at | "POU domain, class 4, transcription factor 2" | POU4F2 | 1.58 | 2E−05 |
| 235498_at | hypothetical protein MGC22773 | MGC22773 | 1.58 | 7E−05 |
| 1558603_at | plasminogen-like | PLGL | 1.57 | 3E−05 |
| 1555035_a_at | Usher syndrome 3A | USH3A | 1.57 | 6E−05 |
| 217603_at | "ATPase, H+ transporting, lysosomal V0 subunit a isoform 2" | ATP6V0A2 | 1.57 | 8E−06 |
| 207859_s_at | "cholinergic receptor, nicotinic, beta polypeptide 3" | CHRNB3 | 1.57 | 2E−08 |
| 1559624_at | Serine/threonine kinase 32A | STK32A | 1.57 | 5E−05 |
| 242765_at | Myelin-associated oligodendrocyte basic protein | MOBP | 1.57 | 1E−05 |
| 239955_at | Transcribed locus | NA | 1.57 | 5E−06 |
| 209604_s_at | GATA binding protein 3 | GATA3 | 1.57 | 6E−06 |
| 218792_s_at | B-box and SPRY domain containing | BSPRY | 1.57 | 7E−06 |
| 210865_at | "Fas ligand (TNF superfamily, member 6)" | FASLG | 1.57 | 9E−09 |
| 223245_at | spermatid perinuclear RNA binding protein | STRBP | 1.57 | 3E−14 |
| 215512_at | membrane-associated ring finger (C3HC4) 6 | 6-Mar | 1.57 | 6E−07 |
| 1558561_at | histocompatibility (minor) 13 | HM13 | 1.57 | 6E−08 |
| 207759_s_at | disrupted in schizophrenia 1 | DISC1 | 1.57 | 1E−08 |
| 1569462_x_at | "potassium channel, subfamily T, member 1" | KCNT1 | 1.57 | 3E−05 |
| 230983_at | B-cell novel protein 1 | BCNP1 | 1.57 | 1E−08 |
| 242130_at | NA | NA | 1.57 | 6E−06 |
| 230262_at | "CDNA FLJ30377 fis, clone BRACE2007952" | NA | 1.57 | 6E−07 |
| 238210_at | RYK receptor-like tyrosine kinase | RYK | 1.56 | 4E−06 |
| 232024_at | "GTPase, IMAP family member 2" | GIMAP2 | 1.56 | 2E−10 |
| 1555785_a_at | 5'-3' exoribonuclease 1 | XRN1 | 1.56 | 9E−09 |
| 207164_s_at | zinc finger protein 238 | ZNF238 | 1.56 | 7E−06 |
| 230217_at | hypothetical protein MGC34646 | MGC34646 | 1.56 | 6E−06 |
| 213631_x_at | "CDNA FLJ40920 fis, clone UTERU2005905" | NA | 1.56 | 5E−10 |
| 230499_at | Baculoviral IAP repeat-containing 3 | BIRC3 | 1.56 | 6E−08 |
| 211226_at | galanin receptor 2 | GALR2 | 1.56 | 9E−05 |
| 219209_at | interferon induced with helicase C domain 1 | IFIH1 | 1.56 | 1E−06 |
| 1561206_at | kelch-like 8 (Drosophila) | KLHL8 | 1.56 | 2E−07 |
| 1560665_at | serine carboxypeptidase 1 | SCPEP1 | 1.56 | 2E−06 |
| 1553120_at | claspin homolog (Xenopus laevis) | CLSPN | 1.56 | 6E−05 |
| 1554253_a_at | LAG1 longevity assurance homolog 3 (S. cerevisiae) | LASS3 | 1.56 | 5E−08 |
| 244565_at | Similar to Hmx2 protein | NA | 1.56 | 5E−05 |
| 231291_at | Gastric inhibitory polypeptide receptor | GIPR | 1.56 | 5E−05 |
| 38241_at | "butyrophilin, subfamily 3, member A3" | BTN3A3 | 1.56 | 1E−10 |
| 1552491_at | isopentenyl-diphosphate delta isomerase 2 | IDI2 | 1.56 | 2E−05 |
| 226070_at | hypothetical protein LOC286257 | LOC286257 | 1.56 | 2E−11 |
| 220684_at | T-box 21 | TBX21 | 1.56 | 1E−10 |
| 222812_s_at | "ras homolog gene family, member F (in filopodia)" | RHOF | 1.56 | 4E−09 |
| 206249_at | mitogen-activated protein kinase kinase kinase 13 | MAP3K13 | 1.55 | 9E−05 |
| 1569540_at | NA | NA | 1.55 | 6E−06 |
| 236281_x_at | 5-hydroxytryptamine (serotonin) receptor 7 (adenylate cyclase-coupled) | HTR7 | 1.55 | 8E−05 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 1564757_a_at | hypothetical protein BC015395 | LOC130940 | 1.55 | 4E−05 |
| 224046_s_at | phosphodiesterase 7A | PDE7A | 1.55 | 4E−09 |
| 229168_at | "collagen, type XXIII, alpha 1" | COL23A1 | 1.55 | 3E−08 |
| 229419_at | "F-box and WD-40 domain protein 7 (archipelago homolog, *Drosophila*)" | FBXW7 | 1.55 | 1E−11 |
| 221080_s_at | "family with sequence similarity 31, member C" | FAM31C | 1.55 | 1E−09 |
| 221339_at | "olfactory receptor, family 10, subfamily C, member 1" | OR10C1 | 1.55 | 2E−08 |
| 219066_at | hypothetical protein MDS018 | MDS018 | 1.55 | 6E−13 |
| 205101_at | MHC class II transactivator | MHC2TA | 1.55 | 3E−05 |
| 209703_x_at | DKFZP586A0522 protein | DKFZP586A0522 | 1.55 | 6E−07 |
| 1553681_a_at | perforin 1 (pore forming protein) | PRF1 | 1.55 | 2E−13 |
| 219786_at | "metallothionein-like 5, testis-specific (tesmin)" | MTL5 | 1.55 | 1E−07 |
| 243764_at | V-set and immunoglobulin domain containing 1 | VSIG1 | 1.55 | 2E−06 |
| 231112_at | Small nuclear ribonucleoprotein polypeptide E | SNRPE | 1.55 | 6E−07 |
| 227002_at | chromosome 9 open reading frame 59 | C9orf59 | 1.55 | 5E−09 |
| 1557145_at | Serine/threonine kinase 38 | STK38 | 1.55 | 1E−06 |
| 242211_x_at | hypothetical protein KIAA1924 | KIAA1924 | 1.55 | 3E−07 |
| 209007_s_at | NPD014 protein | NPD014 | 1.55 | 2E−12 |
| 218811_at | chromosome 7 open reading frame 19 | C7orf19 | 1.55 | 1E−09 |
| 243430_at | seizure related 6 homolog (mouse) | SEZ6 | 1.55 | 4E−05 |
| 213947_s_at | nucleoporin 210 kDa | NUP210 | 1.55 | 7E−06 |
| 231599_x_at | "D4, zinc and double PHD fingers family 1" | DPF1 | 1.55 | 3E−05 |
| 206776_x_at | acrosomal vesicle protein 1 | ACRV1 | 1.54 | 5E−10 |
| 211531_x_at | proline-rich protein BstNI subfamily 1 | PRB1 | 1.54 | 6E−05 |
| 233343_at | NA | NA | 1.54 | 2E−07 |
| 219683_at | frizzled homolog 3 (*Drosophila*) | FZD3 | 1.54 | 6E−07 |
| 204950_at | "caspase recruitment domain family, member 8" | CARD8 | 1.54 | 4E−13 |
| 217291_at | NA | NA | 1.54 | 7E−05 |
| 226433_at | ring finger protein 157 | RNF157 | 1.54 | 1E−06 |
| 209863_s_at | tumor protein p73-like | TP73L | 1.54 | 2E−09 |
| 205739_x_at | Zinc finger protein (ZFD25) | ZFD25 | 1.54 | 2E−10 |
| 239149_at | Bromodomain containing 4 | BRD4 | 1.54 | 2E−05 |
| 206261_at | zinc finger protein 239 | ZNF239 | 1.54 | 3E−10 |
| 231796_at | EPH receptor A8 | EPHA8 | 1.54 | 1E−07 |
| 211828_s_at | TRAF2 and NCK interacting kinase | TNIK | 1.54 | 1E−08 |
| 210934_at | B lymphoid tyrosine kinase | BLK | 1.54 | 2E−08 |
| 1565131_x_at | Mitogen-activated protein kinase kinase kinase 2 | MAP3K2 | 1.54 | 3E−05 |
| 208341_x_at | chorionic somatomammotropin hormone 2 | CSH2 | 1.54 | 5E−08 |
| 211573_x_at | "transglutaminase 2 (C polypeptide, protein-glutamine-gamma-glutamyltransferase)" | TGM2 | 1.54 | 4E−05 |
| 1569614_s_at | lipocalin 8 | LCN8 | 1.54 | 9E−05 |
| 205659_at | histone deacetylase 9 | HDAC9 | 1.54 | 1E−06 |
| 1552788_a_at | helicase (DNA) B | HELB | 1.54 | 5E−05 |
| 205801_s_at | RAS guanyl releasing protein 3 (calcium and DAG-regulated) | RASGRP3 | 1.54 | 2E−06 |
| 1552555_at | polyserase-2 | FLJ90661 | 1.54 | 4E−07 |
| 1565588_at | SP140 nuclear body protein | SP140 | 1.54 | 2E−06 |
| 213756_s_at | heat shock transcription factor 1 | HSF1 | 1.54 | 5E−09 |
| 1562026_at | WNK lysine deficient protein kinase 2 | WNK2 | 1.53 | 2E−06 |
| 220987_s_at | chromosome 11 open reading frame 17 | chromosome 11 open reading frame 17 | likely ortholog of rat SNF1/AMP-activated protein kinase | likely ortholog of rat SNF1/AMP-activated protein kinase | C11orf17 | SNARK | 1.53 | 2E−08 |
| 210894_s_at | centrosomal protein 2 | CEP2 | 1.53 | 8E−06 |
| 205009_at | "trefoil factor 1 (breast cancer, estrogen-inducible sequence expressed in)" | TFF1 | 1.53 | 3E−05 |
| 222951_s_at | ankyrin repeat domain 5 | ANKRD5 | 1.53 | 3E−05 |
| 211333_s_at | "Fas ligand (TNF superfamily, member 6)" | FASLG | 1.53 | 3E−08 |
| 215086_at | Inhibitor of Bruton agammaglobulinemia tyrosine kinase | IBTK | 1.53 | 6E−05 |
| 221209_s_at | otoraplin | OTOR | 1.53 | 6E−05 |
| 205733_at | Bloom syndrome | BLM | 1.53 | 4E−11 |
| 224156_x_at | interleukin 17 receptor B | IL17RB | 1.53 | 2E−08 |
| 202558_s_at | "stress 70 protein chaperone, microsome-associated, 60 kDa" | STCH | 1.53 | 1E−07 |
| 211368_s_at | "caspase 1, apoptosis-related cysteine protease (interleukin 1, beta, convertase)" | CASP1 | 1.53 | 6E−10 |
| 226474_at | nucleotide-binding oligomerization domains 27 | NOD27 | 1.53 | 3E−08 |
| 206353_at | cytochrome c oxidase subunit VIa polypeptide 2 | COX6A2 | 1.53 | 7E−07 |
| 211516_at | "interleukin 5 receptor, alpha" | IL5RA | 1.53 | 4E−06 |
| 236240_at | hypothetical protein FLJ21106 | FLJ21106 | 1.53 | 2E−07 |
| 224451_x_at | Rho GTPase activating protein 9 | Rho GTPase activating protein 9 | ARHGAP9 | 1.53 | 1E−07 |
| 219112_at | Rap guanine nucleotide exchange factor (GEF) 6 | RAPGEF6 | 1.53 | 1E−10 |
| 231962_at | "adaptor-related protein complex 4, beta 1 subunit" | AP4B1 | 1.53 | 2E−07 |
| 207408_at | "solute carrier family 22 (organic cation transporter), member 14" | SLC22A14 | 1.53 | 2E−10 |
| 233575_s_at | "transducin-like enhancer of split 4 (E(sp1) homolog, *Drosophila*)" | TLE4 | 1.53 | 2E−06 |
| 1553549_at | vomeronasal 1 receptor 2 | VN1R2 | 1.53 | 5E−05 |
| 1554116_s_at | "poly (ADP-ribose) polymerase family, member 11" | PARP11 | 1.53 | 9E−06 |
| 1558755_x_at | hypothetical protein LOC284390 | LOC284390 | 1.53 | 3E−10 |
| 207359_at | "calcium/calmodulin-dependent protein kinase kinase 2, beta" | CAMKK2 | 1.53 | 8E−05 |
| 211194_s_at | tumor protein p73-like | TP73L | 1.53 | 5E−05 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 220958_at | Hypothetical protein FLJ20574 | FLJ20574 | 1.53 | 5E−06 |
| 210038_at | "protein kinase C, theta" | PRKCQ | 1.52 | 4E−09 |
| 224209_s_at | guanine deaminase | GDA | 1.52 | 9E−05 |
| 234943_at | "casein kinase 1, epsilon | TPTE/TPIP pseudogene | similar to TPTE and PTEN homologous inositol lipid phosphatase isoform alpha; TPTE and PTEN homologous inositol lipid phosphatase" | CSNK1E | LOC387593 | LOC400927 | 1.52 | 5E−07 |
| 225795_at | hypothetical gene supported by AL449243 | LOC91689 | 1.52 | 1E−08 |
| 242968_at | NA | NA | 1.52 | 1E−07 |
| 242970_at | KIAA1463 protein | KIAA1463 | 1.52 | 3E−06 |
| 210234_at | "glutamate receptor, metabotropic 4" | GRM4 | 1.52 | 1E−07 |
| 241920_x_at | hypothetical protein FLJ21439 | FLJ21439 | 1.52 | 9E−10 |
| 231612_at | testis development protein NYD-SP26 | NYD-SP26 | 1.52 | 8E−05 |
| 230756_at | hypothetical protein MGC33414 | MGC33414 | 1.52 | 6E−06 |
| 239554_at | Ring finger protein 13 | RNF13 | 1.52 | 5E−05 |
| 214791_at | hypothetical protein BC004921 | LOC93349 | 1.52 | 2E−12 |
| 234820_at | MAS1 oncogene-like | MAS1L | 1.52 | 2E−05 |
| 205235_s_at | M-phase phosphoprotein 1 | MPHOSPH1 | 1.52 | 6E−06 |
| 220989_s_at | amnionless homolog (mouse) | amnionless homolog (mouse) | AMN | 1.52 | 1E−04 |
| 226525_at | Serine/threonine kinase 17b (apoptosis-inducing) | STK17B | 1.52 | 3E−11 |
| 205586_x_at | VGF nerve growth factor inducible | VGF | 1.52 | 8E−06 |
| 1570231_at | "LATS, large tumor suppressor, homolog 1 (Drosophila)" | LATS1 | 1.52 | 5E−05 |
| 226117_at | TRAF-interacting protein with a forkhead-associated domain | TIFA | 1.52 | 2E−14 |
| 214572_s_at | insulin-like 3 (Leydig cell) | INSL3 | 1.52 | 7E−05 |
| 211044_at | tripartite motif-containing 14 | tripartite motif-containing 14 | TRIM14 | 1.52 | 3E−06 |
| 228607_at | "2'-5'-oligoadenylate synthetase 2, 69/71 kDa" | OAS2 | 1.52 | 9E−07 |
| 1558754_at | hypothetical protein LOC284390 | LOC284390 | 1.52 | 2E−06 |
| 220390_at | hypothetical protein FLJ23598 | FLJ23598 | 1.52 | 9E−05 |
| 219413_at | acyl-Coenzyme A binding domain containing 4 | ACBD4 | 1.52 | 2E−07 |
| 225178_at | tetratricopeptide repeat domain 14 | TTC14 | 1.52 | 1E−08 |
| 204733_at | "kallikrein 6 (neurosin, zyme)" | KLK6 | 1.52 | 8E−07 |
| 232963_at | Constitutive photomorphogenic protein | COP1 | 1.52 | 1E−06 |
| 221874_at | maba1 | KIAA1324 | 1.51 | 2E−05 |
| 236061_at | PR domain containing 15 | PRDM15 | 1.51 | 2E−05 |
| 227499_at | Transcribed locus | NA | 1.51 | 2E−06 |
| 241923_x_at | NA | NA | 1.51 | 3E−06 |
| 208442_s_at | "ataxia telangiectasia mutated (includes complementation groups A, C and D)" | ATM | 1.51 | 3E−07 |
| 205013_s_at | adenosine A2a receptor | ADORA2A | 1.51 | 1E−12 |
| 223325_at | thioredoxin domain containing 11 | TXNDC11 | 1.51 | 3E−10 |
| 1552586_at | "transient receptor potential cation channel, subfamily V, member 3" | TRPV3 | 1.51 | 5E−06 |
| 232234_at | Src-like-adaptor 2 | SLA2 | 1.51 | 1E−06 |
| 232706_s_at | hypothetical protein PP2447 | PP2447 | 1.51 | 1E−05 |
| 1557718_at | "protein phosphatase 2, regulatory subunit B (B56), gamma isoform" | PPP2R5C | 1.51 | 2E−07 |
| 207798_s_at | ataxin 2-like | ATXN2L | 1.51 | 1E−05 |
| 221680_s_at | ets variant gene 7 (TEL2 oncogene) | ETV7 | 1.51 | 4E−09 |
| 242174_at | Zinc finger and BTB domain containing 10 | ZBTB10 | 1.51 | 3E−05 |
| 1569490_at | fibronectin type III domain containing 3B | FNDC3B | 1.51 | 2E−07 |
| 1555407_s_at | "FGD1 family, member 3" | FGD3 | 1.51 | 6E−08 |
| 1555734_x_at | "adaptor-related protein complex 1, sigma 3 subunit" | AP1S3 | 1.51 | 3E−05 |
| 243570_at | KIAA0102 gene product | KIAA0102 | 1.51 | 7E−09 |
| 1553067_a_at | gonadotropin-releasing hormone (type 2) receptor 2 | GNRHR2 | 1.51 | 2E−05 |
| 211079_s_at | dual-specificity tyrosine-(Y)-phosphorylation regulated kinase 1A | dual-specificity tyrosine-(Y)-phosphorylation regulated kinase 1A | DYRK1A | 1.51 | 1E−06 |
| 230551_at | "Shinc-4 mRNA, partial sequence" | NA | 1.51 | 3E−05 |
| 1552554_a_at | "caspase recruitment domain family, member 12" | CARD12 | 1.51 | 1E−05 |
| 212079_s_at | "myeloid/lymphoid or mixed-lineage leukemia (trithorax homolog, Drosophila)" | MLL | 1.51 | 3E−09 |
| 205563_at | KiSS-1 metastasis-suppressor | KISS1 | 1.51 | 4E−09 |
| 217823_s_at | "ubiquitin-conjugating enzyme E2, J1 (UBC6 homolog, yeast)" | UBE2J1 | 1.51 | 7E−11 |
| 218796_at | chromosome 20 open reading frame 42 | C20orf42 | 1.50 | 4E−05 |
| 233403_x_at | transmembrane 6 superfamily member 2 | TM6SF2 | 1.50 | 2E−06 |
| 221297_at | "G protein-coupled receptor, family C, group 5, member D" | GPRC5D | 1.50 | 2E−06 |
| 231210_at | hypothetical protein LOC283129 | LOC283129 | 1.50 | 6E−05 |
| 211367_s_at | "caspase 1, apoptosis-related cysteine protease (interleukin 1, beta, convertase)" | CASP1 | 1.50 | 4E−08 |
| 224044_at | "ras homolog gene family, member T1" | RHOT1 | 1.50 | 2E−08 |
| 220216_at | hypothetical protein FLJ11267 | FLJ11267 | 1.50 | 3E−09 |
| 239162_at | NA | NA | 1.50 | 5E−06 |
| 222729_at | "F-box and WD-40 domain protein 7 (archipelago homolog, Drosophila)" | FBXW7 | 1.50 | 2E−11 |
| 217824_at | "ubiquitin-conjugating enzyme E2, J1 (UBC6 homolog, yeast)" | UBE2J1 | 1.50 | 6E−08 |
| 1559500_at | KIAA0804 protein | KIAA0804 | 1.50 | 2E−06 |
| 1555772_a_at | cell division cycle 25A | CDC25A | 1.50 | 9E−05 |
| 206216_at | serine/threonine kinase 23 | STK23 | 1.50 | 2E−11 |
| 224882_at | acetyl-Coenzyme A synthetase 2 (AMP forming)-like | ACAS2L | 1.50 | 1E−10 |
| 218751_s_at | "F-box and WD-40 domain protein 7 (archipelago homolog, Drosophila)" | FBXW7 | 1.50 | 2E−12 |

TABLE 5-continued

Gene expression associated with the L subtype of RA.

| ProbeID | NETAFFX: GeneTitle | NETAFFX: GeneSymbol | Fold Change | p-value |
|---|---|---|---|---|
| 207102_at | "aldo-keto reductase family 1, member D1 (delta 4-3-ketosteroid-5-beta-reductase)" | AKR1D1 | 1.50 | 4E−05 |
| 226132_s_at | hypothetical protein FLJ31434 | FLJ31434 | 1.50 | 3E−08 |
| 213297_at | hypothetical protein FLJ22318 | FLJ22318 | 1.50 | 6E−12 |
| 208486_at | dopamine receptor D5 | DRD5 | 1.50 | 9E−06 |

TABLE 6

Gene expression associated with the M subtype of RA.

| ProbeID | NETAFFX: GeneTitle | NETAFFX: GeneSymbol | Fold Change | p-value |
|---|---|---|---|---|
| 231755_at | "interleukin 1 family, member 8 (eta)" | IL1F8 | 15.91 | 9E−05 |
| 206239_s_at | "serine protease inhibitor, Kazal type 1" | SPINK1 | 10.07 | 4E−04 |
| 206067_s_at | Wilms tumor 1 | WT1 | 9.44 | 5E−08 |
| 204580_at | matrix metalloproteinase 12 (macrophage elastase) | MMP12 | 8.30 | 5E−07 |
| 1552394_a_at | hypothetical protein FLJ25421 | FLJ25421 | 7.89 | 2E−04 |
| 214974_x_at | chemokine (C-X-C motif) ligand 5 | CXCL5 | 7.83 | 8E−10 |
| 219890_at | "C-type lectin domain family 5, member A" | CLEC5A | 7.36 | 2E−07 |
| 215101_s_at | chemokine (C-X-C motif) ligand 5 | CXCL5 | 7.34 | 2E−07 |
| 212657_s_at | interleukin 1 receptor antagonist | IL1RN | 6.79 | 4E−08 |
| 1552393_at | hypothetical protein FLJ25421 | FLJ25421 | 6.11 | 6E−04 |
| 230966_at | interleukin 4 induced 1 | IL4I1 | 4.82 | 5E−09 |
| 216243_s_at | interleukin 1 receptor antagonist | IL1RN | 4.65 | 2E−08 |
| 209696_at | "fructose-1,6-bisphosphatase 1" | FBP1 | 4.30 | 3E−08 |
| 211506_s_at | interleukin 8 | IL8 | 4.22 | 1E−06 |
| 206881_s_at | "leukocyte immunoglobulin-like receptor, subfamily A (without TM domain), member 3" | LILRA3 | 3.95 | 6E−06 |
| 232629_at | prokineticin 2 | PROK2 | 3.81 | 2E−04 |
| 219874_at | "solute carrier family 12 (potassium/chloride transporters), member 8" | SLC12A8 | 3.77 | 1E−09 |
| 212659_s_at | interleukin 1 receptor antagonist | IL1RN | 3.72 | 3E−07 |
| 205220_at | G protein-coupled receptor 109B \| G protein-coupled receptor 109B | GPR109B | 3.71 | 4E−05 |
| 210842_at | neuropilin 2 | NRP2 | 3.64 | 2E−05 |
| 216015_s_at | cold autoinflammatory syndrome 1 | CIAS1 | 3.61 | 2E−09 |
| 230147_at | coagulation factor II (thrombin) receptor-like 2 | F2RL2 | 3.45 | 8E−07 |
| 217078_s_at | CD300A antigen | CD300A | 3.30 | 4E−07 |
| 202628_s_at | "serine (or cysteine) proteinase inhibitor, clade E (nexin, plasminogen activator inhibitor type 1), member 1" | SERPINE1 | 3.27 | 1E−07 |
| 216953_s_at | Wilms tumor 1 | WT1 | 3.26 | 5E−04 |
| 202859_x_at | interleukin 8 | IL8 | 3.19 | 2E−05 |
| 211527_x_at | vascular endothelial growth factor | VEGF | 3.03 | 2E−13 |
| 223484_at | normal mucosa of esophagus specific 1 | NMES1 | 3.03 | 7E−07 |
| 216598_s_at | chemokine (C-C motif) ligand 2 | CCL2 | 2.99 | 3E−13 |
| 203290_at | "major histocompatibility complex, class II, DQ alpha 1 \| major histocompatibility complex, class II, DQ alpha 1 \| major histocompatibility complex, class II, DQ alpha 2 \| major histocompatibility complex, class II, DQ alpha 2" | HLA-DQA1 \| HLA-DQA2 | 2.94 | 3E−04 |
| 208606_s_at | "wingless-type MMTV integration site family, member 4 \| wingless-type MMTV integration site family, member 4" | WNT4 | 2.93 | 5E−04 |
| 214014_at | CDC42 effector protein (Rho GTPase binding) 2 | CDC42EP2 | 2.90 | 4E−04 |
| 209122_at | adipose differentiation-related protein | ADFP | 2.90 | 7E−06 |
| 223767_at | G protein-coupled receptor 84 | GPR84 | 2.84 | 9E−08 |
| 202219_at | "solute carrier family 6 (neurotransmitter transporter, creatine), member 8" | SLC6A8 | 2.77 | 5E−05 |
| 211924_s_at | "plasminogen activator, urokinase receptor \| plasminogen activator, urokinase receptor" | PLAUR | 2.74 | 7E−12 |
| 205709_s_at | CDP-diacylglycerol synthase (phosphatidate cytidylyltransferase) 1 | CDS1 | 2.69 | 7E−07 |
| 209949_at | "neutrophil cytosolic factor 2 (65 kDa, chronic granulomatous disease, autosomal 2)" | NCF2 | 2.68 | 1E−09 |
| 230030_at | heparan sulfate 6-O-sulfotransferase 2 | HS6ST2 | 2.66 | 6E−04 |
| 213831_at | "major histocompatibility complex, class II, DQ alpha 1" | HLA-DQA1 | 2.65 | 1E−04 |
| 213338_at | Ras-induced senescence 1 | RIS1 | 2.65 | 4E−12 |
| 210845_s_at | "plasminogen activator, urokinase receptor" | PLAUR | 2.60 | 8E−13 |
| 218498_s_at | ERO1-like (S. cerevisiae) | ERO1L | 2.60 | 6E−09 |
| 220023_at | apolipoprotein B48 receptor | APOB48R | 2.59 | 6E−08 |
| 210512_s_at | vascular endothelial growth factor | VEGF | 2.56 | 5E−11 |

TABLE 6-continued

Gene expression associated with the M subtype of RA.

| ProbeID | NETAFFX: GeneTitle | NETAFFX: GeneSymbol | Fold Change | p-value |
|---|---|---|---|---|
| 205114_s_at | "chemokine (C-C motif) ligand 3 | chemokine (C-C motif) ligand 3-like 1 | chemokine (C-C motif) ligand 3-like, centromeric" | CCL3 | CCL3L1 | MGC12815 | 2.53 | 2E-04 |
| 214038_at | chemokine (C-C motif) ligand 8 | CCL8 | 2.53 | 6E-07 |
| 206482_at | PTK6 protein tyrosine kinase 6 | PTK6 | 2.50 | 4E-06 |
| 224762_at | tumor differentially expressed 2-like | TDE2L | 2.46 | 4E-06 |
| 219386_s_at | SLAM family member 8 | SLAMF8 | 2.45 | 5E-08 |
| 205648_at | wingless-type MMTV integration site family member 2 | WNT2 | 2.43 | 7E-05 |
| 204533_at | chemokine (C-X-C motif) ligand 10 | CXCL10 | 2.40 | 4E-07 |
| 201313_at | "enolase 2 (gamma, neuronal)" | ENO2 | 2.39 | 5E-06 |
| 202627_s_at | "serine (or cysteine) proteinase inhibitor, clade E (nexin, plasminogen activator inhibitor type 1), member 1" | SERPINE1 | 2.37 | 7E-07 |
| 204656_at | SHB (Src homology 2 domain containing) adaptor protein B | SHB | 2.35 | 4E-10 |
| 214435_x_at | v-ral simian leukemia viral oncogene homolog A (ras related) | RALA | 2.34 | 9E-08 |
| 212171_x_at | vascular endothelial growth factor | VEGF | 2.32 | 2E-14 |
| 220016_at | hypothetical protein MGC5395 | MGC5395 | 2.30 | 4E-06 |
| 202638_s_at | "intercellular adhesion molecule 1 (CD54), human rhinovirus receptor" | ICAM1 | 2.30 | 2E-17 |
| 217159_x_at | sialic acid binding Ig-like lectin 7 | SIGLEC7 | 2.28 | 5E-04 |
| 201952_at | NA | NA | 2.25 | 3E-09 |
| 1555214_a_at | "C-type lectin domain family 7, member A" | CLEC7A | 2.25 | 2E-04 |
| 229309_at | "Adrenergic, beta-1-, receptor" | ADRB1 | 2.24 | 2E-08 |
| 222646_s_at | ERO1-like (S. cerevisiae) | ERO1L | 2.24 | 2E-07 |
| 212374_at | fem-1 homolog b (C. elegans) | FEM1B | 2.23 | 2E-05 |
| 202856_s_at | "solute carrier family 16 (monocarboxylic acid transporters), member 3" | SLC16A3 | 2.23 | 4E-10 |
| 205071_x_at | X-ray repair complementing defective repair in Chinese hamster cells 4 | XRCC4 | 2.23 | 6E-05 |
| 219047_s_at | hypothetical protein FLJ13479 | FLJ13479 | 2.22 | 6E-06 |
| 213324_at | v-src sarcoma (Schmidt-Ruppin A-2) viral oncogene homolog (avian) | SRC | 2.22 | 2E-08 |
| 206503_x_at | promyelocytic leukemia | PML | 2.20 | 2E-05 |
| 242871_at | membrane progestin receptor gamma | MPRG | 2.20 | 1E-04 |
| 208438_s_at | Gardner-Rasheed feline sarcoma viral (v-fgr) oncogene homolog | FGR | 2.19 | 2E-09 |
| 205875_s_at | three prime repair exonuclease 1 | TREX1 | 2.18 | 5E-04 |
| 220066_at | "caspase recruitment domain family, member 15" | CARD15 | 2.18 | 3E-08 |
| 201951_at | Activated leukocyte cell adhesion molecule | ALCAM | 2.17 | 8E-10 |
| 210233_at | interleukin 1 receptor accessory protein | IL1RAP | 2.14 | 8E-10 |
| 202637_s_at | "intercellular adhesion molecule 1 (CD54), human rhinovirus receptor" | ICAM1 | 2.13 | 8E-14 |
| 217818_s_at | "actin related protein 2/3 complex, subunit 4, 20 kDa" | ARPC4 | 2.12 | 6E-04 |
| 211013_x_at | promyelocytic leukemia | PML | 2.12 | 1E-05 |
| 209933_s_at | CD3OOA antigen | CD300A | 2.12 | 1E-06 |
| 220333_at | membrane progestin receptor gamma | MPRG | 2.12 | 4E-06 |
| 205786_s_at | "integrin, alpha M (complement component receptor 3, alpha; also known as CD11b (p170), macrophage antigen alpha polypeptide) | integrin, alpha M (complement component receptor 3, alpha; also known as CD11b (p170), macrophage antigen alpha polypeptide . . ." | ITGAM | 2.10 | 2E-09 |
| 204174_at | arachidonate 5-lipoxygenase-activating protein | ALOX5AP | 2.10 | 1E-06 |
| 205722_s_at | GDNF family receptor alpha 2 | GFRA2 | 2.10 | 6E-04 |
| 209875_s_at | "secreted phosphoprotein 1 (osteopontin, bone sialoprotein I, early T-lymphocyte activation 1)" | SPP1 | 2.09 | 3E-05 |
| 223303_at | UNC-112 related protein 2 | URP2 | 2.09 | 4E-08 |
| 226111_s_at | zinc finger protein 385 | ZNF385 | 2.09 | 2E-09 |
| 223019_at | chromosome 9 open reading frame 88 | C9orf88 | 2.08 | 4E-12 |
| 215485_s_at | "intercellular adhesion molecule 1 (CD54), human rhinovirus receptor" | ICAM1 | 2.07 | 1E-12 |
| 219434_at | triggering receptor expressed on myeloid cells 1 | TREM1 | 2.05 | 3E-08 |
| 214841_at | cornichon homolog 3 (Drosophila) | CNIH3 | 2.05 | 7E-06 |
| 221698_s_at | "C-type lectin domain family 7, member A | C-type lectin domain family 7, member A" | CLEC7A | 2.05 | 5E-09 |
| 223855_s_at | G protein-coupled receptor 24 | GPR24 | 2.04 | 1E-04 |
| 202790_at | claudin 7 | CLDN7 | 2.04 | 4E-06 |
| 1554952_at | "NACHT, leucine rich repeat and PYD containing 12" | NALP12 | 2.03 | 9E-09 |
| 205241_at | SCO cytochrome oxidase deficient homolog 2 (yeast) | SCO2 | 2.03 | 1E-13 |
| 207387_s_at | glycerol kinase | GK | 2.02 | 4E-08 |
| 201250_s_at | "solute carrier family 2 (facilitated glucose transporter), member 1" | SLC2A1 | 2.02 | 1E-05 |
| 206267_s_at | megakaryocyte-associated tyrosine kinase | MATK | 2.02 | 1E-05 |
| 238423_at | synaptotagmin-like 3 | SYTL3 | 2.01 | 2E-05 |
| 1555349_a_at | "integrin, beta 2 (antigen CD18 (p95), lymphocyte function-associated antigen 1; macrophage antigen 1 (mac-1) beta subunit)" | ITGB2 | 2.01 | 2E-06 |

TABLE 6-continued

Gene expression associated with the M subtype of RA.

| ProbeID | NETAFFX: GeneTitle | NETAFFX: GeneSymbol | Fold Change | p-value |
|---|---|---|---|---|
| 221908_at | Hypothetical protein FLJ14627 | FLJ14627 | 2.00 | 6E−05 |
| 243611_at | hypothetical protein FLJ14966 | FLJ14966 | 1.99 | 4E−05 |
| 221779_at | MICAL-like 1 | MICAL-L1 | 1.99 | 4E−07 |
| 209053_s_at | Wolf-Hirschhorn syndrome candidate 1 | WHSC1 | 1.98 | 5E−04 |
| 202855_s_at | "solute carrier family 16 (monocarboxylic acid transporters), member 3" | SLC16A3 | 1.98 | 3E−08 |
| 226088_at | "zinc finger, DHHC domain containing 12" | ZDHHC12 | 1.98 | 8E−06 |
| 1555167_s_at | pre-B-cell colony enhancing factor 1 | PBEF1 | 1.98 | 2E−04 |
| 218223_s_at | CK2 interacting protein 1; HQ0024c protein | CKIP-1 | 1.97 | 9E−10 |
| 204508_s_at | carbonic anhydrase XII | CA12 | 1.96 | 2E−06 |
| 205721_at | GDNF family receptor alpha 2 | GFRA2 | 1.96 | 4E−06 |
| 235568_at | hypothetical protein LOC199675 | LOC199675 | 1.95 | 9E−06 |
| 211312_s_at | WNT1 inducible signaling pathway protein 1 | WISP1 | 1.95 | 7E−04 |
| 205098_at | chemokine (C-C motif) receptor 1 | CCR1 | 1.95 | 6E−11 |
| 237623_at | Cystatin C (amyloid angiopathy and cerebral hemorrhage) | CST3 | 1.95 | 4E−05 |
| 218567_x_at | dipeptidylpeptidase 3 | DPP3 | 1.95 | 3E−04 |
| 214866_at | "plasminogen activator, urokinase receptor" | PLAUR | 1.94 | 6E−11 |
| 204446_s_at | arachidonate 5-lipoxygenase | ALOX5 | 1.94 | 2E−06 |
| 209660_at | "transthyretin (prealbumin, amyloidosis type I)" | TTR | 1.93 | 8E−06 |
| 214366_s_at | arachidonate 5-lipoxygenase | ALOX5 | 1.92 | 1E−05 |
| 205485_at | ryanodine receptor 1 (skeletal) | RYR1 | 1.92 | 1E−06 |
| 203963_at | carbonic anhydrase XII | CA12 | 1.92 | 6E−07 |
| 202912_at | adrenomedullin | ADM | 1.91 | 5E−04 |
| 55081_at | MICAL-like 1 | MICAL-L1 | 1.91 | 1E−09 |
| 214164_x_at | carbonic anhydrase XII | CA12 | 1.91 | 1E−08 |
| 219978_s_at | nucleolar and spindle associated protein 1 | NUSAP1 | 1.90 | 6E−04 |
| 202910_s_at | CD97 antigen | CD97 | 1.90 | 5E−09 |
| 232608_x_at | "caspase recruitment domain family, member 14" | CARD14 | 1.90 | 3E−04 |
| 210152_at | "leukocyte immunoglobulin-like receptor, subfamily B (with TM and ITIM domains), member 4" | LILRB4 | 1.90 | 2E−06 |
| 1555756_a_at | "C-type lectin domain family 7, member A" | CLEC7A | 1.89 | 1E−06 |
| 225316_at | hypothetical protein FLJ14490 | FLJ14490 | 1.89 | 7E−04 |
| 219634_at | carbohydrate (chondroitin 4) sulfotransferase 11 | CHST11 | 1.89 | 1E−09 |
| 205099_s_at | chemokine (C-C motif) receptor 1 | CCR1 | 1.88 | 4E−08 |
| 226869_at | Full length insert cDNA clone ZD77F06 | NA | 1.88 | 5E−08 |
| 1553133_at | chromosome 9 open reading frame 72 | C9orf72 | 1.88 | 7E−07 |
| 228302_x_at | calcium/calmodulin-dependent protein kinase II | CaMKIINalpha | 1.88 | 3E−04 |
| 205165_at | "cadherin, EGF LAG seven-pass G-type receptor 3 (flamingo homolog, *Drosophila*)" | CELSR3 | 1.88 | 5E−04 |
| 219385_at | SLAM family member 8 | SLAMF8 | 1.87 | 1E−05 |
| 224374_s_at | elastin microfibril interfacer 2 \| elastin microfibril interfacer 2 | EMILIN2 | 1.87 | 1E−14 |
| 202803_s_at | "integrin, beta 2 (antigen CD18 (p95), lymphocyte function-associated antigen 1; macrophage antigen 1 (mac-1) beta subunit)" | ITGB2 | 1.87 | 9E−07 |
| 207091_at | "purinergic receptor P2X, ligand-gated ion channel, 7" | P2RX7 | 1.86 | 1E−06 |
| 215966_x_at | NA | NA | 1.86 | 3E−08 |
| 229404_at | twist homolog 2 (*Drosophila*) | TWIST2 | 1.86 | 2E−05 |
| 1559399_s_at | "zinc finger, CCHC domain containing 10" | ZCCHC10 | 1.85 | 4E−10 |
| 204655_at | NA | NA | 1.85 | 2E−05 |
| 204490_s_at | CD44 antigen (homing function and Indian blood group system) | CD44 | 1.84 | 2E−10 |
| 226389_s_at | Rap guanine nucleotide exchange factor (GEF) 1 | RAPGEF1 | 1.83 | 5E−12 |
| 1554036_at | zinc finger and BTB domain containing 24 | ZBTB24 | 1.82 | 2E−04 |
| 218627_at | hypothetical protein FLJ11259 | FLJ11259 | 1.81 | 3E−14 |
| 214501_s_at | "H2A histone family, member Y" | H2AFY | 1.81 | 2E−09 |
| 239217_x_at | "ATP-binding cassette, sub-family C (CFTR/MRP), member 3" | ABCC3 | 1.81 | 4E−04 |
| 217507_at | "solute carrier family 11 (proton-coupled divalent metal ion transporters), member 1" | SLC11A1 | 1.81 | 4E−05 |
| 238044_at | "Transcribed locus, moderately similar to XP_529341.1 LOC450700 [*Pan troglodytes*]" | NA | 1.81 | 9E−06 |
| 202998_s_at | lysyl oxidase-like 2 | LOXL2 | 1.81 | 1E−04 |
| 202998_s_at | lysyl oxidase-like 2 | LOXL2 | 1.81 | 1E−04 |
| 205349_at | "guanine nucleotide binding protein (G protein), alpha 15 (Gq class)" | GNA15 | 1.81 | 7E−09 |
| 206420_at | "immunoglobulin superfamily, member 6" | IGSF6 | 1.81 | 1E−07 |
| 226354_at | "lactamase, beta" | LACTB | 1.81 | 2E−13 |
| 206991_s_at | chemokine (C-C motif) receptor 5 | CCR5 | 1.81 | 1E−05 |
| 215977_x_at | glycerol kinase | GK | 1.80 | 4E−06 |
| 209835_x_at | CD44 antigen (homing function and Indian blood group system) | CD44 | 1.80 | 2E−10 |
| 219360_s_at | "transient receptor potential cation channel, subfamily M, member 4" | TRPM4 | 1.80 | 3E−04 |
| 207075_at | cold autoinflammatory syndrome 1 | CIAS1 | 1.79 | 1E−06 |
| 207376_at | VENT-like homeobox 2 | VENTX2 | 1.79 | 8E−08 |
| 200629_at | tryptophanyl-tRNA synthetase | WARS | 1.79 | 6E−06 |
| 215223_s_at | "superoxide dismutase 2, mitochondrial" | SOD2 | 1.78 | 3E−05 |

TABLE 6-continued

Gene expression associated with the M subtype of RA.

| ProbeID | NETAFFX: GeneTitle | NETAFFX: GeneSymbol | Fold Change | p-value |
|---|---|---|---|---|
| 214978_s_at | "protein tyrosine phosphatase, receptor type, f polypeptide (PTPRF), interacting protein (liprin), alpha 4" | PPFIA4 | 1.78 | 6E−05 |
| 212014_x_at | CD44 antigen (homing function and Indian blood group system) | CD44 | 1.78 | 4E−09 |
| 213520_at | NA | NA | 1.78 | 5E−04 |
| 209267_s_at | "solute carrier family 39 (zinc transporter), member 8" | SLC39A8 | 1.78 | 1E−05 |
| 223952_x_at | dehydrogenase/reductase (SDR family) member 9 | DHRS9 | 1.78 | 7E−05 |
| 224009_x_at | dehydrogenase/reductase (SDR family) member 9 | DHRS9 | 1.77 | 9E−05 |
| 215498_s_at | mitogen-activated protein kinase kinase 3 \| mitogen-activated protein kinase kinase 3 | MAP2K3 | 1.77 | 8E−09 |
| 1554131_at | KIAA1128 | KIAA1128 | 1.76 | 1E−04 |
| 201890_at | ribonucleotide reductase M2 polypeptide | RRM2 | 1.76 | 1E−04 |
| 204440_at | "CD83 antigen (activated B lymphocytes, immunoglobulin superfamily)" | CD83 | 1.74 | 2E−05 |
| 229763_at | Forkhead box P4 \| Activating signal cointegrator 1 complex subunit 2 | FOXP4 \| ASCC2 | 1.74 | 3E−04 |
| 208018_s_at | hemopoietic cell kinase | HCK | 1.74 | 2E−09 |
| 215867_x_at | carbonic anhydrase XII | CA12 | 1.74 | 1E−07 |
| 222817_at | "hydroxy-delta-5-steroid dehydrogenase, 3 beta- and steroid delta-isomerase 7" | HSD3B7 | 1.74 | 4E−05 |
| 230283_at | neuralized-like 2 (Drosophila) | NEURL2 | 1.73 | 1E−04 |
| 203570_at | lysyl oxidase-like 1 | LOXL1 | 1.73 | 1E−07 |
| 211725_s_at | BH3 interacting domain death agonist \| BH3 interacting domain death agonist | BID | 1.73 | 1E−12 |
| 223398_at | chromosome 9 open reading frame 89 | C9orf89 | 1.73 | 3E−09 |
| 209193_at | NA | NA | 1.73 | 1E−07 |
| 205640_at | "aldehyde dehydrogenase 3 family, member B1" | ALDH3B1 | 1.73 | 2E−05 |
| 229975_at | Transcribed locus | NA | 1.73 | 5E−04 |
| 1552914_a_at | B7 homolog 3 | B7H3 | 1.72 | 4E−04 |
| 207697_x_at | "leukocyte immunoglobulin-like receptor, subfamily B (with TM and ITIM domains), member 2" | LILRB2 | 1.72 | 2E−07 |
| 210146_x_at | "leukocyte immunoglobulin-like receptor, subfamily B (with TM and ITIM domains), member 2 \| leukocyte immunoglobulin-like receptor, subfamily B (with TM and ITIM domains), member 6" | LILRB2 \| LILRB6 | 1.71 | 7E−06 |
| 212268_at | "serine (or cysteine) proteinase inhibitor, clade B (ovalbumin), member 1" | SERPINB1 | 1.71 | 3E−14 |
| 219799_s_at | dehydrogenase/reductase (SDR family) member 9 | DHRS9 | 1.71 | 2E−04 |
| 213693_s_at | "Mucin 1, transmembrane" | MUC1 | 1.70 | 2E−04 |
| 202207_at | ADP-ribosylation factor-like 7 | ARL7 | 1.70 | 7E−08 |
| 210042_s_at | cathepsin Z | CTSZ | 1.70 | 1E−06 |
| 1557458_s_at | SHB (Src homology 2 domain containing) adaptor protein B | SHB | 1.70 | 2E−10 |
| 204182_s_at | zinc finger protein 297B | ZNF297B | 1.70 | 2E−06 |
| 214500_at | "H2A histone family, member Y" | H2AFY | 1.69 | 2E−10 |
| 209191_at | "tubulin, beta 6" | TUBB6 | 1.69 | 4E−09 |
| 218169_at | Vac14 homolog (S. cerevisiae) | VAC14 | 1.69 | 2E−07 |
| 204401_at | "potassium intermediate/small conductance calcium-activated channel, subfamily N, member 4" | KCNN4 | 1.69 | 2E−06 |
| 226722_at | "family with sequence similarity 20, member C" | FAM20C | 1.69 | 9E−06 |
| 217739_s_at | pre-B-cell colony enhancing factor 1 | PBEF1 | 1.69 | 1E−04 |
| 225440_at | 1-acylglycerol-3-phosphate O-acyltransferase 3 | AGPAT3 | 1.68 | 7E−06 |
| 203835_at | glycoprotein A repetitions predominant | GARP | 1.68 | 2E−05 |
| 217388_s_at | kynureninase (L-kynurenine hydrolase) | KYNU | 1.68 | 2E−05 |
| 219631_at | low density lipoprotein-related protein 12 | LRP12 | 1.68 | 1E−05 |
| 213942_at | "EGF-like-domain, multiple 3" | EGFL3 | 1.68 | 3E−05 |
| 212472_at | flavoprotein oxidoreductase MICAL2 | MICAL2 | 1.67 | 3E−04 |
| 212472_at | flavoprotein oxidoreductase MICAL2 | MICAL2 | 1.67 | 3E−04 |
| 225687_at | chromosome 20 open reading frame 129 | C20orf129 | 1.67 | 2E−04 |
| 223502_s_at | "tumor necrosis factor (ligand) superfamily, member 13b" | TNFSF13B | 1.66 | 9E−06 |
| 213274_s_at | cathepsin B | CTSB | 1.66 | 2E−09 |
| 228499_at | "6-phosphofructo-2-kinase/fructose-2,6-biphosphatase 4" | PFKFB4 | 1.66 | 9E−05 |
| 224880_at | v-ral simian leukemia viral oncogene homolog A (ras related) | RALA | 1.66 | 2E−09 |
| 209230_s_at | p8 protein (candidate of metastasis 1) | P8 | 1.66 | 6E−04 |
| 204879_at | lung type-I cell membrane-associated glycoprotein | T1A-2 | 1.65 | 3E−05 |
| 219763_at | KIAA1608 | KIAA1608 | 1.65 | 1E−08 |
| 201389_at | "integrin, alpha 5 (fibronectin receptor, alpha polypeptide)" | ITGA5 | 1.65 | 2E−06 |
| 206342_x_at | iduronate 2-sulfatase (Hunter syndrome) | IDS | 1.65 | 7E−09 |
| 218840_s_at | NAD synthetase 1 | NADSYN1 | 1.64 | 4E−04 |
| 224282_s_at | 1-acylglycerol-3-phosphate O-acyltransferase 3 | AGPAT3 | 1.64 | 6E−05 |
| 228124_at | chromosome 20 open reading frame 22 | C20orf22 | 1.64 | 5E−07 |
| 204445_s_at | arachidonate 5-lipoxygenase | ALOX5 | 1.64 | 5E−04 |
| 212488_at | "Collagen, type V, alpha 1" | COL5A1 | 1.64 | 8E−04 |
| 212488_at | "Collagen, type V, alpha 1" | COL5A1 | 1.64 | 8E−04 |
| 210889_s_at | "Fc fragment of IgG, low affinity IIb, receptor (CD32)" | FCGR2B | 1.64 | 2E−04 |
| 202788_at | mitogen-activated protein kinase-activated protein kinase 3 | MAPKAPK3 | 1.64 | 2E−09 |
| 210513_s_at | vascular endothelial growth factor | VEGF | 1.64 | 2E−09 |

TABLE 6-continued

Gene expression associated with the M subtype of RA.

| ProbeID | NETAFFX: GeneTitle | NETAFFX: GeneSymbol | Fold Change | p-value |
|---|---|---|---|---|
| 217167_x_at | glycerol kinase | GK | 1.63 | 4E−05 |
| 202626_s_at | v-yes-1 Yamaguchi sarcoma viral related oncogene homolog | v-yes-1 Yamaguchi sarcoma viral related oncogene homolog | LYN | 1.63 | 1E−08 |
| 207765_s_at | KIAA1539 | KIAA1539 | 1.63 | 7E−09 |
| 203671_at | thiopurine S-methyltransferase | TPMT | 1.63 | 2E−11 |
| 1557915_s_at | glutathione S-transferase omega 1 | GSTO1 | 1.63 | 1E−10 |
| 219448_at | hypothetical protein FLJ20533 | FLJ20533 | 1.63 | 5E−06 |
| 204158_s_at | "T-cell, immune regulator 1, ATPase, H+ transporting, lysosomal V0 protein a isoform 3" | TCIRG1 | 1.63 | 5E−06 |
| 210735_s_at | carbonic anhydrase XII | CA12 | 1.63 | 4E−06 |
| 207939_x_at | "RNA binding protein S1, serine-rich domain" | RNPS1 | 1.63 | 1E−06 |
| 201231_s_at | "enolase 1, (alpha)" | ENO1 | 1.63 | 2E−11 |
| 221882_s_at | transmembrane protein 8 (five membrane-spanning domains) | TMEM8 | 1.63 | 2E−07 |
| 219053_s_at | Hypothetical protein FLJ20847 | FLJ20847 | 1.62 | 4E−14 |
| 219648_at | likely ortholog of mouse dilute suppressor | DSU | 1.62 | 9E−05 |
| 204924_at | toll-like receptor 2 | TLR2 | 1.62 | 4E−05 |
| 223683_at | "zinc finger, MYND domain containing 15" | ZMYND15 | 1.61 | 8E−06 |
| 218309_at | calcium/calmodulin-dependent protein kinase II | CaMKIINalpha | 1.61 | 1E−04 |
| 205205_at | "v-rel reticuloendotheliosis viral oncogene homolog B, nuclear factor of kappa light polypeptide gene enhancer in B-cells 3 (avian)" | RELB | 1.61 | 4E−11 |
| 1557905_s_at | CD44 antigen (homing function and Indian blood group system) | CD44 | 1.61 | 1E−06 |
| 213113_s_at | "solute carrier family 43, member 3" | SLC43A3 | 1.61 | 2E−10 |
| 218779_x_at | EPS8-like 1 | EPS8L1 | 1.61 | 4E−04 |
| 205174_s_at | glutaminyl-peptide cyclotransferase (glutaminyl cyclase) | QPCT | 1.60 | 3E−04 |
| 227396_at | "Homo sapiens, clone IMAGE: 4454331, mRNA" | NA | 1.60 | 7E−06 |
| 203561_at | "Fc fragment of IgG, low affinity IIa, receptor (CD32)" | FCGR2A | 1.60 | 1E−05 |
| 212849_at | axin 1 | AXIN1 | 1.60 | 5E−08 |
| 229055_at | Transcribed locus | NA | 1.60 | 6E−08 |
| 211057_at | receptor tyrosine kinase-like orphan receptor 1 | receptor tyrosine kinase-like orphan receptor 1 | ROR1 | 1.60 | 1E−04 |
| 226944_at | HtrA serine peptidase 3 | HTRA3 | 1.60 | 3E−05 |
| 202206_at | ADP-ribosylation factor-like 7 | ARL7 | 1.59 | 2E−06 |
| 201743_at | CD14 antigen | CD14 antigen | CD14 | 1.59 | 3E−08 |
| 230498_at | G protein-coupled receptor 24 | GPR24 | 1.59 | 5E−07 |
| 210612_s_at | synaptojanin 2 | SYNJ2 | 1.59 | 6E−04 |
| 210612_s_at | synaptojanin 2 | SYNJ2 | 1.59 | 6E−04 |
| 35820_at | GM2 ganglioside activator | GM2A | 1.58 | 3E−07 |
| 1553375_at | BTB (POZ) domain containing 9 | BTBD9 | 1.58 | 7E−04 |
| 221042_s_at | "calmin (calponin-like, transmembrane)" | CLMN | 1.58 | 1E−05 |
| 217995_at | sulfide quinone reductase-like (yeast) | SQRDL | 1.58 | 9E−07 |
| 1554406_a_at | "C-type lectin domain family 7, member A" | CLEC7A | 1.58 | 1E−07 |
| 235735_at | NA | NA | 1.58 | 6E−06 |
| 1560060_s_at | vacuolar protein sorting 37C (yeast) | VPS37C | 1.58 | 4E−13 |
| 207540_s_at | spleen tyrosine kinase | SYK | 1.58 | 6E−05 |
| 218145_at | tribbles homolog 3 (Drosophila) | TRIB3 | 1.58 | 1E−04 |
| 204657_s_at | SHB (Src homology 2 domain containing) adaptor protein B | SHB | 1.58 | 7E−07 |
| 224950_at | prostaglandin F2 receptor negative regulator | PTGFRN | 1.57 | 1E−05 |
| 232510_s_at | dipeptidylpeptidase 3 | DPP3 | 1.57 | 2E−07 |
| 1554503_a_at | osteoclast-associated receptor | OSCAR | 1.57 | 1E−04 |
| 203952_at | activating transcription factor 6 | ATF6 | 1.57 | 1E−04 |
| 226497_s_at | Fms-related tyrosine kinase 1 (vascular endothelial growth factor/vascular permeability factor receptor) | FLT1 | 1.57 | 5E−05 |
| 201470_at | glutathione S-transferase omega 1 | GSTO1 | 1.56 | 2E−10 |
| 219090_at | "solute carrier family 24 (sodium/potassium/calcium exchanger), member 3" | SLC24A3 | 1.56 | 1E−03 |
| 205707_at | interleukin 17 receptor | IL17R | 1.56 | 2E−06 |
| 220253_s_at | low density lipoprotein-related protein 12 | LRP12 | 1.56 | 8E−07 |
| 213011_s_at | triosephosphate isomerase 1 | TPI1 | 1.56 | 8E−10 |
| 227060_at | "tumor necrosis factor receptor superfamily, member 19-like" | TNFRSF19L | 1.56 | 9E−04 |
| 207671_s_at | "vitelliform macular dystrophy (Best disease, bestrophin)" | VMD2 | 1.56 | 3E−04 |
| 227757_at | cullin 4A | CUL4A | 1.56 | 3E−04 |
| 226140_s_at | OTU domain containing 1 | OTUD1 | 1.56 | 8E−10 |
| 209545_s_at | receptor-interacting serine-threonine kinase 2 | RIPK2 | 1.56 | 3E−09 |
| 218009_s_at | protein regulator of cytokinesis 1 | PRC1 | 1.56 | 1E−04 |
| 202208_s_at | ADP-ribosylation factor-like 7 | ARL7 | 1.56 | 1E−06 |
| 203045_at | ninjurin 1 | NINJ1 | 1.56 | 4E−07 |
| 207168_s_at | "H2A histone family, member Y" | H2AFY | 1.55 | 9E−10 |
| 221654_s_at | ubiquitin specific protease 3 | USP3 | 1.55 | 2E−09 |
| 203402_at | "potassium voltage-gated channel, shaker-related subfamily, beta member 2" | KCNAB2 | 1.55 | 3E−05 |
| 203923_s_at | "cytochrome b-245, beta polypeptide (chronic granulomatous disease)" | CYBB | 1.55 | 1E−04 |
| 202897_at | "protein tyrosine phosphatase, non-receptor type substrate 1" | PTPNS1 | 1.55 | 3E−09 |

TABLE 6-continued

Gene expression associated with the M subtype of RA.

| ProbeID | NETAFFX: GeneTitle | NETAFFX: GeneSymbol | Fold Change | p-value |
|---|---|---|---|---|
| 201848_s_at | BCL2/adenovirus E1B 19 kDa interacting protein 3 | BNIP3 | 1.55 | 3E−06 |
| 202625_at | V-yes-1 Yamaguchi sarcoma viral related oncogene homolog \| V-yes-1 Yamaguchi sarcoma viral related oncogene homolog | LYN | 1.55 | 2E−09 |
| 1565951_s_at | choroideremia-like (Rab escort protein 2) | CHML | 1.55 | 1E−04 |
| 41660_at | "cadherin, EGF LAG seven-pass G-type receptor 1 (flamingo homolog, Drosophila)" | CELSR1 | 1.55 | 7E−04 |
| 215499_at | Mitogen-activated protein kinase kinase 3 \| Mitogen-activated protein kinase kinase 3 | MAP2K3 | 1.55 | 2E−07 |
| 203409_at | "damage-specific DNA binding protein 2, 48 kDa" | DDB2 | 1.55 | 2E−06 |
| 224733_at | chemokine-like factor super family 3 | CKLFSF3 | 1.55 | 4E−10 |
| 204858_s_at | endothelial cell growth factor 1 (platelet-derived) | ECGF1 | 1.54 | 4E−05 |
| 201849_at | BCL2/adenovirus E1B 19 kDa interacting protein 3 | BNIP3 | 1.54 | 3E−06 |
| 225955_at | "meteorin, glial cell differentiation regulator-like" | METRNL | 1.54 | 2E−08 |
| 222768_s_at | CGI-09 protein | CGI-09 | 1.54 | 3E−09 |
| 204575_s_at | matrix metalloproteinase 19 | MMP19 | 1.54 | 2E−05 |
| 208002_s_at | brain acyl-CoA hydrolase | BACH | 1.54 | 2E−06 |
| 225738_at | Rap guanine nucleotide exchange factor (GEF) 1 | RAPGEF1 | 1.54 | 2E−11 |
| 1553134_s_at | chromosome 9 open reading frame 72 | C9orf72 | 1.54 | 4E−04 |
| 227337_at | low density lipoprotein receptor-related protein binding protein | Lrp2bp | 1.53 | 2E−04 |
| 221539_at | eukaryotic translation initiation factor 4E binding protein 1 | EIF4EBP1 | 1.53 | 9E−05 |
| 216180_s_at | synaptojanin 2 | SYNJ2 | 1.53 | 4E−04 |
| 235678_at | GM2 ganglioside activator | GM2A | 1.53 | 2E−07 |
| 202087_s_at | cathepsin L | CTSL | 1.53 | 2E−06 |
| 213716_s_at | secreted and transmembrane 1 | SECTM1 | 1.53 | 2E−05 |
| 201963_at | acyl-CoA synthetase long-chain family member 1 | ACSL1 | 1.53 | 5E−06 |
| 223811_s_at | chromosome 7 open reading frame 20 | C7orf20 | 1.53 | 7E−05 |
| 212671_s_at | "major histocompatibility complex, class II, DQ alpha 1 \| major histocompatibility complex, class II, DQ alpha 2" | HLA-DQA1 \| HLA-DQA2 | 1.53 | 9E−04 |
| 207275_s_at | acyl-CoA synthetase long-chain family member 1 | ACSL1 | 1.53 | 3E−04 |
| 209166_s_at | "mannosidase, alpha, class 2B, member 1" | MAN2B1 | 1.53 | 6E−08 |
| 208308_s_at | glucose phosphate isomerase | GPI | 1.53 | 1E−07 |
| 202329_at | c-src tyrosine kinase | CSK | 1.53 | 1E−06 |
| 205684_s_at | chromosome 9 open reading frame 55 | C9orf55 | 1.53 | 1E−08 |
| 210589_s_at | "glucosidase, beta; acid (includes glucosylceramidase)" | GBA | 1.52 | 9E−05 |
| 222868_s_at | interleukin 18 binding protein | IL18BP | 1.52 | 6E−06 |
| 201587_s_at | interleukin-1 receptor-associated kinase 1 | IRAK1 | 1.52 | 3E−09 |
| 207224_s_at | sialic acid binding Ig-like lectin 7 | SIGLEC7 | 1.52 | 1E−04 |
| 1554309_at | "eukaryotic translation initiation factor 4 gamma, 3" | EIF4G3 | 1.52 | 4E−04 |
| 228153_at | IBR domain containing 2 | IBRDC2 | 1.52 | 7E−07 |
| 217984_at | ribonuclease T2 | RNASET2 | 1.52 | 4E−05 |
| 200840_at | lysyl-tRNA synthetase | KARS | 1.52 | 4E−07 |
| 218039_at | nucleolar and spindle associated protein 1 | NUSAP1 | 1.52 | 1E−06 |
| 226459_at | phosphoinositide-3-kinase adaptor protein 1 | PIK3AP1 | 1.52 | 1E−06 |
| 224937_at | prostaglandin F2 receptor negative regulator | PTGFRN | 1.51 | 3E−04 |
| 224937_at | prostaglandin F2 receptor negative regulator | PTGFRN | 1.51 | 3E−04 |
| 201079_at | synaptogyrin 2 | SYNGR2 | 1.51 | 1E−05 |
| 242288_s_at | elastin microfibril interfacer 2 | EMILIN2 | 1.51 | 1E−05 |
| 201761_at | "methylenetetrahydrofolate dehydrogenase (NADP+ dependent) 2, methenyltetrahydrofolate cyclohydrolase" | MTHFD2 | 1.51 | 2E−08 |
| 226071_at | thrombospondin repeat containing 1 | TSRC1 | 1.51 | 5E−07 |
| 224859_at | B7 homolog 3 | B7H3 | 1.51 | 1E−05 |
| 214175_x_at | PDZ and LIM domain 4 | PDLIM4 | 1.51 | 1E−03 |
| 223378_at | NA | NA | 1.51 | 2E−05 |
| 202009_at | PTK9L protein tyrosine kinase 9-like (A6-related protein) | PTK9L | 1.51 | 3E−12 |
| 219040_at | coronin 7 | CORO7 | 1.51 | 2E−04 |
| 228745_at | Hypothetical protein FLJ13611 | FLJ13611 | 1.51 | 6E−08 |
| 221894_at | aarF domain containing kinase 2 | ADCK2 | 1.51 | 2E−05 |
| 235359_at | ELLP3030 | UNQ3030 | 1.50 | 7E−05 |
| 217933_s_at | leucine aminopeptidase 3 | LAP3 | 1.50 | 1E−05 |
| 1555841_at | similar to RIKEN cDNA 5730528L13 gene | MGC17337 | 1.50 | 9E−08 |
| 201779_s_at | ring finger protein 13 | RNF13 | 1.50 | 1E−08 |
| 201066_at | cytochrome c-1 | CYC1 | 1.50 | 4E−08 |

TABLE 7

Gene expression associated with the F2 subtype of RA.

| ProbeID | NETAFFX: GeneTitle | NETAFFX: GeneSymbol | Fold Change | p-value |
|---|---|---|---|---|
| 206552_s_at | "tachykinin, precursor 1 (substance K, substance P, neurokinin 1, neurokinin 2, neuromedin L, neurokinin alpha, neuropeptide K, neuropeptide gamma)" | TAC1 | 10.84 | 3E−05 |
| 204712_at | WNT inhibitory factor 1 | WIF1 | 8.21 | 5E−07 |
| 241412_at | betacellulin | BTC | 5.75 | 2E−12 |
| 223836_at | Ksp37 protein | KSP37 | 5.58 | 2E−08 |
| 237466_s_at | hedgehog interacting protein | HHIP | 5.34 | 1E−07 |
| 206423_at | angiopoietin-like 7 | ANGPTL7 | 5.31 | 3E−06 |
| 206315_at | cytokine receptor-like factor 1 | CRLF1 | 4.87 | 5E−20 |
| 207326_at | betacellulin | BTC | 4.48 | 7E−11 |
| 209613_s_at | "alcohol dehydrogenase IB (class I), beta polypeptide" | ADH1B | 4.42 | 8E−05 |
| 204933_s_at | "tumor necrosis factor receptor superfamily, member 11b (osteoprotegerin)" | TNFRSF11B | 3.79 | 8E−08 |
| 214680_at | "neurotrophic tyrosine kinase, receptor, type 2" | NTRK2 | 3.78 | 8E−13 |
| 206262_at | "alcohol dehydrogenase 1C (class I), gamma polypeptide" | ADH1C | 3.78 | 4E−06 |
| 201525_at | apolipoprotein D | APOD | 3.74 | 1E−05 |
| 207174_at | glypican 5 | GPC5 | 3.71 | 4E−05 |
| 211276_at | transcription elongation factor A (SII)-like 2 | TCEAL2 | 3.70 | 4E−13 |
| 230593_at | Transcribed locus | NA | 3.67 | 1E−05 |
| 231798_at | noggin | NOG | 3.60 | 1E−06 |
| 223775_at | hedgehog interacting protein | HHIP | 3.58 | 1E−06 |
| 206002_at | G protein-coupled receptor 64 | GPR64 | 3.52 | 3E−15 |
| 235050_at | "solute carrier family 2 (facilitated glucose transporter), member 12" | SLC2A12 | 3.33 | 1E−06 |
| 38037_at | heparin-binding EGF-like growth factor | HBEGF | 3.33 | 3E−09 |
| 221795_at | "neurotrophic tyrosine kinase, receptor, type 2" | NTRK2 | 3.29 | 8E−10 |
| 203662_s_at | tropomodulin 1 | TMOD1 | 3.24 | 1E−10 |
| 210155_at | "myocilin, trabecular meshwork inducible glucocorticoid response" | MYOC | 3.24 | 3E−08 |
| 221796_at | "neurotrophic tyrosine kinase, receptor, type 2" | NTRK2 | 3.24 | 1E−12 |
| 206737_at | "wingless-type MMTV integration site family, member 11" | WNT11 | 3.24 | 4E−07 |
| 204469_at | "protein tyrosine phosphatase, receptor-type, Z polypeptide 1" | PTPRZ1 | 3.22 | 8E−10 |
| 212444_at | "CDNA clone IMAGE: 6025865, partial cds" | NA | 3.18 | 1E−08 |
| 213317_at | Chloride intracellular channel 5 | CLIC5 | 3.15 | 1E−09 |
| 1556037_s_at | hedgehog interacting protein | HHIP | 3.14 | 3E−10 |
| 204932_at | "tumor necrosis factor receptor superfamily, member 11b (osteoprotegerin)" | TNFRSF11B | 3.09 | 1E−07 |
| 219295_s_at | procollagen C-endopeptidase enhancer 2 | PCOLCE2 | 3.05 | 5E−16 |
| 205397_x_at | "SMAD, mothers against DPP homolog 3 (Drosophila)" | SMAD3 | 2.97 | 2E−14 |
| 224212_s_at | "protocadherin alpha 9 \| protocadherin alpha subfamily C, 2 \| protocadherin alpha subfamily C, 1 \| protocadherin alpha 13 \| protocadherin alpha 12 \| protocadherin alpha 11 \| protocadherin alpha 10 \| protocadherin alpha 8 \| protocadherin alpha 7 \| prot . . ." | PCDHA9 \| PCDHAC2 \| PCDHAC1 \| PCDHA13 \| PCDHA12 \| PCDHA11 \| PCDHA10 \| PCDHA8 \| PCDHA7 \| PCDHA6 \| PCDHA5 \| PCDHA4 \| PCDHA3 \| PCDHA2 \| PCDHA1 | 2.96 | 2E−06 |
| 211485_s_at | fibroblast growth factor 18 | FGF18 | 2.96 | 1E−05 |
| 220076_at | "ankylosis, progressive homolog (mouse)" | ANKH | 2.90 | 1E−10 |
| 228796_at | copine IV | CPNE4 | 2.87 | 5E−06 |
| 207317_s_at | calsequestrin 2 (cardiac muscle) | CASQ2 | 2.86 | 9E−07 |
| 214040_s_at | "gelsolin (amyloidosis, Finnish type)" | GSN | 2.85 | 3E−11 |
| 206227_at | "cartilage intermediate layer protein, nucleotide pyrophosphohydrolase" | CILP | 2.85 | 2E−06 |
| 207292_s_at | mitogen-activated protein kinase 7 | MAPK7 | 2.84 | 3E−14 |
| 205883_at | zinc finger and BTB domain containing 16 | ZBTB16 | 2.82 | 3E−05 |
| 229929_at | SPRY domain-containing SOCS box protein SSB-4 | SSB4 | 2.77 | 1E−05 |
| 219866_at | chloride intracellular channel 5 | CLIC5 | 2.77 | 1E−09 |
| 213176_s_at | latent transforming growth factor beta binding protein 4 | LTBP4 | 2.75 | 8E−10 |
| 231729_s_at | calcyphosine | CAPS | 2.72 | 8E−06 |
| 1555997_s_at | insulin-like growth factor binding protein 5 | IGFBP5 | 2.71 | 1E−05 |
| 227803_at | ectonucleotide pyrophosphatase/phosphodiesterase 5 (putative function) | ENPP5 | 2.69 | 2E−08 |
| 206941_x_at | NA | NA | 2.68 | 1E−07 |
| 227782_at | Similar to B230208J24Rik protein | NA | 2.68 | 9E−18 |
| 209616_s_at | carboxylesterase 1 (monocyte/macrophage serine esterase 1) | CES1 | 2.67 | 5E−07 |
| 220484_at | mucolipin 3 | MCOLN3 | 2.67 | 6E−07 |
| 218180_s_at | EPS8-like 2 | EPS8L2 | 2.67 | 5E−07 |

TABLE 7-continued

Gene expression associated with the F2 subtype of RA.

| ProbeID | NETAFFX: GeneTitle | NETAFFX: GeneSymbol | Fold Change | p-value |
|---|---|---|---|---|
| 1555800_at | zinc finger protein 533 | ZNF533 | 2.66 | 2E−06 |
| 214961_at | KIAA0774 | KIAA0774 | 2.63 | 4E−05 |
| 235367_at | myopalladin | MYPN | 2.63 | 4E−06 |
| 230360_at | collomin | COLM | 2.63 | 4E−09 |
| 229176_at | "Ankylosis, progressive homolog (mouse)" | ANKH | 2.56 | 3E−10 |
| 203821_at | heparin-binding EGF-like growth factor | HBEGF | 2.51 | 2E−08 |
| 217628_at | Chloride intracellular channel 5 | CLIC5 | 2.49 | 5E−05 |
| 203463_s_at | epsin 2 | EPN2 | 2.49 | 1E−05 |
| 230081_at | "phosphatidylinositol-specific phospholipase C, X domain containing 3" | PLCXD3 | 2.48 | 2E−07 |
| 204442_x_at | latent transforming growth factor beta binding protein 4 | LTBP4 | 2.48 | 5E−09 |
| 244353_s_at | NA | NA | 2.47 | 5E−07 |
| 229019_at | zinc finger protein 533 | ZNF533 | 2.47 | 3E−07 |
| 206404_at | fibroblast growth factor 9 (glia-activating factor) | FGF9 | 2.45 | 6E−06 |
| 227401_at | interleukin 17D | IL17D | 2.45 | 2E−12 |
| 223093_at | "ankylosis, progressive homolog (mouse)" | ANKH | 2.45 | 2E−12 |
| 204223_at | proline arginine-rich end leucine-rich repeat protein | PRELP | 2.45 | 5E−09 |
| 223315_at | netrin 4 | NTN4 | 2.44 | 5E−15 |
| 205325_at | phytanoyl-CoA hydroxylase interacting protein | PHYHIP | 2.42 | 2E−06 |
| 204714_s_at | "coagulation factor V (proaccelerin, labile factor)" | F5 | 2.42 | 6E−08 |
| 221926_s_at | interleukin 17 receptor C | IL17RC | 2.41 | 8E−09 |
| 212741_at | monoamine oxidase A | MAOA | 2.41 | 2E−08 |
| 204731_at | "transforming growth factor, beta receptor III (betaglycan, 300 kDa)" | TGFBR3 | 2.38 | 1E−08 |
| 219747_at | hypothetical protein FLJ23191 | FLJ23191 | 2.37 | 3E−14 |
| 206987_x_at | fibroblast growth factor 18 | FGF18 | 2.37 | 2E−05 |
| 219140_s_at | "retinol binding protein 4, plasma" | RBP4 | 2.34 | 3E−08 |
| 222043_at | "clusterin (complement lysis inhibitor, SP-40,40, sulfated glycoprotein 2, testosterone-repressed prostate message 2, apolipoprotein J)" | CLU | 2.34 | 6E−13 |
| 205182_s_at | zinc finger protein 324 | ZNF324 | 2.34 | 1E−05 |
| 211029_x_at | fibroblast growth factor 18 | fibroblast growth factor 18 | FGF18 | 2.33 | 3E−05 |
| 228224_at | proline arginine-rich end leucine-rich repeat protein | PRELP | 2.33 | 4E−07 |
| 206614_at | growth differentiation factor 5 (cartilage-derived morphogenetic protein-1) | GDF5 | 2.33 | 1E−06 |
| 1555801_s_at | zinc finger protein 533 | ZNF533 | 2.33 | 1E−05 |
| 1561396_at | EPH receptor A6 | EPHA6 | 2.32 | 3E−07 |
| 238441_at | "CDNA clone IMAGE: 5288757, partial cds" | NA | 2.31 | 4E−07 |
| 228873_at | "collagen, type XXII, alpha 1" | COL22A1 | 2.30 | 2E−05 |
| 203068_at | kelch-like 21 (Drosophila) | KLHL21 | 2.29 | 2E−08 |
| 201539_s_at | four and a half LIM domains 1 | FHL1 | 2.26 | 1E−08 |
| 210397_at | "defensin, beta 1" | DEFB1 | 2.25 | 2E−05 |
| 215913_s_at | "GULP, engulfment adaptor PTB domain containing 1" | GULP1 | 2.24 | 6E−09 |
| 231029_at | Transcribed locus | NA | 2.23 | 6E−08 |
| 203424_s_at | insulin-like growth factor binding protein 5 | IGFBP5 | 2.21 | 8E−05 |
| 205158_at | "ribonuclease, RNase A family, 4" | RNASE4 | 2.21 | 4E−16 |
| 210823_s_at | "protein tyrosine phosphatase, receptor type, S" | PTPRS | 2.21 | 1E−07 |
| 204237_at | "GULP, engulfment adaptor PTB domain containing 1" | GULP1 | 2.20 | 3E−14 |
| 204713_s_at | "coagulation factor V (proaccelerin, labile factor)" | F5 | 2.19 | 7E−08 |
| 225879_at | likely homolog of yeast SEN54 | SEN54L | 2.18 | 9E−09 |
| 212713_at | microfibrillar-associated protein 4 | MFAP4 | 2.18 | 9E−07 |
| 227762_at | Transcribed locus | NA | 2.18 | 7E−05 |
| 200965_s_at | actin binding LIM protein 1 | ABLIM1 | 2.17 | 1E−08 |
| 224059_s_at | numb homolog (Drosophila)-like | NUMBL | 2.16 | 6E−05 |
| 209355_s_at | phosphatidic acid phosphatase type 2B | PPAP2B | 2.16 | 2E−09 |
| 219949_at | leucine rich repeat containing 2 | LRRC2 | 2.15 | 8E−10 |
| 211958_at | insulin-like growth factor binding protein 5 | IGFBP5 | 2.15 | 1E−07 |
| 203706_s_at | frizzled homolog 7 (Drosophila) | FZD7 | 2.15 | 7E−15 |
| 212062_at | "ATPase, Class II, type 9A" | ATP9A | 2.14 | 1E−10 |
| 207336_at | SRY (sex determining region Y)-box 5 | SOX5 | 2.14 | 2E−09 |
| 203851_at | insulin-like growth factor binding protein 6 | IGFBP6 | 2.13 | 3E−07 |
| 205265_s_at | aortic preferentially expressed protein 1 | APEG1 | 2.13 | 2E−06 |
| 230083_at | Ubiquitin specific protease 53 | USP53 | 2.12 | 5E−10 |
| 204389_at | monoamine oxidase A | MAOA | 2.12 | 5E−06 |
| 1555958_at | NA | NA | 2.11 | 6E−11 |
| 205100_at | glutamine-fructose-6-phosphate transaminase 2 | GFPT2 | 2.10 | 1E−10 |
| 231817_at | ubiquitin specific protease 53 | USP53 | 2.10 | 6E−11 |
| 201801_s_at | "solute carrier family 29 (nucleoside transporters), member 1" | SLC29A1 | 2.10 | 9E−14 |
| 227702_at | "cytochrome P450, family 4, subfamily X, polypeptide 1" | CYP4X1 | 2.09 | 2E−07 |
| 206243_at | tissue inhibitor of metalloproteinase 4 | TIMP4 | 2.09 | 2E−05 |
| 229674_at | SERTA domain containing 4 | SERTAD4 | 2.08 | 8E−07 |
| 208792_s_at | "clusterin (complement lysis inhibitor, SP-40,40, sulfated glycoprotein 2, testosterone-repressed prostate message 2, apolipoprotein J)" | CLU | 2.07 | 3E−10 |
| 210298_x_at | four and a half LIM domains 1 | FHL1 | 2.07 | 8E−08 |

TABLE 7-continued

Gene expression associated with the F2 subtype of RA.

| ProbeID | NETAFFX: GeneTitle | NETAFFX: GeneSymbol | Fold Change | p-value |
|---|---|---|---|---|
| 201149_s_at | "tissue inhibitor of metalloproteinase 3 (Sorsby fundus dystrophy, pseudoinflammatory)" | TIMP3 | 2.06 | 1E−11 |
| 226192_at | "Transcribed locus, strongly similar to XP_496055.1 similar to p40 [Homo sapiens]" | NA | 2.06 | 6E−08 |
| 223094_s_at | "ankylosis, progressive homolog (mouse)" | ANKH | 2.06 | 6E−07 |
| 203108_at | "G protein-coupled receptor, family C, group 5, member A" | GPCR5A | 2.06 | 5E−06 |
| 203661_s_at | tropomodulin 1 | TMOD1 | 2.05 | 3E−11 |
| 209283_at | "crystallin, alpha B" | CRYAB | 2.04 | 2E−09 |
| 224657_at | mitogen-inducible gene 6 | MIG-6 | 2.04 | 4E−08 |
| 224325_at | frizzled homolog 8 (Drosophila) | frizzled homolog 8 (Drosophila) | FZD8 | 2.04 | 2E−13 |
| 227405_s_at | frizzled homolog 8 (Drosophila) | FZD8 | 2.03 | 1E−13 |
| 204736_s_at | chondroitin sulfate proteoglycan 4 (melanoma-associated) | CSPG4 | 2.03 | 1E−06 |
| 204235_s_at | "GULP, engulfment adaptor PTB domain containing 1" | GULP1 | 2.03 | 8E−12 |
| 237054_at | Ectonucleotide pyrophosphatase/phosphodiesterase 5 (putative function) | ENPP5 | 2.03 | 3E−05 |
| 238489_at | "Transcribed locus, moderately similar to NP_694983.1 DHHC-containing protein 20 [Homo sapiens]" | NA | 2.01 | 2E−05 |
| 204796_at | Echinoderm microtubule associated protein like 1 | EML1 | 2.00 | 1E−13 |
| 220744_s_at | WD repeat domain 10 | WDR10 | 2.00 | 5E−05 |
| 212730_at | desmuslin | DMN | 2.00 | 2E−06 |
| 204776_at | thrombospondin 4 | THBS4 | 2.00 | 5E−07 |
| 212328_at | KIAA1102 protein | KIAA1102 | 1.99 | 8E−10 |
| 220110_s_at | nuclear RNA export factor 3 | NXF3 | 1.99 | 1E−05 |
| 219825_at | "cytochrome P450, family 26, subfamily B, polypeptide 1" | CYP26B1 | 1.99 | 6E−06 |
| 229310_at | kelch repeat and BTB (POZ) domain containing 9 | KBTBD9 | 1.98 | 4E−16 |
| 203705_s_at | frizzled homolog 7 (Drosophila) | FZD7 | 1.98 | 1E−13 |
| 213800_at | complement factor H | CFH | 1.98 | 1E−10 |
| 209905_at | homeo box A9 | HOXA9 | 1.96 | 4E−07 |
| 205591_at | olfactomedin 1 | OLFM1 | 1.96 | 2E−10 |
| 227821_at | "leucine-rich repeat LGI family, member 4" | LGI4 | 1.95 | 8E−05 |
| 239488_at | Protein phosphatase 1 (formerly 2C)-like | PPM1L | 1.94 | 1E−06 |
| 237465_at | hypothetical gene supported by BC062741 | LOC401151 | 1.94 | 3E−06 |
| 205606_at | low density lipoprotein receptor-related protein 6 | LRP6 | 1.94 | 4E−05 |
| 231781_s_at | leucine rich repeat containing 2 | LRRC2 | 1.93 | 2E−09 |
| 205498_at | growth hormone receptor | GHR | 1.93 | 1E−09 |
| 227892_at | "cDNA clone IMAGE: 5288757, partial cds" | NA | 1.93 | 2E−05 |
| 203088_at | fibulin 5 | FBLN5 | 1.93 | 9E−07 |
| 220442_at | UDP-N-acetyl-alpha-D-galactosamine: polypeptide N-acetylgalactosaminyltransferase 4 (GalNAc-T4) | GALNT4 | 1.92 | 1E−05 |
| 214505_s_at | four and a half LIM domains 1 | FHL1 | 1.92 | 5E−07 |
| 210674_s_at | "protocadherin alpha 9 | protocadherin alpha subfamily C, 2 | protocadherin alpha subfamily C, 1 | protocadherin alpha 13 | protocadherin alpha 12 | protocadherin alpha 11 | protocadherin alpha 10 | protocadherin alpha 8 | protocadherin alpha 7 | prot . . ." | PCDHA9 | PCDHAC2 | PCDHAC1 | PCDHA13 | PCDHA12 | PCDHA11 | PCDHA10 | PCDHA8 | PCDHA7 | PCDHA6 | PCDHA5 | PCDHA4 | PCDHA3 | PCDHA2 | PCDHA1 | 1.92 | 1E−05 |
| 201148_s_at | "tissue inhibitor of metalloproteinase 3 (Sorsby fundus dystrophy, pseudoinflammatory)" | TIMP3 | 1.92 | 4E−12 |
| 212327_at | KIAA1102 protein | KIAA1102 | 1.91 | 7E−13 |
| 204396_s_at | G protein-coupled receptor kinase 5 | GRK5 | 1.91 | 1E−15 |
| 218532_s_at | hypothetical protein FLJ20152 | FLJ20152 | 1.90 | 3E−11 |
| 231778_at | distal-less homeo box 3 | DLX3 | 1.90 | 5E−07 |
| 227058_at | hypothetical protein FLJ14834 | FLJ14834 | 1.90 | 7E−11 |
| 202686_s_at | AXL receptor tyrosine kinase | AXL | 1.89 | 4E−13 |
| 1553706_at | HtrA serine peptidase 4 | HTRA4 | 1.89 | 3E−05 |
| 210473_s_at | G protein-coupled receptor 125 | GPR125 | 1.89 | 3E−10 |
| 218484_at | NADH: ubiquinone oxidoreductase MLRQ subunit homolog | LOC56901 | 1.89 | 2E−06 |
| 219764_at | frizzled homolog 10 (Drosophila) | FZD10 | 1.89 | 9E−10 |
| 212230_at | phosphatidic acid phosphatase type 2B | PPAP2B | 1.88 | 2E−09 |
| 204578_at | KIAA0377 gene product | KIAA0377 | 1.88 | 2E−05 |
| 203786_s_at | tumor protein D52-like 1 | TPD52L1 | 1.88 | 1E−06 |
| 227341_at | Chromosome 10 open reading frame 30 | C10orf30 | 1.88 | 8E−06 |
| 210372_s_at | tumor protein D52-like 1 | TPD52L1 | 1.88 | 2E−06 |
| 221408_x_at | protocadherin beta 12 | PCDHB12 | 1.88 | 7E−07 |
| 212736_at | chromosome 16 open reading frame 45 | C16orf45 | 1.88 | 3E−12 |

TABLE 7-continued

Gene expression associated with the F2 subtype of RA.

| ProbeID | NETAFFX: GeneTitle | NETAFFX: GeneSymbol | Fold Change | p-value |
|---|---|---|---|---|
| 213497_at | ankyrin repeat and BTB (POZ) domain containing 2 | ABTB2 | 1.87 | 2E−13 |
| 201147_s_at | "tissue inhibitor of metalloproteinase 3 (Sorsby fundus dystrophy, pseudoinflammatory)" | TIMP3 | 1.87 | 1E−12 |
| 216017_s_at | NGFI-A binding protein 2 (EGR1 binding protein 2) | NAB2 | 1.87 | 2E−06 |
| 229797_at | mucolipin 3 | MCOLN3 | 1.87 | 1E−05 |
| 210619_s_at | hyaluronoglucosaminidase 1 | HYAL1 | 1.87 | 1E−09 |
| 221317_x_at | protocadherin beta 6 | PCDHB6 | 1.87 | 8E−07 |
| 201926_s_at | "decay accelerating factor for complement (CD55, Cromer blood group system)" | DAF | 1.87 | 1E−08 |
| 204388_s_at | monoamine oxidase A | MAOA | 1.86 | 1E−06 |
| 215305_at | "platelet-derived growth factor receptor, alpha polypeptide" | PDGFRA | 1.86 | 2E−05 |
| 211607_x_at | "epidermal growth factor receptor (erythroblastic leukemia viral (v-erb-b) oncogene homolog, avian) | epidermal growth factor receptor (erythroblastic leukemia viral (v-erb-b) oncogene homolog, avian)" | EGFR | 1.86 | 2E−06 |
| 229337_at | ubiquitin specific protease 2 | USP2 | 1.86 | 1E−05 |
| 204797_s_at | echinoderm microtubule associated protein like 1 | EML1 | 1.84 | 9E−11 |
| 204310_s_at | natriuretic peptide receptor B/guanylate cyclase B (atrionatriuretic peptide receptor B) | NPR2 | 1.84 | 8E−11 |
| 225817_at | cingulin-like 1 | CGNL1 | 1.84 | 1E−08 |
| 205086_s_at | hypothetical protein 384D8_6 | 384D8-2 | 1.83 | 4E−06 |
| 208202_s_at | PHD finger protein 15 | PHF15 | 1.83 | 5E−06 |
| 209683_at | NA | NA | 1.83 | 7E−11 |
| 220043_s_at | antigen p97 (melanoma associated) identified by monoclonal antibodies 133.2 and 96.5 | MFI2 | 1.83 | 9E−05 |
| 205613_at | B/K protein | LOC51760 | 1.83 | 3E−05 |
| 216949_s_at | polycystic kidney disease 1 (autosomal dominant) | PKD1 | 1.82 | 2E−06 |
| 202289_s_at | "transforming, acidic coiled-coil containing protein 2" | TACC2 | 1.82 | 7E−12 |
| 205384_at | FXYD domain containing ion transport regulator 1 (phospholemman) | FXYD1 | 1.82 | 2E−08 |
| 212226_s_at | phosphatidic acid phosphatase type 2B | PPAP2B | 1.81 | 2E−06 |
| 223475_at | LCCL domain containing cysteine-rich secretory protein 1 | LCRISP1 | 1.81 | 3E−05 |
| 203425_s_at | insulin-like growth factor binding protein 5 | IGFBP5 | 1.81 | 8E−05 |
| 206850_at | RAS-related on chromosome 22 | RRP22 | 1.81 | 1E−08 |
| 218692_at | hypothetical protein FLJ20366 | FLJ20366 | 1.81 | 1E−07 |
| 208791_at | "clusterin (complement lysis inhibitor, SP-40,40, sulfated glycoprotein 2, testosterone-repressed prostate message 2, apolipoprotein J)" | CLU | 1.80 | 1E−07 |
| 218500_at | mesenchymal stem cell protein DSCD75 | LOC51337 | 1.80 | 3E−06 |
| 206480_at | leukotriene C4 synthase | LTC4S | 1.80 | 6E−08 |
| 201188_s_at | "inositol 1,4,5-triphosphate receptor, type 3" | ITPR3 | 1.80 | 7E−08 |
| 224210_s_at | "peroxisomal membrane protein 4, 24 kDa" | PXMP4 | 1.80 | 3E−07 |
| 213397_x_at | "ribonuclease, RNase A family, 4" | RNASE4 | 1.80 | 6E−13 |
| 226901_at | hypothetical protein LOC284018 | LOC284018 | 1.79 | 1E−12 |
| 203355_s_at | pleckstrin and Sec7 domain containing 3 | PSD3 | 1.79 | 2E−06 |
| 225627_s_at | KIAA1573 protein | KIAA1573 | 1.79 | 2E−06 |
| 221272_s_at | chromosome 1 open reading frame 21 | chromosome 1 open reading frame 21 | C1orf21 | 1.78 | 2E−05 |
| 244623_at | Transcribed locus | NA | 1.78 | 6E−05 |
| 205236_x_at | "superoxide dismutase 3, extracellular" | SOD3 | 1.78 | 9E−09 |
| 228255_at | "amyotrophic lateral sclerosis 2 (juvenile) chromosome region, candidate 4" | ALS2CR4 | 1.78 | 3E−08 |
| 244130_at | Transcribed locus | NA | 1.78 | 2E−05 |
| 201860_s_at | "plasminogen activator, tissue" | PLAT | 1.77 | 1E−07 |
| 218613_at | pleckstrin and Sec7 domain containing 3 | PSD3 | 1.77 | 6E−08 |
| 232099_at | protocadherin beta 16 | PCDHB16 | 1.77 | 8E−07 |
| 1556427_s_at | similar to hypothetical protein | LOC221091 | 1.77 | 5E−10 |
| 206171_at | adenosine A3 receptor | ADORA3 | 1.76 | 3E−06 |
| 1557292_a_at | mucolipin 3 | MCOLN3 | 1.76 | 9E−05 |
| 229657_at | Hypothetical gene supported by AK096885; AK098084 | NA | 1.76 | 1E−08 |
| 201802_at | "solute carrier family 29 (nucleoside transporters), member 1" | SLC29A1 | 1.76 | 2E−14 |
| 203426_s_at | insulin-like growth factor binding protein 5 | IGFBP5 | 1.76 | 4E−05 |
| 228716_at | hypothetical gene supported by AK096885; AK098084 | LOC401059 | 1.76 | 1E−07 |
| 217626_at | "aldo-keto reductase family 1, member C1 (dihydrodiol dehydrogenase 1; 20-alpha (3-alpha)-hydroxysteroid dehydrogenase) | aldo-keto reductase family 1, member C2 (dihydrodiol dehydrogenase 2; bile acid binding protein; 3-alpha hydroxysteroid dehydroge . . ." | AKR1C1 | AKR1C2 | 1.75 | 8E−06 |
| 201925_s_at | "decay accelerating factor for complement (CD55, Cromer blood group system)" | DAF | 1.75 | 5E−07 |
| 204066_s_at | "centaurin, gamma 2" | CENTG2 | 1.75 | 8E−06 |
| 1554008_at | oncostatin M receptor | OSMR | 1.74 | 2E−05 |
| 221204_s_at | cartilage acidic protein 1 | CRTAC1 | 1.74 | 2E−06 |
| 210299_s_at | four and a half LIM domains 1 | FHL1 | 1.74 | 4E−07 |
| 229916_at | ectonucleotide pyrophosphatase/phosphodiesterase 6 | ENPP6 | 1.74 | 9E−07 |

TABLE 7-continued

Gene expression associated with the F2 subtype of RA.

| ProbeID | NETAFFX: GeneTitle | NETAFFX: GeneSymbol | Fold Change | p-value |
|---|---|---|---|---|
| 202342_s_at | tripartite motif-containing 2 | TRIM2 | 1.74 | 1E−09 |
| 227899_at | vitrin | VIT | 1.74 | 1E−08 |
| 228608_at | Voltage gated channel like 1 | VGCNL1 | 1.74 | 1E−06 |
| 206638_at | 5-hydroxytryptamine (serotonin) receptor 2B | HTR2B | 1.74 | 9E−05 |
| 1553572_a_at | cytoglobin | CYGB | 1.74 | 2E−06 |
| 226189_at | "Homo sapiens, clone IMAGE: 4794726, mRNA" | NA | 1.73 | 5E−05 |
| 204041_at | monoamine oxidase B | MAOB | 1.73 | 1E−06 |
| 238451_at | "membrane protein, palmitoylated 7 (MAGUK p55 subfamily member 7)" | MPP7 | 1.73 | 1E−05 |
| 219902_at | betaine-homocysteine methyltransferase 2 | BHMT2 | 1.73 | 2E−08 |
| 1568868_at | NA | NA | 1.73 | 4E−05 |
| 205398_s_at | "SMAD, mothers against DPP homolog 3 (Drosophila)" | SMAD3 | 1.73 | 5E−08 |
| 209894_at | leptin receptor | LEPR | 1.72 | 3E−05 |
| 209019_s_at | PTEN induced putative kinase 1 | PINK1 | 1.72 | 4E−09 |
| 204284_at | "protein phosphatase 1, regulatory (inhibitor) subunit 3C" | PPP1R3C | 1.72 | 3E−06 |
| 209243_s_at | paternally expressed 3 | PEG3 | 1.72 | 5E−06 |
| 228554_at | MRNA; cDNA DKFZp586G0321 (from clone DKFZp586G0321) | NA | 1.72 | 3E−05 |
| 220407_s_at | "transforming growth factor, beta 2" | TGFB2 | 1.71 | 8E−10 |
| 225871_at | six transmembrane epithelial antigen of prostate 2 | STEAP2 | 1.71 | 2E−07 |
| 206163_at | mab-21-like 1 (C. elegans) | MAB21L1 | 1.70 | 9E−05 |
| 202724_s_at | forkhead box O1A (rhabdomyosarcoma) | FOXO1A | 1.70 | 5E−12 |
| 214721_x_at | CDC42 effector protein (Rho GTPase binding) 4 | CDC42EP4 | 1.70 | 2E−07 |
| 40524_at | "protein tyrosine phosphatase, non-receptor type 21" | PTPN21 | 1.70 | 6E−06 |
| 202669_s_at | ephrin-B2 | EFNB2 | 1.69 | 2E−05 |
| 221667_s_at | heat shock 22 kDa protein 8 | HSPB8 | 1.69 | 2E−06 |
| 232305_at | 3-hydroxymethyl-3-methylglutaryl-Coenzyme A lyase-like 1 | HMGCLL1 | 1.69 | 1E−05 |
| 200636_s_at | "protein tyrosine phosphatase, receptor type, F" | PTPRF | 1.69 | 7E−07 |
| 202341_s_at | tripartite motif-containing 2 | TRIM2 | 1.69 | 2E−06 |
| 218510_x_at | hypothetical protein FLJ20152 | FLJ20152 | 1.69 | 8E−09 |
| 201984_s_at | "epidermal growth factor receptor (erythroblastic leukemia viral (v-erb-b) oncogene homolog, avian)" | EGFR | 1.68 | 7E−08 |
| 1554705_at | hypothetical protein MGC45780 | MGC45780 | 1.68 | 5E−05 |
| 211110_s_at | androgen receptor (dihydrotestosterone receptor; testicular feminization; spinal and bulbar muscular atrophy; Kennedy disease) | AR | 1.68 | 5E−09 |
| 1555950_a_at | "decay accelerating factor for complement (CD55, Cromer blood group system)" | DAF | 1.67 | 8E−08 |
| 227898_s_at | hypothetical protein FLJ38705 | FLJ38705 | 1.67 | 8E−06 |
| 202862_at | fumarylacetoacetate hydrolase (fumarylacetoacetase) | FAH | 1.67 | 6E−11 |
| 214682_at | Hypothetical protein LOC339047 | LOC339047 | 1.67 | 4E−07 |
| 48031_r_at | chromosome 5 open reading frame 4 | C5orf4 | 1.67 | 1E−06 |
| 205019_s_at | vasoactive intestinal peptide receptor 1 | VIPR1 | 1.67 | 3E−06 |
| 209789_at | "coronin, actin binding protein, 2B" | CORO2B | 1.67 | 9E−07 |
| 219922_s_at | latent transforming growth factor beta binding protein 3 | LTBP3 | 1.66 | 4E−10 |
| 37022_at | proline arginine-rich end leucine-rich repeat protein | PRELP | 1.66 | 7E−06 |
| 235076_at | nuclear domain 10 protein | NDP52 | 1.65 | 6E−06 |
| 200637_s_at | "protein tyrosine phosphatase, receptor type, F" | PTPRF | 1.65 | 2E−06 |
| 223092_at | "ankylosis, progressive homolog (mouse)" | ANKH | 1.64 | 1E−07 |
| 227419_x_at | placenta-specific 9 | PLAC9 | 1.64 | 4E−07 |
| 236325_at | NA | NA | 1.64 | 1E−06 |
| 212494_at | tensin like C1 domain containing phosphatase | TENC1 | 1.64 | 2E−09 |
| 226602_s_at | similar to breakpoint cluster region isoform m | LOC440820 | 1.64 | 2E−12 |
| 223796_at | contactin associated protein-like 3 | similar to cell recognition molecule CASPR3 | CNTNAP3 | LOC389734 | 1.63 | 5E−06 |
| 229487_at | Early B-cell factor | EBF | 1.63 | 4E−07 |
| 225867_at | "mental retardation, X-linked 85" | MRX85 | 1.63 | 2E−08 |
| 204036_at | "endothelial differentiation, lysophosphatidic acid G-protein-coupled receptor, 2" | EDG2 | 1.63 | 6E−10 |
| 204287_at | synaptogyrin 1 | SYNGR1 | 1.63 | 3E−05 |
| 204161_s_at | ectonucleotide pyrophosphatase/phosphodiesterase 4 (putative function) | ENPP4 | 1.62 | 2E−06 |
| 229000_at | zinc finger protein 77 (pT1) | ZNF77 | 1.62 | 4E−05 |
| 222423_at | Nedd4 family interacting protein 1 | NDFIP1 | 1.62 | 2E−14 |
| 204037_at | "endothelial differentiation, lysophosphatidic acid G-protein-coupled receptor, 2" | EDG2 | 1.62 | 3E−09 |
| 219188_s_at | LRP16 protein | LRP16 | 1.62 | 5E−09 |
| 205404_at | hydroxysteroid (11-beta) dehydrogenase 1 | HSD11B1 | 1.62 | 1E−05 |
| 226959_at | NA | NA | 1.62 | 3E−05 |
| 206176_at | bone morphogenetic protein 6 | BMP6 | 1.62 | 2E−06 |
| 1552789_at | hypothetical protein FLJ32803 | FLJ32803 | 1.62 | 1E−08 |
| 1558680_s_at | "phosphodiesterase 1A, calmodulin-dependent" | PDE1A | 1.61 | 4E−05 |
| 205407_at | reversion-inducing-cysteine-rich protein with kazal motifs | RECK | 1.61 | 7E−08 |
| 219039_at | "sema domain, immunoglobulin domain (Ig), transmembrane domain (TM) and short cytoplasmic domain, (semaphorin) 4C" | SEMA4C | 1.61 | 2E−07 |

TABLE 7-continued

Gene expression associated with the F2 subtype of RA.

| ProbeID | NETAFFX: GeneTitle | NETAFFX: GeneSymbol | Fold Change | p-value |
|---|---|---|---|---|
| 224975_at | nuclear factor I/A | NFIA | 1.61 | 1E−08 |
| 226197_at | "Transcribed locus, strongly similar to XP_496055.1 similar to p40 [Homo sapiens]" | NA | 1.61 | 2E−07 |
| 226360_at | zinc and ring finger 3 | ZNRF3 | 1.61 | 4E−07 |
| 208396_s_at | "phosphodiesterase 1A, calmodulin-dependent" | PDE1A | 1.61 | 1E−06 |
| 213364_s_at | Sorting nexin 1 | SNX1 | 1.61 | 1E−08 |
| 225990_at | brother of CDO | BOC | 1.60 | 1E−05 |
| 200635_sat | "protein tyrosine phosphatase, receptor type, F" | PTPRF | 1.60 | 3E−05 |
| 203510_at | met proto-oncogene (hepatocyte growth factor receptor) | MET | 1.60 | 2E−06 |
| 226322_at | ARG99 protein | ARG99 | 1.60 | 3E−07 |
| 205168_at | "discoidin domain receptor family, member 2" | DDR2 | 1.60 | 1E−06 |
| 232746_at | Chemokine orphan receptor 1 | CMKOR1 | 1.59 | 1E−07 |
| 238669_at | prostaglandin-endoperoxide synthase 1 (prostaglandin G/H synthase and cyclooxygenase) | PTGS1 | 1.59 | 1E−06 |
| 229974_at | Ellis van Creveld syndrome 2 (limbin) | EVC2 | 1.59 | 5E−08 |
| 223611_s_at | ligand of numb-protein X | LNX | 1.59 | 9E−06 |
| 226402_at | "cytochrome P450, family 2, subfamily U, polypeptide 1" | CYP2U1 | 1.59 | 1E−08 |
| 207031_at | bagpipe homeobox homolog 1 (Drosophila) | BAPX1 | 1.59 | 2E−05 |
| 235849_at | hypothetical protein MGC45780 | MGC45780 | 1.59 | 3E−08 |
| 218656_s_at | lipoma HMGIC fusion partner | LHFP | 1.59 | 7E−07 |
| 205225_at | estrogen receptor 1 | ESR1 | 1.58 | 1E−08 |
| 1553347_s_at | "potassium voltage-gated channel, shaker-related subfamily, member 6" | KCNA6 | 1.58 | 9E−05 |
| 1553995_a_at | "5'-nucleotidase, ecto (CD73)" | NT5E | 1.58 | 2E−05 |
| 219354_at | hypothetical protein FLJ11078 | FLJ11078 | 1.58 | 5E−07 |
| 223603_at | zinc finger protein 179 | ZNF179 | 1.58 | 2E−05 |
| 211959_at | insulin-like growth factor binding protein 5 | IGFBP5 | 1.58 | 2E−05 |
| 224990_at | hypothetical protein LOC201895 | LOC201895 | 1.58 | 3E−11 |
| 222890_at | HSPC065 protein | HSPC065 | 1.58 | 2E−07 |
| 213131_at | olfactomedin 1 | OLFM1 | 1.58 | 7E−09 |
| 212977_at | chemokine orphan receptor 1 | CMKOR1 | 1.58 | 3E−07 |
| 203762_s_at | dynein 2 light intermediate chain | D2LIC | 1.57 | 2E−10 |
| 231969_at | NA | NA | 1.57 | 3E−05 |
| 201566_x_at | "inhibitor of DNA binding 2, dominant negative helix-loop-helix protein" | ID2 | 1.57 | 7E−06 |
| 202242_at | transmembrane 4 superfamily member 2 | TM4SF2 | 1.57 | 6E−07 |
| 214620_x_at | peptidylglycine alpha-amidating monooxygenase | PAM | 1.57 | 2E−09 |
| 225274_at | prenylcysteine oxidase 1 | PCYOX1 | 1.56 | 2E−13 |
| 228728_at | hypothetical protein FLJ21986 | FLJ21986 | 1.56 | 3E−07 |
| 218824_at | hypothetical protein FLJ10781 | FLJ10781 | 1.56 | 5E−05 |
| 233547_x_at | "phosphodiesterase 1A, calmodulin-dependent" | PDE1A | 1.56 | 6E−05 |
| 205083_at | aldehyde oxidase 1 | AOX1 | 1.56 | 1E−05 |
| 227326_at | Transmembrane anchor protein 1 | TMAP1 | 1.56 | 2E−06 |
| 201120_s_at | progesterone receptor membrane component 1 | PGRMC1 | 1.56 | 7E−08 |
| 207076_s_at | argininosuccinate synthetase | ASS | 1.56 | 1E−10 |
| 214651_s_at | homeo box A9 | HOXA9 | 1.56 | 2E−06 |
| 236644_at | ring finger protein 180 | RNF180 | 1.56 | 6E−05 |
| 209209_s_at | "pleckstrin homology domain containing, family C (with FERM domain) member 1" | PLEKHC1 | 1.56 | 1E−06 |
| 230231_at | "CDNA: FLJ23131 fis, clone LNG08502" | NA | 1.56 | 3E−05 |
| 210973_s_at | "fibroblast growth factor receptor 1 (fms-related tyrosine kinase 2, Pfeiffer syndrome)" | FGFR1 | 1.56 | 4E−09 |
| 227126_at | Transcribed locus | NA | 1.55 | 5E−08 |
| 218285_s_at | dehydrogenase/reductase (SDR family) member 6 | DHRS6 | 1.55 | 4E−10 |
| 219038_at | "zinc finger, CW type with coiled-coil domain 2" | ZCWCC2 | 1.55 | 3E−08 |
| 202017_at | "epoxide hydrolase 1, microsomal (xenobiotic)" | EPHX1 | 1.55 | 1E−06 |
| 213512_at | chromosome 14 open reading frame 79 | C14orf79 | 1.55 | 5E−05 |
| 218062_x_at | CDC42 effector protein (Rho GTPase binding) 4 | CDC42EP4 | 1.55 | 4E−06 |
| 210665_at | tissue factor pathway inhibitor (lipoprotein-associated coagulation inhibitor) | TFPI | 1.55 | 3E−05 |
| 201983_s_at | "epidermal growth factor receptor (erythroblastic leukemia viral (v-erb-b) oncogene homolog, avian)" | EGFR | 1.55 | 5E−07 |
| 211596_s_at | leucine-rich repeats and immunoglobulin-like domains 1 \| leucine-rich repeats and immunoglobulin-like domains 1 | LRIG1 | 1.55 | 9E−07 |
| 201468_s_at | "NAD(P)H dehydrogenase, quinone 1" | NQO1 | 1.55 | 9E−05 |
| 209522_s_at | carnitine acetyltransferase | CRAT | 1.55 | 2E−06 |
| 203343_at | UDP-glucose dehydrogenase | UGDH | 1.55 | 2E−07 |
| 228184_at | dispatched homolog 1 (Drosophila) | DISP1 | 1.55 | 7E−07 |
| 213093_at | "protein kinase C, alpha" | PRKCA | 1.55 | 2E−05 |
| 235956_at | KIAA1377 protein | KIAA1377 | 1.54 | 3E−07 |
| 202457_s_at | "protein phosphatase 3 (formerly 2B), catalytic subunit, alpha isoform (calcineurin A alpha)" | PPP3CA | 1.54 | 6E−10 |
| 226632_at | cytoglobin | CYGB | 1.54 | 3E−05 |
| 226571_s_at | "Protein tyrosine phosphatase, receptor type, S" | PTPRS | 1.54 | 1E−08 |
| 205651_x_at | Rap guanine nucleotide exchange factor (GEF) 4 | RAPGEF4 | 1.54 | 5E−07 |

TABLE 7-continued

Gene expression associated with the F2 subtype of RA.

| ProbeID | NETAFFX: GeneTitle | NETAFFX: GeneSymbol | Fold Change | p-value |
|---|---|---|---|---|
| 212848_s_at | chromosome 9 open reading frame 3 | C9orf3 | 1.54 | 5E−07 |
| 203464_s_at | epsin 2 | EPN2 | 1.54 | 9E−12 |
| 221045_s_at | period homolog 3 (Drosophila) | PER3 | 1.54 | 9E−06 |
| 215039_at | NA | NA | 1.54 | 2E−05 |
| 227719_at | NA | NA | 1.54 | 2E−05 |
| 212325_at | KIAA1102 protein | KIAA1102 | 1.54 | 6E−10 |
| 206007_at | proteoglycan 4 | PRG4 | 1.53 | 7E−05 |
| 213227_at | progesterone receptor membrane component 2 | PGRMC2 | 1.53 | 3E−08 |
| 204570_at | cytochrome c oxidase subunit VIIa polypeptide 1 (muscle) | COX7A1 | 1.53 | 4E−07 |
| 204395_s_at | G protein-coupled receptor kinase 5 | GRK5 | 1.53 | 2E−09 |
| 230624_at | "solute carrier family 25, member 27" | SLC25A27 | 1.53 | 1E−05 |
| 215945_s_at | tripartite motif-containing 2 | TRIM2 | 1.53 | 8E−07 |
| 225946_at | Chromosome 12 open reading frame 2 | C12orf2 | 1.53 | 7E−05 |
| 227188_at | chromosome 21 open reading frame 63 | C21orf63 | 1.53 | 7E−06 |
| 226382_at | hypothetical protein LOC283070 | LOC283070 | 1.53 | 1E−05 |
| 1552476_s_at | "phospholipase C, delta 3" | PLCD3 | 1.53 | 5E−06 |
| 218418_s_at | ankyrin repeat domain 25 | ANKRD25 | 1.53 | 2E−08 |
| 213169_at | Clone TUA8 Cri-du-chat region mRNA | NA | 1.53 | 9E−05 |
| 233136_at | "poly(A) binding protein, cytoplasmic 5" | PABPC5 | 1.53 | 5E−06 |
| 202328_s_at | polycystic kidney disease 1 (autosomal dominant) | PKD1 | 1.52 | 3E−07 |
| 226375_at | Lemur tyrosine kinase 2 | LMTK2 | 1.52 | 1E−05 |
| 230246_at | placenta-specific 9 | PLAC9 | 1.52 | 6E−05 |
| 227308_x_at | latent transforming growth factor beta binding protein 3 | LTBP3 | 1.52 | 3E−12 |
| 207895_at | N-acetylated alpha-linked acidic dipeptidase-like 1 | NAALADL1 | 1.52 | 1E−05 |
| 203803_at | prenylcysteine oxidase 1 | PCYOX1 | 1.52 | 6E−10 |
| 1553994_at | "5'-nucleotidase, ecto (CD73)" | NT5E | 1.51 | 8E−05 |
| 212719_at | "pleckstrin homology domain containing, family E (with leucine rich repeats) member 1" | PLEKHE1 | 1.51 | 5E−09 |
| 226931_at | ARG99 protein | ARG99 | 1.51 | 6E−06 |
| 202916_s_at | "family with sequence similarity 20, member B" | FAM20B | 1.51 | 8E−12 |
| 226380_at | "Protein tyrosine phosphatase, non-receptor type 21" | PTPN21 | 1.51 | 6E−07 |
| 225868_at | tripartite motif-containing 47 | TRIM47 | 1.51 | 6E−05 |
| 202723_s_at | forkhead box O1A (rhabdomyosarcoma) | FOXO1A | 1.51 | 2E−06 |
| 1553682_at | F-box and leucine-rich repeat protein 14 | FBXL14 | 1.50 | 6E−05 |
| 224973_at | "family with sequence similarity 46, member A" | FAM46A | 1.50 | 4E−07 |
| 242033_at | ring finger protein 180 | RNF180 | 1.50 | 4E−05 |
| 212239_at | "phosphoinositide-3-kinase, regulatory subunit 1 (p85 alpha)" | PIK3R1 | 1.50 | 3E−07 |

TABLE 8

Gene expression associated with the F1 subtype of RA.

| ProbeID | NETAFFX: GeneTitle | NETAFFX: GeneSymbol | Fold Change | p-value |
|---|---|---|---|---|
| 204848_x_at | "hemoglobin, gamma A | hemoglobin, gamma A | hemoglobin, gamma G | hemoglobin, gamma G" | HBG1 | HBG2 | 8.93 | 4E−06 |
| 205959_at | matrix metalloproteinase 13 (collagenase 3) | matrix metalloproteinase 13 (collagenase 3) | MMP13 | 8.89 | 2E−09 |
| 213790_at | A disintegrin and metalloproteinase domain 12 (meltrin alpha) | ADAM12 | 6.77 | 4E−12 |
| 228165_at | hypothetical protein DKFZp547D2210 | DKFZp547D2210 | 4.76 | 6E−07 |
| 205523_at | hyaluronan and proteoglycan link protein 1 | HAPLN1 | 4.74 | 6E−05 |
| 228703_at | "procollagen-proline, 2-oxoglutarate 4-dioxygenase (proline 4-hydroxylase), alpha polypeptide III" | P4HA3 | 4.74 | 7E−20 |
| 202952_s_at | a disintegrin and metalloproteinase domain 12 (meltrin alpha) | ADAM12 | 4.58 | 1E−11 |
| 204419_x_at | "hemoglobin, gamma G | hemoglobin, gamma G" | HBG2 | 4.21 | 6E−05 |
| 228640_at | BH-protocadherin (brain-heart) | PCDH7 | 4.20 | 5E−16 |
| 227372_s_at | BAI1-associated protein 2-like 1 | BAIAP2L1 | 4.10 | 1E−11 |
| 205902_at | "potassium intermediate/small conductance calcium-activated channel, subfamily N, member 3" | KCNN3 | 4.07 | 2E−08 |
| 203798_s_at | visinin-like 1 | VSNL1 | 4.06 | 7E−16 |
| 219454_at | "EGF-like-domain, multiple 6" | EGFL6 | 3.86 | 5E−13 |
| 222862_s_at | adenylate kinase 5 | AK5 | 3.75 | 1E−07 |
| 203936_s_at | "matrix metalloproteinase 9 (gelatinase B, 92 kDa gelatinase, 92 kDa type IV collagenase)" | MMP9 | 3.74 | 2E−06 |
| 223721_s_at | "DnaJ (Hsp40) homolog, subfamily C, member 12" | DNAJC12 | 3.73 | 2E−11 |
| 230895_at | Hyaluronan and proteoglycan link protein 1 | HAPLN1 | 3.54 | 4E−05 |
| 213425_at | "wingless-type MMTV integration site family, member 5A | wingless-type MMTV integration site family, member 5A" | WNT5A | 3.47 | 1E−13 |
| 1554863_s_at | docking protein 5 | DOK5 | 3.45 | 1E−05 |

TABLE 8-continued

Gene expression associated with the F1 subtype of RA.

| ProbeID | NETAFFX: GeneTitle | NETAFFX: GeneSymbol | Fold Change | p-value |
| --- | --- | --- | --- | --- |
| 223121_s_at | secreted frizzled-related protein 2 | SFRP2 | 3.42 | 5E−07 |
| 207118_s_at | matrix metalloproteinase 23B \| matrix metalloproteinase 23A | MMP23B \| MMP23A | 3.39 | 6E−05 |
| 204379_s_at | "fibroblast growth factor receptor 3 (achondroplasia, thanatophoric dwarfism)" | FGFR3 | 3.34 | 2E−08 |
| 232122_s_at | NA | NA | 3.07 | 6E−11 |
| 227860_at | carboxypeptidase X (M14 family) | CPXM | 3.06 | 2E−09 |
| 223722_at | "DnaJ (Hsp40) homolog, subfamily C, member 12" | DNAJC12 | 3.04 | 3E−07 |
| 230204_at | Hyaluronan and proteoglycan link protein 1 | HAPLN1 | 3.03 | 4E−05 |
| 230464_at | "endothelial differentiation, sphingolipid G-protein-coupled receptor, 8" | EDG8 | 2.92 | 5E−12 |
| 210134_x_at | short stature homeobox 2 | SHOX2 | 2.91 | 1E−07 |
| 202935_s_at | "SRY (sex determining region Y)-box 9 (campomelic dysplasia, autosomal sex-reversal)" | SOX9 | 2.91 | 1E−07 |
| 213059_at | cAMP responsive element binding protein 3-like 1 | CREB3L1 | 2.91 | 3E−19 |
| 205990_s_at | "wingless-type MMTV integration site family, member 5A" | WNT5A | 2.90 | 2E−13 |
| 225681_at | collagen triple helix repeat containing 1 | CTHRC1 | 2.89 | 3E−12 |
| 1554697_at | "a disintegrin-like and metalloprotease (reprolysin type) with thrombospondin type 1 motif, 9" | ADAMTS9 | 2.89 | 8E−08 |
| 221697_at | MAP1 light chain 3-like protein 2 \| MAP1 light chain 3-like protein 2 | LOC440738 | 2.88 | 4E−05 |
| 203184_at | fibrillin 2 (congenital contractural arachnodactyly) | FBN2 | 2.84 | 4E−07 |
| 218976_at | "DnaJ (Hsp40) homolog, subfamily C, member 12" | DNAJC12 | 2.83 | 1E−11 |
| 212489_at | "Collagen, type V, alpha 1" | COL5A1 | 2.83 | 5E−13 |
| 209800_at | keratin 16 (focal non-epidermolytic palmoplantar keratoderma) | KRT16 | 2.83 | 8E−05 |
| 205524_s_at | hyaluronan and proteoglycan link protein 1 | HAPLN1 | 2.78 | 9E−05 |
| 226814_at | "a disintegrin-like and metalloprotease (reprolysin type) with thrombospondin type 1 motif, 9" | ADAMTS9 | 2.76 | 1E−08 |
| 206933_s_at | hexose-6-phosphate dehydrogenase (glucose 1-dehydrogenase) | H6PD | 2.76 | 1E−10 |
| 205131_x_at | "C-type lectin domain family 11, member A" | CLEC11A | 2.75 | 1E−12 |
| 205375_at | MyoD family inhibitor | MDFI | 2.74 | 6E−12 |
| 236044_at | phosphatidic acid phosphatase type 2 domain containing 1 | PPAPDC1 | 2.72 | 9E−12 |
| 1554293_at | tau tubulin kinase 2 | TTBK2 | 2.72 | 7E−08 |
| 215271_at | tenascin N | TNN | 2.72 | 3E−05 |
| 206842_at | "potassium voltage-gated channel, Shal-related subfamily, member 1" | KCND1 | 2.71 | 1E−06 |
| 227971_at | Nik related kinase | NRK | 2.70 | 2E−11 |
| 206376_at | "solute carrier family 6 (neurotransmitter transporter), member 15" | SLC6A15 | 2.68 | 3E−06 |
| 205381_at | leucine rich repeat containing 17 | LRRC17 | 2.67 | 8E−12 |
| 211396_at | "Fc fragment of IgG, low affinity IIc, receptor for (CD32)" | FCGR2C | 2.67 | 5E−08 |
| 224941_at | "pregnancy-associated plasma protein A, pappalysin 1" | PAPPA | 2.64 | 4E−05 |
| 209035_at | midkine (neurite growth-promoting factor 2) | MDK | 2.64 | 6E−09 |
| 210151_s_at | dual-specificity tyrosine-(Y)-phosphorylation regulated kinase 3 | DYRK3 | 2.62 | 1E−07 |
| 1555256_at | Ellis van Creveld syndrome 2 (limbin) | EVC2 | 2.62 | 4E−09 |
| 204358_s_at | fibronectin leucine rich transmembrane protein 2 | FLRT2 | 2.59 | 6E−14 |
| 219894_at | MAGE-like 2 | MAGEL2 | 2.59 | 5E−10 |
| 236258_at | chromosome 20 open reading frame 151 | C20orf151 | 2.57 | 5E−06 |
| 204359_at | fibronectin leucine rich transmembrane protein 2 | FLRT2 | 2.57 | 5E−13 |
| 235510_at | Usher syndrome 1C binding protein 1 | USHBP1 | 2.56 | 9E−07 |
| 233030_at | adiponutrin | ADPN | 2.56 | 5E−06 |
| 203325_s_at | "collagen, type V, alpha 1" | COL5A1 | 2.56 | 2E−12 |
| 204281_at | TEA domain family member 4 | TEAD4 | 2.54 | 2E−09 |
| 224207_x_at | matrix metalloproteinase 28 | MMP28 | 2.53 | 3E−09 |
| 215446_s_at | lysyl oxidase | LOX | 2.52 | 1E−09 |
| 212473_s_at | flavoprotein oxidoreductase MICAL2 | MICAL2 | 2.52 | 1E−09 |
| 205866_at | ficolin (collagen/fibrinogen domain containing) 3 (Hakata antigen) | FCN3 | 2.52 | 6E−05 |
| 211175_at | G protein-coupled receptor 45 | GPR45 | 2.51 | 9E−10 |
| 201107_s_at | thrombospondin 1 | THBS1 | 2.50 | 6E−05 |
| 1553027_a_at | kelch-like 4 (Drosophila) | KLHL4 | 2.49 | 3E−06 |
| 205535_s_at | BH-protocadherin (brain-heart) | PCDH7 | 2.49 | 4E−08 |
| 211899_s_at | TNF receptor-associated factor 4 | TRAF4 | 2.48 | 2E−06 |
| 236179_at | "Cadherin 11, type 2, OB-cadherin (osteoblast)" | CDH11 | 2.48 | 1E−13 |
| 200884_at | "creatine kinase, brain" | CKB | 2.48 | 3E−06 |
| 236245_at | outer dense fiber of sperm tails 3-like 1 | ODF3L1 | 2.46 | 3E−05 |
| 223122_s_at | secreted frizzled-related protein 2 | SFRP2 | 2.45 | 4E−07 |
| 211062_s_at | carboxypeptidase Z \| carboxypeptidase Z | CPZ | 2.45 | 2E−06 |
| 204123_at | "ligase III, DNA, ATP-dependent" | LIG3 | 2.44 | 2E−10 |
| 219263_at | ring finger protein 128 | RNF128 | 2.43 | 6E−07 |
| 219555_s_at | uncharacterized bone marrow protein BM039 | BM039 | 2.42 | 1E−05 |

TABLE 8-continued

Gene expression associated with the F1 subtype of RA.

| ProbeID | NETAFFX: GeneTitle | NETAFFX: GeneSymbol | Fold Change | p-value |
|---|---|---|---|---|
| 213155_at | KIAA0523 protein | KIAA0523 | 2.42 | 1E−05 |
| 217430_x_at | NA | NA | 2.41 | 2E−10 |
| 228367_at | alpha-kinase 2 | ALPK2 | 2.41 | 2E−10 |
| 230240_at | Transcribed locus | NA | 2.40 | 2E−08 |
| 205656_at | protocadherin 17 | PCDH17 | 2.40 | 7E−05 |
| 220289_s_at | absent in melanoma 1-like | AIM1L | 2.40 | 2E−05 |
| 213085_s_at | KIBRA protein | KIBRA | 2.40 | 9E−08 |
| 205031_at | ephrin-B3 | EFNB3 | 2.39 | 3E−05 |
| 206234_s_at | matrix metalloproteinase 17 (membrane-inserted) | MMP17 | 2.39 | 2E−06 |
| 206655_s_at | "glycoprotein Ib (platelet), beta polypeptide" | GP1BB | 2.38 | 2E−06 |
| 218051_s_at | hypothetical protein FLJ12442 | FLJ12442 | 2.37 | 3E−11 |
| 203823_at | regulator of G-protein signalling 3 | RGS3 | 2.37 | 1E−09 |
| 218653_at | solute carrier family 25 (mitochondrial carrier; ornithine transporter) member 15 | SLC25A15 | 2.36 | 2E−06 |
| 207714_s_at | "serine (or cysteine) proteinase inhibitor, clade H (heat shock protein 47), member 1, (collagen binding protein 1)" | SERPINH1 | 2.36 | 3E−12 |
| 202148_s_at | pyrroline-5-carboxylate reductase 1 | PYCR1 | 2.35 | 3E−17 |
| 204600_at | EPH receptor B3 | EPHB3 | 2.35 | 1E−11 |
| 219602_s_at | "family with sequence similarity 38, member B" | FAM38B | 2.34 | 8E−08 |
| 213170_at | glutathione peroxidase 7 | GPX7 | 2.34 | 4E−14 |
| 210477_x_at | mitogen-activated protein kinase 8 | MAPK8 | 2.34 | 1E−08 |
| 239542_at | NA | NA | 2.32 | 7E−06 |
| 227289_at | hypothetical protein LOC144997 | LOC144997 | 2.31 | 6E−05 |
| 202311_s_at | "collagen, type I, alpha 1" | COL1A1 | 2.31 | 1E−08 |
| 210323_at | tektin 2 (testicular) | TEKT2 | 2.31 | 4E−05 |
| 214608_s_at | eyes absent homolog 1 (Drosophila) | EYA1 | 2.31 | 2E−06 |
| 204904_at | "gap junction protein, alpha 4, 37 kDa (connexin 37)" | GJA4 | 2.30 | 2E−08 |
| 204826_at | cyclin F | CCNF | 2.30 | 8E−07 |
| 211233_x_at | estrogen receptor 1 | ESR1 | 2.30 | 1E−08 |
| 206201_s_at | mesenchyme homeo box 2 (growth arrest-specific homeo box) | MEOX2 | 2.29 | 3E−07 |
| 221730_at | "collagen, type V, alpha 2" | COL5A2 | 2.29 | 2E−12 |
| 235545_at | DEP domain containing 1 | DEPDC1 | 2.29 | 2E−05 |
| 207379_at | EGF-like repeats and discoidin I-like domains 3 | EDIL3 | 2.29 | 4E−08 |
| 220979_s_at | "ST6 (alpha-N-acetyl-neuraminyl-2,3-beta-galactosyl-1,3)-N-acetylgalactosaminide alpha-2,6-sialyltransferase 5 | ST6 (alpha-N-acetyl-neuraminyl-2,3-beta-galactosyl-1,3)-N-acetylgalactosaminide alpha-2,6-sialyltransferase 5" | ST6GALNAC5 | 2.28 | 6E−08 |
| 244533_at | NA | NA | 2.28 | 3E−08 |
| 220093_at | anthrax toxin receptor 1 | ANTXR1 | 2.28 | 8E−05 |
| 235944_at | hemicentin | FIBL-6 | 2.27 | 2E−10 |
| 233026_s_at | PDZ domain containing 3 | PDZK3 | 2.27 | 3E−07 |
| 200644_at | MARCKS-like 1 | MARCKSL1 | 2.26 | 6E−08 |
| 203434_s_at | "membrane metallo-endopeptidase (neutral endopeptidase, enkephalinase, CALLA, CD10)" | MME | 2.26 | 6E−07 |
| 228128_x_at | "pregnancy-associated plasma protein A, pappalysin 1" | PAPPA | 2.25 | 2E−06 |
| 205262_at | "potassium voltage-gated channel, subfamily H (eag-related), member 2" | KCNH2 | 2.25 | 1E−10 |
| 213869_x_at | Thy-1 cell surface antigen | Thy-1 co-transcribed | THY1 | LOC94105 | 2.25 | 8E−10 |
| 206547_s_at | "protein phosphatase, EF hand calcium-binding domain 1" | PPEF1 | 2.24 | 1E−07 |
| 204078_at | synaptonemal complex protein SC65 | SC65 | 2.24 | 2E−14 |
| 238732_at | "collagen, type XXIV, alpha 1" | COL24A1 | 2.23 | 7E−11 |
| 236689_at | ring finger protein 151 | RNF151 | 2.23 | 2E−07 |
| 206528_at | "transient receptor potential cation channel, subfamily C, member 6" | TRPC6 | 2.23 | 3E−13 |
| 243502_at | "Gap junction protein, alpha 7, 45 kDa (connexin 45)" | GJA7 | 2.22 | 4E−10 |
| 223574_x_at | "protein phosphatase 2 (formerly 2A), regulatory subunit B (PR 52), gamma isoform" | PPP2R2C | 2.22 | 5E−07 |
| 223587_s_at | amnionless homolog (mouse) | AMN | 2.22 | 1E−08 |
| 218638_s_at | "spondin 2, extracellular matrix protein" | SPON2 | 2.22 | 5E−07 |
| 219401_at | xylosyltransferase II | XYLT2 | 2.21 | 1E−07 |
| 1557176_a_at | chromosome 14 open reading frame 37 | C14orf37 | 2.20 | 5E−11 |
| 204298_s_at | lysyl oxidase | LOX | 2.19 | 7E−08 |
| 206754_s_at | "cytochrome P450, family 2, subfamily B, polypeptide 6" | CYP2B6 | 2.19 | 8E−06 |
| 228814_at | retinoblastoma binding protein 6 | RBBP6 | 2.19 | 2E−08 |
| 209031_at | "Immunoglobulin superfamily, member 4" | IGSF4 | 2.18 | 3E−06 |
| 1438_at | EPH receptor B3 | EPHB3 | 2.18 | 2E−12 |
| 227557_at | "scavenger receptor class F, member 2" | SCARF2 | 2.17 | 3E−08 |
| 211071_s_at | ALL1-fused gene from chromosome 1q | ALL1-fused gene from chromosome 1q | AF1Q | 2.17 | 1E−09 |
| 210095_s_at | insulin-like growth factor binding protein 3 | IGFBP3 | 2.17 | 3E−07 |
| 206758_at | endothelin 2 | EDN2 | 2.17 | 6E−05 |
| 1558643_s_at | EGF-like repeats and discoidin I-like domains 3 | EDIL3 | 2.16 | 1E−11 |
| 234605_at | CDC14 cell division cycle 14 homolog B (S. cerevisiae) | CDC14B | 2.16 | 6E−05 |
| 226891_at | chromosome 3 open reading frame 21 | C3orf21 | 2.15 | 8E−05 |

TABLE 8-continued

Gene expression associated with the F1 subtype of RA.

| ProbeID | NETAFFX: GeneTitle | NETAFFX: GeneSymbol | Fold Change | p-value |
|---|---|---|---|---|
| 235343_at | Hypothetical protein FLJ12505 | FLJ12505 | 2.15 | 7E−06 |
| 202936_s_at | "SRY (sex determining region Y)-box 9 (campomelic dysplasia, autosomal sex-reversal)" | SOX9 | 2.15 | 2E−06 |
| 228080_at | layilin | LOC143903 | 2.14 | 2E−13 |
| 213640_s_at | lysyl oxidase | LOX | 2.14 | 2E−05 |
| 204941_s_at | "aldehyde dehydrogenase 3 family, member B2" | ALDH3B2 | 2.14 | 8E−05 |
| 218898_at | membrane protein expressed in epithelial-like lung adenocarcinoma | CT120 | 2.13 | 2E−17 |
| 222461_s_at | hect domain and RLD 2 | HERC2 | 2.13 | 1E−06 |
| 229942_at | Transcribed locus | NA | 2.13 | 3E−11 |
| 201981_at | "pregnancy-associated plasma protein A, pappalysin 1" | PAPPA | 2.12 | 2E−08 |
| 204040_at | ring finger protein 144 | RNF144 | 2.11 | 4E−12 |
| 1561853_a_at | interleukin 23 receptor | IL23R | 2.11 | 7E−05 |
| 205612_at | multimerin 1 | MMRN1 | 2.11 | 2E−05 |
| 211709_s_at | "C-type lectin domain family 11, member A | C-type lectin domain family 11, member A" | CLEC11A | 2.09 | 4E−11 |
| 209082_s_at | "collagen, type XVIII, alpha 1" | COL18A1 | 2.09 | 4E−13 |
| 210783_x_at | "C-type lectin domain family 11, member A" | CLEC11A | 2.08 | 4E−06 |
| 211685_s_at | neurocalcin delta | neurocalcin delta | NCALD | 2.08 | 2E−11 |
| 202007_at | nidogen (enactin) | NID | 2.08 | 3E−11 |
| 226769_at | similar to RIKEN cDNA 1110018M03 | LOC387758 | 2.07 | 1E−05 |
| 219310_at | chromosome 20 open reading frame 39 | C20orf39 | 2.07 | 4E−06 |
| 242100_at | chondroitin sulfate synthase 3 | CSS3 | 2.07 | 4E−10 |
| 213695_at | paraoxonase 3 | PON3 | 2.06 | 5E−05 |
| 223170_at | DKFZP564K1964 protein | DKFZP564K1964 | 2.06 | 1E−10 |
| 213707_s_at | distal-less homeo box 5 | DLX5 | 2.05 | 2E−05 |
| 204464_s_at | endothelin receptor type A | EDNRA | 2.05 | 5E−13 |
| 1554989_at | KIAA0317 | KIAA0317 | 2.04 | 5E−05 |
| 203636_at | midline 1 (Opitz/BBB syndrome) | MID1 | 2.04 | 5E−12 |
| 204463_s_at | endothelin receptor type A | EDNRA | 2.03 | 1E−07 |
| 243409_at | Forkhead box L1 | FOXL1 | 2.03 | 4E−05 |
| 1553889_at | G protein-coupled receptor MRGX2 | MRGX2 | 2.03 | 9E−05 |
| 227314_at | "Integrin, alpha 2 (CD49B, alpha 2 subunit of VLA-2 receptor)" | ITGA2 | 2.03 | 3E−11 |
| 221729_at | "collagen, type V, alpha 2" | COL5A2 | 2.02 | 2E−11 |
| 214234_s_at | "cytochrome P450, family 3, subfamily A, polypeptide 5" | CYP3A5 | 2.02 | 1E−04 |
| 204468_s_at | tyrosine kinase with immunoglobulin-like and EGF-like domains 1 | TIE1 | 2.02 | 3E−07 |
| 223235_s_at | SPARC related modular calcium binding 2 | SMOC2 | 2.02 | 1E−10 |
| 202409_at | putative insulin-like growth factor II associated protein | LOC492304 | 2.01 | 2E−05 |
| 238805_at | similar to RIKEN cDNA 2310030G06 gene | MGC14839 | 2.01 | 1E−06 |
| 208224_at | homeo box B1 | HOXB1 | 2.01 | 4E−09 |
| 208850_s_at | Thy-1 cell surface antigen | Thy-1 co-transcribed | THY1 | LOC94105 | 2.01 | 2E−09 |
| 202894_at | EPH receptor B4 | EPHB4 | 2.01 | 2E−10 |
| 239286_at | "Cadherin 11, type 2, OB-cadherin (osteoblast)" | CDH11 | 2.00 | 2E−09 |
| 202068_s_at | low density lipoprotein receptor (familial hypercholesterolemia) | LDLR | 2.00 | 3E−05 |
| 1558342_x_at | DIX domain containing 1 | DIXDC1 | 2.00 | 1E−08 |
| 206106_at | mitogen-activated protein kinase 12 | MAPK12 | 2.00 | 1E−09 |
| 218730_s_at | "osteoglycin (osteoinductive factor, mimecan)" | OGN | 2.00 | 4E−06 |
| 207039_at | "cyclin-dependent kinase inhibitor 2A (melanoma, p16, inhibits CDK4)" | CDKN2A | 2.00 | 8E−05 |
| 205226_at | platelet-derived growth factor receptor-like | PDGFRL | 1.99 | 6E−07 |
| 202067_s_at | low density lipoprotein receptor (familial hypercholesterolemia) | LDLR | 1.99 | 3E−05 |
| 218717_s_at | leprecan-like 1 | LEPREL1 | 1.99 | 4E−09 |
| 209081_s_at | "collagen, type XVIII, alpha 1" | COL18A1 | 1.99 | 4E−14 |
| 215125_s_at | "UDP glycosyltransferase 1 family, polypeptide A10 | UDP glycosyltransferase 1 family, polypeptide A8 | UDP glycosyltransferase 1 family, polypeptide A7 | UDP glycosyltransferase 1 family, polypeptide A6 | UDP glycosyltransferase 1 family, polypeptide . . ." | UGT1A10 | UGT1A8 | UGT1A7 | UGT1A6 | UGT1A5 | UGT1A9 | UGT1A4 | UGT1A1 | UGT1A3 | 1.99 | 2E−05 |
| 219686_at | serine/threonine kinase 32B | STK32B | 1.98 | 2E−06 |
| 211234_x_at | estrogen receptor 1 | ESR1 | 1.98 | 3E−07 |
| 1564746_at | hypothetical protein BC009732 | LOC133308 | 1.97 | 1E−07 |
| 238169_at | Transcribed locus | NA | 1.97 | 9E−09 |
| 203780_at | epithelial V-like antigen 1 | EVA1 | 1.96 | 4E−06 |
| 218629_at | smoothened homolog (Drosophila) | SMO | 1.96 | 5E−05 |
| 219102_at | "reticulocalbin 3, EF-hand calcium binding domain" | RCN3 | 1.96 | 7E−11 |

TABLE 8-continued

Gene expression associated with the F1 subtype of RA.

| ProbeID | NETAFFX: GeneTitle | NETAFFX: GeneSymbol | Fold Change | p-value |
|---|---|---|---|---|
| 209841_s_at | leucine rich repeat neuronal 3 | LRRN3 | 1.96 | 1E−04 |
| 211343_s_at | "collagen, type XIII, alpha 1" | COL13A1 | 1.96 | 2E−07 |
| 214347_s_at | dopa decarboxylase (aromatic L-amino acid decarboxylase) | DDC | 1.96 | 1E−06 |
| 203637_s_at | midline 1 (Opitz/BBB syndrome) | MID1 | 1.94 | 2E−12 |
| 222856_at | "apelin, AGTRL1 ligand" | APLN | 1.94 | 8E−06 |
| 207011_s_at | PTK7 protein tyrosine kinase 7 | PTK7 | 1.94 | 1E−13 |
| 219419_at | chromosome 18 open reading frame 22 | C18orf22 | 1.93 | 2E−05 |
| 222548_s_at | mitogen-activated protein kinase kinase kinase 4 | MAP4K4 | 1.92 | 3E−15 |
| 219556_at | hypothetical protein FLJ13909 | FLJ13909 | 1.92 | 1E−07 |
| 228776_at | "Gap junction protein, alpha 7, 45 kDa (connexin 45)" | GJA7 | 1.91 | 3E−11 |
| 209427_at | smoothelin | SMTN | 1.91 | 2E−10 |
| 220807_at | "hemoglobin, theta 1 | hemoglobin, theta 1" | HBQ1 | 1.90 | 7E−05 |
| 1554398_at | lysozyme-like | LYG2 | 1.90 | 9E−05 |
| 208370_s_at | Down syndrome critical region gene 1 | DSCR1 | 1.90 | 3E−06 |
| 213435_at | SATB family member 2 | SATB2 | 1.90 | 1E−06 |
| 226244_at | "C-type lectin domain family 14, member A" | CLEC14A | 1.90 | 1E−06 |
| 209812_x_at | "caspase 2, apoptosis-related cysteine protease (neural precursor cell expressed, developmentally down-regulated 2)" | CASP2 | 1.90 | 2E−06 |
| 227204_at | par-6 partitioning defective 6 homolog gamma (C. elegans) | PARD6G | 1.90 | 2E−11 |
| 223594_at | hypothetical protein DKFZp434K2435 | DKFZp434K2435 | 1.90 | 6E−09 |
| 227468_at | carnitine palmitoyltransferase 1C | CPT1C | 1.89 | 4E−08 |
| 1557000_at | hypothetical protein LOC339768 | LOC339768 | 1.89 | 5E−11 |
| 225790_at | methionine sulfoxide reductase B3 | MSRB3 | 1.89 | 6E−09 |
| 232566_at | nucleolar protein family 6 (RNA-associated) | NOL6 | 1.88 | 3E−09 |
| 213125_at | olfactomedin-like 2B | OLFML2B | 1.88 | 3E−09 |
| 200907_s_at | palladin | KIAA0992 | 1.88 | 6E−09 |
| 206775_at | cubilin (intrinsic factor-cobalamin receptor) | CUBN | 1.88 | 3E−05 |
| 1552672_a_at | "immunoglobulin superfamily, member 3" | IGSF3 | 1.88 | 5E−07 |
| 1559394_a_at | Receptor tyrosine kinase-like orphan receptor 1 | ROR1 | 1.87 | 2E−06 |
| 230722_at | NA | NA | 1.87 | 1E−13 |
| 219390_at | "FK506 binding protein 14, 22 kDa" | FKBP14 | 1.87 | 1E−11 |
| 212558_at | "sprouty homolog 1, antagonist of FGF signaling (Drosophila)" | SPRY1 | 1.87 | 3E−05 |
| 211140_s_at | "caspase 2, apoptosis-related cysteine protease (neural precursor cell expressed, developmentally down-regulated 2)" | CASP2 | 1.87 | 1E−09 |
| 61734_at | "reticulocalbin 3, EF-hand calcium binding domain" | RCN3 | 1.87 | 4E−11 |
| 206571_s_at | mitogen-activated protein kinase kinase kinase 4 | MAP4K4 | 1.86 | 3E−10 |
| 1562528_at | RAR-related orphan receptor A | RORA | 1.86 | 8E−06 |
| 227850_x_at | CDC42 effector protein (Rho GTPase binding) 5 | CDC42EP5 | 1.86 | 8E−10 |
| 202112_at | von Willebrand factor | VWF | 1.86 | 1E−08 |
| 209890_at | transmembrane 4 superfamily member 9 | transmembrane 4 superfamily member 9 | TM4SF9 | 1.86 | 6E−10 |
| 207173_x_at | "cadherin 11, type 2, OB-cadherin (osteoblast)" | CDH11 | 1.85 | 1E−11 |
| 213139_at | snail homolog 2 (Drosophila) | SNAI2 | 1.85 | 7E−08 |
| 226960_at | DMC | UNQ473 | 1.84 | 3E−05 |
| 220226_at | "transient receptor potential cation channel, subfamily M, member 8" | TRPM8 | 1.84 | 3E−05 |
| 204141_at | "tubulin, beta 2" | TUBB2 | 1.84 | 1E−07 |
| 209030_s_at | "immunoglobulin superfamily, member 4" | IGSF4 | 1.84 | 1E−05 |
| 40016_g_at | microtubule associated serine/threonine kinase family member 4 | MAST4 | 1.83 | 3E−06 |
| 40687_at | "gap junction protein, alpha 4, 37 kDa (connexin 37)" | GJA4 | 1.83 | 4E−07 |
| 234610_at | heat shock 70 kD protein 12B | HSPA12B | 1.83 | 4E−08 |
| 204017_at | KDEL (Lys-Asp-Glu-Leu) endoplasmic reticulum protein retention receptor 3 | KDELR3 | 1.83 | 1E−10 |
| 204901_at | beta-transducin repeat containing | BTRC | 1.83 | 1E−05 |
| 206116_s_at | tropomyosin 1 (alpha) | TPM1 | 1.82 | 2E−09 |
| 208851_s_at | Thy-1 cell surface antigen | Thy-1 co-transcribed | THY1 | LOC94105 | 1.82 | 5E−10 |
| 205289_at | bone morphogenetic protein 2 | BMP2 | 1.82 | 1E−05 |
| 201445_at | "calponin 3, acidic" | CNN3 | 1.82 | 1E−05 |
| 206310_at | "serine protease inhibitor, Kazal type 2 (acrosin-trypsin inhibitor)" | SPINK2 | 1.82 | 3E−05 |
| 242671_at | Midline 1 (Opitz/BBB syndrome) | MID1 | 1.81 | 2E−07 |
| 218181_s_at | mitogen-activated protein kinase kinase kinase 4 | MAP4K4 | 1.81 | 3E−12 |
| 205578_at | receptor tyrosine kinase-like orphan receptor 2 | ROR2 | 1.81 | 3E−07 |
| 229369_at | V-set and immunoglobulin domain containing 2 | VSIG2 | 1.81 | 2E−06 |
| 214043_at | "Protein tyrosine phosphatase, receptor type, D" | PTPRD | 1.81 | 2E−06 |
| 207172_s_at | "cadherin 11, type 2, OB-cadherin (osteoblast)" | CDH11 | 1.80 | 1E−10 |
| 213345_at | "nuclear factor of activated T-cells, cytoplasmic, calcineurin-dependent 4" | NFATC4 | 1.80 | 8E−07 |
| 201792_at | AE binding protein 1 | AEBP1 | 1.80 | 7E−07 |
| 224817_at | SH3 multiple domains 1 | SH3MD1 | 1.80 | 3E−10 |

TABLE 8-continued

Gene expression associated with the F1 subtype of RA.

| ProbeID | NETAFFX: GeneTitle | NETAFFX: GeneSymbol | Fold Change | p-value |
|---|---|---|---|---|
| 228748_at | "CD59 antigen p18-20 (antigen identified by monoclonal antibodies 16.3A5, EJ16, EJ30, EL32 and G344)" | CD59 | 1.79 | 1E−08 |
| 213362_at | "Protein tyrosine phosphatase, receptor type, D" | PTPRD | 1.79 | 4E−06 |
| 200906_s_at | palladin | KIAA0992 | 1.79 | 5E−07 |
| 201416_at | SRY (sex determining region Y)-box 4 | SOX4 | 1.79 | 8E−05 |
| 234994_at | KIAA1913 | KIAA1913 | 1.79 | 6E−10 |
| 209655_s_at | transmembrane 4 superfamily member 10 | TM4SF10 | 1.79 | 5E−05 |
| 205122_at | transmembrane protein with EGF-like and two follistatin-like domains 1 | TMEFF1 | 1.78 | 6E−09 |
| 212915_at | PDZ domain containing RING finger 3 | PDZRN3 | 1.78 | 7E−07 |
| 217287_s_at | "transient receptor potential cation channel, subfamily C, member 6" | TRPC6 | 1.78 | 3E−08 |
| 242979_at | Transcribed locus | NA | 1.77 | 1E−08 |
| 205453_at | homeo box B2 | HOXB2 | 1.77 | 8E−07 |
| 233365_at | "Cleavage stimulation factor, 3' pre-RNA, subunit 2, 64 kDa, tau variant" | CSTF2T | 1.77 | 5E−05 |
| 213496_at | plasticity related gene 1 | LPPR4 | 1.77 | 5E−05 |
| 210330_at | "sarcoglycan, delta (35 kDa dystrophin-associated glycoprotein)" | SGCD | 1.76 | 3E−10 |
| 204115_at | "guanine nucleotide binding protein (G protein), gamma 11" | GNG11 | 1.76 | 2E−09 |
| 214319_at | Hypothetical protein CG003 | 13CDNA73 | 1.76 | 2E−06 |
| 220014_at | mesenchymal stem cell protein DSC54 | LOC51334 | 1.76 | 4E−05 |
| 225782_at | methionine sulfoxide reductase B3 | MSRB3 | 1.75 | 2E−07 |
| 204686_at | insulin receptor substrate 1 | IRS1 | 1.75 | 2E−08 |
| 218834_s_at | "heat shock 70 kDa protein 5 (glucose-regulated protein, 78 kDa) binding protein 1" | HSPA5BP1 | 1.75 | 2E−06 |
| 202008_s_at | nidogen (enactin) | NID | 1.75 | 6E−09 |
| 209656_s_at | transmembrane 4 superfamily member 10 | TM4SF10 | 1.75 | 8E−06 |
| 202450_s_at | cathepsin K (pycnodysostosis) | CTSK | 1.75 | 4E−14 |
| 213252_at | SH3 multiple domains 1 | SH3MD1 | 1.75 | 3E−09 |
| 209561_at | thrombospondin 3 | THBS3 | 1.74 | 5E−06 |
| 204688_at | "sarcoglycan, epsilon" | SGCE | 1.74 | 3E−06 |
| 205303_at | "potassium inwardly-rectifying channel, subfamily J, member 8" | KCNJ8 | 1.74 | 2E−08 |
| 228054_at | transmembrane protein 44 | TMEM44 | 1.74 | 4E−05 |
| 228067_at | similar to 2010300C02Rik protein | MGC42367 | 1.73 | 3E−06 |
| 202503_s_at | KIAA0101 | KIAA0101 | 1.73 | 5E−05 |
| 219637_at | hypothetical protein FLJ12584 | FLJ12584 | 1.73 | 1E−06 |
| 238478_at | Basonuclin 2 | BNC2 | 1.73 | 1E−08 |
| 220272_at | basonuclin 2 | BNC2 | 1.73 | 1E−09 |
| 202871_at | TNF receptor-associated factor 4 | TRAF4 | 1.73 | 7E−08 |
| 201505_at | "laminin, beta 1" | LAMB1 | 1.73 | 1E−08 |
| 229172_at | heat shock 70 kD protein 12B | HSPA12B | 1.72 | 3E−07 |
| 225735_at | KIAA1223 protein | KIAA1223 | 1.72 | 3E−09 |
| 217791_s_at | "aldehyde dehydrogenase 18 family, member A1" | ALDH18A1 | 1.72 | 2E−11 |
| 41037_at | TEA domain family member 4 | TEAD4 | 1.72 | 3E−07 |
| 217963_s_at | nerve growth factor receptor (TNFRSF16) associated protein 1 | NGFRAP1 | 1.72 | 3E−08 |
| 225611_at | microtubule associated serine/threonine kinase family member 4 | MAST4 | 1.71 | 3E−06 |
| 212533_at | WEE1 homolog (S. pombe) | WEE1 | 1.71 | 3E−07 |
| 221870_at | EH-domain containing 2 | EHD2 | 1.71 | 5E−07 |
| 218839_at | hairy/enhancer-of-split related with YRPW motif 1 | HEY1 | 1.71 | 2E−08 |
| 219134_at | "EGF, latrophilin and seven transmembrane domain containing 1" | ELTD1 | 1.71 | 4E−08 |
| 238583_at | methionine sulfoxide reductase B3 | MSRB3 | 1.71 | 2E−06 |
| 202712_s_at | "creatine kinase, mitochondrial 1 (ubiquitous)" | CKMT1 | 1.71 | 3E−06 |
| 212651_at | Rho-related BTB domain containing 1 | RHOBTB1 | 1.71 | 4E−11 |
| 209633_at | "protein phosphatase 2 (formerly 2A), regulatory subunit B", alpha" | PPP2R3A | 1.70 | 2E−05 |
| 1553620_at | tripartite motif-containing 42 | TRIM42 | 1.70 | 5E−06 |
| 1568618_a_at | UDP-N-acetyl-alpha-D-galactosamine: polypeptide N-acetylgalactosaminyltransferase 1 (GalNAc-T1) | GALNT1 | 1.70 | 2E−09 |
| 226282_at | Full length insert cDNA clone ZE03F06 | NA | 1.70 | 8E−05 |
| 206607_at | Cas-Br-M (murine) ecotropic retroviral transforming sequence | CBL | 1.70 | 2E−06 |
| 212364_at | myosin IB | MYO1B | 1.69 | 1E−09 |
| 242668_x_at | sperm associated antigen 4-like | SPAG4L | 1.69 | 3E−05 |
| 209694_at | 6-pyruvoyltetrahydropterin synthase | PTS | 1.69 | 1E−11 |
| 202949_s_at | four and a half LIM domains 2 | FHL2 | 1.69 | 2E−07 |
| 212950_at | G protein-coupled receptor 116 | GPR116 | 1.69 | 2E−09 |
| 212365_at | myosin IB | MYO1B | 1.69 | 7E−11 |
| 1562529_s_at | RAR-related orphan receptor A | RORA | 1.69 | 9E−05 |
| 208664_s_at | tetratricopeptide repeat domain 3 | TTC3 | 1.68 | 3E−07 |
| 222722_at | "osteoglycin (osteoinductive factor, mimecan)" | OGN | 1.68 | 1E−05 |
| 214844_s_at | docking protein 5 | DOK5 | 1.68 | 6E−05 |
| 224942_at | "pregnancy-associated plasma protein A, pappalysin 1" | PAPPA | 1.68 | 8E−05 |
| 228563_at | NA | NA | 1.68 | 6E−09 |
| 230972_at | ankyrin repeat domain 9 | ANKRD9 | 1.68 | 2E−06 |
| 226905_at | hypothetical protein MGC45871 | MGC45871 | 1.68 | 9E−06 |
| 204136_at | "collagen, type VII, alpha 1 (epidermolysis bullosa, dystrophic, dominant and recessive)" | COL7A1 | 1.67 | 1E−06 |

TABLE 8-continued

Gene expression associated with the F1 subtype of RA.

| ProbeID | NETAFFX: GeneTitle | NETAFFX: GeneSymbol | Fold Change | p-value |
|---|---|---|---|---|
| 221401_at | "calcium channel, voltage-dependent, gamma subunit 5" | CACNG5 | 1.67 | 1E−05 |
| 222101_s_at | dachsous 1 (*Drosophila*) | DCHS1 | 1.67 | 5E−08 |
| 231175_at | chromosome 6 open reading frame 65 | C6orf65 | 1.67 | 4E−07 |
| 222675_s_at | BAI1-associated protein 2-like 1 | BAIAP2L1 | 1.67 | 2E−07 |
| 207390_s_at | smoothelin | SMTN | 1.67 | 5E−08 |
| 204983_s_at | glypican 4 | GPC4 | 1.67 | 4E−06 |
| 203150_at | Rab9 effector p40 | RAB9P40 | 1.67 | 5E−09 |
| 33579_i_at | galanin receptor 3 | GALR3 | 1.67 | 5E−06 |
| 200897_s_at | palladin | KIAA0992 | 1.66 | 4E−08 |
| 219522_at | four jointed box 1 (*Drosophila*) | FJX1 | 1.66 | 2E−06 |
| 210987_x_at | Tropomyosin 1 (alpha) | TPM1 | 1.66 | 2E−07 |
| 205304_s_at | "potassium inwardly-rectifying channel, subfamily J, member 8" | KCNJ8 | 1.66 | 2E−07 |
| 208663_s_at | tetratricopeptide repeat domain 3 | TTC3 | 1.66 | 4E−10 |
| 225322_s_at | hypothetical protein FLJ22175 | FLJ22175 | 1.66 | 1E−04 |
| 206702_at | "TEK tyrosine kinase, endothelial (venous malformations, multiple cutaneous and mucosal)" | TEK | 1.66 | 3E−06 |
| 212642_s_at | human immunodeficiency virus type I enhancer binding protein 2 | HIVEP2 | 1.66 | 2E−05 |
| 208661_s_at | tetratricopeptide repeat domain 3 | TTC3 | 1.66 | 7E−13 |
| 228396_at | NA | NA | 1.66 | 2E−07 |
| 226893_at | "V-abl Abelson murine leukemia viral oncogene homolog 2 (arg, Abelson-related gene)" | ABL2 | 1.65 | 3E−05 |
| 201681_s_at | "discs, large homolog 5 (*Drosophila*)" | DLG5 | 1.65 | 5E−06 |
| 221024_s_at | "solute carrier family 2 (facilitated glucose transporter), member 10 ǀ solute carrier family 2 (facilitated glucose transporter), member 10" | SLC2A10 | 1.65 | 2E−08 |
| 201261_x_at | biglycan | BGN | 1.65 | 2E−05 |
| 205104_at | syntaphilin | SNPH | 1.65 | 3E−06 |
| 224998_at | chemokine-like factor super family 4 | CKLFSF4 | 1.65 | 3E−09 |
| 225736_at | F-box protein 22 | FBXO22 | 1.65 | 4E−05 |
| 226876_at | hypothetical protein MGC45871 | MGC45871 | 1.65 | 7E−06 |
| 226950_at | Activin A receptor type II-like 1 | ACVRL1 | 1.65 | 6E−05 |
| 222416_at | "aldehyde dehydrogenase 18 family, member A1" | ALDH18A1 | 1.65 | 7E−12 |
| 237411_at | "a disintegrin-like and metalloprotease (reprolysin type) with thrombospondin type 1 motif, 6" | ADAMTS6 | 1.64 | 6E−05 |
| 225613_at | microtubule associated serine/threonine kinase family member 4 | MAST4 | 1.64 | 3E−07 |
| 207119_at | "protein kinase, cGMP-dependent, type I" | PRKG1 | 1.64 | 1E−06 |
| 208073_x_at | tetratricopeptide repeat domain 3 | TTC3 | 1.64 | 8E−14 |
| 224746_at | KIAA1522 protein | KIAA1522 | 1.64 | 4E−05 |
| 210135_s_at | short stature homeobox 2 | SHOX2 | 1.64 | 1E−05 |
| 204400_at | embryonal Fyn-associated substrate | EFS | 1.64 | 2E−05 |
| 204966_at | brain-specific angiogenesis inhibitor 2 | BAI2 | 1.64 | 4E−06 |
| 219051_x_at | "meteorin, glial cell differentiation regulator" | METRN | 1.64 | 2E−08 |
| 237929_at | LOC146853 | LOC146853 | 1.64 | 8E−05 |
| 201418_s_at | SRY (sex determining region Y)-box 4 | SOX4 | 1.64 | 1E−06 |
| 207264_at | KDEL (Lys-Asp-Glu-Leu) endoplasmic reticulum protein retention receptor 3 | KDELR3 | 1.64 | 5E−06 |
| 215074_at | myosin IB | MYO1B | 1.63 | 2E−05 |
| 210645_s_at | tetratricopeptide repeat domain 3 | TTC3 | 1.63 | 2E−11 |
| 201724_s_at | UDP-N-acetyl-alpha-D-galactosamine: polypeptide N-acetylgalactosaminyltransferase 1 (GalNAc-T1) | GALNT1 | 1.63 | 3E−09 |
| 209596_at | adlican | DKFZp564I1922 | 1.63 | 7E−06 |
| 210986_s_at | tropomyosin 1 (alpha) | TPM1 | 1.63 | 4E−07 |
| 205164_at | glycine C-acetyltransferase (2-amino-3-ketobutyrate coenzyme A ligase) | GCAT | 1.63 | 4E−05 |
| 200757_s_at | calumenin | CALU | 1.62 | 5E−08 |
| 233025_at | PDZ domain containing 3 | PDZK3 | 1.62 | 2E−05 |
| 232269_x_at | "meteorin, glial cell differentiation regulator" | METRN | 1.62 | 6E−09 |
| 227399_at | Colon carcinoma related protein | FLJ38507 | 1.62 | 1E−05 |
| 227481_at | membrane associated guanylate kinase interacting protein-like 1 | MAGI1 | 1.62 | 4E−05 |
| 44783_s_at | hairy/enhancer-of-split related with YRPW motif 1 | HEY1 | 1.62 | 5E−09 |
| 222937_s_at | matrix metalloproteinase 28 | MMP28 | 1.62 | 1E−06 |
| 235204_at | "COX15 homolog, cytochrome c oxidase assembly protein (yeast)" | COX15 | 1.61 | 3E−07 |
| 208682_s_at | "melanoma antigen family D, 2" | MAGED2 | 1.61 | 1E−08 |
| 232080_at | "HECT, C2 and WW domain containing E3 ubiquitin protein ligase 2" | HECW2 | 1.61 | 4E−05 |
| 211651_s_at | "laminin, beta 1 ǀ laminin, beta 1" | LAMB1 | 1.61 | 1E−07 |
| 213221_s_at | SNF1-like kinase 2 | SNF1LK2 | 1.61 | 7E−05 |
| 217312_s_at | "collagen, type VII, alpha 1 (epidermolysis bullosa, dystrophic, dominant and recessive)" | COL7A1 | 1.61 | 9E−05 |
| 210869_s_at | melanoma cell adhesion molecule | MCAM | 1.61 | 8E−05 |
| 225009_at | chemokine-like factor super family 4 | CKLFSF4 | 1.61 | 1E−08 |
| 222803_at | phosphoribosyl transferase domain containing 1 | PRTFDC1 | 1.61 | 9E−08 |

TABLE 8-continued

Gene expression associated with the F1 subtype of RA.

| ProbeID | NETAFFX: GeneTitle | NETAFFX: GeneSymbol | Fold Change | p-value |
|---|---|---|---|---|
| 207265_s_at | KDEL (Lys-Asp-Glu-Leu) endoplasmic reticulum protein retention receptor 3 | KDELR3 | 1.60 | 5E−10 |
| 213905_x_at | biglycan | serologically defined colon cancer antigen 33 | BGN | SDCCAG33 | 1.60 | 5E−06 |
| 213012_at | "neural precursor cell expressed, developmentally down-regulated 4" | NEDD4 | 1.60 | 1E−09 |
| 210958_s_at | microtubule associated serine/threonine kinase family member 4 | MAST4 | 1.60 | 8E−06 |
| 1568779_a_at | "extracellular matrix protein 2, female organ and adipocyte specific" | ECM2 | 1.60 | 6E−08 |
| 204854_at | leprecan-like 2 | LEPREL2 | 1.60 | 4E−06 |
| 45297_at | EH-domain containing 2 | EHD2 | 1.60 | 4E−07 |
| 212641_at | human immunodeficiency virus type I enhancer binding protein 2 | HIVEP2 | 1.60 | 3E−05 |
| 221880_s_at | hypothetical gene supported by AK075564; BC060873 | LOC400451 | 1.59 | 1E−05 |
| 221599_at | PTD015 protein | PTD015 | 1.59 | 8E−05 |
| 215017_s_at | formin binding protein 1-like | FNBP1L | 1.59 | 1E−06 |
| 216235_s_at | endothelin receptor type A | EDNRA | 1.59 | 1E−06 |
| 210993_s_at | "SMAD, mothers against DPP homolog 1 (*Drosophila*)" | SMAD1 | 1.59 | 3E−05 |
| 207836_s_at | RNA binding protein with multiple splicing | RBPMS | 1.59 | 5E−07 |
| 213577_at | squalene epoxidase | SQLE | 1.59 | 8E−05 |
| 201307_at | septin 11 | 11-Sep | 1.59 | 9E−13 |
| 205911_at | parathyroid hormone receptor 1 | PTHR1 | 1.59 | 4E−05 |
| 222258_s_at | SH3-domain binding protein 4 | SH3BP4 | 1.58 | 2E−06 |
| 212667_at | "secreted protein, acidic, cysteine-rich (osteonectin)" | SPARC | 1.58 | 1E−07 |
| 209576_at | "guanine nucleotide binding protein (G protein), alpha inhibiting activity polypeptide 1" | GNAI1 | 1.58 | 5E−07 |
| 203038_at | "protein tyrosine phosphatase, receptor type, K" | PTPRK | 1.58 | 3E−10 |
| 201723_s_at | UDP-N-acetyl-alpha-D-galactosamine: polypeptide N-acetylgalactosaminyltransferase 1 (GalNAc-T1) | GALNT1 | 1.58 | 3E−08 |
| 220174_at | hypothetical protein FLJ23420 | FLJ23420 | 1.58 | 6E−05 |
| 211592_s_at | NA | NA | 1.58 | 1E−05 |
| 216269_s_at | "elastin (supravalvular aortic stenosis, Williams-Beuren syndrome)" | ELN | 1.58 | 5E−05 |
| 1554195_a_at | NA | NA | 1.58 | 2E−05 |
| 226408_at | TEA domain family member 2 | TEAD2 | 1.58 | 2E−05 |
| 227998_at | S100 calcium binding protein A16 | S100A16 | 1.57 | 2E−07 |
| 241355_at | Hairless homolog (mouse) | HR | 1.57 | 3E−07 |
| 200755_s_at | calumenin | CALU | 1.57 | 4E−07 |
| 209373_at | BENE protein | BENE | 1.57 | 3E−05 |
| 218176_at | "melanoma antigen family F, 1" | MAGEF1 | 1.57 | 3E−10 |
| 213230_at | paraneoplastic antigen | HUMPPA | 1.57 | 3E−06 |
| 225731_at | KIAA1223 protein | KIAA1223 | 1.57 | 2E−09 |
| 204976_s_at | "Alport syndrome, mental retardation, midface hypoplasia and elliptocytosis chromosomal region, gene 1" | AMMECR1 | 1.56 | 1E−11 |
| 205635_at | huntingtin-associated protein interacting protein (duo) | HAPIP | 1.56 | 1E−05 |
| 205020_s_at | ADP-ribosylation factor-like 4A | ARL4A | 1.56 | 6E−05 |
| 201655_s_at | Heparan sulfate proteoglycan 2 (perlecan) | HSPG2 | 1.56 | 5E−06 |
| 210830_s_at | paraoxonase 2 | PON2 | 1.56 | 2E−06 |
| 231420_at | gametogenetin | GGN | 1.56 | 8E−05 |
| 201722_s_at | UDP-N-acetyl-alpha-D-galactosamine: polypeptide N-acetylgalactosaminyltransferase 1 (GalNAc-T1) | GALNT1 | 1.56 | 4E−08 |
| 235723_at | basonuclin 2 | BNC2 | 1.56 | 1E−06 |
| 212951_at | G protein-coupled receptor 116 | GPR116 | 1.56 | 2E−07 |
| 227295_at | IKK interacting protein | IKIP | 1.55 | 5E−11 |
| 204518_s_at | peptidylprolyl isomerase C (cyclophilin C) | PPIC | 1.55 | 7E−08 |
| 203797_at | visinin-like 1 | VSNL1 | 1.55 | 3E−06 |
| 206236_at | G protein-coupled receptor 4 | GPR4 | 1.55 | 7E−06 |
| 209087_x_at | melanoma cell adhesion molecule | MCAM | 1.55 | 4E−05 |
| 219145_at | latrophilin 1 | LPHN1 | 1.55 | 5E−08 |
| 210300_at | RAS (RAD and GEM)-like GTP-binding 1 | REM1 | 1.55 | 4E−07 |
| 220027_s_at | Ras interacting protein 1 | RASIP1 | 1.55 | 1E−05 |
| 203060_s_at | 3'-phosphoadenosine 5'-phosphosulfate synthase 2 | PAPSS2 | 1.55 | 2E−05 |
| 203488_at | latrophilin 1 | LPHN1 | 1.54 | 2E−07 |
| 202515_at | "discs, large homolog 1 (*Drosophila*)" | DLG1 | 1.54 | 3E−08 |
| 221767_x_at | High density lipoprotein binding protein (vigilin) | HDLBP | 1.54 | 8E−07 |
| 1553530_a_at | "integrin, beta 1 (fibronectin receptor, beta polypeptide, antigen CD29 includes MDF2, MSK12)" | ITGB1 | 1.54 | 2E−06 |
| 222547_at | mitogen-activated protein kinase kinase kinase kinase 4 | MAP4K4 | 1.54 | 2E−09 |
| 217904_s_at | beta-site APP-cleaving enzyme 1 | BACE1 | 1.54 | 3E−05 |
| 236261_at | Oxysterol binding protein-like 6 | OSBPL6 | 1.54 | 1E−06 |
| 218162_at | olfactomedin-like 3 | OLFML3 | 1.53 | 8E−06 |
| 204992_s_at | profilin 2 | PFN2 | 1.53 | 2E−09 |

TABLE 8-continued

Gene expression associated with the F1 subtype of RA.

| ProbeID | NETAFFX: GeneTitle | NETAFFX: GeneSymbol | Fold Change | p-value |
|---|---|---|---|---|
| 207034_s_at | GLI-Kruppel family member GLI2 | GLI2 | 1.53 | 4E−06 |
| 220778_x_at | "sema domain, transmembrane domain (TM), and cytoplasmic domain, (semaphorin) 6B" | SEMA6B | 1.53 | 3E−06 |
| 1554127_s_at | methionine sulfoxide reductase B3 | MSRB3 | 1.53 | 1E−07 |
| 221529_s_at | plasmalemma vesicle associated protein | PLVAP | 1.53 | 1E−06 |
| 203558_at | cullin 7 | CUL7 | 1.53 | 9E−05 |
| 203744_at | high-mobility group box 3 | HMGB3 | 1.53 | 2E−06 |
| 204517_at | peptidylprolyl isomerase C (cyclophilin C) | PPIC | 1.53 | 8E−10 |
| 213249_at | F-box and leucine-rich repeat protein 7 | FBXL7 | 1.53 | 8E−08 |
| 222462_s_at | beta-site APP-cleaving enzyme 1 | BACE1 | 1.52 | 8E−11 |
| 217975_at | WW domain binding protein 5 | WBP5 | 1.52 | 1E−09 |
| 200770_s_at | "laminin, gamma 1 (formerly LAMB2)" | LAMC1 | 1.52 | 2E−05 |
| 202975_s_at | Rho-related BTB domain containing 3 | RHOBTB3 | 1.52 | 3E−05 |
| 219076_s_at | "peroxisomal membrane protein 2, 22 kDa" | PXMP2 | 1.52 | 2E−05 |
| 202828_s_at | matrix metalloproteinase 14 (membrane-inserted) | MMP14 | 1.51 | 2E−05 |
| 228327_x_at | "Meis1, myeloid ecotropic viral integration site 1 homolog 3 (mouse)" | MEIS3 | 1.51 | 7E−05 |
| 203810_at | "DnaJ (Hsp40) homolog, subfamily B, member 4" | DNAJB4 | 1.51 | 8E−05 |
| 204619_s_at | chondroitin sulfate proteoglycan 2 (versican) | CSPG2 | 1.51 | 1E−05 |
| 227660_at | anthrax toxin receptor 1 | ANTXR1 | 1.51 | 3E−05 |
| 201876_at | paraoxonase 2 | PON2 | 1.51 | 9E−07 |
| 213959_s_at | KIAA1005 protein | KIAA1005 | 1.51 | 2E−05 |
| 226911_at | hypothetical protein FLJ39155 | FLJ39155 | 1.51 | 1E−06 |
| 207829_s_at | BCL2/adenovirus E1B 19 kDa interacting protein 1 | BNIP1 | 1.51 | 1E−05 |
| 223237_x_at | "adaptor-related protein complex 2, alpha 1 subunit" | AP2A1 | 1.51 | 3E−05 |
| 225688_s_at | "pleckstrin homology-like domain, family B, member 2" | PHLDB2 | 1.51 | 4E−05 |
| 204556_s_at | DAZ interacting protein 1 | DZIP1 | 1.51 | 3E−09 |
| 244126_at | peroxisomal biogenesis factor 11 gamma | PEX11G | 1.50 | 4E−08 |
| 227569_at | ligand of numb-protein X 2 | LNX2 | 1.50 | 4E−09 |
| 225202_at | Rho-related BTB domain containing 3 | RHOBTB3 | 1.50 | 3E−05 |
| 218894_s_at | mago-nashi homolog | FLJ10292 | 1.50 | 1E−06 |

What is claimed is:

1. A method of treating a subject with rheumatoid arthritis, comprising the steps of:
   (a) obtaining a biological sample from the subject;
   (b) measuring in the biological sample expression of a combination of proteins comprising ICAM1 and CXCL13 in an immunoassay using monoclonal antibodies that specifically bind to the ICAM1 protein and the CXCL13 protein;
   (c) determining whether the expression of the proteins is elevated in the biological sample relative to a control sample; and
   (d) administering an effective amount of a rheumatoid arthritis (RA) therapeutic agent to treat the subject based on whether the expression of the ICAM1 protein or the CXCL13 protein is elevated, wherein the RA therapeutic agent is a tumor necrosis factor-alpha inhibitor or an anti-interleukin 6 receptor agent.

2. The method of claim 1, wherein step (c) comprises determining that expression of the ICAM1 protein is elevated.

3. The method of claim 2, wherein the ICAM1 protein is sICAM1.

4. The method of claim 1, wherein the biological sample is serum.

5. The method of claim 1, wherein the immunoassay is an ELISA.

6. The method of claim 1, wherein step (c) comprises determining that expression of the CXCL13 protein is elevated.

7. The method of claim 1, wherein step (c) comprises determining that expression of the ICAM1 protein is not elevated.

8. The method of claim 1, wherein step (c) comprises determining that expression of the CXCL13 protein is not elevated.

9. The method of claim 1, wherein step (d) comprises administering an effective amount of the tumor necrosis factor-alpha inhibitor.

10. The method of claim 1, wherein step (d) comprises administering an effective amount of the anti-interleukin 6 receptor agent.

11. A method of measuring protein expression, comprising the steps of:
    (a) obtaining a serum sample from a subject with rheumatoid arthritis; and
    (b) measuring in the biological sample expression of a combination of proteins comprising ICAM1 and CXCL13 in an immunoassay using monoclonal antibodies that specifically bind to the ICAM1 protein and the CXCL13 protein.

12. The method of claim 11, wherein the immunoassay is an ELISA.

13. The method of claim 11, wherein the ICAM1 protein is sICAM1.

14. The method of claim 11, further comprising determining that expression of the ICAM1 protein is elevated.

15. The method of claim 11, further comprising determining that expression of the CXCL13 protein is elevated.

16. The method of claim 11, further comprising determining that expression of the ICAM1 protein is not elevated.

17. The method of claim 11, further comprising determining that expression of the CXCL13 protein is not elevated.

* * * * *